US011414665B2

(12) United States Patent
Zhang et al.

(10) Patent No.: US 11,414,665 B2
(45) Date of Patent: Aug. 16, 2022

(54) NUCLEIC ACID, COMPOSITION AND CONJUGATE COMPRISING THE SAME, AND PREPARATION METHOD AND USE THEREOF

(71) Applicant: SUZHOU RIBO LIFE SCIENCE CO., LTD., Suzhou (CN)

(72) Inventors: Hongyan Zhang, Suzhou (CN); Shan Gao, Suzhou (CN); Daiwu Kang, Suzhou (CN)

(73) Assignee: SUZHOU RIBO LIFE SCIENCE CO., LTD., Jiangsu (CN)

( * ) Notice: Subject to any disclaimer, the term of this patent is extended or adjusted under 35 U.S.C. 154(b) by 0 days.

(21) Appl. No.: 16/763,058

(22) PCT Filed: Nov. 29, 2018

(86) PCT No.: PCT/CN2018/118300
§ 371 (c)(1),
(2) Date: May 11, 2020

(87) PCT Pub. No.: WO2019/105435
PCT Pub. Date: Jun. 6, 2019

(65) Prior Publication Data
US 2021/0277400 A1    Sep. 9, 2021

(30) Foreign Application Priority Data

Dec. 1, 2017  (CN) .......................... 201711249378.5
Dec. 29, 2017  (CN) .......................... 201711478933.1

(51) Int. Cl.
| | |
|---|---|
| *C12N 15/11* | (2006.01) |
| *C12N 15/113* | (2010.01) |
| *A61P 31/20* | (2006.01) |
| *A61K 31/713* | (2006.01) |

(52) U.S. Cl.
CPC .......... *C12N 15/1131* (2013.01); *A61P 31/20* (2018.01); *A61K 31/713* (2013.01); *C12N 2310/14* (2013.01); *C12N 2310/315* (2013.01); *C12N 2310/321* (2013.01); *C12N 2310/322* (2013.01); *C12N 2310/344* (2013.01); *C12N 2310/351* (2013.01); *C12N 2320/32* (2013.01)

(58) Field of Classification Search
None
See application file for complete search history.

(56) References Cited

U.S. PATENT DOCUMENTS

| | | | |
|---|---|---|---|
| 8,344,125 B2 | 1/2013 | Manoharan et al. | |
| 10,130,651 B2 | 11/2018 | Wooddell et al. | |
| 10,246,708 B2 | 4/2019 | Kasperkovitz et al. | |
| 2003/0206887 A1* | 11/2003 | Morrissey .............. | C12N 15/86 424/93.2 |
| 2010/0063132 A1 | 3/2010 | Kim et al. | |
| 2013/0005793 A1 | 1/2013 | Chin et al. | |
| 2013/0158021 A1 | 6/2013 | Dong et al. | |
| 2014/0179768 A1 | 6/2014 | Bettencourt et al. | |
| 2014/0194489 A1 | 7/2014 | Bumcrot et al. | |
| 2014/0343123 A1 | 11/2014 | Prakash et al. | |
| 2015/0174260 A1 | 6/2015 | Yang et al. | |
| 2015/0191726 A1 | 7/2015 | Manoharan et al. | |
| 2015/0247143 A1 | 9/2015 | Fitzgerald et al. | |
| 2015/0263948 A1 | 9/2015 | Jan et al. | |
| 2016/0017335 A1 | 1/2016 | Borodovsky et al. | |
| 2016/0186180 A1 | 6/2016 | Bettencourt et al. | |
| 2017/0000815 A1 | 1/2017 | Fitzgerald et al. | |
| 2018/0087054 A1 | 3/2018 | Querbes et al. | |
| 2018/0216114 A1 | 8/2018 | Fitzgerald et al. | |
| 2019/0062749 A1 | 2/2019 | Zhang | |
| 2019/0202855 A1 | 7/2019 | Sakamuri et al. | |
| 2019/0255091 A1 | 8/2019 | Li et al. | |
| 2019/0292547 A1 | 9/2019 | Li et al. | |

FOREIGN PATENT DOCUMENTS

| | | |
|---|---|---|
| AU | 2014208251 A1 | 8/2014 |
| CA | 2 930 393 A1 | 6/2009 |
| CN | 101603042 A * | 12/2009 |
| CN | 102083983 A | 6/2011 |
| CN | 102140458 A | 8/2011 |

(Continued)

OTHER PUBLICATIONS

Machine translation of CN 101603042, 2009, pp. 1-14 (Year: 2009).*
International Search Report (PCT/ISA/210) dated Feb. 28, 2019, by the National Intellectual Property Administration, PRC as the International Searching Authority for International Application No. PCT/CN2018/118300, and an English translation of the Report.
Su et al., "Progress on Inhibition of Hepatitis B Virus by siRNA Strategy", China Biotechnology. vol. 34, No. 9, Sep. 15, 2014 (Sep. 15, 2014), pp. 102-105 (English abstract).
Ren et al., "Stable Inhibition of Hepatitis B Virus Expression and Replication by Expressed siRNA", Biochemical and Biophysical Research Communications, vol. 335, No. 4, Oct. 7, 2005 (Oct. 7, 2005), pp. 1051-1058 (English abstract).
Beaucage et al., "Advances in the Synthesis of Oligonucleotides by the Phosphoramidite Approach", Tetrahedron, 1992, vol. 28, No. 12, pp. 2223-2311.

(Continued)

*Primary Examiner* — Ekaterina Poliakova-Georgantas
(74) *Attorney, Agent, or Firm* — Buchanan Ingersoll & Rooney PC

(57) ABSTRACT

Provided are an siRNA for inhibiting expression of a Hepatitis B virus gene, and a pharmaceutical composition and conjugate containing the siRNA. Each nucleotide in the siRNA is an independently modified or unmodified nucleotide; the siRNA comprises a sense strand and an antisense strand; the sense strand comprises a nucleotide sequence A; the length of the nucleotide sequence A is the same as that of a nucleotide sequence as shown in SEQ ID NO: 1, and the number of the nucleotide differences is not more than three; the antisense strand comprises a nucleotide sequence B; and the length of the nucleotide sequence B is the same as that of a nucleotide sequence as shown in SEQ ID NO: 2, and number of nucleotide differences is not more than three.

26 Claims, 5 Drawing Sheets

Specification includes a Sequence Listing.

(56) References Cited

FOREIGN PATENT DOCUMENTS

| | | | |
|---|---|---|---|
| CN | 102140461 | A | 8/2011 |
| CN | 103380113 | A | 10/2013 |
| CN | 104107437 | A | 10/2014 |
| CN | 105378082 | A | 3/2016 |
| EP | 2 669 377 | A2 | 12/2013 |
| EP | 2 990 410 | A1 | 3/2016 |
| EP | 3 312 281 | A2 | 4/2018 |
| WO | 2004078181 | A1 | 9/2004 |
| WO | 2006096018 | A1 | 9/2006 |
| WO | 2009/073809 | A2 | 6/2009 |
| WO | 2009/082607 | A2 | 7/2009 |
| WO | 2010/012244 | A1 | 2/2010 |
| WO | 2010/101951 | A1 | 9/2010 |
| WO | 2011/139702 | A2 | 11/2011 |
| WO | 2012/024170 | A2 | 2/2012 |
| WO | 2012037254 | A1 | 3/2012 |
| WO | 2012/068176 | A1 | 5/2012 |
| WO | 2012/083185 | A2 | 6/2012 |
| WO | 2014/025805 | A1 | 2/2014 |
| WO | 2014/079629 | A1 | 5/2014 |
| WO | 2014/089313 | A1 | 6/2014 |
| WO | 2014/179626 | A2 | 11/2014 |
| WO | 2015/006740 | A2 | 1/2015 |
| WO | 2015/168532 | A2 | 11/2015 |
| WO | 2015/188197 | A2 | 12/2015 |
| WO | 2016/077321 | A1 | 5/2016 |
| WO | 2016/081444 | A1 | 5/2016 |
| WO | 2016/149331 | A2 | 9/2016 |
| WO | 2016/179342 | A2 | 11/2016 |
| WO | 2016/206626 | A1 | 12/2016 |
| WO | 2017/015175 | A1 | 1/2017 |
| WO | 2017/035340 | A1 | 3/2017 |
| WO | 2017/120397 | A1 | 7/2017 |
| WO | 2018/027106 | A2 | 2/2018 |
| WO | 2018/140920 | A1 | 8/2018 |
| WO | 2020/093053 | A1 | 5/2020 |

OTHER PUBLICATIONS

Dong et al., "Lipopeptide nanoparticles for potent and selective siRNA delivery in rodents and nonhuman primates", Proceedings of the National Academy of Sciences, Feb. 2014, www.pnas.org/cgi/doi/10.1073/pnas.1322937111 (6 pages).

Greene et al., "Protection for the Hydroxyl Group, Including 1,2- and 1,3-DIOLS", Protective Groups in Organic Synthesis, Third Edition, 1999 John Wiley & Sons, Inc. pp. 17-245 (229 pages).

Khvorova et al., "The chemical evolution of oligonucleotide therapies of clinical utility", Nature Biotechnology Advance Online Publication, Feb. 27, 2017; doi:10.1038/nbt.3765 (11 pages).

Love et al., "Lipid-like materials for low-dose, in vivo gene silencing", Proceedings of the National Academy of Sciences, Feb. 2, 2010, vol. 107, No. 5, 1864-1869, with correction. (7 pages).

Matsuda et al., "siRNA Conjugates Carrying Sequentially Assembled Trivalent N-Acetylgalactosamine Linked Through Nucleosides Elicit Robust Gene Silencing In Vivo in Hepatocytes", ACS Chemical Biology, 2015, vol. 10, No. 5, pp. 1181-1187.

Nair et al., "Multivalent N-Acetylgalactosamine-Conjugated siRNA Localizes in Hepatocytes and Elicits Robust RNAi-Mediated Gene Silencing", Journal of the American Chemical Society, 2014, vol. 136, pp. 16958-16961.

Rajeev et al., "Hepatocyte-Specific Delivery of siRNAs Conjugated to Novel Non-nucleosidic Trivalent N-Acetylgalactosamine Elicits Robust Gene Silencing in Vivo", ChemBioChem, 2015, vol. 16, pp. 903-908.

Ui-Tei et al., "Functional dissection of siRNA sequence by systematic DNA substitution: modified siRNA with a DNA seed arm is a powerful tool for mammalian gene silencing with significantly reduced off-target effect", Nucleic Acids Rearch, 2008, vol. 36, No. 7, pp. 2136-2151.

Watts et al., "Chemically modified siRNA: tools and applications", Drug Discovery Today, Oct. 2008, vol. 13, Nos. 19/20, pp. 842-855.

Wooddell et al., "Hepatocyte-targeted RNAi Therapeutics for the Treatment of Chronic Hepatitis B Virus Infection", Molecular Therapy. Feb. 26, 2013. doi:10.1038/mt.2013.31 (13 pages).

Dong et al., "A Novel packaging system of recombinant AAV5/5 vector", Chinese Journal of Biotechnology, May 25, 2010, vol. 26, No. 5, pp. 679-686, with an English abstract.

Extended European Search Report dated Aug. 9, 2021, by the European Patent Office in corresponding European Patent Application No. 18883362.8. (9 pages).

* cited by examiner

NUCLEIC ACID, COMPOSITION AND CONJUGATE COMPRISING THE SAME, AND PREPARATION METHOD AND USE THEREOF

SEQUENCE LISTING

Incorporated by reference herein in its entirety is a computer-readable sequence listing submitted via EFS-Web and identified as follows: One (10,208 byte ASCII (Text)) file named "16763058 Amended Sequence Listing.txt" created on Oct. 30, 2020.

BACKGROUND OF THE INVENTION

Viral hepatitis type B (also known as hepatitis type B or hepatitis B) is an infectious disease, which is a serious threat to the world, especially to China. At present, interferons and nucleoside analogues are two major kinds of globally recognized drugs for the prevention/treatment of hepatitis B; however, these two drugs have various drawbacks, e.g., being prone to development of drug resistance after use or having limited uses. For example, interferons are susceptible to cause adverse reactions; and nucleoside analogues have the problems of drug resistance and disease recurrence after drug withdrawal. Therefore, the most ideal means for treatment of hepatitis B should undoubtedly be to silence viral gene expression of the virus at gene level to block the generation and replication of HBV, thereby fundamentally reducing the virus metabolism and the infection of hepatic cells. Based on the mechanism of RNA interference (RNAi), small interfering RNA (siRNA) can inhibit or block the expression of any target gene of interest, e.g., a gene triggering a disease such as cancer, in a sequence-specific manner, thereby achieving the purpose of treating diseases.

Stabilization modification of siRNA and its delivery system are two key technologies in the development of small RNA drugs.

SUMMARY OF THE INVENTION

In some embodiments, provided herein is a siRNA capable of inhibiting the expression of hepatitis B virus (HBV) gene, which comprises a sense strand and an antisense strand, each nucleotide in the siRNA being independently a modified or unmodified nucleotide; wherein the sense strand comprises a nucleotide sequence I, and the antisense strand comprises a nucleotide sequence II; the nucleotide sequence I and the nucleotide sequence II are at least partly reverse complementary to form a double-stranded region; wherein the nucleotide sequence I comprises a nucleotide sequence A, which has the same length as the nucleotide sequence shown in SEQ ID NO: 1 with no more than 3 nucleotide differences; and the nucleotide sequence II comprises a nucleotide sequence B, which has the same length as the nucleotide sequence shown in SEQ ID NO: 2 with no more than 3 nucleotide differences:

```
                                       (SEQ ID NO: 1)
        5'-UGCUAUGCCUCAUCUUCUZ-3';

(SEQ ID NO: 2)
        5'-Z'AGAAGAUGAGGCAUAGCA-3';
``` wherein Z is A; Z' is U; and
the nucleotide sequence A comprises a nucleotide $Z_A$ at the position corresponding to Z; the nucleotide sequence B comprises a nucleotide $Z'_B$ at the position corresponding to Z'; the nucleotide $Z'_B$ is the first nucleotide at 5' terminal of the antisense strand.

In some embodiments, provided herein is a pharmaceutical composition comprising the siRNA disclosed herein and a pharmaceutically acceptable carrier.

In some embodiments, provided herein is a siRNA conjugate comprising the siRNA disclosed herein and a conjugating group conjugated to the siRNA.

In some embodiments, provided herein is use of the siRNA, and/or pharmaceutical composition and/or siRNA conjugate of the present disclosure in the manufacture of a medicament for treating and/or preventing pathological conditions or diseases caused by hepatitis B virus (HBV) infection.

In some embodiments, provided herein is a method for treating and/or preventing pathological conditions or diseases caused by HBV infection, comprising administering to a subject in need thereof an effective amount of the siRNA, and/or pharmaceutical composition and/or siRNA conjugate of the present disclosure.

In some embodiments, provided herein is a kit comprising the siRNA and/or pharmaceutical composition and/or siRNA conjugate of the present disclosure.

INCORPORATION BY REFERENCE

All publications, patents, and patent applications mentioned in this description are herein incorporated by reference to the same extent as if each individual publication, patent, or patent application was specifically and individually indicated to be incorporated by reference.

DETAILED DESCRIPTION OF THE INVENTION

Figure 1:
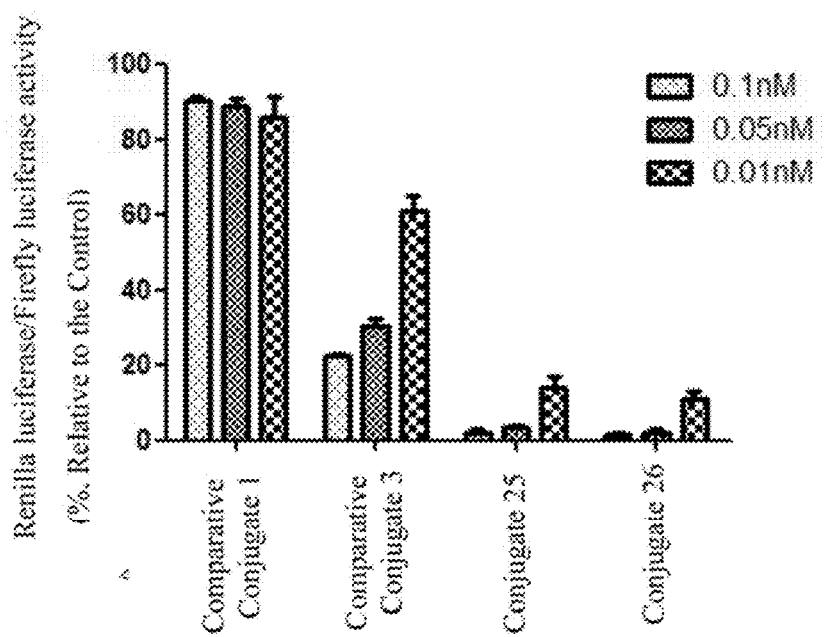
FIG. 1 shows the results of the inhibitory activity of Conjugates 25 and 26 in vitro.

The specific embodiments of the present disclosure are described in detail as below. It should be understood that the specific embodiments described herein are only used to illustrate and explain the present disclosure and are not intended to limit the present disclosure in any respect.

Definitions

In the context of the present disclosure, HBV gene refers to the gene having a DNA sequence as shown in Genbank Accession No. NC_003977.1.

In the context of the present disclosure, unless otherwise specified, C, G, U, A, and T represent the base composition of the nucleotides; d represents that the nucleotide adjacent to the right side of the letter d is a deoxyribonucleotide; m represents that the nucleotide adjacent to the left side of the letter m is a methoxy modified nucleotide; f represents that the nucleotide adjacent to the left side of the letter f is a fluoro modified nucleotide; s represents that the two nucleotides adjacent to both sides of the letter s are linked by a phosphorothioate linkage; P1 represents that the nucleotide adjacent to the right side of P1 is a 5'-phosphate nucleotide or a 5'-phosphate analogue modified nucleotide, especially a vinyl phosphate modified nucleotide (expressed as VP in the Examples below), a 5'-phosphate nucleotide (expressed as P in the Examples below) or a 5'-thiophosphate modified nucleotide (expressed as Ps in the Examples below).

In the context of the present disclosure, the "fluoro modified nucleotide" refers to a nucleotide formed by substituting the 2'-hydroxy of the ribose group of the nucleotide with a fluorine atom. The "non-fluoro modified nucleotide" refers to a nucleotide formed by substituting the 2'-hydroxy of the ribose group of the nucleotide with a non-fluoro group, or a nucleotide analogue. The "nucleotide analogue" refers to a group that can replace a nucleotide in a nucleic acid, while structurally differs from an adenine ribonucleotide, a guanine ribonucleotide, a cytosine ribonucleotide, a uracil ribonucleotide or thymine deoxyribonucleotide, such as an isonucleotide, a bridged nucleic acid (BNA) nucleotide or an acyclic nucleotide. The methoxy modified nucleotide refers to a nucleotide formed by substituting the 2'-hydroxy of the ribose group with a methoxy group.

In the context of the present disclosure, expressions "complementary" and "reverse complementary" are interchangeably used herein, and have the meaning well-known in the art, namely, the bases in one strand are paired complementarily with those in another strand in a double-stranded nucleic acid molecule. In DNAs, a purine base adenine (A) is always paired with a pyrimidine base thymine (T) (or a uracil (U) in RNAs); and a purine base guanine (G) is always paired with a pyrimidine base cytosine (C). Each base pair comprises a purine and a pyrimidine. While adenines in one strand are always paired with thymines (or uracils) in another strand, and guanines paired with cytosines, these two strands are considered as being complementary each other; and the sequence of a strand may be deduced from the sequence of its complementary strand. Correspondingly, a "mispairing" means that the bases at corresponding sites are not present in a complementary pair in a double-stranded nucleic acid.

In the context of the present disclosure, unless otherwise specified, "basically reverse complementary" means that there is no more than 3 base mispairings between two nucleotide sequences. "Substantially reverse complementary" means that there is no more than 1 base mispairing between two nucleotide sequences. "Completely complementary" means that there is no base mispairing in two nucleotide sequences.

In the context of the present disclosure, a "nucleotide difference" between one nucleotide sequence and another nucleotide sequence refers to a change of the base type of the nucleotides at the same position therebetween. For example, in the case that a nucleotide base in the second sequence is A while the nucleotide base at the same position in the first sequence is U, C, G or T, these two nucleotide sequences are considered as having a nucleotide difference at this position. In some embodiments, if a nucleotide at a position is replaced with an abasic nucleotide or a nucleotide analogue, it is also considered that there is a nucleotide difference at the position.

In the context of the present disclosure, particularly in the description of the method for preparing the conjugating molecule or the siRNA conjugate described herein, unless otherwise specified, the "nucleoside monomer" refers to, according to the type and sequence of the nucleotides in the siRNA or siRNA conjugate to be prepared, "unmodified or modified RNA phosphoramidites" (the RNA phosphoramidites are also called as "Nucleoside phosphoramidites" elsewhere) used in a "solid phase phosphoramidite synthesis", which is well-known in the art for synthesis of RNA. Nucleoside monomers used herein can all be commercially available.

As used herein, a dash ("—") that is not positioned between two letters or symbols is used to indicate the attachment position of a substituent. For example, —$C_1$-$C_{10}$ alkyl-$NH_2$ is attached through the $C_1$-$C_{10}$ alkyl.

As used herein, "optional" or "optionally" is meant that the subsequently described event or condition may or may not occur, and that the description includes instances wherein the event or condition may occur and instances wherein the event or condition may not occur. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically infeasible and/or inherently unstable.

As used herein, "alkyl" refers to straight chain and branched chain having the indicated number of carbon atoms, usually from 1 to 20 carbon atoms, for example 1 to 10 carbon atoms, such as 1 to 8 or 1 to 6 carbon atoms. For example, $C_1$-$C_6$ alkyl encompasses both straight and branched chain alkyl of from 1 to 6 carbon atoms. When an alkyl residue having a specific number of carbon atoms is named, all branched and straight chain versions having that number of carbon atoms are intended to be encompassed; thus, for example, "butyl" is meant to include n-butyl, sec-butyl, isobutyl and t-butyl; "propyl" includes n-propyl and isopropyl. Alkylene is a subset of alkyl, referring to the same residues as alkyl, but having two attachment positions.

As used herein, "alkenyl" refers to an unsaturated branched or straight-chain alkyl group having at least one carbon-carbon double bond which is obtained by removal of one hydrogen molecule from adjacent carbon atoms of the parent alkyl. The group may be in either cis or trans configuration of the double bond(s). Typical alkenyl groups include, but are not limited to, ethenyl; propenyls such as prop-1-en-1-yl, prop-1-en-2-yl, prop-2-en-1-yl (allyl), prop-2-en-2-yl; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl; and the like. In certain embodiments, an alkenyl group has from 2 to 20 carbon atoms and in other embodiments, from 2 to 10, 2 to 8, or 2 to 6 carbon atoms. Alkenylene is a subset of alkenyl, referring to the same residues as alkenyl, but having two attachment positions.

As used herein, "alkynyl" refers to an unsaturated branched or straight-chain alkyl group having at least one carbon-carbon triple bond which is obtained by removal of two hydrogen molecules from adjacent carbon atoms of the parent alkyl. Typical alkynyl groups include, but are not limited to, ethynyl; propynyls such as prop-1-yn-1-yl, prop-2-yn-1-yl; butynyls such as but-1-yn-1-yl, but-1-yn-3-yl, but-3-yn-1-yl; and the like. In certain embodiments, an alkynyl group has from 2 to 20 carbon atoms and in other embodiments, from 2 to 10, 2 to 8, or 2 to 6 carbon atoms. Alkynylene is a subset of alkynyl, referring to the same residues as alkynyl, but having two attachment positions.

As used herein, "alkoxy" refers to an alkyl group of the indicated number of carbon atoms attached through an oxygen bridge, such as, for example, methoxy, ethoxy, propoxy, isopropoxy, n-butoxy, sec-butoxy, tert-butoxy, pentyloxy, 2-pentyloxy, isopentyloxy, neopentyloxy, hexyloxy, 2-hexyloxy, 3-hexyloxy, 3-methylpentyloxy, and the like. Alkoxy groups will usually have from 1 to 10, 1 to 8, 1 to 6, or 1 to 4 carbon atoms attached through oxygen bridge.

As used herein, "aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon of from six to eighteen carbon atoms, where at least one ring in the ring system is fully unsaturated, i.e., it contains a cyclic, delocalized (4n+2) π-electron system in accordance with the Hückel theory. Aryl groups include, but are not limited to, phenyl, fluorenyl, and naphthyl. Arylene is a subset of aryl, referring to the same residues as aryl, but having two attachment positions.

As used herein, "cycloalkyl" refers to a non-aromatic carbon ring, usually having from 3 to 7 ring carbon atoms. The ring may be saturated or have one or more carbon-carbon double bonds. Examples of cycloalkyl groups include cyclopropyl, cyclobutyl, cyclopentyl, cyclopentenyl, cyclohexyl, and cyclohexenyl, as well as bridged and caged ring groups such as norbornane.

As used herein, "halo" or "halogen" refers to fluoro, chloro, bromo, and iodo, and the term "halogen" includes fluorine, chlorine, bromine, and iodine.

As used herein, "haloalkyl" refers to alkyl as defined above with the specified number of carbon atoms being substituted with one or more halogen atoms, up to the maximum allowable number of halogen atoms. Examples of haloalkyl include, but are not limited to, trifluoromethyl, difluoromethyl, 2-fluoroethyl, and penta-fluoroethyl.

"Heterocyclyl" refers to a stable 3- to 18-membered non-aromatic ring radical that comprises two to twelve carbon atoms and from one to six heteroatoms selected from nitrogen, oxygen or sulfur. Unless stated otherwise in the description, heterocyclyl is a monocyclic, bicyclic, tricyclic or tetracyclic ring system, which may include fused or bridged ring systems. The heteroatoms in the heterocyclyl radical may be optionally oxidized. One or more nitrogen atoms, if present, are optionally quaternized. The heterocyclyl radical is partially or fully saturated. The heterocyclyl may be attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrimidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxa-thiomorpholinyl, and 1,1-dioxa-thiomorpholinyl.

"Heteroaryl" refers to a radical derived from a 3- to 18-membered aromatic ring radical that comprises two to seventeen carbon atoms and from one to six heteroatoms selected from nitrogen, oxygen or sulfur. As used herein, heteroaryl radical may be a monocyclic, bicyclic, tricyclic or tetracyclic ring system, wherein at least one ring in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxazolyl, benzofuranyl, benzoxazolyl, benzo[d]thiazolyl, benzothiadiazolyl, benzo[b][1,4]dioxazolyl, benzo[b][1,4]oxazolyl, 1,4-benzodioxazolyl, benzonaphthofuranyl, benzodiazolyl, benzodioxaphenyl, benzopyranyl, benzopyranonyl, benzofuranyl, benzofuranonyl, benzothienyl, benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothienyl, furanyl, furanonyl, furo[3,2-c]pyridinyl, 5,6,7,8,9,10-hexahydrocyclohepta[d]pyrimidinyl, 5,6,7,8,9,10-hexahydrocycloocta[d]pyridazinyl, 5,6,7,8,9,10-hexahydrocycloocta[d]pyridinyl, isothiazolyl, indazolyl, imidazolyl, indolyl, isoindolyl, indolinyl, isoindolinyl, isoquinolyl, indolizinyl, isoxazolyl, 5,8-methano-5,6,7,8-tetrahydroquinazolinyl, naphthyridinonyl, 1,6-naphthyridinonyl, oxadiazolyl, 2-oxoazepinyl, oxazolyl, oxalyl, 5,6,6a,7,8,9,10,10a-octahydrobenzo[h]quinazolinyl, 1-phenyl-1H-pyrrolyl, phenazinyl, phenothiazinyl, phenoxazinyl, phthalyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thienyl.

Various hydroxyl protecting groups may be used in the present disclosure. In general, protecting groups render chemical functionalities inert to specific reaction conditions, and may be attached to and removed from such functionalities in a molecule without substantially damaging the remainder of the molecule. Representative hydroxyl protecting groups are disclosed by Beaucage, et al., *Tetrahedron* 1992, 48, 2223-2311, and also by Greene and Wuts, Protective Groups in Organic Synthesis, Chapter 2, 2d ed, John Wiley & Sons, New York, 1991, each of which is hereby incorporated by reference in their entirety. In some embodiments, the protecting group is stable under basic conditions but may be removed under acidic conditions. In some embodiments, non-exclusive examples of the hydroxyl protecting groups that may be used herein include dimethoxytrityl (DMT), monomethoxytrityl, 9-phenylxanthen-9-yl (Pixyl) and 9-(p-methoxyphenyl)xanthen-9-yl (Mox). In some embodiments, non-exclusive examples of hydroxyl protecting groups that may be used herein comprises Tr (trityl), MMTr (4-methoxytrityl), DMTr (4,4'-dimethoxytrityl), and TMTr (4,4',4"-trimethoxytrityl).

The term "subject", as used herein, refers to any animal, e.g., a mammal or marsupial. Subject of the present disclosure includes but are not limited to human, non-human primate (e.g., rhesus or other kinds of macaque), mouse, pig, horse, donkey, cow, sheep, rat and fowl of any kind.

As used herein, "treating", "palliatively treating", or "ameliorating" are used interchangeably herein. These terms refer to an approach for obtaining advantageous or desired results, including but not limited to, therapeutic benefit. By "therapeutic benefit" is meant eradication or improvement of potential disorder being treated. Also, a therapeutic benefit is achieved by eradication or amelioration of one or more of physiological symptoms associated with the potential disorder such that an improvement is observed in the patient, notwithstanding that the patient may still be afflicted with the potential disorder.

As used herein, "prevention" and "preventing" are used interchangeably. These terms refer to an approach for obtaining advantageous or desired results, including but not limited to, a prophylactic benefit. For "prophylactic benefit", the conjugates or compositions may be administered to a subject at risk of developing a particular disease, or to a subject reporting one or more of the physiological symptoms of the disease, even though the diagnosis of this disease may not have been made.

siRNA

Provided herein is a siRNA capable of inhibiting the expression of hepatitis B virus (HBV) gene.

The siRNA disclosed herein comprises nucleotide groups as basic building units. It is well-known to those skilled in the art that the nucleotide comprises a phosphate group, a ribose group and a base. Detailed illustrations relating to such groups are omitted here.

CN102140458B has disclosed a siRNA that specifically inhibits HBV gene and studied various chemical modification strategies of the siRNA. This study found that different modification strategies have completely different impacts on the parameters of the siRNA, such as stability, biological activity, and cytotoxicity. In this study, seven effective modification manners were confirmed. Compared with unmodified siRNA, the siRNA obtained by one of the seven modification manners showed increased stability in blood, while maintaining substantially equal inhibitory activity as that of the unmodified siRNA.

The siRNA disclosed herein comprises a sense strand and an antisense strand, each nucleotide in the siRNA being independently a modified or unmodified nucleotide, wherein the sense strand comprises a nucleotide sequence I; the antisense strand comprises a nucleotide sequence II; the nucleotide sequence I and the nucleotide sequence II are at least partly reverse complementary to form a double-stranded region; wherein the nucleotide sequence I comprises nucleotide sequence A, which has the same length as the nucleotide sequence shown in SEQ ID NO: 1 with no more than 3 nucleotide differences; and the nucleotide sequence II comprises nucleotide sequence B, which has the same length as the nucleotide sequence shown in SEQ ID NO: 2 with no more than 3 nucleotide differences:

(SEQ ID NO: 1)
5'-UGCUAUGCCUCAUCUUCUZ-3';

(SEQ ID NO: 2)
5'-Z'AGAAGAUGAGGCAUAGCA-3';

wherein Z is A; Z' is U; and the nucleotide sequence A comprises nucleotide $Z_A$ at the position corresponding to Z; the nucleotide sequence B comprises nucleotide $Z'_B$ at the position corresponding to Z'; the nucleotide $Z'_B$ is the first nucleotide at 5' terminal of the antisense strand.

In this context, the term "position corresponding" means being at the same position in the nucleotide sequences when counting from the same terminal of the nucleotide sequences. For example, the first nucleotide at the 3' terminal of the nucleotide sequence A is a nucleotide at the position corresponding to the first nucleotide at the 3' terminal of SEQ ID NO: 1.

In some embodiments, the sense strand only comprises the nucleotide sequence I, and the antisense strand only comprises the nucleotide sequence II.

In some embodiments, the nucleotide sequence A has no more than 1 nucleotide difference over the nucleotide sequence shown in SEQ ID NO: 1; and/or the nucleotide sequence B has no more than 1 nucleotide difference over the nucleotide sequence shown in SEQ ID NO: 2.

In some embodiments, the nucleotide difference between the nucleotide sequence B and the nucleotide sequence shown in SEQ ID NO: 2 includes a difference at the position of $Z'_B$, and $Z'_B$ is selected from A, C or G. In some embodiments, the nucleotide difference is a difference at the position of $Z'_B$, $Z'_B$ is selected from A, C or G, and $Z_A$ is a nucleotide complementary to $Z'_B$. These nucleotide differences will not significantly reduce the ability of the siRNA conjugates to inhibit the target gene, and such siRNA conjugates comprising the nucleotide differences are also within the scope of this disclosure.

In some embodiments, the nucleotide sequence A is basically reverse complementary, substantially reverse complementary, or completely reverse complementary to the nucleotide sequence B. The "basically reverse complementary" means that there is no more than 3 base mispairings between two nucleotide sequences. The "substantially reverse complementary" means that there is no more than 1 base mispairing between two nucleotide sequences. The "completely reverse complementary" means that there is no mispairing between two nucleotide sequences.

In some embodiments, the nucleotide sequence A is a nucleotide sequence shown in SEQ ID NO: 3; and the nucleotide sequence B is a nucleotide sequence shown in SEQ ID NO: 4:

(SEQ ID NO: 3)
5'-UGCUAUGCCUCAUCUUCUZ$_A$-3';

(SEQ ID NO: 4)
5'-Z'$_B$AGAAGAUGAGGCAUAGCA-3';

wherein the $Z'_B$ is the first nucleotide at 5' terminal of the antisense strand; $Z_A$ is selected from A, U, G or C, and $Z'_B$ is a nucleotide complementary to $Z_A$; and in some embodiments, $Z_A$ is A, and $Z'_B$ is U.

The sense strand and antisense strand have the same or different lengths. The sense strand is 19-23 nucleotides in length, and the antisense strand is 20-26 nucleotides in length. As such, the length ratio of the sense strand to the antisense strand in the siRNA of the present disclosure may be 19/20, 19/21, 19/22, 19/23, 19/24, 19/25, 19/26, 20/20, 20/21, 20/22, 20/23, 20/24, 20/25, 20/26, 21/20, 21/21, 21/22, 21/23, 21/24, 21/25, 21/26, 22/20, 22/21, 22/22, 22/23, 22/24, 22/25, 22/26, 23/20, 23/21, 23/22, 23/23, 23/24, 23/25 or 23/26. In some embodiments, the length ratio of the sense strand to the antisense strand in the siRNA of the present disclosure is 19/21, 21/23 or 23/25.

According to one embodiment of the present disclosure, the sense strand and antisense strand have the same length. The nucleotide sequence I further comprises a nucleotide sequence III; and the nucleotide sequence II further comprises a nucleotide sequence IV. The nucleotide sequence III and the nucleotide sequence IV independently of one another are 1-4 nucleotides in length; the nucleotide sequence III is linked to 5' terminal of the nucleotide sequence A; the nucleotide sequence IV is linked to 3' terminal of the nucleotide sequence B; and the nucleotide sequence III and the nucleotide sequence IV have the same length.

The nucleotide sequence III may be complementary or may not be complementary to the nucleotide sequence IV. In order to enhance the stability of the siRNA, in some embodiments, the nucleotide sequence III is at least partly complementary to the nucleotide sequence IV; in some embodiments, the nucleotide sequence III is complementary to more than 80% or 90% of the bases in the nucleotide sequence IV; in some embodiments, the nucleotide sequence III is substantially reverse complementary or completely reverse complementary to the nucleotide sequence IV; the "substantially reverse complementary" means that there is no more than 1 base mispairing between two nucleotide sequences; the "completely reverse complementary" means that there is no mispairing in two nucleotide sequences; and in some embodiments, the nucleotide sequence III is completely reverse complementary to the nucleotide sequence IV. As such, the sense strand and antisense strand of the siRNA have the same length, and the length ratio thereof is 20/20, 21/21, 22/22, or 23/23. In some embodiments, the length ratio of the sense strand to the antisense strand in the siRNA is 21/21 or 23/23.

In some embodiments, the nucleotide sequence III and the nucleotide sequence IV both are 1 nucleotide in length. The base of the nucleotide sequence III is G, and the base of the nucleotide sequence IV is C; in this case, the length ratio of the sense strand to the antisense strand is 20/20. Alternatively, the nucleotide sequence III and the nucleotide sequence IV both are 2 nucleotides in length; in the direction from 5' terminal to 3' terminal, the base composition of the nucleotide sequence III is AG, and the base composition of the nucleotide sequence IV is CU; in this case, the length ratio of the sense strand to the antisense strand is 21/21. Alternatively, the nucleotide sequence III and the nucleotide sequence IV both are 3 nucleotides in length; in the direction from 5' terminal to 3' terminal, the base composition of the nucleotide sequence III is AAG, and the base composition of the nucleotide sequence IV is CUU; in this case, the length ratio of the sense strand to the antisense strand is 22/22. Alternatively, the nucleotide sequence III and the nucleotide sequence IV both are 4 nucleotides in length; in the direction from 5' terminal to 3' terminal, the base composition of the nucleotide sequence III is CAAG, and the base composition of the nucleotide sequence IV is CUUG; in this case, the length ratio of the sense strand to the antisense strand is 23/23. In some embodiments, the nucleotide sequence III and the nucleotide sequence IV both are 2 nucleotides in length; in the direction from 5' terminal to 3' terminal, the base composition of the nucleotide sequence III is AG, and the base composition of the nucleotide sequence IV is CU; in this case, the length ratio of the sense strand to the antisense strand is 21/21.

In some embodiments, the nucleotide sequence III has the same length and is completely reverse complementary to the nucleotide sequence IV. Thus, if the bases of the nucleotide sequence III are given, the bases of the nucleotide sequence IV are also determined.

In some embodiments, the sense strand and antisense strand have different lengths. The nucleotide sequence II further comprises a nucleotide sequence V, which is 1-3 nucleotides in length and is linked to 3' terminal of the antisense strand, thereby forming a 3' overhang of the antisense strand. As such, the length ratio of the sense strand to the antisense strand in the siRNA of the present disclosure may be 19/20, 19/21, 19/22, 20/21, 20/22, 20/23, 21/22, 21/23, 21/24, 22/23, 22/24, 22/25, 23/24, 23/25, or 23/26. In some embodiments, the nucleotide sequence V is 2 nucleotides in length. As such, the length ratio of the sense strand to the antisense strand in the siRNA of the present disclosure may be 19/21, 21/23 or 23/25.

Each nucleotide in the nucleotide sequence V may be any nucleotide. In order to facilitate synthesis and decrease the cost of synthesis, the nucleotide sequence V is 2 consecutive thymidine deoxyribonucleotides (TT) or 2 consecutive uridine ribonucleotides (UU); in order to increase affinity of the antisense strand of the siRNA for the target mRNA, the nucleotide sequence V is complementary to the nucleotides at the corresponding positions of the target mRNA. Thus, in some embodiments, the length ratio of the sense strand to the antisense strand in the siRNA of the present disclosure is 19/21 or 21/23. In this case, the siRNA of the present disclosure has better silencing activity against mRNA.

In some embodiments, the sense strand of the siRNA comprises the nucleotide sequence shown in SEQ ID NO: 3, and the antisense strand of the siRNA comprises the nucleotide sequence shown in SEQ ID NO: 5:

```
                                            (SEQ ID NO: 3)
5'-UGCUAUGCCUCAUCUUCUZ_A-3';

(SEQ ID NO: 5)
5'-Z'_BAGAAGAUGAGGCAUAGCAGC-3';
``` alternatively, the sense strand of the siRNA comprises the nucleotide sequence shown in SEQ ID NO: 3, and the antisense strand of the siRNA comprises the nucleotide sequence shown in SEQ ID NO: 6:

```
                                            (SEQ ID NO: 3)
5'-UGCUAUGCCUCAUCUUCUZ_A-3';

(SEQ ID NO: 6)
5'-Z'_BAGAAGAUGAGGCAUAGCAUU-3';
``` wherein the nucleotide $Z'_B$ is the first nucleotide at 5' terminal of the antisense strand; $Z_A$ is selected from A, U, G or C; and $Z'_B$ is a nucleotide complementary to $Z_A$.

According to some specific embodiments of the present disclosure, the siRNA disclosed herein is siHBVS1 or siHBVS2:

```
siHBVS1
Sense strand:
                                            (SEQ ID NO: 1)
5'-UGCUAUGCCUCAUCUUCUZ-3',
```

-continued

Antisense strand:
(SEQ ID NO: 7)
5'-Z'AGAAGAUGAGGCAUAGCAGC-3', siHBVS2
Sense strand:
(SEQ ID NO: 1)
5'-UGCUAUGCCUCAUCUUCUZ-3', Antisense strand:
(SEQ ID NO: 8)
5'-Z'AGAAGAUGAGGCAUAGCAUU-3'.

As described above, each nucleotide in the siRNA of the present disclosure is independently a modified or unmodified nucleotide. In some embodiments, the nucleotides in the siRNA of the present disclosure are unmodified nucleotides. In some embodiments, some or all nucleotides in the siRNA of the present disclosure are modified nucleotides. Such modifications on the nucleotide would not cause significant decrease or loss of the function of the siRNA conjugate of the present disclosure to inhibit the expression of HBV gene.

In some embodiments, the siRNA of the present disclosure comprises at least one modified nucleotide. In the context of the present disclosure, the term "modified nucleotide" used herein refers to a nucleotide formed by substituting the 2'-hydroxy of the ribose group of the nucleotide with other groups, a nucleotide analogue, or a nucleotide with modified base. The modified nucleotides would not cause significant decrease or loss of the function of the siRNA conjugate to inhibit the expression of HBV gene. For example, the modified nucleotides disclosed by J. K. Watts, G. F. Deleavey and M. J. Damha, Chemically Modified siRNA: tools and applications. Drug Discov Today, 2008.13 (19-20): p. 842-55 may be selected.

In some embodiments, at least one nucleotide in the sense strand or antisense strand of the siRNA provided by the present disclosure is a modified nucleotide, and/or at least one phosphate is a phosphate group with modification. In other words, at least a portion of the phosphate and/or ribose groups in phosphate-ribose backbone of at least one single strand in the sense strand and the antisense strand are phosphate and/or ribose groups with modified groups.

In some embodiments, all nucleotides in the sense strand and/or the antisense strand are modified nucleotides. In some embodiments, each nucleotide in the sense strand and the antisense strand of the siRNA provided by the present disclosure is independently a fluoro modified nucleotide or a non-fluoro modified nucleotide.

The inventors of the present disclosure have surprisingly found that the siRNA described herein has achieved a high degree of balance between the stability in serum and the gene silencing efficiency in animal experiments.

In some embodiments, the fluoro modified nucleotides are located within the nucleotide sequences A and B; and in the direction from 5' terminal to 3' terminal, the nucleotides at positions 7, 8 and 9 of the nucleotide sequence A are fluoro modified nucleotides; and in the direction from 5' terminal to 3' terminal, the nucleotides at positions 2, 6, 14 and 16 of the nucleotide sequence B are fluoro modified nucleotides.

In some embodiments, the fluoro modified nucleotides are located within the nucleotide sequences A and B; no more than 5 fluoro modified nucleotides are present in the nucleotide sequence A, and in the direction from 5' terminal to 3' terminal, the nucleotides at positions 7, 8 and 9 in the nucleotide sequence A are fluoro modified nucleotides; no more than 7 fluoro modified nucleotides are present in the nucleotide sequence B, and the nucleotides at positions 2, 6, 14 and 16 in the nucleotide sequence B are fluoro modified nucleotides.

In some embodiments, in the direction from 5' terminal to 3' terminal, the nucleotides at positions 7, 8 and 9 or 5, 7, 8 and 9 of the nucleotide sequence A in the sense strand are fluoro modified nucleotides, and the nucleotides at the other positions in the sense strand are non-fluoro modified nucleotides; and in the direction from 5' terminal to 3' terminal, the nucleotides at positions 2, 6, 14 and 16 or 2, 6, 8, 9, 14 and 16 of the nucleotide sequence B in the antisense strand are fluoro modified nucleotides, and the nucleotides at the other positions in the antisense strand are non-fluoro modified nucleotides.

In the context of the present disclosure, the "fluoro modified nucleotide" refers to a nucleotide formed by substituting the 2'-hydroxy of the ribose group thereof with a fluorine atom, having a structure as shown by Formula (101). The "non-fluoro modified nucleotide" refers to a nucleotide formed by substituting the 2'-hydroxy of the ribose group thereof with a non-fluoro group, or a nucleotide analogue. In some embodiments, each non-fluoro modified nucleotide is independently selected from the group consisting of a nucleotide formed by substituting the 2'-hydroxy of the ribose group thereof with a non-fluoro group, and a nucleotide analogue.

A nucleotide formed by substituting the 2'-hydroxy of the ribose group with a non-fluoro group is well-known in the art, such as, the nucleotide can be one of 2'-alkoxy modified nucleotides, 2'-substituted alkoxy modified nucleotides, 2'-alkyl modified nucleotides, 2'-substituted alkyl modified nucleotides, 2'-amino modified nucleotides, 2'-substituted amino modified nucleotides, and 2'-deoxy nucleotides.

In some embodiments, the 2'-alkoxy modified nucleotide is a methoxy modified nucleotide (2'-OMe) as shown by Formula (102). The 2'-substituted alkoxy modified nucleotide may be, for example, a 2'-O-methoxyethyl modified nucleotide (2'-MOE) as shown by Formula (103). The 2'-amino modified nucleotide (2'-$NH_2$) is as shown by Formula (104). The 2'-deoxy nucleotide (DNA) is as shown by Formula (105).

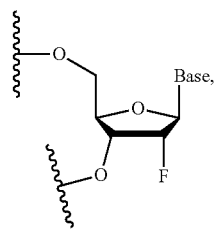

Formula (101)

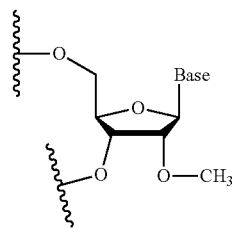

Formula (102)

Formula (103)

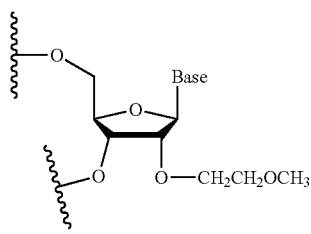

Formula (104)

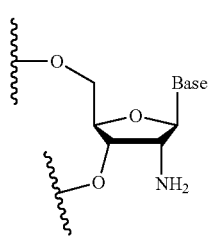

Formula (105)

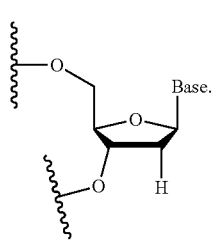

A "nucleotide analogue" refers to a group that can replace a nucleotide in the nucleic acid, while structurally differs from an adenine ribonucleotide, a guanine ribonucleotide, a cytosine ribonucleotide, a uracil ribonucleotide or thymine deoxyribonucleotide. In some embodiments, the nucleotide analogue may be such as an isonucleotide, a bridged nucleic acid (BNA) nucleotide or an acyclic nucleotide.

A BNA nucleotide is a nucleotide that is constrained or inaccessible. BNA can contain a 5-, 6-membered or even a 7-membered ring bridged structure with a "fixed" C3'-endo sugar puckering. The bridge is typically incorporated at the 2'- and 4'-position of the ribose to afford a 2', 4'-BNA nucleotide, such as LNA, ENA and cET BNA, which are as shown by Formulae (106), (107) and (108), respectively.

Formula (106)

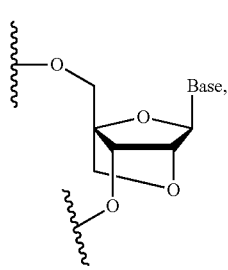

Formula (107)

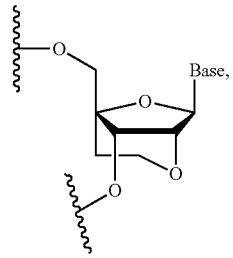

Formula (108)

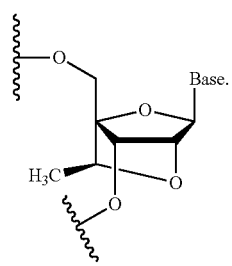

An acyclic nucleotide is a nucleotide in which the ribose ring is opened, such as an unlocked nucleic acid (UNA) and a glycerol nucleic acid (GNA), which are respectively as shown by Formulae (109) and (110).

Formula (109)

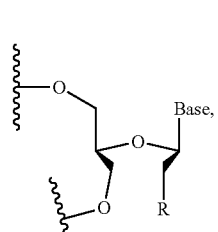

Formula (110)

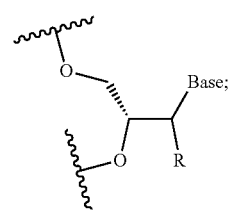

wherein R is H, OH or alkoxy (O-alkyl).

An isonucleotide is a nucleotide in which the position of the base on the ribose ring is changed, such as a compound in which the base is transposed from position-1' to position-2' or 3' on the ribose ring, as shown by Formula (111) or (112):

Formula (111)

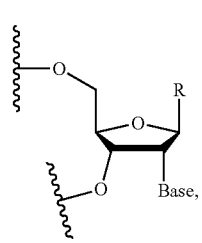

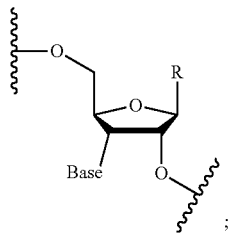

Formula (112)

wherein Base represents a base, such as A, U, G, C or T; and R is H, OH, F or a non-fluoro group described above.

In some embodiments, a nucleotide analogue is selected from isonucleotide, LNA, ENA, cET, UNA, or GNA. In some embodiments, each non-fluoro modified nucleotide is a methoxy modified nucleotide. In the context of the disclosure, the methoxy modified nucleotide refers to a nucleotide formed by substituting the 2'-hydroxy of the ribose group with a methoxy group.

In the context of the disclosure, a "fluoro modified nucleotide", a "2'-fluoro modified nucleotide", a "nucleotide in which 2'-hydroxy of a ribose group is substituted with fluoro" and a "2'-fluororibosyl" have the same meaning, referring to a compound having a structure as shown by Formula (207) that is formed by substituting 2'-hydroxy of the nucleotide with fluoro. A "methoxy modified nucleotide", a "2'-methoxy modified nucleotide", a "nucleotide in which 2'-hydroxy of a ribose group is substituted with methoxy" and a "2'-methoxyribosyl" have the same meaning, referring to a compound having a structure as shown by Formula (208) that is formed by substituting 2'-hydroxy of the ribose group thereof with methoxy.

In some embodiments, the siRNA of the present disclosure is a siRNA with the following modifications: in the direction from 5' terminal to 3' terminal, the nucleotides at positions 7, 8 and 9 or 5, 7, 8 and 9 of the nucleotide sequence A in the sense strand are fluoro modified nucleotides, and the nucleotides at the other positions in the sense strand are methoxy modified nucleotides; and the nucleotides at positions 2, 6, 14 and 16 or 2, 6, 8, 9, 14 and 16 of the nucleotide sequence B in the antisense strand are fluoro modified nucleotides, and the nucleotides at the other positions in the antisense strand are methoxy modified nucleotides.

In some embodiments, the siRNA of the disclosure is a siRNA with the following modifications: in the direction from 5' terminal to 3' terminal, the nucleotides at positions 5, 7, 8 and 9 of the nucleotide sequence A in the sense strand of the siRNA are fluoro modified nucleotides, and the nucleotides at the other positions in the sense strand of the siRNA are methoxy modified nucleotides; and in the direction from 5' terminal to 3' terminal, the nucleotides at positions 2, 6, 8, 9, 14 and 16 of the nucleotide sequence B in the antisense strand of the siRNA are fluoro modified nucleotides, and the nucleotides at the other positions in the antisense strand of the siRNA are methoxy modified nucleotides;

alternatively, in the direction from 5' terminal to 3' terminal, the nucleotides at positions 5, 7, 8 and 9 of the nucleotide sequence A in the sense strand of the siRNA are fluoro modified nucleotides, and the nucleotides at the other positions in the sense strand of the siRNA are methoxy modified nucleotides; and in the direction from 5' terminal to 3' terminal, the nucleotides at positions 2, 6, 14 and 16 of the nucleotide sequence B in the antisense strand of the siRNA are fluoro modified nucleotides, and the nucleotides at the other positions in the antisense strand of the siRNA are methoxy modified nucleotides;

alternatively, in the direction from 5' terminal to 3' terminal, the nucleotides at positions 7, 8 and 9 of the nucleotide sequence A in the sense strand of the siRNA are fluoro modified nucleotides, and the nucleotides at the other positions in the sense strand of the siRNA are methoxy modified nucleotides; and in the direction from 5' terminal to 3' terminal, the nucleotides at positions 2, 6, 14 and 16 of the nucleotide sequence B in the antisense strand of the siRNA are fluoro modified nucleotides, and the nucleotides at the other positions in the antisense strand of the siRNA are methoxy modified nucleotides.

In other words, the ribose groups in phosphate-ribose backbone of the siRNA respectively have the following modifying groups: in the direction from 5' terminal to 3' terminal, the ribose groups of the nucleotides at positions 5, 7, 8 and 9 of the nucleotide sequence A in the sense strand of the siRNA are 2'-fluororibosyl, and the ribose groups of the nucleotides at the other positions in the sense strand of the siRNA are 2'-methoxyribosyl; and in the direction from 5' terminal to 3' terminal, the ribose groups of the nucleotides at positions 2, 6, 8, 9, 14 and 16 of the nucleotide sequence B in the antisense strand of the siRNA are 2'-fluororibosyl, and the ribose groups of the nucleotides at the other positions in the antisense strand of the siRNA are 2'-methoxyribosyl;

alternatively, in the direction from 5' terminal to 3' terminal, the ribose groups of the nucleotides at positions 5, 7, 8 and 9 of the nucleotide sequence A in the sense strand of the siRNA are 2'-fluororibosyl, and the ribose groups of the nucleotides at the other positions in the sense strand of the siRNA are 2'-methoxyribosyl; and in the direction from 5' terminal to 3' terminal, the ribose groups of the nucleotides at positions 2, 6, 14 and 16 of the nucleotide sequence B in the antisense strand of the siRNA are 2'-fluororibosyl, and the ribose groups of the nucleotides at the other positions in the antisense strand of the siRNA are 2'-methoxyribosyl;

alternatively, in the direction from 5' terminal to 3' terminal, the ribose groups of the nucleotides at positions 7, 8 and 9 of the nucleotide sequence A in the sense strand of the siRNA are 2'-fluororibosyl, and the ribose groups of the nucleotides at the other positions in the sense strand of the siRNA are 2'-methoxyribosyl; and in the direction from 5' terminal to 3' terminal, the ribose groups of the nucleotides at positions 2, 6, 14 and 16 of the nucleotide sequence B in the antisense strand of the siRNA are 2'-fluororibosyl, and the ribose groups of the nucleotides at the other positions in the antisense strand of the siRNA are 2'-methoxyribosyl.

In some embodiments, the siRNA provided herein is siHBVS3, siHBVS4, siHBVS5, or siHBVS6:

```
siHBVS3
Sense strand:
                                              (SEQ ID NO: 9)
5'-UmGmCmUmAmUmGfCfCfUmCmAmUmCmUmCmUmAm-3', Antisense strand:
                                             (SEQ ID NO: 10)
5'-UmAfGmAmAmGfAmUmGmAmGmGmCmAfUmAfGmCmAmGmCm-3', siHBVS4
Sense strand:
                                              (SEQ ID NO: 9)
5'-UmGmCmUmAmUmGfCfCfUmCmAmUmCmUmCmUmAm-3',
```

-continued

Antisense strand:
(SEQ ID NO: 11)
5'-UmAfGmAmAmGfAmUmGmAmGmGmCmAfUmAfGmCmAmUmUm-3', siHBVS5
Sense strand:
(SEQ ID NO: 12)
5'-UmGmCmUmAfUmGfCfCfUmCmAmUmCmUmUmCmUmAm-3', Antisense strand:
(SEQ ID NO: 13)
5'-UmAfGmAmAmGfAmUfGfAmGmGmCmAfUmAfGmCmAmGmCm-3', siHBVS6
Sense strand:
(SEQ ID NO: 12)
5'-UmGmCmUmAfUmGfCfCfUmCmAmUmCmUmUmCmUmAm-3', Antisense strand:
(SEQ ID NO: 14)
5'-UmAfGmAmAmGfAmUfGfAmGmGmCmAfUmAfGmCmAmUmUm-3', wherein C, G, U, and A represent the base composition of the nucleotides; m represents that the nucleotide adjacent to the left side of the letter m is a methoxy modified nucleotide; f represents that the nucleotide adjacent to the left side of the letter f is a fluoro modified nucleotide.

The siRNA with the above modifications can not only have lower cost, but also cause that the ribonucleases in the blood cannot easily cleave the nucleic acid, so as to increase the stability of the nucleic acid and enable the nucleic acid to have stronger resistance against nuclease hydrolysis.

In some embodiments, at least a portion of the phosphate groups in phosphate-ribose backbone of at least one single strand in the sense strand and the antisense strand of the siRNA provided by the present disclosure are phosphate groups with modified groups. In some embodiments, the phosphate groups with modified groups are phosphorothioate groups formed by substituting at least one oxygen atom in a phosphodiester bond in the phosphate groups with a sulfur atom; and in some embodiments, the phosphate groups with modified groups are phosphorothioate groups having a structure as shown by Formula (1):

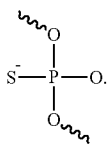

Formula (1)

This modification can stabilize the double-stranded structure of the siRNA, thereby maintaining high specificity and high affinity of base pairing.

In some embodiments, in the siRNA provided by the present disclosure, a phosphorothioate linkage exists in at least one of the following positions: the position between the first and the second nucleotides at either terminal of the sense strand or antisense strand, the position between the second and the third nucleotides at either terminal of the sense strand or antisense strand, or connection combination thereof. In some embodiments, a phosphorothioate linkage exists at all the above positions except for 5' terminal of the sense strand. In some embodiments, a phosphorothioate linkage exists at all the above positions except for 3' terminal of the sense strand. In some embodiments, a phosphorothioate linkage exists in at least one of the following positions: the position between the first and second nucleotides at 5' terminal of the sense strand;

the position between the second and third nucleotides at 5' terminal of the sense strand;

the position between the first and second nucleotides at 3' terminal of the sense strand;

the position between the second and third nucleotides at 3' terminal of the sense strand;

the position between the first and second nucleotides at 5' terminal of the antisense strand;

the position between the second and third nucleotides at 5' terminal of the antisense strand;

the position between the first and second nucleotides at 3' terminal of the antisense strand; and the position between the second and third nucleotides at 3' terminal of the antisense strand.

In some embodiments, phosphorothioate linkages are present at the position between the first and second nucleotides at 5' terminal of the sense strand of the siRNA, the position between the second and third nucleotides at 5' terminal of the sense strand of the siRNA, the position between the first and second nucleotides at 5' terminal of the antisense strand of the siRNA, the position between the second and third nucleotides at 5' terminal of the antisense strand of the siRNA, the position between the first and second nucleotides at 3' terminal of the antisense strand of the siRNA, and the position between the second and third nucleotides at 3' terminal of the antisense strand of the siRNA.

In some embodiments, the siRNA provided by the present disclosure is siHBVS7, siHBVS8, siHBVS9 or siHBVS10:

siHBVS7
Sense strand:
(SEQ ID NO: 15)
5'-UmsGmsCmUmAmUmGfCfCfUmCmAmUmCmUmUmCmUmAm-3', AntiSense strand:
(SEQ ID NO: 16)
5'-UmsAfsGmAmAmGfAmUmGmAmGmGmCmAfUmAfGmCmAmsGmsCm-3', siHBVS8
Sense strand:
(SEQ ID NO: 15)
5'-UmsGmsCmUmAmUmGfCfCfUmCmAmUmCmUmUmCmUmAm-3', AntiSense strand:
(SEQ ID NO: 17)
5'-UmsAfsGmAmAmGfAmUmGmAmGmGmCmAfUmAfGmCmAmsUmsUm-3', siHBVS9
Sense strand:
(SEQ ID NO: 18)
5'-UmsGmsCmUmAfUmGfCfCfUmCmAmUmCmUmUmCmUmAm-3', AntiSense strand:
(SEQ ID NO: 19)
5'-UmsAfsGmAmAmGfAmUfGfAmGmGmCmAfUmAfGmCmAmsGmsCm-3', siHBVS10
Sense strand:
(SEQ ID NO: 18)
5'-UmsGmsCmUmAfUmGfCfCfUmCmAmUmCmUmUmCmUmAm-3', AntiSense strand:
(SEQ ID NO: 20)
5'-UmsAfsGmAmAmGfAmUfGfAmGmGmCmAfUmAfGmCmAmsUmsUm-3', wherein C, G, U, and A represent the base composition of the nucleotides; m represents that the nucleotide adjacent to the left side of the letter m is a methoxy modified nucleotide; f represents that the nucleotide adjacent to the left side of the letter f is a fluoro modified nucleotide; s represents that the two nucleotides adjacent to both sides of the letter s are linked by a phosphorothioate linkage.

In some embodiments, the nucleotide at 5'-terminal in the antisense strand of the siRNA is a 5'-phosphate nucleotide or a 5'-phosphate analogue modified nucleotide.

Typical 5'-phosphate nucleotides or 5'-phosphate analogue modified nucleotides are well known to those skilled in the art; for example, the 5'-phosphate nucleotides may have the following structure:

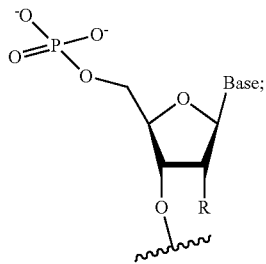

Formula (2)

for another example, Anastasia Khvorova and Jonathan K. Watts, The chemical evolution of oligonucleotide therapies of clinical utility. Nature Biotechnology, 2017, 35(3): 238-48 disclosed the following four 5'-phosphate analogue modified nucleotides:

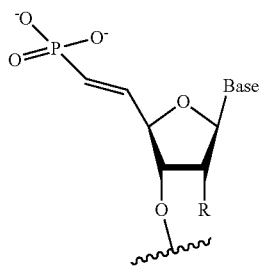

Formula (3)

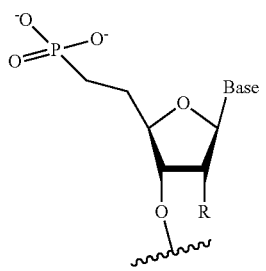

Formula (4)

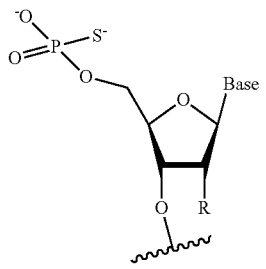

Formula (5)

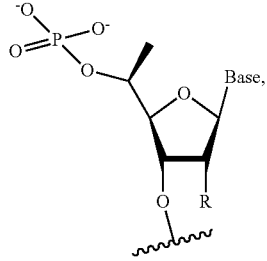

Formula (6)

wherein R represents a group selected from the group consisting of H, OH, methoxy and F; and "Base" represents a base selected from A, U, C, G, or T.

In some embodiments, the 5'-phosphate nucleotide is a nucleotide with 5'-phosphate modification as shown by Formula (2); the 5'-phosphate analogue modified nucleotide is a nucleotide with 5'-(E)-vinylphosphonat (E-VP) modification as shown by Formula (3) or a phosphorothioate modified nucleotide as shown by Formula (5).

In some embodiments, the siRNA provided by the present disclosure is siHBVS11, siHBVS12, siHBVS13, siHBVS14, siHBVS15, siHBVS16, siHBVS17 or siHBVS18:

```
siHBVS11
Sense strand:
                                    (SEQ ID NO: 9)
5'-UmGmCmUmAmUmGfCfCfUmCmAmUmCmUmUmCmUmAm-3', AntiSense strand:
                                    (SEQ ID NO: 21)
5'-P1-UmAfGmAmAmGfAmUmGmAmGmGmCmAfUmAfGmCmAm GmCm-3', siHBVS12
Sense strand:
                                    (SEQ ID NO: 9)
5'-UmGmCmUmAmUmGfCfCfUmCmAmUmCmUmUmCmUmAm-3', AntiSense strand:
                                    (SEQ ID NO: 22)
5'-P1-UmAfGmAmAmGfAmUmGmAmGmGmCmAfUmAfGmCmAm UmUm-3', siHBVS13
Sense strand:
                                    (SEQ ID NO: 12)
5'-UmGmCmUmAfUmGfCfCfUmCmAmUmCmUmUmCmUmAm-3', AntiSense strand:
                                    (SEQ ID NO: 23)
5'-P1-UmAfGmAmAmGfAmUfGfAmGmGmCmAfUmAfGmCmAm GmCm-3', siHBVS14
Sense strand:
                                    (SEQ ID NO: 12)
5'-UmGmCmUmAfUmGfCfCfUmCmAmUmCmUmUmCmUmAm-3', AntiSense strand:
                                    (SEQ ID NO: 24)
5'-P1-UmAfGmAmAmGfAmUfGfAmGmGmCmAfUmAfGmCmAm UmUm-3',
```

-continued siHBVS15
Sense strand:
(SEQ ID NO: 15)
5'-UmsGmsCmUmAmUmGfCfCfUmCmAmUmCmUmCmUmAm-3', AntiSense strand:
(SEQ ID NO: 25)
5'-P1-UmsAfsGmAmAmGfAmUmGmAmGmGmCmAfUmAfGmCmAms GmsCm-3', siHBVS16
Sense strand:
(SEQ ID NO: 15)
5'-UmsGmsCmUmAmUmGfCfCfUmCmAmUmCmUmCmUmAm-3', AntiSense strand:
(SEQ ID NO: 26)
5'-P1-UmsAfsGmAmAmGfAmUmGmAmGmGmCmAfUmAfGmCmAms UmsUm-3', siHBVS17
Sense strand:
(SEQ ID NO: 18)
5'-UmsGmsCmUmAfUmGfCfCfUmCmAmUmCmUmCmUmAm-3', AntiSense strand:
(SEQ ID NO: 27)
5'-P1-UmsAfsGmAmAmGfAmUfGfAmGmGmCmAfUmAfGmCmAms GmsCm-3', siHBVS18
Sense strand:
(SEQ ID NO: 18)
5'-UmsGmsCmUmAfUmGfCfCfUmCmAmUmCmUmCmUmAm-3', AntiSense strand:
(SEQ ID NO: 28)
5'-P1-UmsAfsGmAmAmGfAmUfGfAmGmGmCmAfUmAfGmCmAms UmsUm-3';

wherein C, G, U, and A represent the base composition of the nucleotides; m represents that the nucleotide adjacent to the left side of the letter m is a methoxy modified nucleotide; f represents that the nucleotide adjacent to the left side of the letter f is a fluoro modified nucleotide; s represents that the two nucleotides adjacent to both sides of the letter s are linked by a phosphorothioate linkage; P1 represents that the nucleotide adjacent to the right side of P1 is a 5'-phosphate nucleotide or a 5'-phosphate analogue modified nucleotide.

The inventors of the present disclosure have surprisingly found that the siRNA provided herein has significantly enhanced plasma and lysosomal stability, while maintaining higher gene-suppressing activity.

The siRNA provided herein can be obtained by conventional methods in the art for preparing siRNA, e.g., solid phase synthesis and liquid phase synthesis methods. Therein, commercial customization services have already been available for solid phase synthesis. A modified nucleotide can be introduced into the siRNA of the present disclosure by using a nucleotide monomer having a corresponding modification, wherein the methods for preparing a nucleotide monomer having a corresponding modification and the methods for introducing a modified nucleotide into a siRNA are also well-known to those skilled in the art.

Pharmaceutical Composition

The present disclosure provides is a pharmaceutical composition comprising the siRNA described above as an active ingredient, and a pharmaceutically acceptable carrier.

The pharmaceutically acceptable carrier may be a carrier conventionally used in the field of siRNA administration, for example, but is not limited to, one or more of magnetic nanoparticles such as Fe3O4- and Fe2O3-based nanoparticles, carbon nanotubes, mesoporous silicon, calcium phosphate nanoparticles, polyethylenimine (PEI), polyamidoamine (PAMAM) dendrimer, poly(L-lysine) (PLL), chitosan, 1,2-dioleoyl-3-trimethylammonium-propane (DOTAP), poly(D&L-lactic/glycolic acid) copolymer (PLGA), poly(2-aminoethyl ethylene phosphate) (PPEEA) and poly(2-dimethylaminoethyl methacrylate) (PDMAEMA), and derivatives thereof.

In the pharmaceutical composition according to some embodiments, there are no special requirements for the contents of the siRNA and the pharmaceutically acceptable carrier. In some embodiments, the weight ratio of the siRNA to the pharmaceutically acceptable carrier is 1:(1-500), and in some embodiments, the weight ratio is 1:(1-50).

In some embodiments, the pharmaceutical composition may also contain other pharmaceutically acceptable excipients, which may be one or more of the various formulations or compounds conventionally used in the art. For example, said other pharmaceutically acceptable excipients may include at least one of a pH buffer, a protective agent and an osmotic pressure regulator.

The pH buffer may be tris(hydroxymethyl) aminomethane hydrochloride buffer solution with a pH of 7.5-8.5, and/or phosphate buffer solution with a pH of 5.5-8.5, such as phosphate buffer solution with a pH of 5.5-8.5.

The protective agent may be at least one of inositol, sorbitol, sucrose, trehalose, mannose, maltose, lactose and glucose. The content of the protective agent may be from 0.01 wt % to 30 wt % based on the total weight of the pharmaceutical composition.

The osmotic pressure regulator may be sodium chloride and/or potassium chloride. The content of the osmotic pressure regulator allows the osmotic pressure of the pharmaceutical composition to be 200-700 milliosmol/kg. Depending on the desired osmotic pressure, those skilled in the art can readily determine the content of the osmotic pressure regulator.

In some embodiments, the pharmaceutical composition may be a liquid formulation, for example, an injection solution; or a lyophilized powder for injection, which is mixed with a liquid excipient to form a liquid formulation when performing administration. The liquid formulation may, but is not limited to, be used for administration by subcutaneous, intramuscular or intravenous injection, and also may, but is not limited to, be administrated to the lung by spray, or to other organ tissues (such as the liver) through the lung by spray. In some embodiments, the pharmaceutical composition is used for administration by intravenous injection.

In some embodiments, the pharmaceutical composition may be in the form of a liposome formulation. In some embodiments, the pharmaceutically acceptable carrier used in the liposome formulation comprises an amine-containing transfection compound (hereinafter also referred to as an organic amine), a helper lipid and/or a PEGylated lipid. Therein, the organic amine, the helper lipid and the PEGylated lipid may be respectively selected from one or more of the amine-containing transfection compounds or the pharmaceutically acceptable salts or derivatives thereof, the helper lipids and the PEGylated lipids described in CN103380113A, which is incorporated herein by reference in its entirety.

In some embodiments, the organic amine may be a compound as shown by Formula (201) described in CN103380113A or a pharmaceutically acceptable salt thereof:

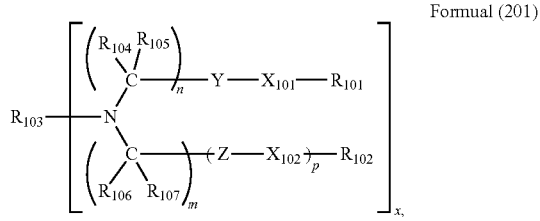

Formual (201)

wherein:

$X_{101}$ and $X_{102}$ independently of one another are selected from O, S, N-A or C-A, wherein A is hydrogen or a $C_1$-$C_{20}$ hydrocarbon chain;

Y and Z independently of one another are selected from C—O, C—S, S—O, CH—OH or $SO_2$;

$R_{101}$, $R_{102}$, $R_{103}$, $R_{104}$, $R_{105}$, $R_{106}$ and $R_{107}$ independently of one another are selected from hydrogen; a cyclic or an acyclic, substituted or unsubstituted, branched or linear aliphatic group; a cyclic or an acyclic, substituted or unsubstituted, branched or linear heteroaliphatic group; a substituted or unsubstituted, branched or linear acyl group; a substituted or unsubstituted, branched or linear aryl group; or a substituted or unsubstituted, branched or linear heteroaryl group;

x is an integer of 1-10;

n is an integer of 1-3; m is an integer of 0-20, p is an integer of 0 or 1, wherein if m=p=0, then $R_{102}$ is hydrogen, and if at least one of n and m is 2, then $R_{103}$ and nitrogen in Formula (201) form a structure as shown by Formula (202) or (203):

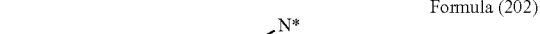

Formula (202)

Formula (203)

wherein g, e and f independently of one another are an integer of 1-6; "HCC" represents a hydrocarbon chain; and each *N represents a nitrogen atom shown in Formula (201).

In some embodiments, $R_{103}$ is a polyamine. In other embodiments, $R_{103}$ is a ketal. In some embodiments, $R_{101}$ and $R_{102}$ in the Formula (201) independently of one another are any of substituted or unsubstituted, branched or linear alkyl or alkenyl groups having between 3-20 carbon atoms (such as between 8-18 carbon atoms) and between 0-4 double bonds (such as between 0-2 double bonds).

In some embodiments, if n and m independently of one another are 1 or 3, $R_{103}$ is any of the following Formulae (204)-(213):

Formula (204)

Formula (205)

Formula (206)

Formula (207)

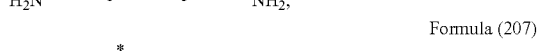

Formula (208)

Formula (209)

Formula (210)

Formula (211)

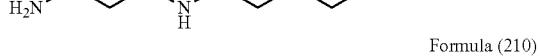

Formula (212)

Formula (213)

wherein in Formulae (204)-(213), g, e and f independently of one another are an integer of 1-6; each "HCC" represents a hydrocarbon chain; and each * shows a potential attachment position of $R_{103}$ to the nitrogen atom in Formula (201), where each H on any * position can be replaced to achieve the attachment to the nitrogen atom in Formula (201).

The compound as shown by Formula (201) may be prepared as described in CN103380113A.

In some embodiments, the organic amine may be an organic amine as shown by Formula (214) and/or an organic amine as shown by Formula (215):

Formula (214)
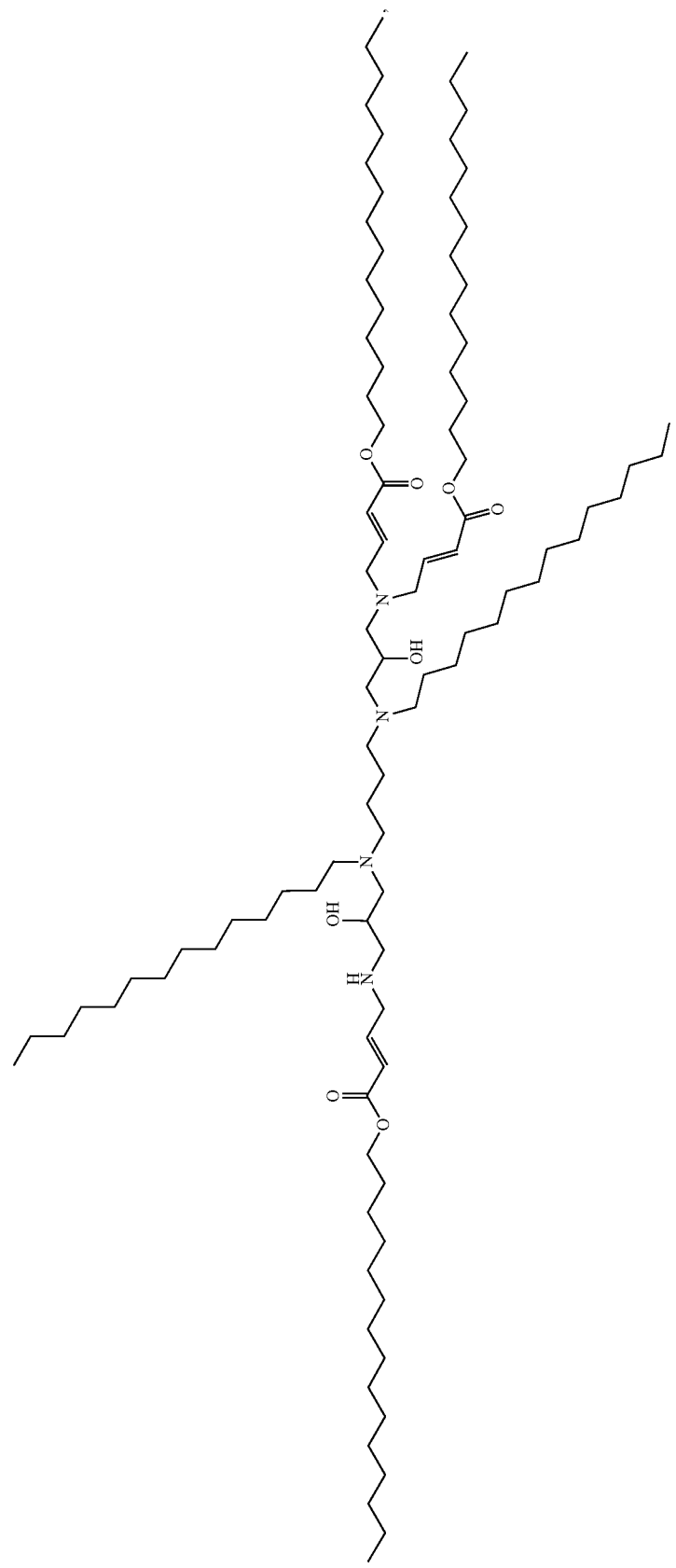

-continued
Formula (215)
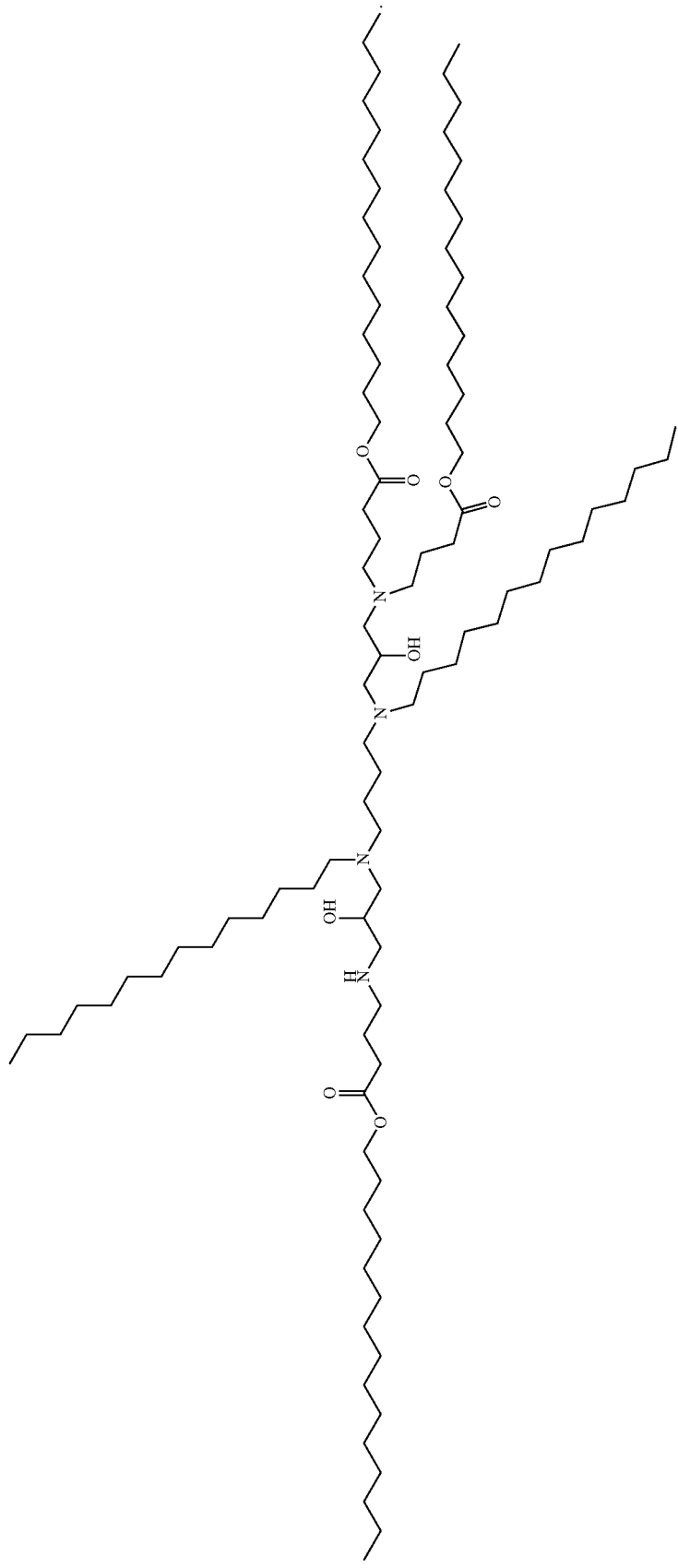

The helper lipid is cholesterol, cholesterol analogue and/or cholesterol derivatives.

The PEGylated lipid may be 1,2-dipalmitoyl-sn-glycero-3-phosphatidylethanolamine-N-[methoxy(polyethylene glycol)]-2000.

In some embodiments, the molar ratio among the organic amine, the helper lipid, and the PEGylated lipid in the pharmaceutical composition is (19.7-80):(19.7-80):(0.3-50); for example, the molar ratio may be (50-70):(20-40):(3-20).

In some embodiments, the pharmaceutical composition particles formed by the siRNA of the present disclosure and the above amine-containing transfection reagents have an average diameter from about 30 nm to about 200 nm, typically from about 40 nm to about 135 nm, and more typically, the average diameter of the liposome particles is from about 50 nm to about 120 nm, from about 50 nm to about 100 nm, from about 60 nm to about 90 nm, or from about 70 nm to about 90 nm, for example, the average diameter of the liposome particles is about 30, 40, 50, 60, 70, 75, 80, 85, 90, 100, 110, 120, 130, 140, 150 or 160 nm.

In some embodiments, in the pharmaceutical composition formed by the siRNA of the present disclosure and the above amine-containing transfection reagents, the weight ratio (weight/weight ratio) of the siRNA to total lipids, e.g., the organic amines, the helper lipids and/or the PEGylated lipids, ranges from about 1:1 to about 1:50, from about 1:1 to about 1:30, from about 1:3 to about 1:20, from about 1:4 to about 1:18, from about 1:5 to about 1:17, from about 1:5 to about 1:15, from about 1:5 to about 1:12, from about 1:6 to about 1:12, or from about 1:6 to about 1:10; for example, the weight ratio of the siRNA of the present disclosure to total lipids is about 1:5, 1:6, 1:7, 1:8, 1:9, 1:10, 1:11, 1:12, 1:13, 1:14, 1:15, 1:16, 1:17 or 1:18.

In some embodiments, the pharmaceutical composition may be marketed with being separate, and used in the form of a liquid formulation. In some embodiments, the pharmaceutical composition formed by the siRNA provided herein and the above pharmaceutically acceptable carrier may be prepared by various known processes, as long as the existing siRNA is replaced with the siRNA provided herein; in some embodiments, the pharmaceutical composition may be prepared according to the following process:

The organic amines, helper lipids and PEGylated lipids are suspended in alcohol at a molar ratio as described above and mixed homogeneously to yield a lipid solution; the alcohol is used in an amount such that the resultant lipid solution is present at a total mass concentration of 2 to 25 mg/mL (e.g., 8 to 18 mg/mL). The alcohol is a pharmaceutically acceptable alcohol, such as an alcohol that is liquid at about room temperature, for example, being one or more of ethanol, propylene glycol, benzyl alcohol, glycerol, PEG 200, PEG 300, PEG 400, such as ethanol.

The siRNA provided herein is dissolved in a buffer salt solution to produce an aqueous solution of the siRNA. The buffer salt solution has a concentration of 0.05 to 0.5 M (such as 0.1 to 0.2 M). The pH of the buffer salt solution is adjusted to 4.0 to 5.5 (such as 5.0 to 5.2). The buffer salt solution is used in an amount such that the siRNA is present at a concentration of less than 0.6 mg/ml (such as 0.2 to 0.4 mg/mL). The buffer salt may be one or more selected from the group consisting of soluble acetate and soluble citrate, such as sodium acetate and/or potassium acetate.

The lipid solution and the aqueous solution of the siRNA are mixed. The product obtained after mixing is incubated at a temperature of 40 to 60° C. for at least 2 minutes (e.g., 5 to 30 minutes) to produce a lipid formulation after incubation. The volume ratio of the lipid solution to the aqueous solution of the siRNA is 1:(2-5), such as 1:4.

The lipid formulation obtained after incubation is concentrated or diluted; the impurities are removed; and then the formulation is sterilized to obtain the pharmaceutical composition provided herein, which has the following physiochemical parameters: a pH of 6.5 to 8, an encapsulation efficiency of more than 80%, a particle size of 40 to 200 nm, a polydispersity index of less than 0.30, and an osmotic pressure of 250 to 400 mOsm/kg; for example, the physicochemical parameters may be as follows: a pH of 7.2 to 7.6, an encapsulation efficiency of more than 90%, a particle size of 60 to 100 nm, a polydispersity index of less than 0.20, and an osmotic pressure of 300 to 400 mOsm/kg.

Therein, the concentration or dilution step may be performed before, after or simultaneously with removal of the impurities. Methods for removing impurities may be any of various existing methods, for example, ultrafiltration with 100 KDa hollow fiber column and PBS at pH 7.4 as ultrafiltration exchange solution using tangential flow system can be used. Methods for sterilization may any of various existing methods, such as filtration sterilization with a 0.22 µm filter.

A First siRNA Conjugate

In one aspect, provided herein is a first siRNA conjugate comprising the siRNA described above and a conjugating group attached to the siRNA.

In the context of the disclosure, unless otherwise stated, "conjugation" refers to two or more chemical moieties each with specific function being linked to each other via a covalent linkage.

Correspondingly, a "conjugate" refers to the compound formed by covalent linkage of individual chemical moieties. Further, a "siRNA conjugate" represents a compound formed by covalently attaching a siRNA and one or more chemical moieties each with specific functions. In this context, the siRNA conjugate disclosed herein is sometimes also referred to as "conjugate". The siRNA conjugate should be understood as the generic term of siRNA conjugates according to the context, the first siRNA conjugate or the second siRNA conjugate. In the context of the present disclosure, a "conjugating molecule" should be understood as a compound capable of being conjugated to a siRNA via reactions, thus finally forming the siRNA conjugate of the present disclosure.

The present disclosure provides a first siRNA conjugate comprising the siRNA described above and a conjugating group attached to the siRNA. Generally speaking, for the first siRNA conjugate, the conjugating group comprises at least one pharmaceutically acceptable targeting group and an optional linker. Moreover, the siRNA, the linker and the targeting group are linked successively. In some embodiments, there are 1 to 6 targeting groups. In some embodiments, there are 2 to 4 targeting groups. The siRNA molecule may be non-covalently or covalently conjugated to the conjugating group, for example, the siRNA molecule is covalently conjugated to the conjugating group. The conjugating site between the siRNA and the conjugating group can be at the 3'-terminal or 5'-terminal of the sense strand of the siRNA, or at the 5'-terminal of the antisense strand, or within the internal sequence of the siRNA. In some embodiments, the conjugating site between the siRNA and the conjugating group is at the 3'-terminal of the sense strand of the siRNA. In some embodiments, the conjugating group is linked to the phosphate group, the 2'-hydroxy group or the base of a nucleotide. In some embodiments, the conjugating group may be linked to a 3'-hydroxy group. In this case, the nucleotides are linked via a 2'-5'-phosphodiester bond. When the conjugating group is linked to a terminal of the siRNA, the conjugating group is typically linked to a phosphate group of a nucleotide; when the conjugating group is linked to an internal sequence of the siRNA, the conjugating group is typically linked to a ribose ring or a base. For specific linking modes, reference may be made to: Muthiah Manoharan et. al. siRNA conjugates carrying sequentially assembled trivalent N-acetylgalactosamine linked through nucleosides elicit robust gene silencing in vivo in hepatocytes. ACS Chemical biology, 2015, 10(5):1181-7.

In some embodiments, the siRNA and the conjugating group can be linked by acid-labile or reducible chemical bonds, and these chemical bonds can be degraded under the acidic environment of cell endosomes, thereby making the siRNA be in free state. For non-degradable conjugating modes, the conjugating group can be linked to the sense strand of the siRNA, thereby minimizing the effect of conjugation on the siRNA activity.

In some embodiments, the pharmaceutically acceptable targeting group may be a ligand conventionally used in the field of siRNA administration, for example, the various ligands described in WO2009082607A2, which is incorporated herein by reference in its entirety.

In some embodiments, the pharmaceutically acceptable targeting group may be selected from one or more of the ligands formed by the following targeting molecules or derivatives thereof: lipophilic molecules, such as cholesterol, bile acids, vitamins such as vitamin E, lipid molecules of different chain lengths; polymers, such as polyethylene glycol; polypeptides, such as cell-penetrating peptide; aptamers; antibodies; quantum dots; saccharides, such as lactose, polylactose, mannose, galactose, N-acetylgalactosamine (GalNAc); folate; or receptor ligands expressed in hepatic parenchymal cells, such as asialoglycoprotein, asialo-sugar residue, lipoproteins (such as high density lipoprotein, low density lipoprotein and the like), glucagon, neurotransmitters (such as adrenaline), growth factors, transferrin and the like.

In some embodiments, each of the ligands is independently selected from a ligand capable of binding to a cell surface receptor. In some embodiments, at least one ligand is a ligand capable of binding to a hepatocyte surface receptor. In some embodiments, at least one ligand is a ligand capable of binding to a mammalian hepatocyte surface receptor. In some embodiments, at least one ligand is a ligand capable of binding to a human hepatocyte surface receptor. In some embodiments, at least one ligand is a ligand capable of binding to a hepatic surface asialoglycoprotein receptor (ASGPR). The types of these ligands are well-known to those skilled in the art and they typically serve the function of binding to specific receptors on the surface of the target cell, thereby mediating delivery of the siRNA linked to the ligand into the target cell.

In some embodiments, the pharmaceutically acceptable targeting group may be any ligand that binds to asialoglycoprotein receptors (ASGP-R) on the surface of mammalian hepatocytes. In one embodiment, each ligand is independently selected from asialoglycoprotein, such as asialoorosomucoid (ASOR) or asialofetuin (ASF). In one embodiment, the ligand is a saccharide or its derivatives.

In some embodiments, at least one ligand is a saccharide. In some embodiments, each ligand is a saccharide. In some embodiments, at least one ligand is a monosaccharide, polysaccharide, modified monosaccharide, modified polysaccharide, or its derivatives. In some embodiments, at least one ligand may be a monosaccharide, disaccharide or trisaccharide. In some embodiments, at least one ligand is a modified saccharide. In some embodiments, each ligand is a modified saccharide. In some embodiments, each ligand is independently selected from polysaccharides, modified polysaccharides, monosaccharides modified monosaccharides, polysaccharide derivatives, or monosaccharide derivatives. In some embodiments, each or at least one ligand may be independently selected from the group consisting of glucose and its derivatives, mannose and its derivatives, galactose and its derivatives, xylose and its derivatives, ribose and its derivatives, fucose and its derivatives, lactose and its derivatives, maltose and its derivatives, arabinose and its derivatives, fructose and its derivatives, and sialic acid.

In some embodiments, each ligand may be independently selected from the group consisting of D-mannopyranose, L-mannopyranose, D-arabinose, D-xylofuranose, L-xylofuranose, D-glucose, L-glucose, D-galactose, L-galactose, α-D-mannofuranose, β-D-mannofuranose, α-D-mannopyranose, β-D-mannopyranose, α-D-glucopyranose, β-D-glucopyranose, α-D-glucofuranose, β-D-glucofuranose, α-D-fructofuranose, α-D-fructopyranose, α-D-galactopyranose, β-D-galactopyranose, α-D-galactofuranose, β-D-galactofuranose, glucosamine, sialic acid, galactosamine, N-acetylgalactosamine, N-trifluoroacetylgalactosamine, N-propionylgalactosamine, N-n-butyrylgalactosamine, N-isobutyrylgalactosamine, 2-amino-3-O—[(R)-1-carboxyethyl]-2-deoxy-β-D-glucopyranose, 2-deoxy-2-methylamino-L-glucopyranose, 4,6-dideoxy-4-formamido-2,3-di-O-methyl-D-mannopyranose, 2-deoxy-2-sulfoamino-D-glucopyranose, N-glycolyl-α-neuraminic acid, 5-thio-β-D-glucopyranose, methyl 2,3,4-tris-O-acetyl-1-thio-6-O-trityl-α-D-glucopyranoside, 4-thio-β-D-galactopyranose, ethyl 3,4,6,7-tetra-O-acetyl-2-deoxy-1,5-dithio-α-D-glucoheptopyranoside, 2,5-anhydro-D-allononitrile, ribose, D-ribose, D-4-thioribose, L-ribose, L-4-thioribose. Additional options of the ligand may be found, for example, in the disclosure of CN105378082A, which is incorporated herein by reference in its entirety.

In some embodiments, the pharmaceutically acceptable targeting group in the first siRNA conjugate may be galactose or N-acetylgalactosamine, wherein the galactose or N-acetylgalactosamine molecules can be mono-, bi-, tri-, or tetra-valent. It should be understood that the terms mono-, bi-, tri-, or tetra-valent described herein respectively mean that the molar ratio of the siRNA molecule to the galactose or N-acetylgalactosamine molecule in the oligonucleotide conjugate is 1:1, 1:2, 1:3 or 1:4, wherein the oligonucleotide conjugate is formed from the siRNA molecule and the conjugating group containing galactose or N-acetylgalactosamine molecule as the targeting group. In some embodiments, the pharmaceutically acceptable targeting group is N-acetylgalactosamine. In some embodiments, when the siRNA of the present disclosure is conjugated to a conjugating group comprising N-acetylgalactosamine, the N-acetylgalactosamine molecule is trivalent or tetravalent. In some embodiments, when the siRNA of the present disclosure is conjugated to a conjugating group containing N-acetylgalactosamine, the N-acetylgalactosamine molecule is trivalent.

When the siRNA described herein is conjugated to a conjugating molecule, the conjugating molecule can be linked to the siRNA molecule via an appropriate linker, and the appropriate linker can be selected by those skilled in the art according to the specific type of the targeting group. The types of these conjugating groups, linkers and targeting groups, and the linking modes with the siRNA may be found in the disclosure of WO2015006740A2, which is incorporated herein by reference in its entirety.

In some embodiments, when the targeting group is N-acetylgalactosamine, a suitable linker may have the following structure as shown by Formula (301):

Formula (301)

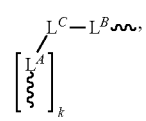

wherein k is an integer of 1-3;

$L^A$ is an amide bond-comprising chain moiety that has a structure as shown by Formula (302), two terminals of which are respectively linked to the targeting group and the $L^C$ moiety via ether bond:

Formula (302)

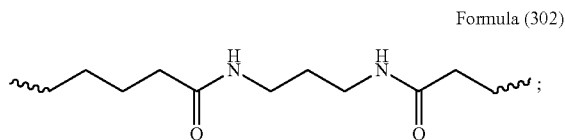

$L^B$ is an N-acylpyrrolidine-comprising chain moiety that has a structure as shown by Formula (303), one terminal of which has a carbonyl group and is linked to the $L^C$ moiety via an amide bond, and the other terminal of which has an oxy-group and is linked to the siRNA via a phosphoester bond:

Formula (303)

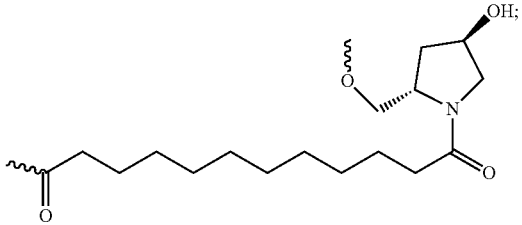

$L^C$ is a bivalent to tetravalent linking group based on hydroxymethyl aminomethane, dihydroxymethyl aminomethane or trihydroxymethyl aminomethane, one terminal of which may be linked to $L^A$ moieties via an ether bond by an oxygen atom, and the other terminal of which is linked to the $L^B$ moiety via amide bond by nitrogen atom.

In some embodiments, when n=3 and $L^C$ is a tetravalent linking group based on trihydroxymethyl aminomethane, the siRNA conjugate formed by linking N-acetylgalactosamine molecules with a siRNA molecule via -($L^A$)3-trihydroxymethyl aminomethane-$L^B$- as a linker has a structure as shown by Formula (304):

Formula (304)

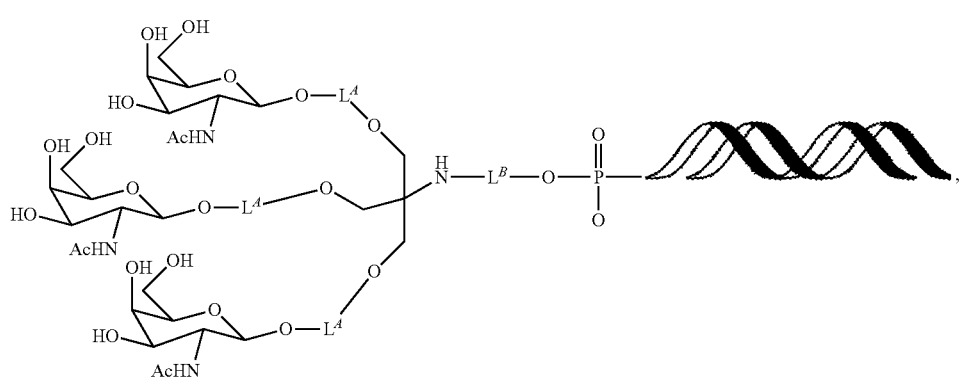

wherein the double helix structure represents a siRNA.

Likewise, the conjugating site between the siRNA and the conjugating molecule can be at the 3'-terminal or 5'-terminal of the sense strand of the siRNA, or at the 5'-terminal of the antisense strand, or within the internal sequence of the siRNA.

In some embodiments, the 3'-terminal of the sense strand of the siRNA of the present disclosure is covalently conjugated to three N-acetylgalactosamine (GalNAc) molecules via a linker -($L^A$)3-trihydroxymethyl aminomethane-$L^B$- to obtain a siRNA conjugate in which the molar ratio of the siRNA molecule to the GalNAc molecule is 1:3 (hereinafter referred to as (GalNAc)$_3$-1-siRNA), and this conjugate has a structure as shown by Formula (305):

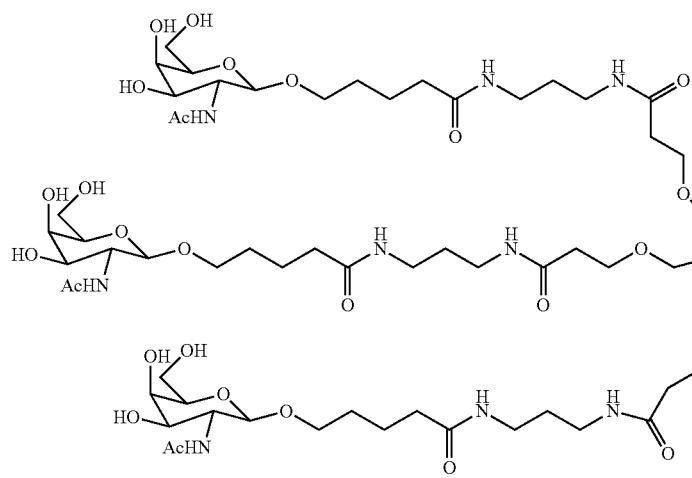

Formula (305)

wherein the double helix structure represents the siRNA; and the linker is linked to the 3'-terminal of the sense strand of the siRNA.

In some embodiments, when the targeting group is N-acetylgalactosamine, a suitable linker may have a structure as shown by Formula (306):

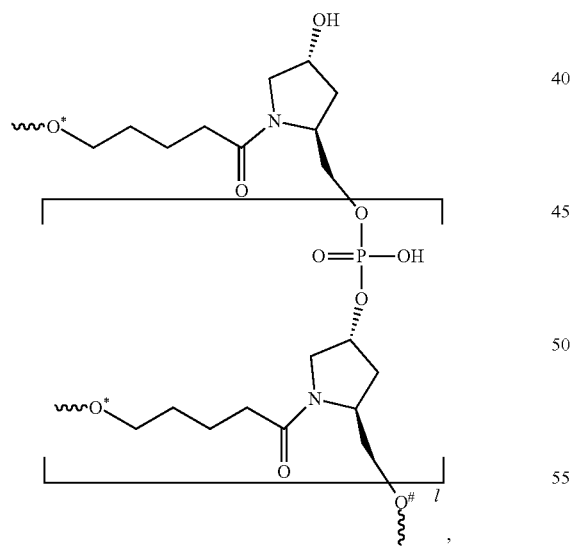

Formula (306)

wherein l is an integer of 0-3;

* represents a site on the linker linked to the targeting group via ether bond; and # represents a site on the linker linked to the siRNA via phosphoester bond.

In some embodiments, when l=2, the siRNA conjugate has a structure as shown by Formula (307):

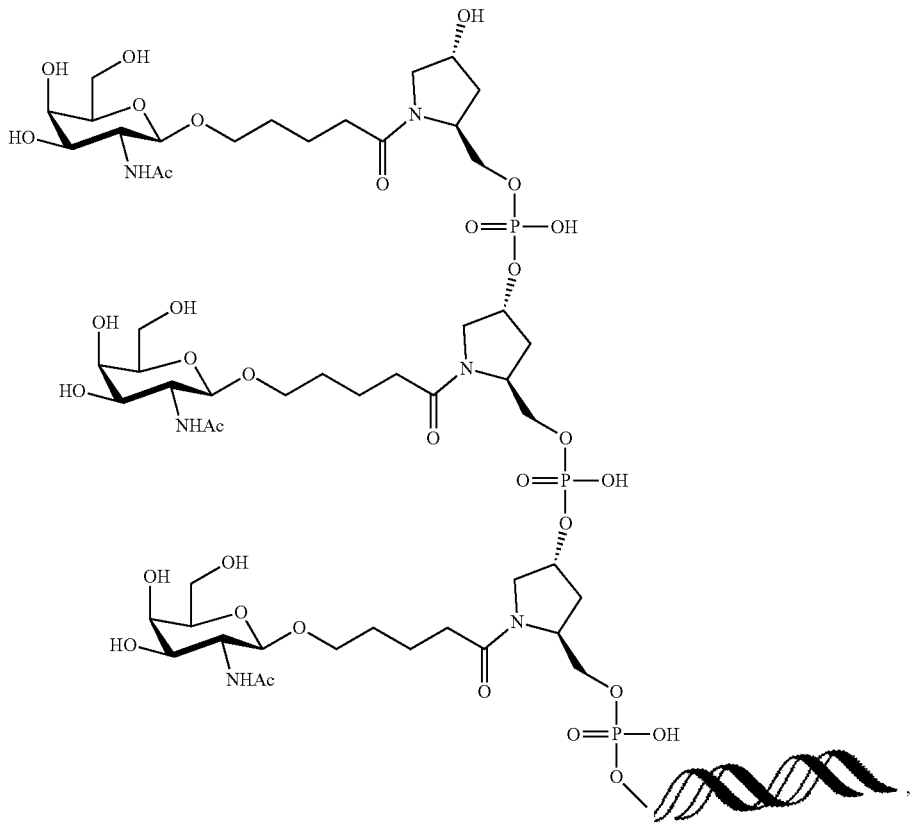

Formula (307)

wherein the double helix structure represents the siRNA; and the linker is linked to the 3'-terminal of the sense strand of the siRNA.

The above conjugates can be synthesized according to the method described in detail in the prior art. For example, WO2015006740A2 has described in detail the preparation methods of various conjugates. The first siRNA conjugate of the present disclosure may be obtained by the methods well known to those skilled in the art. For example, WO2014025805A1 described the preparation method of the conjugate with a structure as shown by Formula (305), and Rajeev et al., ChemBioChem 2015, 16, 903-908 described the preparation method of the conjugate with a structure as shown by Formula (307).

A Second siRNA Conjugate

In some embodiments, the siRNA conjugate is a second siRNA conjugate which has a structure as shown by Formula (308):

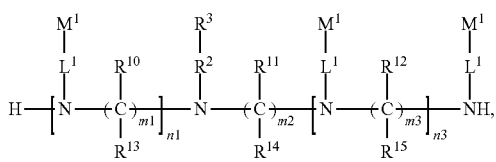

Formula (308)

wherein, n1 is an integer of 1-3, and n3 is an integer of 0-4; m1, m2, and m3 independently of one another are an integer of 2-10;

$R_{10}$, $R_{11}$, $R_{12}$, $R_{13}$, $R_{10}$ and $R_{15}$ independently of one another are independently H, or selected from the group consisting of $C_1$-$C_{10}$ alkyl, $C_1$-$C_{10}$ haloalkyl, and $C_1$-$C_{10}$ alkoxy;

R3 is a group having a structure as shown by Formula (A59):

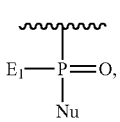

Formula (A59)

wherein E1 is OH, SH or $BH_2$; Nu is the siRNA of the present disclosure;

$R_2$ is a linear alkylene of 1 to 20 carbon atoms in length, wherein one or more carbon atoms are optionally replaced with one or more groups selected from the group consisting of: C(O), NH, O, S, CH=N, S(O)$_2$, $C_2$-$C_{10}$ alkenylene, $C_2$-$C_{10}$ alkynylene, $C_6$-$C_{10}$ arylene, $C_3$-$C_{18}$ heterocyclylene, and $C_5$-$C_{10}$ heteroarylene, and wherein $R_2$ is optionally substituted by one or more substituents selected from the group consisting of: $C_1$-$C_{10}$ alkyl, $C_6$-$C_{10}$ aryl, $C_5$-$C_{10}$ heteroaryl, $C_1$-$C_{10}$ haloalkyl, —O$C_1$-$C_{10}$ alkyl, —O$C_1$-$C_{10}$ alkylphenyl, —$C_1$-$C_{10}$ alkyl-OH, —O$C_1$-$C_{10}$ haloalkyl, —S$C_1$-$C_{10}$ alkyl, —S$C_1$-$C_{10}$ alkylphenyl, —$C_1$-$C_{10}$ alkyl-SH, —S$C_1$-$C_{10}$ haloalkyl, halo, —OH, —SH, —NH$_2$, —$C_1$-$C_{10}$ alkyl-NH$_2$, —N($C_1$-$C_{10}$ alkyl)($C_1$-$C_{10}$ alkyl), —NH($C_1$-$C_{10}$ alkyl), cyano, nitro, —CO$_2$H, —C(O)O($C_1$-$C_{10}$ alkyl), —CON($C_1$-$C_{10}$ alkyl)($C_1$-$C_{10}$ alkyl), —CONH($C_1$-$C_{10}$ alkyl), —CONH$_2$, —NHC(O)($C_1$-$C_{10}$ alkyl), —NHC(O)

(phenyl), —N(C$_1$-C$_{10}$ alkyl)C(O)(C$_1$-C$_{10}$ alkyl), —N(C$_1$-C$_{10}$ alkyl)C(O)(phenyl), —C(O)C$_1$-C$_{10}$ alkyl, —C(O)C$_1$-C$_{10}$ alkylphenyl, —C(O)C$_1$-C$_{10}$ haloalkyl, —OC(O)C$_1$-C$_{10}$ alkyl, —SO$_2$(C$_1$-C$_{10}$ alkyl), —SO$_2$(phenyl), —SO$_2$(C$_1$-C$_{10}$ haloalkyl), —SO$_2$NH$_2$, —SO$_2$NH(C$_1$-C$_{10}$ alkyl), —SO$_2$NH (phenyl), —NHSO$_2$(C$_1$-C$_{10}$ alkyl), —NHSO$_2$(phenyl), and —NHSO$_2$(C$_1$-C$_{10}$ haloalkyl);

each L$_1$ is independently a linear alkylene of 1 to 70 carbon atoms in length, wherein one or more carbon atoms are optionally replaced with one or more groups selected from the group consisting of: C(O), NH, O, S, CH=N, S(O)$_2$, C$_2$-C$_{10}$ alkenylene, C$_2$-C$_{10}$ alkynylene, C$_6$-C$_{10}$ arylene, C$_3$-C$_{18}$ heterocyclylene, and C$_5$-C$_{10}$ heteroarylene, and wherein L$_1$ is optionally substituted by one or more groups selected from the group consisting of: C$_1$-C$_{10}$ alkyl, C$_6$-C$_{10}$ aryl, C$_5$-C$_{10}$ heteroaryl, C$_1$-C$_{10}$ haloalkyl, —OC$_1$-C$_{10}$ alkyl, —OC$_1$-C$_{10}$ alkylphenyl, —C$_1$-C$_{10}$ alkyl-OH, —OC$_1$-C$_{10}$ haloalkyl, —SC$_1$-C$_{10}$ alkyl, —SC$_1$-C$_{10}$ alkylphenyl, —C$_1$-C$_{10}$ alkyl-SH, —SC$_1$-C$_{10}$ haloalkyl, halo, —OH, —SH, —NH$_2$—, —C$_1$-C$_{10}$ alkyl-NH$_2$, —N(C$_1$-C$_{10}$ alkyl)(C$_1$-C$_{10}$ alkyl), —NH(C$_1$-C$_{10}$ alkyl), cyano, nitro, —CO$_2$H, —C(O)O(C$_1$-C$_{10}$ alkyl), —CON(C$_1$-C$_{10}$ alkyl)(C$_1$-C$_{10}$ alkyl), —CONH(C$_1$-C$_{10}$ alkyl), —CONH$_2$, —NHC(O)(C$_1$-C$_{10}$ alkyl), —NHC(O)(phenyl), —N(C$_1$-C$_{10}$ alkyl)C(O)(C$_1$-C$_{10}$ alkyl), —N(C$_1$-C$_{10}$ alkyl)C(O)(phenyl), —C(O)C$_1$-C$_{10}$ alkyl, —C(O)C$_1$-C$_{10}$ alkylphenyl, —C(O) C$_1$-C$_{10}$ haloalkyl, —OC(O)C$_1$-C$_{10}$ alkyl, —SO$_2$(C$_1$-C$_{10}$ alkyl), —SO$_2$(phenyl), —SO$_2$(C$_1$-C$_{10}$ haloalkyl), —SO$_2$NH$_2$, —SO$_2$NH(C$_1$-C$_{10}$ alkyl), —SO$_2$NH(phenyl), —NHSO$_2$(C$_1$-C$_{10}$ alkyl), —NHSO$_2$(phenyl), and —NHSO$_2$ (C$_1$-C$_{10}$ haloalkyl). Moreover, in some embodiments, L$_1$ may be selected from the group consisting of groups A1-A26 or any connection combinations thereof, wherein the structures and definitions of A1-A26 are as follows:

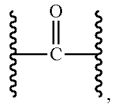 (A1)

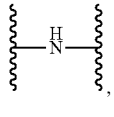 (A2)

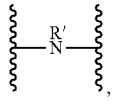 (A3)

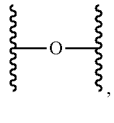 (A4)

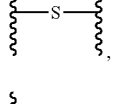 (A5)

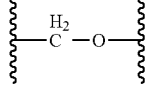 (A6)

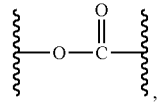 (A7)

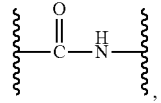 (A8)

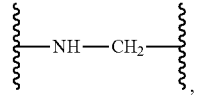 (A9)

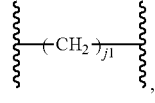 (A10)

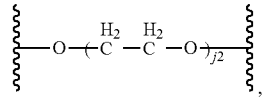 (A11)

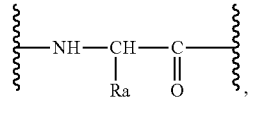 (A12)

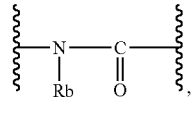 (A13)

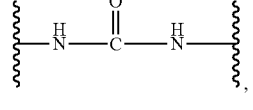 (A14)

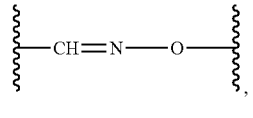 (A15)

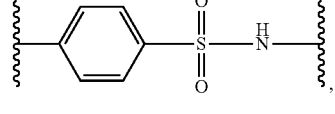 (A16)

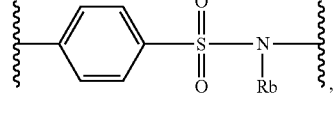 (A17)

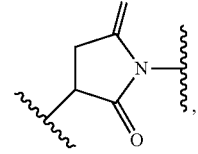 (A18)

wherein j1 is independently an integer of 1-20;
j2 is independently an integer of 1-20;
R' is independently a $C_1$-$C_{10}$ alkyl;
Ra is independently selected from the group consisting of A27-A45:

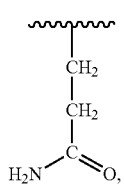
(A39)

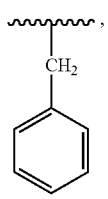
(A40)

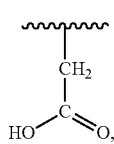
(A41)

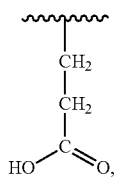
(A42)

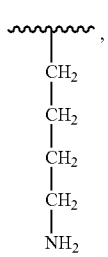
(A43)

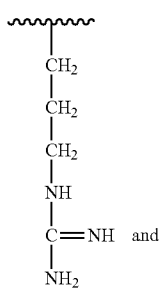
(A44)

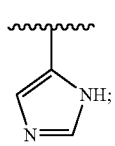
(A45)

Rb is a $C_1$-$C_{10}$ alkyl; and ⁓ represents a site where a group is linked to the rest of the molecule.

A skilled person would readily understand that, though $L_1$ is defined as a linear alkyl for convenience, but it may not be a linear group or be named differently, such as an amine or alkenyl produced by the above replacement and/or substitution. For the purpose of the present disclosure, the length of $L_1$ is the number of the atoms in the chain connecting the two attaching points. For this purpose, a ring produced by replacement of a carbon atom of the linear alkylene, such as a heterocyclylene or heteroarylene, is counted as one atom.

$M_1$ represents a targeting group, of which the definitions and options are the same as described above. In some embodiments, each $M_1$ is independently selected from one of the ligands that have affinity to the asialoglycoprotein receptors (ASGP-R) on the surface of mammalian hepatocytes.

When $M_1$ is a ligand that has affinity to an asialoglycoprotein receptor (ASGP-R) on the surface of mammalian hepatocyte, in some embodiments, n1 may be an integer of 1-3, and n3 may be an integer of 0-4 to ensure that the number of $M_1$ ligand in the conjugate may be at least 2. In some embodiments, n1+n3≥2, so that the number of $M_1$ ligand in the conjugate may be at least 3, thereby allowing the $M_1$ ligand to bind to the asialoglycoprotein receptors on the surface of hepatocytes more conveniently, which may facilitate the endocytosis of the conjugate into cells. Experiments have shown that when the number of $M_1$ ligand is greater than 3, the ease of binding $M_1$ ligand to the asialoglycoprotein receptors on the surface of hepatocytes is not significantly increased. Therefore, in view of various aspects such as the synthesis convenience, structure/process costs and delivery efficiency, in some embodiments, n1 is an integer of 1-2, n3 is an integer of 0-1, and n1+n3 is from 2 to 3.

In some embodiments, when m1, m2, and m3 independently of one another are selected from an integer of 2-10, the steric positions among a plurality of $M_1$ ligands may be fit for binding $M_1$ ligands to the asialoglycoprotein receptors on the surface of hepatocytes. In order to make the conjugate provided by the present disclosure simpler, more convenient to synthesize and/or costs reduced, in some embodiments, m1, m2 and m3 independently of one another are an integer of 2-5, in some embodiments, m1=m2=m3.

It may be understood by those skilled in the art that with $R_{10}$, $R_{11}$, $R_{12}$, $R_{13}$, $R_{14}$, and $R_{15}$ independently of one another being selected from H, $C_1$-$C_{10}$ alkyl, $C_1$-$C_{10}$ haloalkyl, or $C_1$-$C_{10}$ alkoxy, the purpose of the present disclosure may be achieved without changing the properties of the conjugate disclosed herein. In some embodiments, $R_{10}$, $R_{11}$, $R_{12}$, $R_{13}$, $R_{14}$, and $R_{15}$ independently of one another are selected from H, methyl or ethyl. In some embodiments, $R_{10}$, $R_{11}$, $R_{12}$, $R_{13}$, $R_{14}$, and $R_{15}$ are all H.

According to the second siRNA conjugate provided by the present disclosure, $R_3$ is a group having a structure as shown by Formula A59, wherein $E_1$ is OH, SH or $BH_2$, and for easy availability of starting materials, in some embodiments, $E_1$ is OH or SH.

In some embodiments, $R_2$ is selected to achieve the linkage between A59 and the N atom on a nitrogenous backbone. In the context of the present disclosure, a "nitrogenous backbone" refers to a chain structure in which the carbon atoms to which $R_{10}$, $R_{11}$, $R_{12}$, $R_{13}$, $R_{14}$, and $R_{15}$ are attached and the N atoms are linked to each other. In some embodiments, $R_2$ may be any linking group capable of attaching the group as shown by Formula (A59) to the N atom on a nitrogenous backbone by suitable means. In some embodiments, in the case where the siRNA conjugate of the present disclosure is prepared by a solid phase synthesis process, $R_2$ group needs to have both a site linking to the N atom on the nitrogenous backbone and a site linking to the P atom in $R_3$. In some embodiments, in $R_2$, the site linking to the N atom on the nitrogenous backbone forms an amide bond with the N atom, and the site linking to the P atom in $R_3$ forms a phosphoester bond with the P atom. In some embodiments, $R_2$ is B5, B6, B5' or B6':

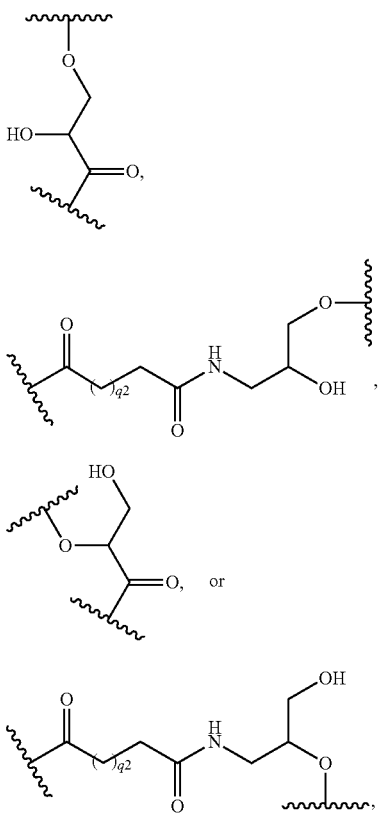

wherein ∼∼∼ represents the site where the groups are covalently linked;

q2 is an integer of 1-10; in some embodiments, q2 is an integer of 1-5.

$L_1$ is used to link the $M_1$ ligand to the N atom on the nitrogenous backbone, thereby providing liver-targeting function for the second siRNA conjugate of the present disclosure. In some embodiments, $L_1$ is selected from the connection combinations of one or more of Formulae A1-A26. In some embodiments, $L_1$ is selected from the connection combinations of one or more of A1, A4, A5, A6, A8, A10, A11, A13. In some embodiments, $L_1$ is selected from the connection combinations of at least two of A1, A4, A8, A10, and A11; in some embodiments, $L_1$ is selected from the connection combinations of at least two groups of A1, A8, and A10.

In some embodiments, the length of $L_1$ may be 3 to 25, 3 to 20, 4 to 15 or 5 to 12 atoms. In some embodiments, $L_1$ is 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 atoms in length.

In some embodiments, j1 is an integer of 2-10, and in some embodiments is an integer of 3-5; in some embodiments, j2 is an integer of 2-10, and in some embodiments is an integer of 3-5. R' is a $C_1$-$C_4$ alkyl, and in some embodiments is one of methyl, ethyl, and isopropyl. Ra is one of A27, A28, A29, A30, and A31, and in some embodiments is A27 or A28. Rb is a $C_1$-$C_5$ alkyl, and in some embodiments is one of methyl, ethyl, isopropyl, and butyl. In some embodiments, j1, j2, R', Ra, and Rb of Formulae A1-A26 are respectively selected to achieve the linkage between the $M_1$ ligands and the N atom on the nitrogenous backbone, and to make the steric position among $M_1$ ligands more suitable for binding $M_1$ ligands to the asialoglycoprotein receptors on the surface of hepatocytes.

In some embodiments, the siRNA conjugate of the present disclosure has a structure as shown by Formula (403), (404), (405), (406), (407), (408), (409), (410), (411), (412), (413), (414), (415), (416), (417), (418), (419), (420), (421), or (422):

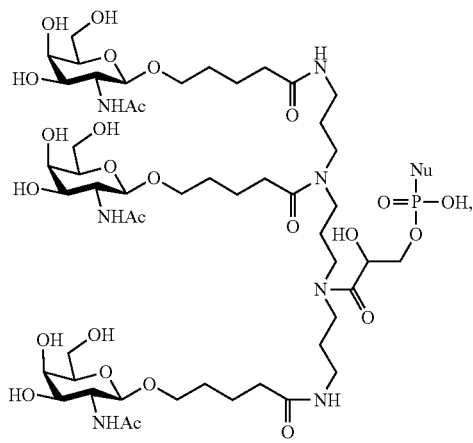

Formula (403)

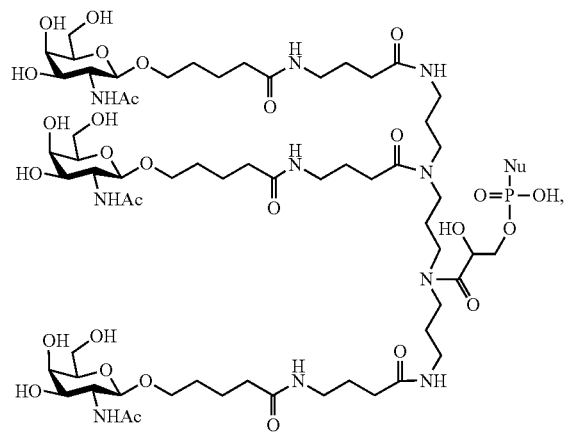

Formula (404)

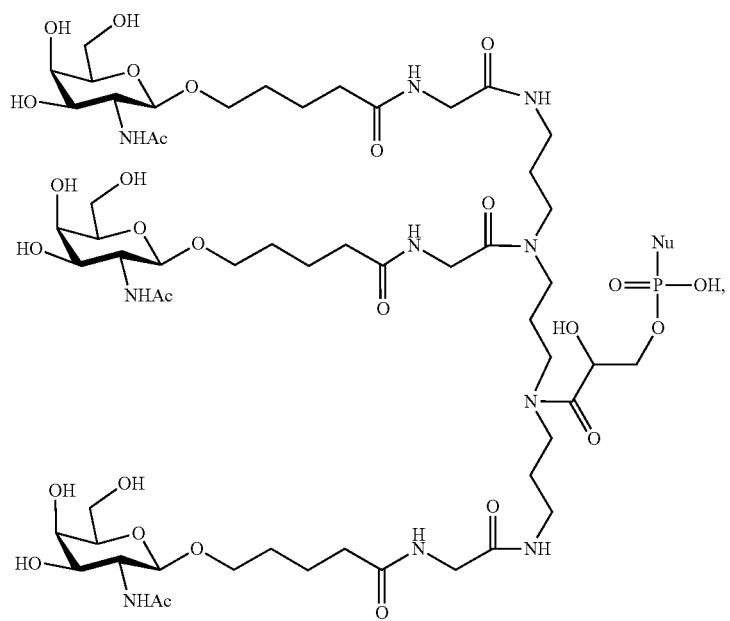
Formula (405)
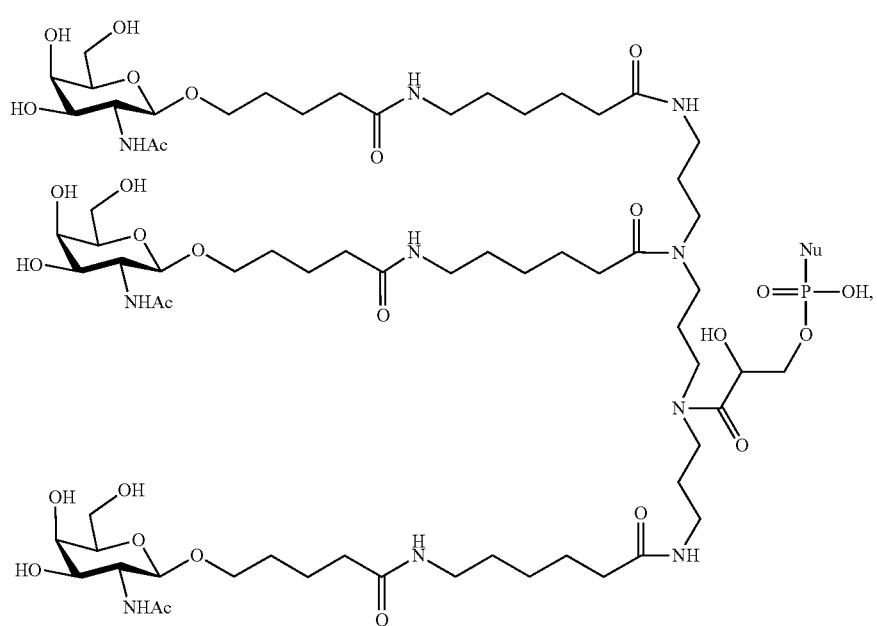
Formula (406)

-continued
Formula (407)
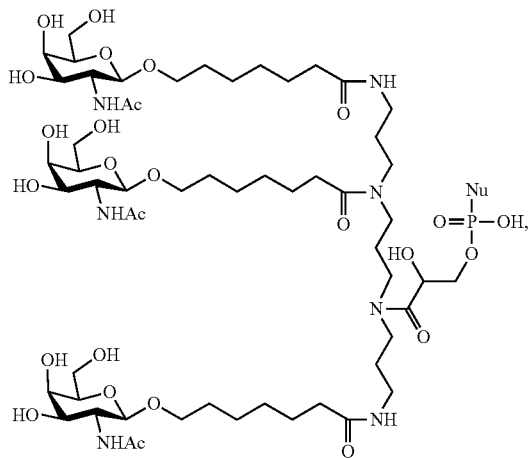
Formula (408)
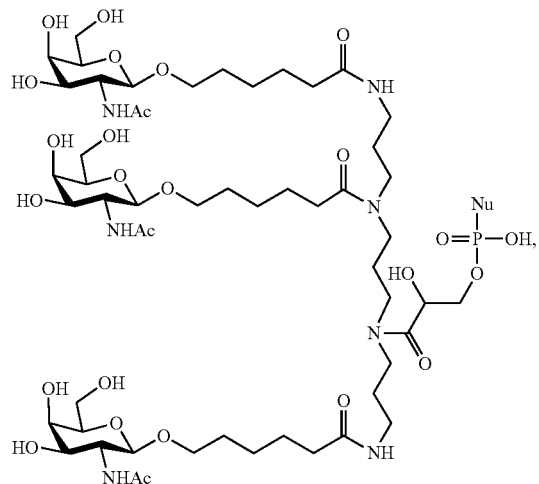
Formula (409)
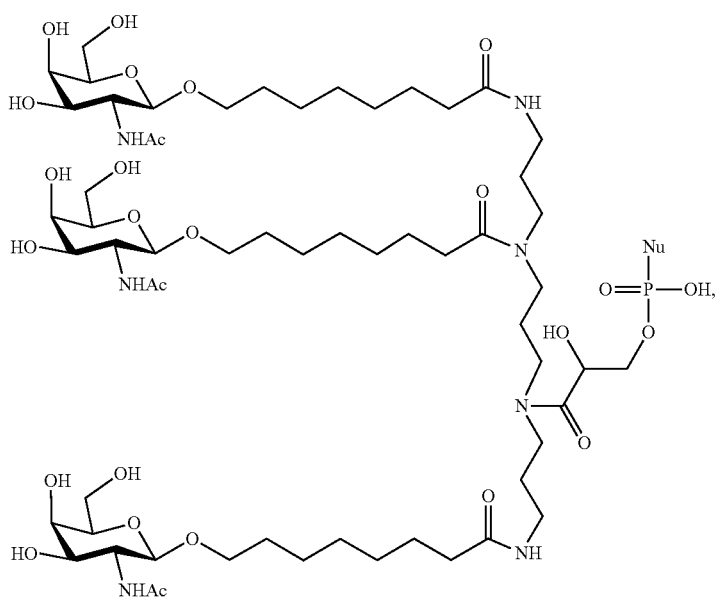

Formula (410)
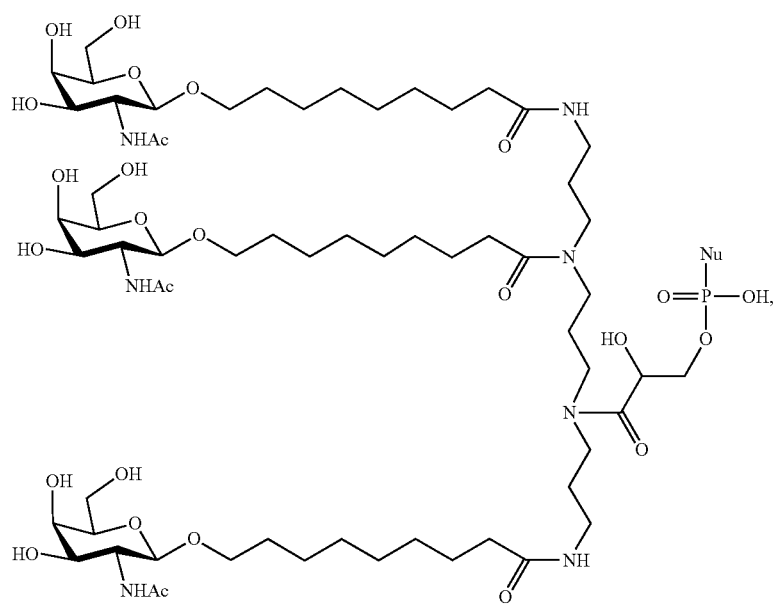
Formula (411)
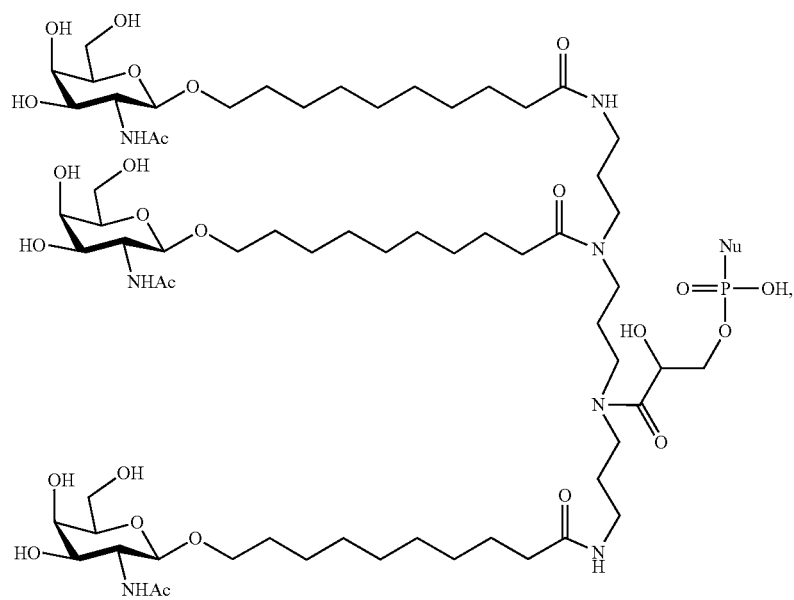

-continued
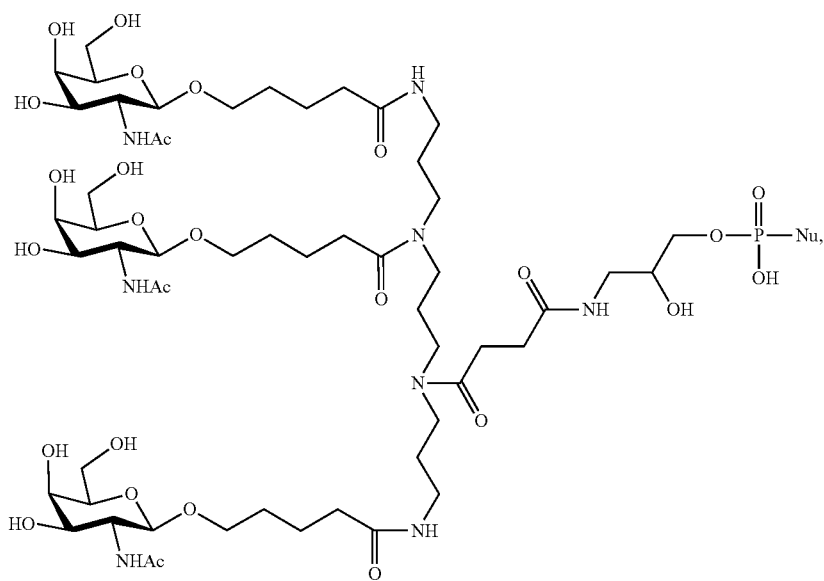
Formula (412)
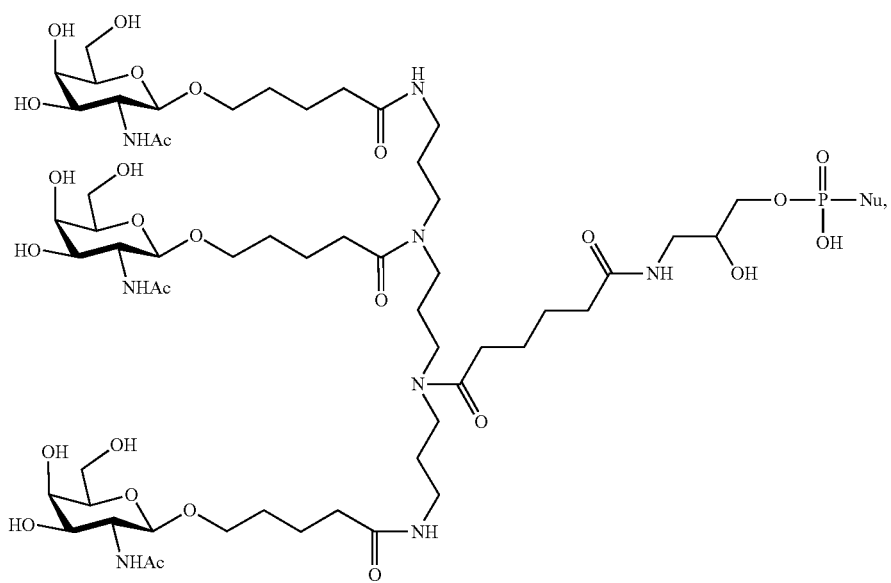
Formula (413)

Formula (414)
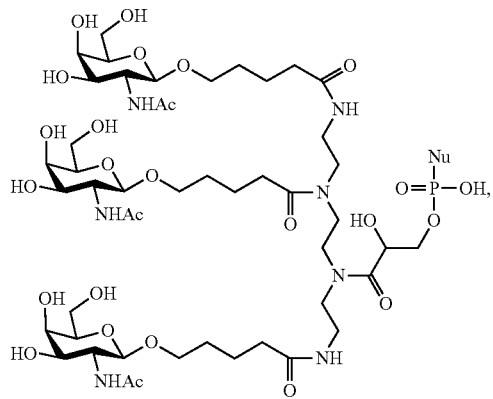
Formula (415)
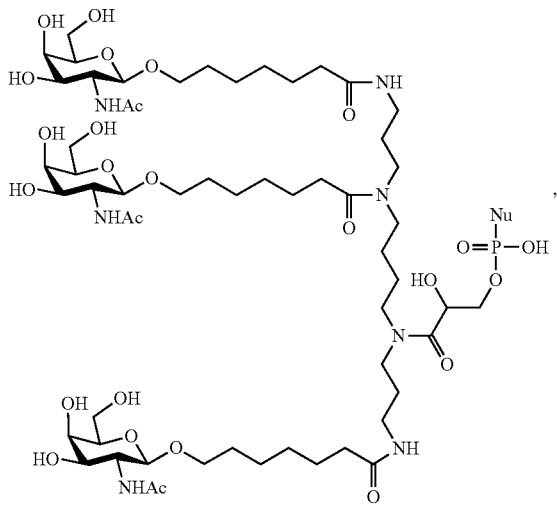
Formula (416)
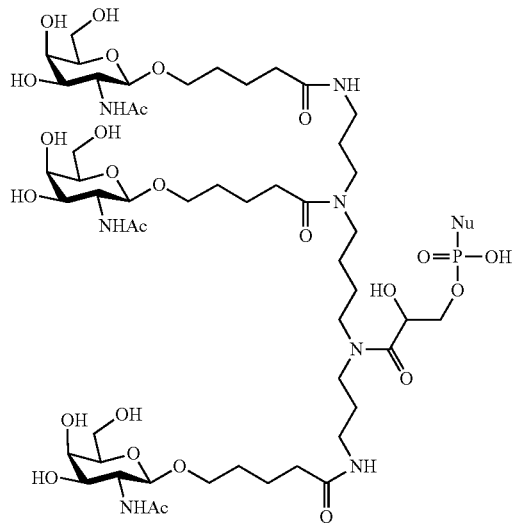
Formula (417)
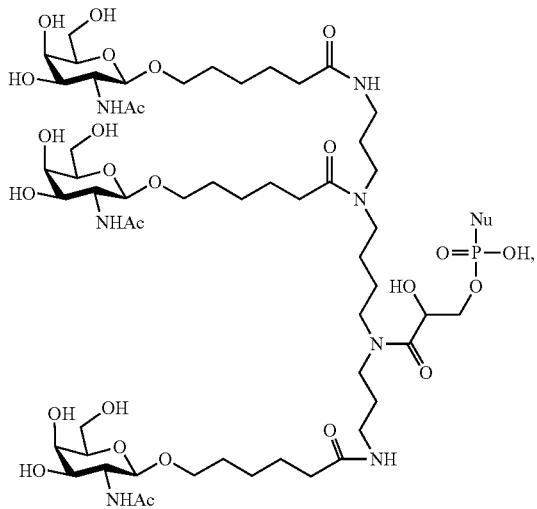

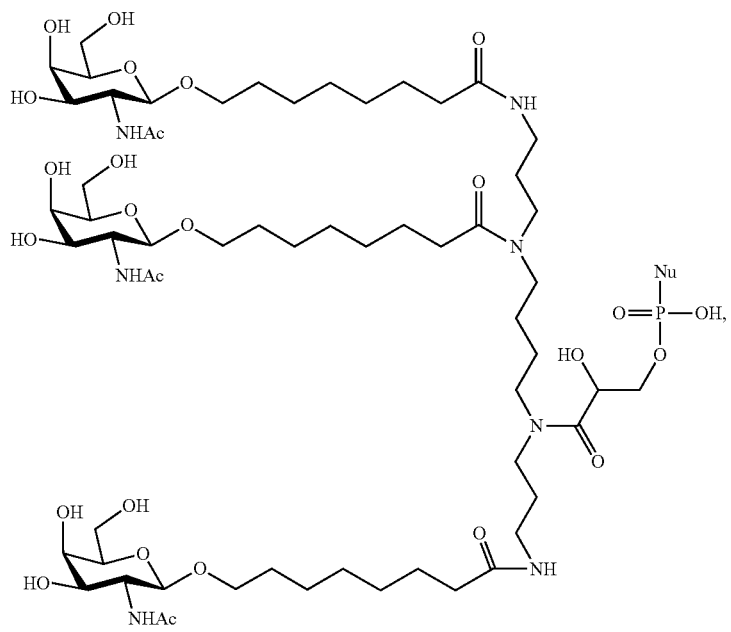
Formula (418)
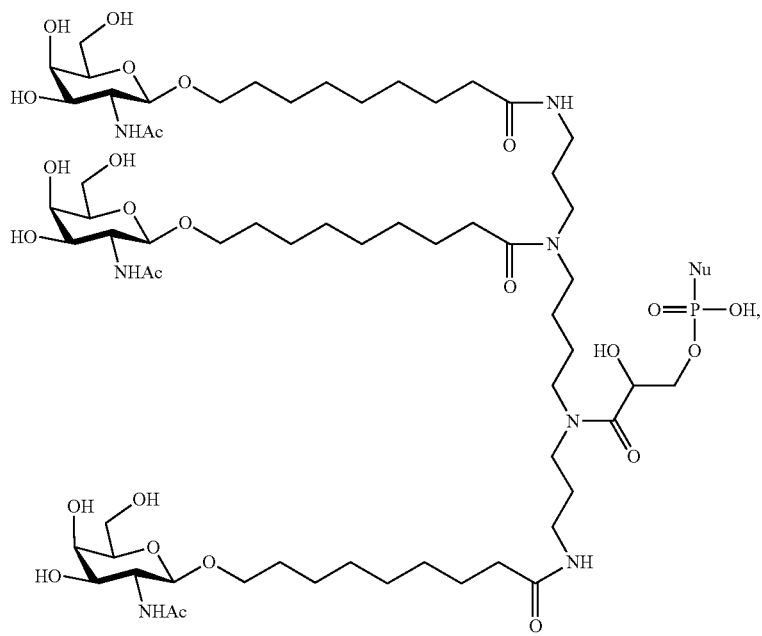
Formula (419)

Formula (420)
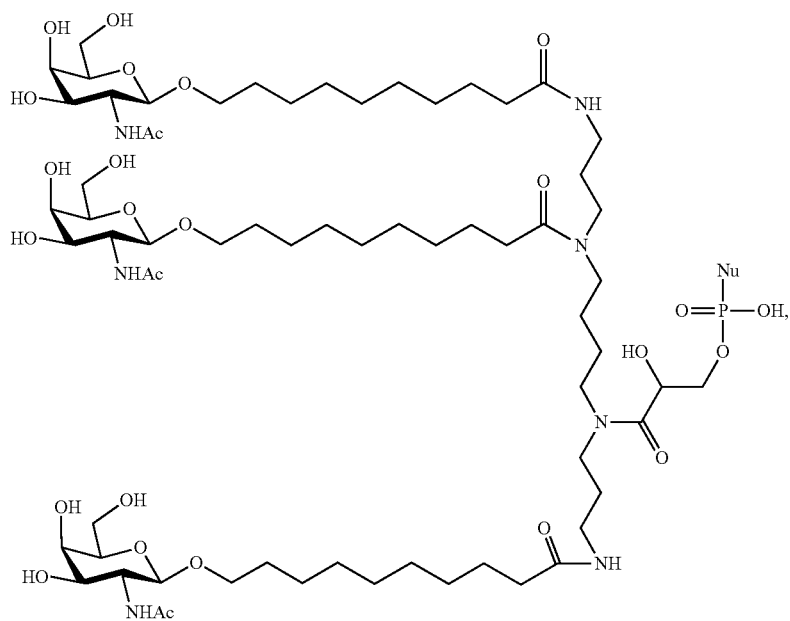
Formula (421)
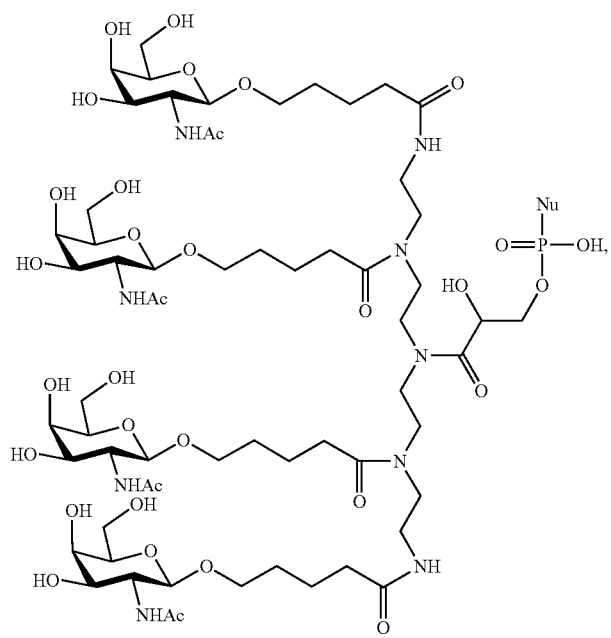

Formula (422)

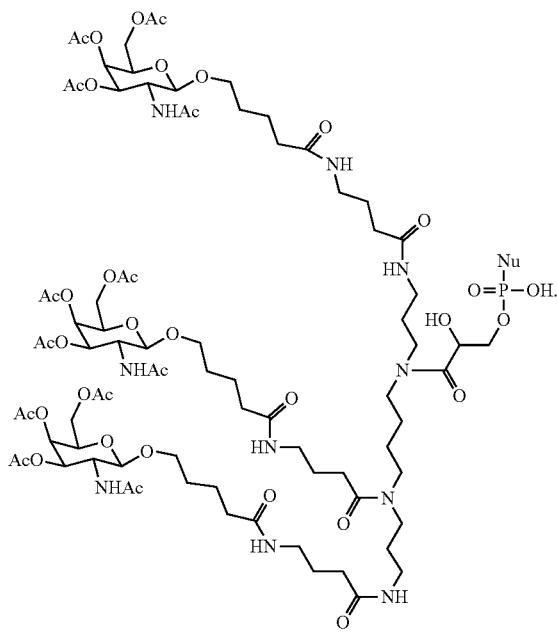

In some embodiments, the P atom in Formula A59 may be linked to any possible position in the siRNA sequence as shown by Nu; for example, the P atom in Formula A59 may be linked to any nucleotide in the sense strand or antisense strand of the siRNA as shown by Nu, and in some embodiments, the P atom in Formula A59 is linked to any nucleotide in the sense strand of the siRNA as shown by Nu. In some embodiments, the P atom in Formula A59 may be linked to a terminal part of the sense strand or antisense strand of the siRNA as shown by Nu, and in some embodiments, the P atom in Formula A59 may be linked to a terminal part of the sense strand of the siRNA as shown by Nu. The terminal part of the siRNA as shown by Nu refers to the first 4 nucleotides counted from the terminal of the sense strand or antisense strand of the siRNA as shown by Nu. In some embodiments, the P atom in Formula A59 is linked to either terminal of the sense strand of the siRNA as shown by Nu. In some embodiments, the P atom in Formula A59 is linked to 3' terminal of the sense strand of the siRNA as shown by Nu. In the case where the P atom in Formula A59 is linked to the above position in the sense strand of the siRNA as shown by Nu, after entering into cells, the second siRNA conjugate can release a separate antisense strand of the siRNA during unwinding, thereby blocking the translation of the HBV mRNA into protein and inhibiting the expression of hepatitis B virus (HBV) gene.

The P atom in Formula A59 may be linked to any possible position of a nucleotide in the siRNA as shown by Nu, for example, to position 5', 2' or 3', or to the base of the nucleotide. In some embodiments, the P atom in Formula A59 may be linked to position 2', 3', or 5' of a nucleotide in the siRNA as shown by Nu by forming a phosphodiester bond. In some embodiments, the P atom in Formula A59 is linked to an oxygen atom formed after deprotonation of 3'-hydroxy of the nucleotide at 3' terminal of the sense strand in the siRNA as shown by Nu, or the P atom in Formula A59 is linked to a nucleotide by substituting a hydrogen atom in 2'-hydroxy of a nucleotide of the sense strand in the siRNA as shown by Nu, or the P atom in Formula A59 is linked to a nucleotide by substituting a hydrogen atom in 5'-hydroxy of the nucleotide at 5' terminal of the sense strand in the siRNA as shown by Nu.

In the siRNA or siRNA conjugate of the present disclosure, adjacent nucleotides are linked via a phosphodiester bond or phosphorothioate diester bond. The non-bridging oxygen or sulfur atom in the phosphodiester bond or phosphorothioate diester bond is negatively charged, and may be present in the form of hydroxy or sulfhydryl group. Moreover, the hydrogen ion in the hydroxy or sulfhydryl group may be partially or completely substituted with a cation. The cation may be any cation, such as a metal cation, an ammonium cation $NH_4^+$ or an organic ammonium cation. In order to increase solubility, in one embodiment, the cation is selected from one or more of alkali metal cation, an ammonium cation formed by a tertiary amine, or a quaternary ammonium cation. The alkali metal ion may be $K^+$ and/or $Na^+$, and the cation formed by a tertiary amine may be an ammonium cation formed by triethylamine and/or N,N-diisopropylethylamine. Thus, the siRNA or the first or second siRNA conjugate of the present disclosure may be at least partially present in the form of salt. In one embodiment, the non-bridging oxygen atom or sulfur atom in the phosphodiester bond or phosphorothioate diester bond at least partly binds to sodium ion. The siRNA or the first or second siRNA conjugate of the present disclosure is present or partially present in the form of sodium salt.

It is well-known to those skilled in the art that a modified nucleotide may be introduced into the siRNA of the present disclosure by a nucleoside monomer with a corresponding modification. The methods for preparing a nucleoside monomer having a corresponding modification and the methods for introducing a modified nucleotide into siRNA are also well-known to those skilled in the art. Modified nucleoside monomers may be either commercially available or may be prepared by known methods.

Preparation of the Second siRNA Conjugate

The second siRNA conjugate as described above may be prepared by any appropriate synthetic routes.

In some embodiments, the second siRNA conjugate of the present disclosure may be prepared by a method comprising: successively linking nucleoside monomers in 3' to 5' direction according to the nucleotide type and sequence in the sense strand and antisense strand of the siRNA respectively, under the condition of phosphoramidite solid phase synthesis, wherein the linking of each nucleoside monomer includes a four-step reaction of deprotection, coupling, capping, and oxidation or sulfurization; isolating the sense strand and the antisense strand of the siRNA; and annealing; wherein the siRNA as shown by Nu is the siRNA of the present disclosure described above.

Moreover, the method further comprises: contacting the compound as shown by Formula (321) with a nucleoside monomer or a nucleotide sequence linked to a solid phase support under the coupling reaction condition and in the presence of a coupling reagent, thereby linking the compound as shown by Formula (321) to the nucleotide sequence through a coupling reaction. Hereinafter, the compound as shown by Formula (321) is also referred to as a conjugating molecule:

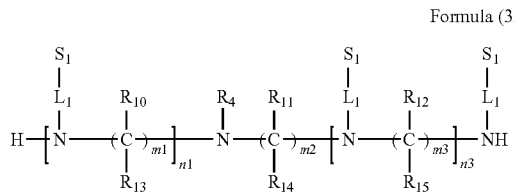

Formula (321)

wherein, $R_4$ is a moiety capable of binding to the siRNA as shown by Nu. In some embodiments, $R_4$ is a moiety capable of binding to the siRNA as shown by Nu via a covalent bond. In some embodiments, $R_4$ is a moiety comprising any functional group that may be conjugated to the siRNA via a phosphodiester bond by a reaction;

each $S_1$ is independently an $M_1$, which is a group formed by substituting all active hydroxyl with the group YCOO—, wherein each Y is independently selected from the group consisting of methyl, trifluoromethyl, difluoromethyl, monofluoromethyl, trichloromethyl, dichloromethyl, monochloromethyl, ethyl, n-propyl, isopropyl, phenyl, halophenyl, and alkylphenyl;

the definitions and options of n1, n3, m1, m2, m3, $R_{10}$, $R_{11}$, $R_{12}$, $R_{13}$, $R_{14}$, $R_{15}$, $L_1$, and $M_1$ are respectively as described above.

$R_4$ is selected to achieve the linkage to the N atom on a nitrogenous backbone and to provide suitable reaction sites for synthesizing the siRNA conjugate of Formula (308). In some embodiments, $R_4$ comprises a $R_2$ linking group or a protected $R_2$ linking group, and can form a functional group having a structure as shown by A59 with the siRNA via a reaction.

In some embodiments, $R_4$ comprises a first functional group that can react with a group on the siRNA as shown by Nu or a nucleoside monomer to form a phosphite ester, and a second functional group that can form a covalent bond with a hydroxy group or an amino group, or comprises a solid phase support linked via the covalent bond. In some embodiments, the first functional group is a phosphoramidite, a hydroxy or a protected hydroxy. In some embodiments, the second functional group is a phosphoramidite, a carboxyl or a carboxylate salt. In some embodiments, the second functional group is a solid phase support linked to the rest of the molecule via a covalent bond formed with a hydroxy group or an amino group. In some embodiments, the solid phase support is linked via a phosphoester bond, a carboxyl ester bond, or an amido bond. In some embodiments, the solid phase support is a resin.

In some embodiments, the first functional group comprises hydroxy, —$OR_k$ or a group as shown by Formula (C3); and/or the second functional group has structure as shown by Formula (C1), (C2), (C3), (C1'), or (C3'):

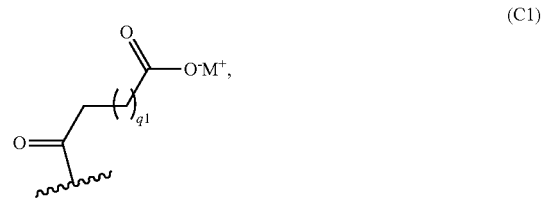

(C1)

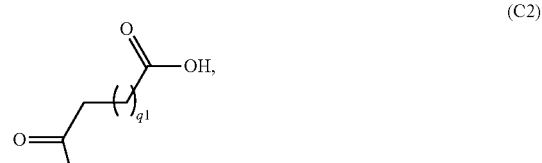

(C2)

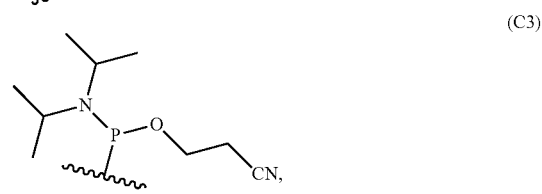

(C3)

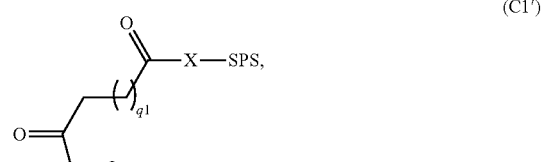

(C1')

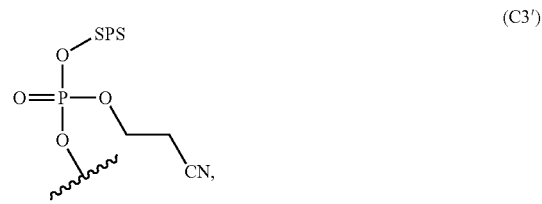

(C3')

wherein q1 is an integer of 1-4, X is O or NH, $M^+$ is a cation, $R_k$ is a hydroxy protecting group, SPS represents a solid phase support, and ⁓ represents the site where a group is covalently linked.

In some embodiments, the first functional group comprises a phosphoramidite group, such as the group as shown by Formula (C3). The phosphoramidite group can form a phosphite ester with a hydroxy (such as a 2'- or 3'-hydroxy) at any position on a nucleotide by coupling reaction, and the phosphite ester can form a phosphodiester bond or phosphorothioate ester bond as shown by Formula (A59) via oxidation or sulfurization, so as to conjugate the conjugating molecule to a siRNA. Here, even if the second functional group does not exist, the compound as shown by Formula (321) will still be able to be conjugated to the nucleotide, without affecting the obtaining of the siRNA conjugate as shown by Formula (308). In this case, after a sense strand or antisense strand of the siRNA has been obtained by a method such as phosphoramidite solid phase synthesis, the compound as shown by Formula (321) is reacted with a hydroxy on the terminal nucleotide of a nucleotide sequence, and form a phosphodiester bond or phosphorothioate linkage by a subsequent oxidation or sulfurization, thereby conjugating the compound as shown by Formula (321) to a siRNA.

In some embodiments, the first functional group comprises a protected hydroxy group. In some embodiments, the second functional group comprises a group that is reactive to a solid phase support to provide a conjugating molecule comprising the solid phase support. In some embodiments, the second functional group comprises a carboxyl, a carboxylate or a phosphoramidite, such as the functional group as shown by Formula (C1), (C2) or (C3). When the second functional group comprises a carboxyl or a carboxylate, the compound as shown by Formula (321) can react via an esterification or an amidation with a hydroxy or an amino group on a solid phase support, such as a resin, to form a conjugating molecule comprising a solid phase support linked via a carboxylate ester bond or an amido bond. When the second functional group comprises a phosphoramidite functional group, the compound as shown by Formula (321) can be coupled with a hydroxy group on a universal solid phase support, such as a resin, and form a conjugating molecule comprising a solid phase support linked via a phosphodiester bond by oxidation. Subsequently, the nucleoside monomers are linked sequentially by a phosphoramidite solid phase synthesis method, starting from the product linked to a solid phase support, thereby obtaining a sense strand or antisense strand of the siRNA linked to the conjugating group. During the solid phase phosphoramidite synthesis, the first functional group is deprotected, followed by coupled with a phosphoramidite group on a nucleoside monomer under coupling reaction condition.

In some embodiments, the first functional group comprises a hydroxy or a protected hydroxy group, and the second functional group comprises a solid phase support linked via the carboxylate ester bond, the amido bond or the phosphodiester bond as shown by Formula (C1') or (C3'). In this case, the nucleoside monomers are linked sequentially by a phosphoramidite solid phase synthesis method, starting from the compound as shown by Formula (321) in place of the solid phase support, thereby obtaining a sense strand or antisense strand of the siRNA linked to a conjugating group.

In some embodiments, the carboxylate may be as shown by —COO-M$^+$, wherein M$^+$ is a cation such as one of a metal cation, an ammonium cation NH4$^+$ or an organic ammonium cation. In one embodiment, the metal cation may be an alkali metal cation, such as K$^+$ or Na$^+$. In order to increase solubility and facilitate the reaction, in some embodiments, the organic ammonium cation is an ammonium cation formed by a tertiary amine, or a quaternary ammonium cation, such as an ammonium cation formed by triethylamine or N,N-diisopropylethylamine. In some embodiments, the carboxylate is a triethylamine carboxylate or an N,N-diisopropylethylamine carboxylate.

In some embodiments, R$_4$ comprises a structure as shown by Formula (B9), (B10), (B9'), (B10'), (B11), (B12), (B11') or (B12'):

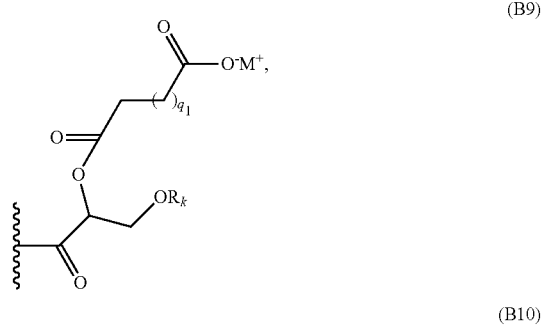

(B9)

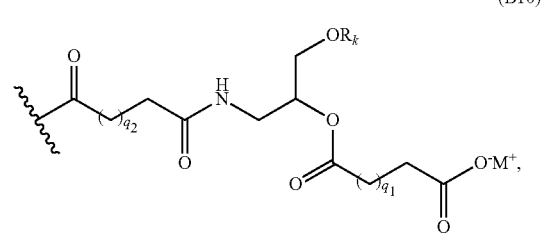

(B10)

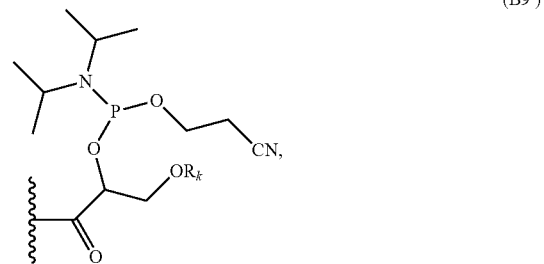

(B9')

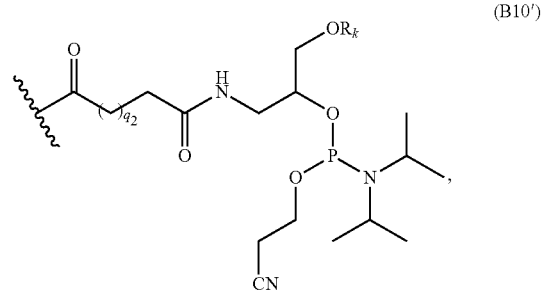

(B10')

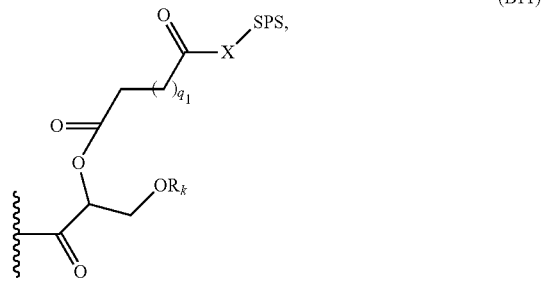

(B11)

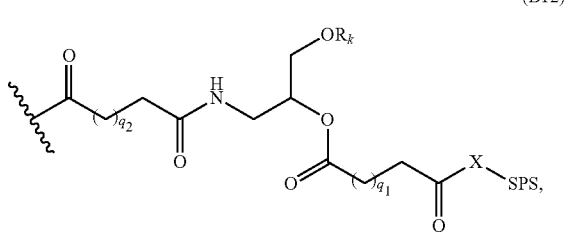

(B12)

-continued

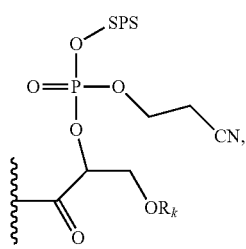
(B11')

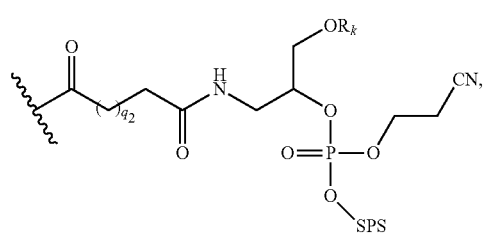
(B12')

wherein $q_1$ is an integer of 1-4, q2 is an integer of 1-10, X is O or NH, $M^+$ is a cation, $R_k$ is a hydroxy protecting group, SPS represents a solid phase support, and ⌇ represents a site where a group is covalently linked. In some embodiments, $q_1$ is 1 or 2. In some embodiments, $q_2$ is an integer of 1-5. In some embodiments, $R_4$ comprises a structure as shown by Formula (B9) or (B10). In some embodiments, $R_4$ comprises a structure as shown by Formula (B11) or (B12).

In some embodiments, $R_k$ is one or more of Tr (trityl), MMTr (4-methoxytrityl), DMTr (4,4'-dimethoxytrityl), and TMTr (4,4',4''-trimethoxytrityl). In some embodiments, $R_k$ may be DMTr, i.e., 4,4'-dimethoxytrityl.

The definition of $L_1$ is as described above. In some embodiments, $L_1$ is used to link the $M_1$ ligand to the N atom on the nitrogenous backbone, thereby providing liver targeting function for the oligonucleotide conjugate. In some embodiments, $L_1$ comprises any one of Formulae A1-A26, or connection combinations thereof.

According to the embodiments described above, those skilled in the art would readily understand that, compared with the phosphoramidite solid phase synthesis methods well-known in the art, a siRNA conjugate in which a conjugating molecule is linked to any possible position of the nucleotide sequence can be obtained through the above first functional group and an optional second functional group. For example, the conjugating molecule is linked to a terminal part of the nucleotide sequence or to a terminal of the nucleotide sequence. Correspondingly, unless otherwise specified, in the following description of the conjugate preparation, when referring to the reactions such as "deprotection", "coupling", "capping", "oxidation", "sulfurization", it will be understood that the reaction conditions and reagents involved in the phosphoramidite solid phase synthesis methods well-known in the art may also be used in these reactions. Exemplary reaction conditions and reagents will be described in detail hereinafter. In some embodiments, each $S_1$ is independently an $M_1$. In some embodiments, each $S_1$ is independently a group formed by protecting at least one active hydroxyl in $M_1$ with a hydroxyl protecting group. In some embodiments, each $S_1$ is independently a group formed by protecting all active hydroxyl in $M_1$, if any, with hydroxyl protecting groups. In some embodiments, any hydroxyl protecting group known to those skilled in the art may be used to protect the active hydroxyl on $M_1$. In some embodiments, the protected hydroxy is expressed as the formula YCOO—, wherein each Y is independently selected from the group consisting of $C_1$-$C_{10}$ alkyl and $C_6$-$C_{10}$ aryl, which is optionally substituted with one or more substituents selected from the group consisting of halo and $C_1$-$C_6$ alkyl. In some embodiments, each Y is independently selected from the group consisting of methyl, trifluoromethyl, difluoromethyl, monofluoromethyl, trichloromethyl, dichloromethyl, monochloromethyl, ethyl, n-propyl, isopropyl, phenyl, halophenyl, and $C_1$-$C_6$ alkylphenyl.

In some embodiments, each $S_1$ is independently selected from the group consisting of Formulae A46-A54:

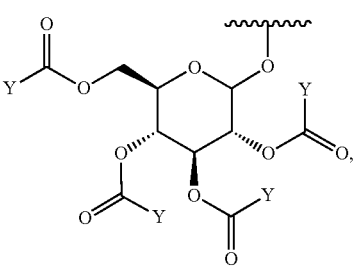
(A46)

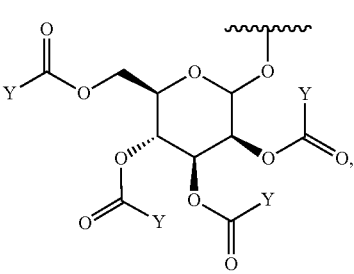
(A47)

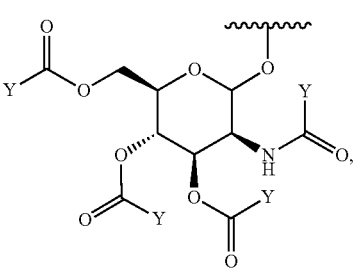
(A48)

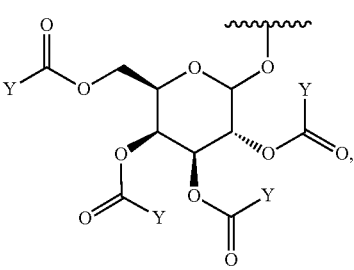
(A49)

(A50)
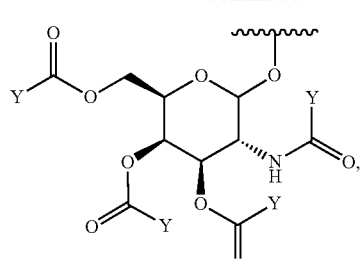

(A51)
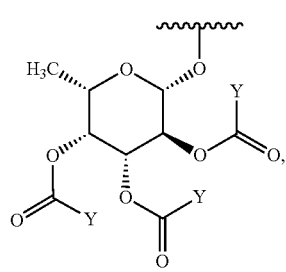

(A52)
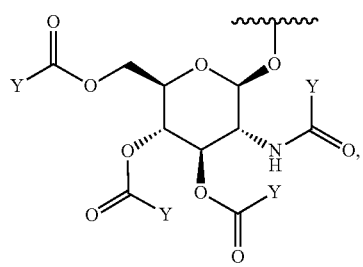

(A53)
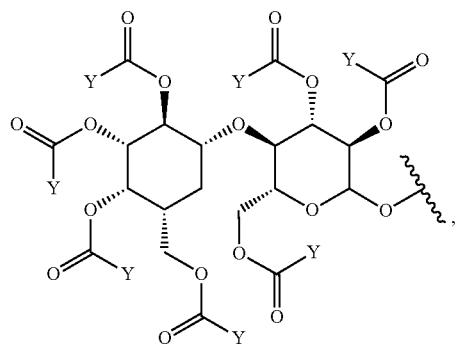

(A54)
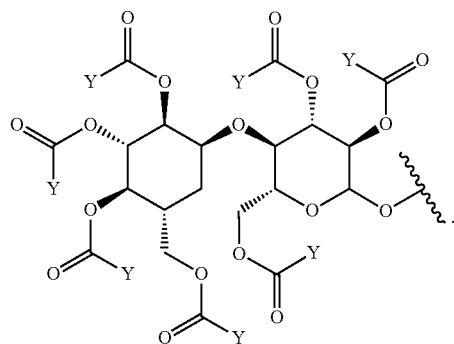

In some embodiments, $S_1$ is Formula A49 or A50.

In some embodiments, each Y is independently selected from one of methyl, trifluoromethyl, difluoromethyl, monofluoromethyl, trichloromethyl, dichloromethyl, monochloromethyl, ethyl, n-propyl, isopropyl, phenyl, halophenyl, and alkylphenyl. For the purpose of simplifying the conjugating molecule of the disclosure, in some embodiments, Y is methyl.

As mentioned previously, the method for preparing the siRNA conjugate of the present disclosure further comprises the following steps: synthesizing the other strand of the siRNA (for example, when a sense strand of the siRNA linked to a conjugating molecule is synthesized in the above step, the method further comprises synthesizing an antisense strand of the siRNA by the solid phase synthesis method, and vice versa); isolating the sense strand and the antisense strand; and annealing. In particular, in the isolating step, the solid phase support linked to the nucleotide sequence and/or conjugating molecule is cut down, while the necessary protecting group is removed (in this case, each $S_1$ group in the compound as shown by Formula (321) is converted to the corresponding $M_1$ ligand), thereby providing a sense strand (or antisense strand) of the siRNA linked to the conjugating molecule and the corresponding antisense strand (or sense strand). The sense strand and the antisense strand are annealed to form a double-stranded RNA structure, thereby providing a siRNA conjugate as shown by Formula (308).

In some embodiments, the method for preparing the siRNA conjugate comprises the following steps: contacting the compound as shown by Formula (321) with the first nucleoside monomer at 3' terminal of the sense strand or antisense strand under coupling reaction condition in the presence of a coupling reagent, thereby linking the compound as shown by Formula (321) to the first nucleotide in the sequence; successively linking nucleoside monomers in 3' to 5' direction to synthesize the sense strand or antisense strand of the siRNA according to the desired nucleotide type and sequence of the sense strand or antisense strand, under the condition of phosphoramidite solid phase synthesis; wherein the compound of Formula (321) is a compound in which $R_4$ comprises a first functional group comprising a protected hydroxy and a second functional group having a structure as shown by Formula (C1') or (C3'); the compound of Formula (321) is deprotected before linking to the first nucleoside monomer; and the linking of each nucleoside monomer comprising a four-step reaction of deprotection, coupling, capping, and oxidation or sulfurization, thus obtaining a sense strand or antisense strand of nucleic acid linked to the conjugating molecule; successively linking nucleoside monomers in 3' to 5' direction to synthesize the sense strand or antisense strand of nucleic acid according to the nucleotide type and sequence of the sense strand or antisense strand, under the condition of phosphoramidite solid phase synthesis; wherein the linking of each nucleoside monomer includes a four-step reaction of deprotection, coupling, capping, and oxidation or sulfurization; removing the protecting groups and cutting down the solid phase support; obtaining the sense strand and the antisense strand of nucleic acid via isolation and purification; and annealing.

In some embodiments, the method for preparing the second siRNA conjugate comprises the following steps: successively linking nucleoside monomers in 3' to 5' direction to synthesize the sense strand and antisense strand according to the nucleotide type and sequence of the sense strand or antisense strand in the double-stranded siRNA; wherein the linking of each nucleoside monomer comprising a four-step reaction of deprotection, coupling, capping, and oxidation or sulfurization, thus obtaining a sense strand linked to the solid phase support and an antisense strand linked to the solid phase support; contacting the compound as shown by Formula (321) with the sense strand linked to the solid phase support or the antisense strand linked to the solid phase support under the coupling reaction condition in the presence of a coupling reagent, thereby linking the compound as shown by Formula (321) to the sense strand or antisense strand; wherein the compound of Formula (321) is a compound in which $R_4$ comprises a phosphoramidite group as the first functional group; removing the protecting groups and cutting down the solid phase support; respectively obtaining the sense strand or antisense strand of the siRNA via isolation and purification; and annealing; wherein the sense strand or antisense strand of the siRNA is linked to a conjugating molecule.

In some embodiments, the P atom in formula A59 is linked to the 3' terminal of the sense strand in the siRNA, and the method for preparing the siRNA conjugate of the present disclosure comprises:

(1) removing the hydroxyl protecting group $R_k$ in the compound of Formula (321) (wherein the compound of Formula (321) is a compound in which $R_4$ comprises a first functional group comprising a protected hydroxy $OR_k$ and a second functional group having a structure as shown by Formula (C1') or (C3')); contacting the product resulting from deprotection with a nucleoside monomer to obtain a nucleoside monomer linked to a solid phase support via the conjugating molecule, under the coupling reaction condition in the presence of a coupling agent;

(2) synthesizing a sense strand of the siRNA in 3' to 5' direction by a phosphoramidite solid phase synthesis method, starting from the nucleoside monomer linked to a solid phase support via the conjugating molecule;

(3) synthesizing an antisense strand of the siRNA by a phosphoramidite solid phase synthesis method; and (4) isolating the sense strand and the antisense strand of the siRNA and annealing the same to obtain the siRNA conjugate of the present disclosure;

wherein in step (1), the method for removing the protecting group $R_k$ in the compound of Formula (321) comprises contacting the compound of Formula (321) with a deprotection agent under the deprotection condition. The deprotection condition comprises a temperature of 0-50° C., and in some embodiments of 15-35° C., and a reaction time of 30-300 seconds, and in some embodiments of 50-150 seconds. The deprotection agent may be selected from one or more of trifluoroacetic acid, trichloroacetic acid, dichloroacetic acid, and monochloroacetic acid, and in some embodiments is dichloroacetic acid. The molar ratio of the deprotection agent to the compound as shown by Formula (321) may be 10:1 to 1000:1, and in some embodiments is 50:1 to 500:1.

The coupling reaction condition and the coupling agent may be any conditions and agents appropriate for the above coupling reaction. In some embodiments, the same condition and reagent as the coupling reaction in the solid phase synthesis method employed are used.

In some embodiments, the coupling reaction condition comprises a reaction temperature of 0-50° C., and in some embodiments of 15-35° C. The molar ratio of the compound of Formula (321) to the nucleoside monomer may be 1:1 to 1:50, and in some embodiments is 1:2 to 1:5. The molar ratio of the compound of Formula (321) to the coupling agent may be 1:1 to 1:50, and in some embodiments is 1:3 to 1:10. The reaction time may be 200-3000 seconds, and in some embodiments is 500-1500 seconds. The coupling agent may be selected from one or more of 1H-tetrazole, 5-ethylthio-1H-tetrazole and 5-benzylthio-1H-tetrazole, and in some embodiments is 5-ethylthio-1H-tetrazole. The coupling reaction may be performed in an organic solvent. The organic solvent may be selected from one or more of anhydrous acetonitrile, anhydrous DMF and anhydrous dichloromethane, and in some embodiments is anhydrous acetonitrile. The amount of the organic solvent may be 3-50 L/mol, and in some embodiments is 5-20 L/mol with respect to the compound as shown by Formula (321).

In step (2), a sense strand S of the siRNA conjugate is synthesized in 3' to 5' direction by the phosphoramidite solid phase synthesis method, starting from the nucleoside monomer linked to a solid phase support via a conjugating molecule prepared in the above steps. In this case, the conjugating molecule is linked to the 3' terminal of the resultant sense strand.

Other conditions for solid phase synthesis described in steps (2) and (3) comprise the deprotection condition for the nucleoside monomer, type and amount of the deprotection agent, the coupling reaction condition, type and amount of the coupling agent, the capping reaction condition, type and amount of the capping agent, the oxidation reaction condition, type and amount of the oxidation agent, the sulfurization reaction condition, and type and amount of the sulfurization agent. Various agents, amounts, and conditions conventionally used in the art are used herein.

In some embodiments, for example, the solid phase synthesis described in steps (2) and (3) can employ the following conditions:

The deprotection condition for the nucleoside monomer comprises a temperature of 0-50° C., and in some embodiments of 15-35° C., and a reaction time of 30-300 seconds, and in some embodiments of 50-150 seconds. The deprotection agent may be selected from one or more of trifluoroacetic acid, trichloroacetic acid, dichloroacetic acid, and monochloroacetic acid, and in some embodiments is dichloroacetic acid. The molar ratio of the deprotection agent to the protecting group of 4,4'-dimethoxytrityl on the solid phase support may be 2:1 to 100:1, and in some embodiments is 3:1 to 50:1.

The coupling reaction condition comprises a temperature of 0-50° C., and in some embodiments of 15-35° C. The molar ratio of the nucleic acid sequence linked to the solid phase support to the nucleoside monomer may be 1:1 to 1:50, and in some embodiments is 1:5 to 1:15. The molar ratio of the nucleic acid sequence linked to the solid phase support to the coupling agent may be 1:1 to 1:100, and in some embodiments is 1:50 to 1:80. The reaction time and the coupling agent are selected as above.

The capping reaction condition comprises a temperature of 0-50° C., and in some embodiments of 15-35° C., and a reaction time of 5-500 seconds, and in some embodiments of 10-100 seconds. The capping agent is selected as above. The molar ratio of the total amount of the capping agent to the nucleic acid sequence linked to the solid phase support may be 1:100 to 100:1, and in some embodiments is 1:10 to 10:1. In the case where equimolar acetic anhydride and N-methylimidazole are used as a capping agent, the molar ratio of acetic anhydride, N-methylimidazole, and the nucleic acid sequence linked to the solid phase support may be 1:1:10-10:10:1, and in some embodiments is 1:1:2-2:2:1.

The oxidation reaction condition comprises a temperature of 0-50° C., and in some embodiments of 15-35° C., and a reaction time of 1-100 seconds, and in some embodiments of 5-50 seconds. In some embodiments, the oxidation agent is iodine (and in some embodiments provided in the form of iodine water). The molar ratio of the oxidation agent to the nucleic acid sequence linked to the solid phase support in the coupling step may be 1:1 to 100:1, and in some embodiments is 5:1 to 50:1. In some embodiments, the oxidation reaction is performed in a mixed solvent of tetrahydrofuran:water:pyridine=3:1:1-1:1:3. The sulfurization reaction condition comprises a temperature of 0-50° C., and in some embodiments of 15-35° C., and a reaction time of 50-2000 seconds, and in some embodiments of 100-1000 seconds. In some embodiments, the sulfurization agent is xanthane hydride. The molar ratio of the sulfurization agent to the nucleic acid sequence linked to the solid phase support in the coupling step may be 10:1 to 1000:1, and in some embodiments is 10:1 to 500:1. In some embodiments, the sulfurization reaction is performed in a mixed solvent of acetonitrile:pyridine=1:3-3:1.

The method further comprises isolating the sense strand and the antisense strand of the siRNA after linking all nucleoside monomers and before the annealing. Methods for isolation are well-known to those skilled in the art and generally comprise cleaving the synthesized nucleotide sequence from the solid phase support, removing protecting groups on bases, phosphate groups and ligands, purifying and desalting.

The synthesized nucleotide sequence may be cleaved from the solid phase support, and the protecting groups on bases, phosphate groups and ligands may be removed, according to conventional cleavage and deprotection methods in the synthesis of siRNA. For example, the resultant nucleotide sequence linked to the solid phase support is contacted with concentrated aqueous ammonia; during deprotection, the protecting group YCOO— in groups A46-A54 is converted to a hydroxyl group, and thus the $S_1$ groups are converted to corresponding $M_1$ groups, providing the conjugate as shown by Formula (308); wherein the concentrated aqueous ammonia may be aqueous ammonia at a concentration of 25-30% by weight. The amount of the concentrated aqueous ammonia may be 0.2 ml/μmol-0.8 ml/μmol with respect to the target siRNA sequence.

When there is at least one 2'-TBDMS protection on the synthesized nucleotide sequence, the method further comprises contacting the nucleotide sequence removed from the solid phase support with triethylamine trihydrofluoride to remove the 2'-TBDMS protection. Here, the resultant target siRNA sequence comprises the corresponding nucleoside having free 2'-hydroxy. The amount of pure triethylamine trihydrofluoride with respect to the target siRNA sequence may be 0.4 ml/μmol-1.0 ml/μmol. As such, the siRNA conjugate as shown by Formula (308) may be obtained.

Methods for purification and desalting are well-known to those skilled in the art. For example, nucleic acid purification may be performed using a preparative ion chromatography purification column with a gradient elution of NaBr or NaCl; after collection and combination of the product, a reverse phase chromatography purification column may be used for desalting.

The non-bridging oxygen or sulfur atom in the phosphodiester bond or phosphorothioate diester bond formed between the nucleotides in the thus-obtained siRNA conjugate is substantially linked to a sodium ion, and the siRNA conjugate is substantially present in the form of a sodium salt. Ion-exchange methods that have been well-known in the art may be used, and the sodium ion may be replaced with hydrogen ion and/or other cations, thereby providing other forms of siRNA conjugates. The cations are as described above.

During synthesis, the purity and molecular weight of the nucleic acid sequence may be determined at any time, in order to better control the synthesis quality. Such determination methods are well-known to those skilled in the art. For example, the purity of the nucleic acid may be determined by ion exchange chromatography, and the molecular weight may be determined by liquid chromatography-mass spectrometry (LC-MS).

Methods for annealing are also well-known to those skilled in the art. For example, the synthesized sense strand (S strand) and antisense strand (AS strand) may be simply mixed in water for injection in an equimolar ratio, heated to 70-95° C., and then cooled at room temperature to form a double-stranded structure via hydrogen bond. Hence, the siRNA conjugate of the present disclosure may be obtained.

After obtaining the conjugate of the present disclosure, in some embodiments, the siRNA conjugate thus synthesized can also be characterized by using the methods such as LC-MS by the means such as molecular weight detection, to confirm that the synthesized siRNA conjugate is the designed siRNA conjugate of interest, and the synthesized siRNA sequence is the desired siRNA sequence to be synthesized, for example, one of the sequences listed in Table 1.

The compound as shown by Formula (321) may be prepared by a method comprising: contacting a compound as shown by Formula (313) with a cyclic anhydride in an organic solvent under the esterification reaction condition in the presence of a base and an esterification catalyst; ion exchanging and isolating the compound as shown by Formula (321):

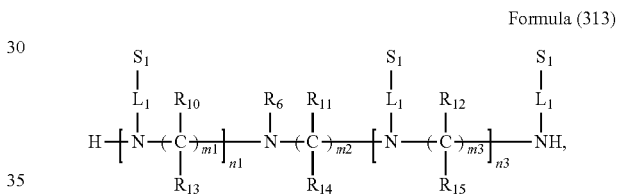

Formula (313)

wherein the definitions and options of n1, n3, m1, m2, m3, $R_{10}$, $R_{11}$, $R_{12}$, $R_{13}$, $R_{14}$, $R_{15}$, $L_1$, and $S_1$ are respectively as described above;

$R_6$ is a group to provide $R_4$ of Formula (321). In some embodiments, for example, $R_6$ has a structure as shown by Formula (A61):

(A61)

wherein $R_l$ is a group capable of linking to the N atom on the nitrogenous backbone, to $R_kO$ and to a free hydroxy group; $R_k$ is a hydroxy protecting group. In this case, a compound as shown by Formula (321) is obtained, wherein $R_4$ comprises a first functional group comprising a hydroxy protecting group and a second functional group having a structure as shown by Formula (C1) or (C2).

The esterification reaction condition includes a reaction temperature of 0-100° C. and a reaction time of 8-48 hours. In some embodiments, the esterification reaction condition comprises a reaction temperature of 10-40° C. and a reaction time of 20-30 hours.

In some embodiments, the organic solvent comprises one or more of an epoxy solvent, an ether solvent, an haloalkane solvent, dimethyl sulfoxide, N,N-dimethylformamide, and N,N-diisopropylethylamine. In some embodiments, the epoxy solvent is dioxane and/or tetrahydrofuran. In some embodiments, the ether solvent is diethyl ether and/or methyl tertbutyl ether. In some embodiments, the haloalkane solvent is one or more of dichloromethane, trichloromethane and 1,2-dichloroethane. In some embodiments, the organic solvent is dichloromethane. The amount of the organic solvent is 3-50 L/mol, and in some embodiments is 5-20 L/mol with respect to the compound as shown by Formula (313).

In some embodiments, the cyclic anhydride is one of succinic anhydride, glutaric anhydride, adipic anhydride or pimelic anhydride. In some embodiments, the cyclic anhydride is succinic anhydride. The molar ratio of the cyclic anhydride to the compound as shown by Formula (313) is 1:1 to 10:1, and in some embodiments is 2:1 to 5:1.

The esterification catalyst may be any catalyst capable of catalyzing the esterification, such as 4-dimethylaminopyridine. The molar ratio of the catalyst to the compound as shown by Formula (313) is 1:1 to 10:1, and in some embodiments is 2:1 to 5:1.

In some embodiments, the base may be any inorganic base, organic base or combination thereof. Regarding the solubility as well as the product stability, the base is an organic base of tertiary amine. In some embodiments, the organic base of tertiary amine is triethylamine or N,N-diisopropylethylamine. The molar ratio of the organic base of tertiary amine to the compound as shown by Formula (313) is 1:1 to 20:1, and in some embodiments is 3:1 to 10:1.

The ion exchanging serves the function of converting the compound as shown by Formula (321) to a desired form of carboxylic acid or salt thereof. The method for ion exchanging is well-known to those skilled in the art, and the above conjugating molecule in which the cation is $M^+$ may be obtained by using suitable ion exchanging solution and ion exchanging condition, which is not described here in detail. In some embodiments, a triethylamine phosphate solution is used in the ion exchanging reaction. In some embodiments, the concentration of the triethylamine phosphate solution is 0.2-0.8 M. In some embodiments, the concentration of the triethylamine phosphate solution is 0.4-0.6 M. In some embodiments, the amount of the triethylamine phosphate solution is 3-6 L/mol, and in further embodiment 4-5 L/mol with respect to the compound as shown by Formula (313).

The compound as shown by Formula (321) may be isolated from the reaction mixture using any suitable isolation methods. In some embodiments, the compound as shown by Formula (321) may be isolated by removal of solvent via evaporation followed by chromatography, for example, using the following chromatographic conditions for the isolation: (1) normal phase purification: 200-300 mesh silica gel filler, with gradient elution of 1 wt % triethylamine-containing dichloromethane:methanol=100:18-100:20; or (2) reverse phase purification: C18 and C8 reverse phase filler, with gradient elution of methanol:acetonitrile=0.1:1-1:0.1. In some embodiments, the solvent may be removed directly to obtain a crude product of the compound as shown by Formula (321), which may be used directly in subsequent reactions.

In some embodiments, the preparation method of the compound as shown by Formula (321) further comprises: contacting the product obtained from the above ion exchanging reaction with a solid phase support with amino or hydroxy groups in an organic solvent under the condensation reaction condition in the presence of a condensing agent and an organic base of tertiary amine. In this case, a compound as shown by Formula (321) is obtained, wherein $R_4$ comprises a first functional group comprising a hydroxy protecting group and a second functional group having a structure as shown by Formula (C1').

The solid phase support is one of the supports used in solid phase synthesis of siRNA, some of which are well-known to those skilled in the art. For example, the solid phase support may be selected from one having an active hydroxy or amino functional group. In some embodiments, the solid phase support is an amino or hydroxy resin. For the purpose of facilitating subsequent solid phase synthesis of nucleic acid, the amino or hydroxy resin has in some embodiments the following parameters: a particle size of 100-400 mesh, and amino or hydroxy surface loading of 0.2-0.5 mmol/g. The ratio of the compound as shown by Formula (321) to the solid phase support is 10 μmol compound per gram of solid phase support (μmol/g) to 400 μmol/g. In some embodiments, the ratio of compound of Formula (321) to the solid phase support is 50 μmol/g to 200 μmol/g.

The organic solvent may be any suitable solvent or mixture of solvents known to those skilled in the art. In some embodiments, the organic solvent is one or more of acetonitrile, an epoxy solvent, an ether solvent, an haloalkane solvent, dimethyl sulfoxide, N,N-dimethylformamide, and N,N-diisopropylethylamine. In some embodiments, the epoxy solvent is dioxane and/or tetrahydrofuran; the ether solvent is diethyl ether and/or methyl tertbutyl ether; the haloalkane solvent is one or more of dichloromethane, trichloromethane and 1,2-dichloroethane. In some embodiments, the organic solvent is acetonitrile. The amount of the organic solvent is 20-200 L/mol, in some embodiments is 50-100 L/mol with respect to the compound as shown by Formula (321).

The condensing agent may be benzotriazol-1-yl-oxytripyrrolidinophosphonium hexafluorophosphate, 3-diethoxyphosphoryl-1,2,3-benzotriazol-4(3H)-one and/or O-benzotriazol-tetramethyluronium hexafluorophosphate. In some embodiments, the condensing agent is O-benzotriazol-tetramethyluronium hexafluorophosphate. The molar ratio of the condensing agent to the compound as shown by Formula (321) is 1:1 to 20:1, and in further embodiments, 1:1 to 5:1.

In some embodiments, the organic base of tertiary amine is triethylamine and/or N,N-diisopropylethylamine, and in some embodiments is N,N-diisopropylethylamine. The molar ratio of the organic base of tertiary amine to the compound as shown by Formula (321) is 1:1 to 20:1, and in some embodiments is 1:1 to 5:1.

In some embodiments, the method for preparing the compound as shown by Formula (321) further comprises: contacting the obtained condensation product with a capping reagent and an acylation catalyst in an organic solvent under the capping reaction condition, and isolating the compound as shown by Formula (321). The capping reaction is used to remove any active functional groups that are not completely reacted, so as to avoid unnecessary by-products in subsequent reactions. The capping reaction condition comprises a reaction temperature of 0-50° C., and in some embodiments of 15-35° C., and a reaction time of 1-10 hours, and in some embodiments, of 3-6 hours. The capping reagent may be a capping agent used in the solid phase synthesis of siRNA, which are well known to those skilled in the art.

In some embodiments, the capping reagent is composed of capping reagent 1 (cap1) and capping reagent 2 (cap2). The capping reagent 1 is N-methylimidazole, and in some embodiments provided as a solution of N-methylimidazole in pyridine/acetonitrile, wherein the volume ratio of pyridine to acetonitrile is 1:10 to 1:1, and in some embodiments is 1:3 to 1:1. In some embodiments, the ratio of the total volume of pyridine and acetonitrile to the volume of N-methylimidazole is 1:1 to 10:1, and in some embodiments is 3:1 to 7:1. The capping reagent 2 is acetic anhydride. In some embodiments is provided as a solution of acetic anhydride in acetonitrile solvent, wherein the volume ratio of acetic anhydride to acetonitrile is 1:1 to 1:10, and in further embodiments is 1:2 to 1:6.

In some embodiments, the ratio of the volume of the mixed solution of N-methylimidazole in pyridine/acetonitrile to the mass of the compound of Formula (321) is 5 ml/g-50 ml/g, and in some embodiments is 15 ml/g-30 ml/g. The ratio of the volume of the solution of acetic anhydride in acetonitrile to the mass of the compound of Formula (321) is 0.5 ml/g-10 ml/g, and in some embodiments is 1 ml/g-5 ml/g.

In some embodiments, the capping reagent uses equimolar acetic anhydride and N-methylimidazole. The organic solvent is one or more of acetonitrile, an epoxy solvent, an ether solvent, an haloalkane solvent, dimethyl sulfoxide, N,N-dimethylformamide, and N,N-diisopropylethylamine. In some embodiments, the organic solvent is acetonitrile. The amount of the organic solvent is 10-50 L/mol, and in some embodiments 5-30 L/mol with respect to the compound as shown by Formula (321).

The acylation catalyst may be selected from any catalyst that may be used for esterification condensation or amidation condensation, such as alkaline heterocyclic compounds. In some embodiments, the acylation catalyst is 4-dimethylaminopyridine. The ratio of the mass of the catalyst to the mass of the compound as shown by Formula (321) may be 0.001:1 to 1:1, and in some embodiments is 0.01:1 to 0.1:1.

The compound as shown by Formula (321) may be isolated from the reaction mixture by any suitable methods. In some embodiments, the compound of Formula (321) may be obtained by sufficiently washing with an organic solvent and filtering to remove unreacted reactants, excess capping reagent and other impurities, wherein the organic solvent is selected from acetonitrile, dichloromethane, or methanol. In some embodiments, the organic solvent is acetonitrile.

In some embodiments, the preparation of the conjugating molecule as shown by Formula (321) comprises contacting a compound as shown by Formula (313) with a phosphorodiamidite in an organic solvent under the coupling reaction condition in the presence of a coupling agent, and isolating the compound as shown by Formula (321). In this case, a compound as shown by Formula (321) is obtained, where $R_4$ comprises a first functional group comprising a hydroxy protecting group and a second functional group having a structure as shown by Formula (C3).

In some embodiments, the coupling reaction condition comprises a reaction temperature of 0-50° C., such as 15-35° C. The molar ratio of the compound of Formula (313) to the phosphorodiamidite may be 1:1 to 1:50, such as 1:5 to 1:15. The molar ratio of the compound of Formula (313) to the coupling agent may be 1:1 to 1:100, such as 1:50 to 1:80. The reaction time may be 200-3000 seconds, such as 500-1500 seconds. The phosphorodiamidite may be, for example, bis(diisopropylamino)(2-cyanoethoxy)phosphine, which may be commercially available or synthesized according to methods well-known in the art. The coupling agent is selected from one or more of 1H-tetrazole, 5-ethylthio-1H-tetrazole and 5-benzylthio-1H-tetrazole, such as 5-ethylthio-1H-tetrazole. The coupling reaction may be performed in an organic solvent. In some embodiments, the organic solvent is selected from one or more of anhydrous acetonitrile, anhydrous DMF and anhydrous dichloromethane, such as anhydrous acetonitrile. The amount of the organic solvent may be 3-50 L/mol, such as 5-20 L/mol with respect to the compound as shown by Formula (313). By performing the coupling reaction, the hydroxy group in the compound (313) reacts with the phosphorodiamidite to form a phosphoramidite group. In some embodiments, the solvent may be removed directly to obtain a crude product of the compound as shown by Formula (321), which may be used directly in subsequent reactions.

In some embodiments, the preparation method of the compound as shown by Formula (321) further comprises: contacting the isolated product with a solid phase support with hydroxy groups in an organic solvent under the coupling reaction condition in the presence of a coupling agent, followed by capping, oxidation, and isolation to obtain the compound as shown by Formula (321), where $R_4$ comprises a first functional group comprising a hydroxy protecting group and a second functional group having a structure as shown by Formula (C3').

In some embodiments, the solid phase support is a support well-known in the art for nucleic acid solid phase synthesis, such as a deprotected universal solid phase support, which is commercially available (such as NittoPhase®HL UnyLinker™ 300 Oligonucleotide Synthesis Support, Kinovate Life Sciences, as shown by Formula B(80):

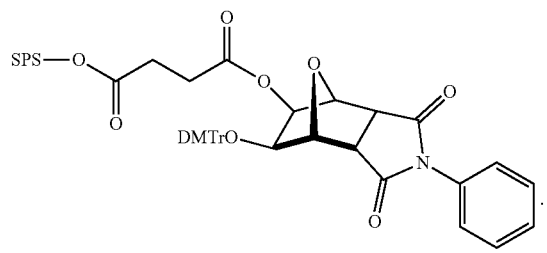

(B80)

A deprotection reaction is well-known in the art. In some embodiments, the deprotection condition comprises a temperature of 0-50° C., such as 15-35° C., and a reaction time of 30-300 seconds, such as 50-150 seconds. The deprotection agent may be selected from one or more of trifluoroacetic acid, trichloroacetic acid, dichloroacetic acid, and monochloroacetic acid. In some embodiments, the deprotection agent is dichloroacetic acid. The molar ratio of the deprotection agent to the protecting group -DMTr (4,4'-dimethoxytrityl) on the solid phase support may be 2:1 to 100:1, such as 3:1 to 50:1. Via such deprotection, reactive free hydroxy groups are obtained on the surface of the solid phase support, thus facilitating the subsequent coupling reaction.

The coupling reaction condition and the coupling agent may be selected as above. Via such coupling reaction, the free hydroxy groups formed in the deprotection react with the phosphoramidite groups, so as to form a phosphite ester linkage.

In some embodiments, the capping reaction condition comprises a temperature of 0-50° C., such as 15-35° C., and a reaction time of 5-500 seconds, such as 10-100 seconds. The selection and amount of the capping agent are as above.

The oxidation reaction condition may comprise a temperature of 0-50° C., such as 15-35° C., and a reaction time of 1-100 seconds, such as 5-50 seconds. The oxidation agent may be, for example, iodine (in some embodiments, provided in the form of iodine water). In some embodiments, the molar ratio of the oxidation agent to the phosphite ester group is 1:1 to 100:1, preferably 5:1 to 50:1. In some embodiments, the oxidation reaction is performed in a mixed solvent of tetrahydrofuran:water:pyridine=3:1:1-1:1:3.

In some embodiments, $R_6$ is a group as shown by Formula B7 or B8:

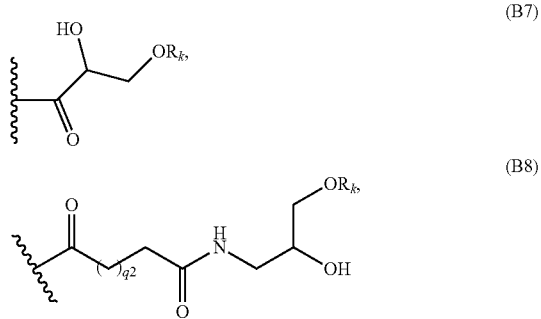

wherein $q_2$ is as defined above.

In this case, the compound shown in the Formula (313) may be prepared by a preparation method comprising: contacting the compound as shown by Formula (314) with a compound as shown by Formula (A-1) or (A-2) in an organic solvent under the amidation reaction condition in the presence of a condensing agent for amidation reaction and an organic base of tertiary amine, followed by isolation:

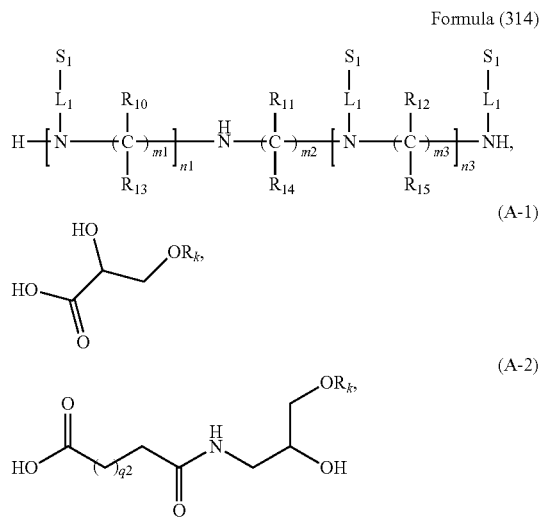

wherein the definitions and options of n1, n3, m1, m2, m3, $R_{10}$, $R_{11}$, $R_{12}$, $R_{13}$, $R_{14}$, $R_{15}$, $L_1$, $S_1$, $q_2$ and $R_k$ are respectively as described above.

The amidation reaction condition may comprise a reaction temperature of 0-100° C. and a reaction time of 1-48 hours. In some embodiments, the amidation reaction condition is a reaction temperature of 10-40° C. and a reaction time of 2-16 hours.

In some embodiments, the organic solvent is one or more of an alcohol solvent, an epoxy solvent, an ether solvent, an haloalkane solvent, dimethyl sulfoxide, N,N-dimethylformamide, and N,N-diisopropylethylamine. In some embodiments, the alcohol solvent is one or more of methanol, ethanol and propanol, and in some embodiments is ethanol. In some embodiments, the epoxy solvent is dioxane and/or tetrahydrofuran. In some embodiments, the ether solvent is diethyl ether and/or methyl tertbutyl ether. In some embodiments, the haloalkane solvent is one or more of dichloromethane, trichloromethane and 1,2-dichloroethane. In some embodiments, the organic solvent is dichloromethane. The amount of the organic solvent is 3-50 L/mol, and in further embodiments 3-20 L/mol with respect to the compound as shown by Formula (314).

In some embodiments, the condensing agent for amidation reaction is benzotriazol-1-yl-oxytripyrrolidinophosphonium hexafluorophosphate, 3-(diethoxyphosphoryl oxy)-1,2,3-benzotrizin-4(3H)-one, 4-(4,6-dimethoxytriazin-2-yl)-4-methylmorpholine hydrochloride, 2-ethoxy-1-ethoxycarbonyl-1,2-dihydroquinoline (EEDQ) or O-benzotriazol-tetramethyluronium hexafluorophosphate, and in further embodiments is 3-(diethoxyphosphoryloxy)-1,2,3-benzotrizin-4(3H)-one. The molar ratio of the condensing agent for amidation reaction to the compound as shown by Formula (314) may be 1:1 to 10:1, and in some embodiments is 2.5:1 to 5:1.

In some embodiments, the organic base of tertiary amine is triethylamine or N,N-diisopropylethylamine, and in some embodiments is N,N-diisopropylethylamine. The molar ratio of the tertiary amine to the compound as shown by Formula (314) may be 3:1 to 20:1, and in some embodiments is 5:1 to 10:1.

The compounds of Formula (A-1) and (A-2) may be prepared by any suitable means. For example, the compound of Formula (A-1) may be prepared by reacting calcium glycerate with DMTrCl, when $R_k$ is a DMTr group. Similarly, the compound of Formula (A-2) may be prepared by firstly contacting 3-amino-1,2-propanediol with a cyclic anhydride which may have 4-13 carbon atoms, and in some embodiments 4-8 carbon atoms, followed by reacting with DMTrCl. It will be readily understood by those skilled in the art that the selection of different cyclic anhydrides corresponds to different values for $q_2$ in the compound of Formula (A-2). For example, when the cyclic anhydride is succinic anhydride, $q_2=1$; when the cyclic anhydride is glutaric anhydride, $q_2=2$, and so on.

In some variations, the compound of Formula (313) can also be prepared by successively reacting the compound as shown by Formula (314) with the cyclic anhydride, 3-amino-1,2-propanediol, and DMTrCl. It will be readily understood by those skilled in the art that these variations would not affect the structure and functions of the compound of Formula (313), and these variations are readily achieved by those skilled in the art on the basis of the above methods.

Similarly, the compound as shown by Formula (313) may be isolated from the reaction mixture by any suitable isolation methods. In some embodiments, the compound as shown by Formula (313) may be isolated by removal of solvent via evaporation followed by chromatography. For example, the following two sets of chromatographic conditions may be used for isolation, (1) normal phase purification: 200-300 mesh silica gel filler, with gradient elution of petroleum ether:ethyl acetate:dichloromethane:N,N-dimethylformamide=1:1:1:0.5-1:1:1:0.6; and (2) reverse phase purification: C18 and C8 reverse phase fillers, with gradient elution of methanol:acetonitrile=0.1:1-1:0.1. In some embodiments, the solvent may be removed directly to obtain a crude product of the compound as shown by Formula (313), which may be directly used in subsequent reactions.

In some embodiments, the compound as shown by Formula (314) may be prepared by a preparation method comprising contacting the compound as shown by Formula (315) with haloacetic acid in an organic solvent under the deprotection reaction condition, followed by isolation:

Formula (315)

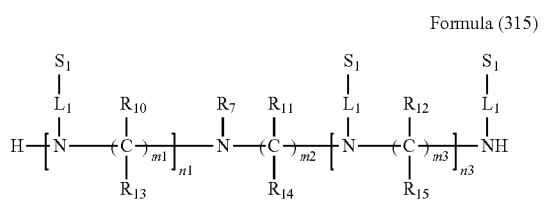

wherein $R_7$ is selected from the groups as shown by Formula (330), (331), (332) and (333), and in some embodiments, $R_7$ has the structure as shown by Formula (330):

Formula (330)

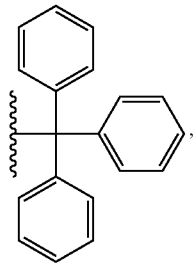

Formula (331)

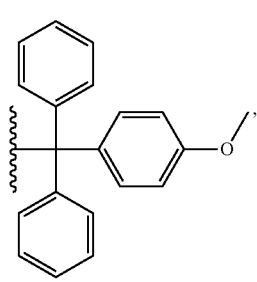

Formula (332)

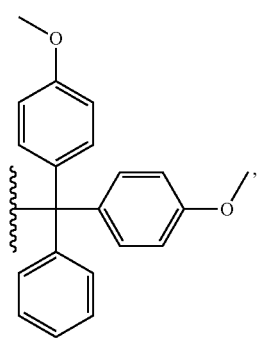

Formula (333)

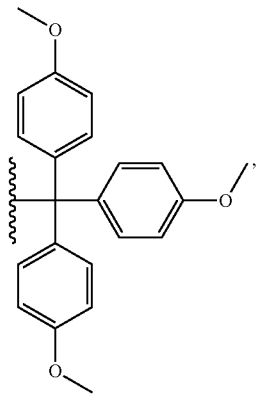

wherein the definitions and options of n1, n3, m1, m2, m3, $R_{10}$, $R_{11}$, $R_{12}$, $R_{13}$, $R_{14}$, $R_{15}$, $L_1$ and $S_1$ are respectively as described above.

The haloacetic acid may be selected from one or more of dichloroacetic acid, trichloroacetic acid, monochloroacetic acid and trifluoroacetic acid, and in some embodiments is dichloroacetic acid.

The deprotection reaction condition may comprise a reaction temperature of 0-100° C. and a reaction time of 0.1-24 hours, and in some embodiments comprises a reaction temperature of 10-40° C. and a reaction time of 0.5-16 hours.

In some embodiments, the organic solvent is one or more of an epoxy solvent, an ether solvent, an haloalkane solvent, dimethyl sulfoxide, N,N-dimethylformamide, and N,N-di-isopropylethylamine. In some embodiments, the epoxy solvent is dioxane and/or tetrahydrofuran. In some embodiments, the ether solvent is diethyl ether and/or methyl tertbutyl ether. In some embodiments, the haloalkane solvent is one or more of dichloromethane, trichloromethane and 1,2-dichloroethane. In some embodiments, the organic solvent is dichloromethane. The amount of the organic solvent is 3-50 L/mol, and in further embodiments 5-20 L/mol with respect to the compound as shown by Formula (315).

The molar ratio of the haloacetic acid to the compound as shown by Formula (315) may be 5:1 to 100:1, and in some embodiments is 10:1 to 50:1.

Similarly, the compound as shown by Formula (314) may be isolated from the reaction mixture by any suitable isolation methods. In some embodiments, the compound as shown by Formula (314) may be isolated by removal of solvent via evaporation followed by chromatography, for example, using the following two sets of chromatographic conditions for isolation, (1) normal phase purification: 200-300 mesh silica gel filler, with gradient elution of dichloromethane:methanol=100:30-100:40; and (2) reverse phase purification: C18 and C8 reverse phase fillers, with gradient elution of methanol:acetonitrile=0.1:1-1:0.1. In some embodiments, the solvent may be removed directly to obtain a crude product of the compound as shown by Formula (314), which may be directly used in subsequent reactions.

The compound as shown by Formula (315) may be prepared by a preparation method comprising contacting the compound as shown by Formula (317) with the compound as shown by Formula (316) in an organic solvent under the condensation reaction condition in the presence of a condensing agent for amidation reaction and an organic base of tertiary amine, followed by isolation:

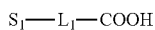

Formula (316)

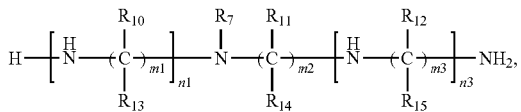

Formula (317)

wherein the definitions and options of n1, n3, m1, m2, m3, $R_7$, $R_{10}$, $R_{11}$, $R_{12}$, $R_{13}$, $R_{14}$, $R_{15}$, $L_1$ and $S_1$ are respectively as described above.

The compound of Formula (316) can be, such as, those disclosed in J. Am. Chem. Soc. 2014, 136, 16958-16961. Alternatively, the compounds of Formula (316) may be prepared by those skilled in the art via various methods. For example, some compounds of Formula (316) may be prepared according to the method disclosed in Example 1 of U.S. Pat. No. 8,106,022 B2, which is incorporated herein by reference in its entirety.

In some embodiments, the condensation reaction condition comprises a reaction temperature of 0-100° C. and a reaction time of 0.1-24 hours. In some embodiments, the reaction temperature is 10-40° C. and the reaction time is 0.5-16 hours.

The molar ratio of the compound as shown by Formula (316) to the compound as shown by Formula (317) may be 2:1 to 10:1, and in some embodiments is 2.5:1 to 5:1.

The organic solvent is one or more of acetonitrile, an epoxy solvent, an ether solvent, an haloalkane solvent, dimethyl sulfoxide, N,N-dimethylformamide and N,N-diisopropylethylamine. In some embodiments, the epoxy solvent is dioxane and/or tetrahydrofuran. In some embodiments, the ether solvent is diethyl ether and/or methyl tertbutyl ether. In some embodiments, the haloalkane solvent is one or more of dichloromethane, trichloromethane and 1,2-dichloroethane. In some embodiments, the organic solvent is acetonitrile. The amount of the organic solvent may be 3-50 L/mol, and in some embodiments is 5-20 L/mol with respect to the compound as shown by Formula (317).

In some embodiments, the condensing agent for amidation reaction is benzotriazol-1-yl-oxytripyrrolidinophosphonium hexafluorophosphate, 3-(diethoxyphosphoryloxy)-1,2,3-benzotrizin-4(3H)-one (DEPBT), O-benzotriazol-tetramethyluronium hexafluorophosphate or 4-(4,6-dimethoxytriazin-2-yl)-4-methylmorpholine hydrochloride, and in some embodiments is 4-(4,6-dimethoxytriazin-2-yl)-4-methylmorpholine hydrochloride. The molar ratio of the condensing agent for amidation reaction to the compound as shown by Formula (317) may be 2:1 to 10:1, and in some embodiments is 2.5:1 to 5:1.

The organic base of tertiary amine may be N-methylmorpholine, triethylamine or N,N-diisopropylethylamine, and in some embodiments is N-methylmorpholine. The molar ratio of the tertiary amine to the compound as shown by Formula (317) may be 3:1 to 20:1, and in some embodiments is 5:1 to 10:1.

Similarly, the compound as shown by Formula (315) may be isolated from the reaction mixture by any suitable isolation methods. In some embodiments, the compound as shown by Formula (315) is isolated by removal of solvent via evaporation followed by chromatography, for example, using the following two sets of chromatographic conditions for isolation, (1) normal phase purification: 200-300 mesh silica gel filler, with gradient elution of dichloromethane:methanol=100:5-100:7; (2) reverse phase purification: C18 and C8 reverse phase fillers, with gradient elution of methanol:acetonitrile=0.1:1-1:0.1. In some embodiments, the solvent is removed directly to obtain a crude product of the compound as shown by Formula (315), which may be used directly in subsequent reactions.

In some embodiments, the compound of Formula (317) is reacted with a sufficient amount of a compound of Formula (316) in one batch to obtain the desired compound of Formula (315), wherein all $S_1$-$L_1$ moieties are identical. In some embodiments, the compound of Formula (317) is reacted in batches with different compounds of Formula (316), i.e., the compounds of Formula (316) having different $L_1$ and/or $S_1$, as desired, so as to obtain the compound of Formula (315) having two or more types of $S_1$ and/or $L_1$ therein. For example, 1 eq of the compound of Formula (317) may be firstly contacted with 2 eq of a first compound of Formula (316) to attach a first $S_1$-$L_1$ moieties to the two terminal primary amine groups in the compound of Formula (317), and then contacted with the (n3+n1−1) eq of a second compound of Formula (316) to attach a second $S_1$-$L_1$ moieties to the (n3+n1−1) secondary amine groups (wherein the definitions and ranges of n3 and n1 are as described above) in the compound of Formula (317).

In some embodiments, the compound as shown by Formula (317) may be prepared by a preparation method comprising contacting the compound as shown by Formula (318) with aqueous methylamine solution under the deprotection reaction condition in the presence of an organic solvent, follow by isolation:

Formula (318)

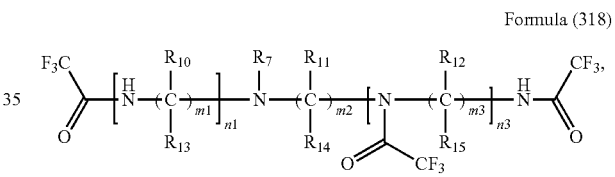

wherein the definitions and options of n1, n3, m1, m2, m3, $R_7$, $R_{10}$, $R_{11}$, $R_{12}$, $R_{13}$, $R_{14}$ and $R_{15}$ are respectively as described above.

The deprotection reaction condition may comprise a reaction temperature of 0-150° C. and a reaction time of 5-72 hours, and in some embodiments comprises a reaction temperature of 20-80° C. and a reaction time of 10-30 hours.

The organic solvent may be selected from alcohols, in some embodiments is one of methanol, ethanol and isopropanol, and in some embodiments is methanol. The amount of the organic solvent may be 1-20 L/mol, and in some embodiments is 1.5-10 L/mol with respect to the compound as shown by Formula (318).

The concentration of the methylamine aqueous solution may be 30%-40% by mass, and the molar ratio of methylamine to the compound as shown by Formula (318) may be 10:1 to 500:1, and in some embodiments is 50:1 to 200:1.

Similarly, the compound as shown by Formula (317) may be isolated from the reaction mixture using any suitable isolation methods. In some embodiments, the compound as shown by Formula (317) may be isolated by removal of solvent via evaporation followed by chromatography, for example, using the following two sets of chromatographic conditions for isolation, (1) normal phase purification: 200-300 mesh silica gel filler, with gradient elution of dichloromethane:methanol:aqueous ammonia (25 wt %)=1:1:0.05-1:1:0.25; and (2) reverse phase purification: C18 and C8 reverse phase fillers, with gradient elution of methanol:

acetonitrile=0.1:1-1:0.1. In some embodiments, the solvent may be removed directly to obtain a crude product of the compound as shown by Formula (317), which may be used directly in subsequent reactions.

The compound as shown by Formula (318) may be prepared by a preparation method comprising contacting the compound as shown by Formula (319) with triphenylchloromethane (TrCl), diphenylethylphenylchloromethane, phenyldiethylphenylchloromethane or triethylphenylchloromethane, and in some embodiments with triphenylchloromethane (TrCl) under a substitution reaction condition in the presence of an organic solvent, followed by isolation:

Formula (319)

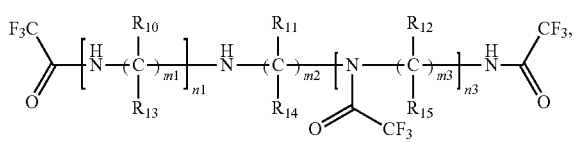

wherein the definitions and options of n1, n3, m1, m2, m3, $R_{10}$, $R_{11}$, $R_{12}$, $R_{13}$, $R_{14}$ and $R_{15}$ are respectively as described above.

The substitution reaction condition may comprise a reaction temperature of 0-100° C. and a reaction time of 5-72 hours, and in some embodiments comprises a reaction temperature of 10-40° C. and a reaction time of 10-30 hours.

Tri phenyl chloromethane (TrCl), di phenyl ethylphenylchloromethane, phenyl di ethyl phenyl chloromethane or tri ethyl phenylchloromethane is commercially available. The molar ratio of tri phenylchloromethane (TrCl), di phenyl ethyl phenyl chloromethane, phenyl diethylphenylchloromethane or triethylphenylchloromethane to the compound as shown by Formula (319) may be 1:1 to 10:1, and in some embodiments is 1:1 to 3:1.

The organic solvent may be one or more of an epoxy solvent, an ether solvent, an haloalkane solvent, dimethyl sulfoxide, N,N-dimethylformamide, and N,N-diisopropylethylamine. In some embodiments, the epoxy solvent is dioxane and/or tetrahydrofuran. In some embodiments, the ether solvent is diethyl ether and/or methyl tertbutyl ether. In some embodiments, the haloalkane solvent is one or more of dichloromethane, trichloromethane and 1,2-dichloroethane. In some embodiments, the organic solvent is dichloromethane. The amount of the organic solvent may be 3-50 L/mol, and in some embodiments is 5-20 L/mol with respect to the compound as shown by Formula (319).

Similarly, the compound as shown by Formula (318) may be isolated from the reaction mixture by any suitable isolation methods. In some embodiments, the compound as shown by Formula (318) may be isolated by removal of solvent via evaporation followed by chromatography, for example, using the following two sets of chromatographic conditions for isolation, (1) normal phase purification: 200-300 mesh silica gel filler, with gradient elution of methanol:dichloromethane=0.01:1-0.5:1 or gradient elution of methanol:dichloromethane:ethyl acetate:petroleum ether=0.1:1:1:1-1:1:1:1; and (2) reverse phase purification: C18 and C8 reverse phase fillers, with gradient elution of methanol:acetonitrile=0.1:1-1:0.1. In some embodiments, the solvent may be removed directly to obtain a crude product of the compound as shown by Formula (318), which may be used directly in subsequent reactions.

In some embodiments, the compound as shown by Formula (319) may be prepared by a preparation method comprising contacting the compound as shown by Formula (320) with ethyl trifluoroacetate in an organic solvent under a substitution reaction condition, followed by isolation:

Formula (320)

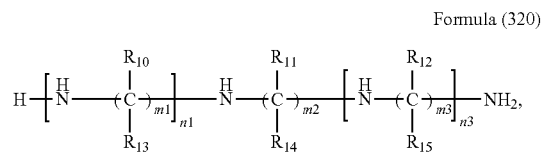

wherein the definitions and options of n1, n3, m1, m2, m3, $R_{10}$, $R_{11}$, $R_{12}$, $R_{13}$, $R_{14}$ and $R_{15}$ are respectively as described above.

In some embodiments, the organic solvent is one or more of acetonitrile, an epoxy solvent, an ether solvent, an haloalkane solvent, dimethyl sulfoxide, N,N-dimethylformamide, and N,N-diisopropylethylamine. In some embodiments, the epoxy solvent is dioxane and/or tetrahydrofuran. In some embodiments, the ether solvent is diethyl ether and/or methyl tertbutyl ether. In some embodiments, the haloalkane solvent is one or more of dichloromethane, trichloromethane and 1,2-dichloroethane. In some embodiments, the organic solvent is acetonitrile. The amount of the organic solvent may be 1-50 L/mol, and in some embodiments is 1-20 L/mol with respect to the compound as shown by Formula (320).

The substitution reaction condition may comprise a reaction temperature of 0-100° C. and a reaction time of 5-72 hours, and in some embodiments comprises a reaction temperature of 10-40° C. and a reaction time of 10-30 hours.

The compound as shown by Formula (320) may be commercially available, or obtained by those skilled in the art via known methods. For example, in the case that m12=m2=m3=3, n1=1, n3=2, while each of $R_{10}$, $R_{11}$, $R_{12}$, $R_{13}$, $R_{14}$ and $R_{15}$ is H, the compound as shown by Formula (320) is commercially available from Alfa Aesar Inc.

The molar ratio of ethyl trifluoroacetate to the compound as shown by Formula (320) may be 2:1 to 10:1, and in some embodiments is 3:1 to 5:1.

Similarly, the compound as shown by Formula (319) may be isolated from the reaction mixture using any suitable isolation methods. In some embodiments, the compound as shown by Formula (319) may be isolated by removal of solvent via evaporation followed by chromatography, for example, using the following two sets of chromatographic conditions for the isolation, (1) normal phase purification: 200-300 mesh silica gel filler, with gradient elution of methanol:dichloromethane=0.01:1-0.5:1 or gradient elution of methanol:dichloromethane:ethyl acetate:petroleum ether=0.1:1:1:1-1:1:1:1; and (2) reverse phase purification: C18 and C8 reverse phase fillers, with gradient elution of methanol:acetonitrile=0.1:1-1:0.1. In some embodiments, the solvent may be removed directly to obtain a crude product of the compound as shown by Formula (319), which may be used directly in subsequent reactions.

The first or second siRNA conjugate of the present disclosure may also be used in combination with other pharmaceutically acceptable excipients, which may be one or more of the various formulations or compounds conventionally used in the art. For details, please refer to the above description of the pharmaceutical composition of the present disclosure as described above.

Use of the siRNA, the pharmaceutical composition comprising the siRNA, the first siRNA conjugate and the second siRNA conjugate of the present disclosure In some embodiments, provided herein is use of the siRNA, the pharmaceutical composition comprising the siRNA, the first siRNA conjugate and the second siRNA conjugate of the present disclosure in the manufacture of a medicament for treating and/or preventing pathological conditions or diseases caused by hepatitis B virus (HBV) infection.

According to one embodiment of the present disclosure, provided herein is a method for treating pathological conditions or diseases caused by HBV infection, comprising administering to a subject the siRNA, the pharmaceutical composition, the first siRNA conjugate and the second siRNA conjugate of the present disclosure.

According to another embodiment of the present disclosure, provided herein is a method for inhibiting the expression of HBV genes in hepatitis cells infected with chronic HBV, comprising contacting the siRNA, the pharmaceutical composition, the first siRNA conjugate and the second siRNA conjugate of the present disclosure with the hepatitis cells infected with chronic HBV.

The pathological condition or disease caused by HBV infection is selected from chronic liver diseases, hepatitis, hepatic fibrosis, or liver proliferative diseases.

The purpose of treating hepatitis B can be achieved based on the mechanism of RNA interference (RNAi) by administering the siRNA and/or the pharmaceutical composition, the first siRNA conjugate and the second siRNA conjugate of the present disclosure to a subject in need thereof. Thus, the siRNA and/or the pharmaceutical composition, the first siRNA conjugate and the second siRNA conjugate of the present disclosure may be used for preventing and/or treating hepatitis B, or for preparing a medicament for preventing and/or treating hepatitis B.

As used herein, the term "administration/administer" refers to placing the siRNA or pharmaceutical composition, the first siRNA conjugate and the second siRNA conjugate of the present disclosure into a subject' body by a method or route where at least, in part, the siRNA or pharmaceutical composition, the first siRNA conjugate and the second siRNA conjugate of the present disclosure is located at a desired site to achieve a desired effect. The administration routes suitable for the method of the present disclosure include topical administration and systemic administration. In general, topical administration results in the delivery of more siRNA or pharmaceutical composition, first siRNA conjugate and second siRNA conjugate to a particular site as compared to the entire body of the subject; while systemic administration results in the delivery of the siRNA or pharmaceutical composition, the first siRNA conjugate and the second siRNA conjugate to basically the whole body of the subject. Considering that the present disclosure is intended to provide means for the prevention and/or treatment of hepatitis B, preferably an administration mode that can deliver drugs to liver.

Any suitable route known in the art can be used for administration to the subject, including, but is not limited to, oral or parenteral routes, including intravenous administration, intramuscular administration, subcutaneous administration, transdermal administration, intratracheal administration (aerosol), pulmonary administration, nasal administration, rectal administration and topical administration (including buccal administration and sublingual administration). The frequency of administration may be once or more times daily, weekly, biweekly, triweekly, monthly, or yearly.

The dose of the siRNA or pharmaceutical composition, the first siRNA conjugate and the second siRNA conjugate of the present disclosure may be a conventional dose in the art, which may be determined according to various parameters, especially age, weight, and gender of the subject. Toxicity and efficacy may be measured in cell cultures or experimental animals by standard pharmaceutical procedures, for example, by determining LD50 (the lethal dose that causes 50% population death) and ED50 (the dose that can cause 50% of the maximum response intensity in a quantitative response, and that causes 50% of the experimental subjects to have a positive response in a qualitative response). The dose ratio between toxicity and efficacy is the therapeutic index, which can be expressed as the ratio of LD50/ED50. The siRNA or pharmaceutical composition, the first siRNA conjugate and the second siRNA conjugate which exhibit a high therapeutic index are preferred. The dose range for human use may be derived based on data obtained from cell culture assays and animal studies.

When administrating the pharmaceutical composition, the first siRNA conjugate and the second siRNA conjugate of the present disclosure, for example, to C57BL/6J or C3H/HeNCrlVr mice, either male or female, with an age of 6 to 12 weeks old and a body weight of 18 to 25 g, when calculated based on the amount of the siRNA in the pharmaceutical composition or the siRNA conjugates: (i) for a pharmaceutical composition formed by a siRNA and a pharmaceutically acceptable carrier, the dosage of siRNA thereof may be 0.001-50 mg/kg body weight, and in further embodiments is 0.01-10 mg/kg body weight, and in still further embodiments is 0.05-5 mg/kg body weight, and in still yet further embodiments is 0.1-3 mg/kg body weight; (ii) for the first and/or second siRNA conjugate formed by a siRNA and a pharmaceutically acceptable conjugating molecule, the dosage of siRNA thereof may be 0.001-100 mg/kg body weight, and in further embodiments is 0.01-50 mg/kg body weight, and in still further embodiments is 0.05-20 mg/kg body weight, and in still yet further embodiments is 0.1-10 mg/kg body weight. The above dosages can be preferred when administrating the siRNA of the present disclosure.

Furthermore, by introducing the siRNA and/or the pharmaceutical composition, the first siRNA conjugate and the second siRNA conjugate of the present disclosure into hepatitis cells infected with chronic HBV, the purpose of inhibiting the expression of HBV gene in the hepatitis cells infected with chronic HBV may also be achieved by the mechanism of RNA interference. In some preferred embodiments, the cells are HepG2.2.15 cells.

In the case where the expression of HBV genes in cells is inhibited by using the method provided by the present disclosure, the amount of the siRNA in the provided siRNA, pharmaceutical composition, first siRNA conjugate or second siRNA conjugate is an amount sufficient to reduce the expression of the target gene and result in an extracellular concentration of 1 pM to 1 µM, or 0.01 nM to 100 nM, or 0.05 nM to 50 nM or 0.05 nM to about 5 nM on the surface of the target cells. The amount required to achieve this local concentration will vary with various factors, including the delivery method, the delivery site, the number of cell layers between the delivery site and the target cells or tissue, the delivery route (topical or systemic), etc. The concentration at the delivery site may be significantly higher than that on the surface of the target cells or tissue.

Kit

Provided herein is a kit comprising an effective amount of at least one of the siRNA, the pharmaceutical composition, the first siRNA conjugate and the second siRNA conjugate of the present disclosure.

In some embodiments, the kits disclosed herein provide modified siRNA in one container. In some embodiments, the kits disclosed herein comprise a container comprising pharmaceutically acceptable excipients. In some embodiments, the kits disclosed herein further comprise additional ingredients, such as stabilizers or preservatives. In some embodiments, the kits comprise at least one additional therapeutic agent in other container than the one comprising the modified siRNA disclosed herein. In some embodiments, the kits comprise an instruction for mixing the modified siRNA with pharmaceutically acceptable carriers and/or adjuvants or other ingredients (if present).

In the kits of the present disclosure, the modified siRNA and pharmaceutically acceptable carriers and/or adjuvants as well as the modified siRNA, pharmaceutical composition, first siRNA conjugate and/or second siRNA conjugate and/or conjugate, and/or pharmaceutically acceptable adjuvants may be provided in any form, e.g., in a liquid form, a dry form, or a lyophilized form. In some embodiments, the modified siRNA and pharmaceutically acceptable carriers and/or adjuvants as well as the pharmaceutical composition and/conjugate and optional pharmaceutically acceptable adjuvants are substantially pure and/or sterile. In some embodiments, sterile water may be provided in the kits of the present disclosure.

Hereinafter, the present disclosure will be further illustrated with reference to the examples, but is not limited thereto.

Advantageous Effects

In some embodiments, the siRNA, composition or siRNA conjugate provided herein can have higher stability, lower toxicity, and/or higher activity in vivo. In some embodiments, the siRNA, siRNA composition or siRNA conjugate provided herein exhibits an inhibition percentage of HBV gene expression of at least 20%, 30%, 40%, 50%, 60%, 70%, 80%, 90%, or 95% in vivo. In some embodiments, the siRNA, siRNA composition or siRNA conjugate provided herein exhibits an inhibition percentage of HBV gene expression in liver of at least 20%, 30%, 40%, 50%, 60%, 70%, 80%, 90%, or 95% in vivo. In some embodiments, the siRNA, siRNA composition or siRNA conjugate provided herein exhibits an inhibition percentage of HBV gene expression in liver in animal models of at least 20%, 30%, 40%, 50%, 60%, 70%, 80%, 90%, or 95% in vivo. In some embodiments, the siRNA, siRNA composition or siRNA conjugate provided herein exhibits an inhibition percentage of HBV surface antigen expression of at least 20%, 30%, 40%, 50%, 60%, 70%, 80%, 90%, or 95% in vivo. In some embodiments, the siRNA, siRNA composition or siRNA conjugate provided herein exhibits no significant off-target effect. An off-target effect may be for example inhibition on normal expression of a gene which is not the target gene. It is considered that if the binding/inhibition of the expression of an off-target gene is 50%, 40%, 30%, 20%, or 10% lower than that of the on-target activity, then the off-target effect is not significant.

In some embodiments, the siRNA conjugates of the present disclosure have better inhibitory activity in vitro.

In some embodiments, the siRNA conjugates of the present disclosure not only have excellent inhibitory effect on the target mRNA, but also show low off-target effect.

In some embodiments, the siRNA conjugates of the present disclosure can remain undegraded in Tritosome for a prolonged period of time, showing good stability.

In some embodiments, the siRNA conjugates of the present disclosure can remain undegraded in human plasma over a period of up to 72 hours, showing excellent stability in human plasma.

In some embodiments, the siRNA conjugates of the present disclosure can remain undegraded in cynomolgus monkey plasma over a period of up to 72 hours, showing excellent stability in monkey plasma.

In some embodiments, the siRNA conjugates of the present disclosure exhibit good inhibitory effect on the target mRNA, having an inhibitory efficiency ranging from 81.73% to 89.22% at 1 mg/kg, and show substantially the same inhibitory effects on different HBV mRNAs.

In some embodiments, the siRNA conjugates of the present disclosure consistently exhibit efficient inhibition against HBsAg and HBV DNA over a period of 85 days.

Additional features and advantages of the present disclosure will be illustrated in detail in the subsequent specific embodiments.

EXAMPLES

Hereinafter, the present disclosure will be described in detail with reference to the examples. Unless otherwise specified, the reagents and culture media used in the following examples are all commercially available, and the procedures used such as nucleic acid electrophoresis and real-time PCR are all performed according to methods described in Molecular Cloning (Cold Spring Harbor Laboratory Press (1989)).

Unless otherwise specified, ratios of the reagents provided below are all calculated by volume ratio (v/v).

The animal models used are as follows:

HBV transgenic mice: C57BL/6-HBV, Strain name: B6-Tg HBV/Vst (1.28 copy, genotype A), purchased from Beijing Vitalstar Biotechnology Co., Ltd. Mice with COI>$10^4$ (hereinafter sometimes referred to as 1.28 copy mice) are selected before experiments;

Low-concentration AAV-HBV transgenic mice: AAV-HBV models prepared according to the literature method (Xiaoyan Dong et al., Chin J Biotech 2010, May 25; 26(5): 679-686) by using rAAV8-1.3HBV, D type (ayw) virus (purchased from Beijing FivePlus Molecular Medicine Institute Co. Ltd., $1\times10^{12}$ viral genome (v.g.)/mL, Lot number 2016123011). The rAAV8-1.3HBV was diluted to $1\times10^{11}$ v.g./mL with sterile PBS. 100 µL of the diluted rAAV8-1.3HBV was injected into each mouse (i.e., $1\times10^{10}$ v.g. per mouse); hereinafter is sometimes referred to as low concentration AAV-HBV model mice, or referred to as AAV-HBV for short.

Preparation Example 1

Preparation of Conjugates 1-2 and 15-16

In this preparation example, Conjugate 1 (hereinafter also referred to as L10-siHB1M1SVP conjugate) and Conjugate 2 (hereinafter also referred to as L10-siHB2M1SVP conjugate) were synthesized. Conjugate 15 (hereinafter also referred to as L10-siHB1M1SP) and Conjugate 16 (hereinafter also referred to as L10-siHB1M1SPs) were scheduled to be synthesized. The conjugates were formed by conjugating L-9 Conjugating Molecule respectively with the siRNAs numbered as siHB1M1SVP, siHB2M1SVP, siHB1M1SP, or siHB1M1SPs. The sequences of the conjugated siRNAs in the conjugates are shown in Table 1.

(1-1) Synthesis of Compound L-10:

Compound L-10 was synthesized according to the following method:

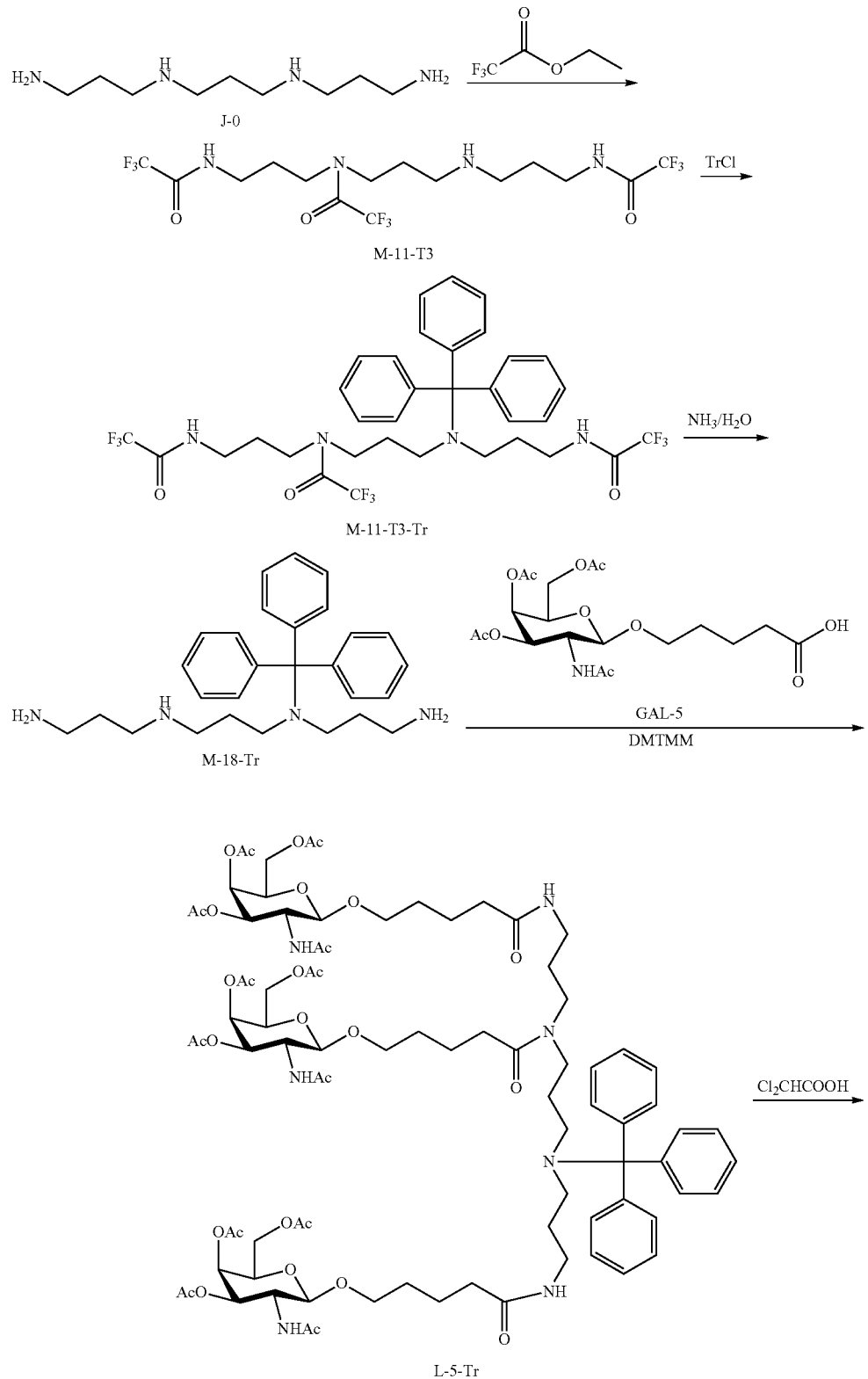

-continued
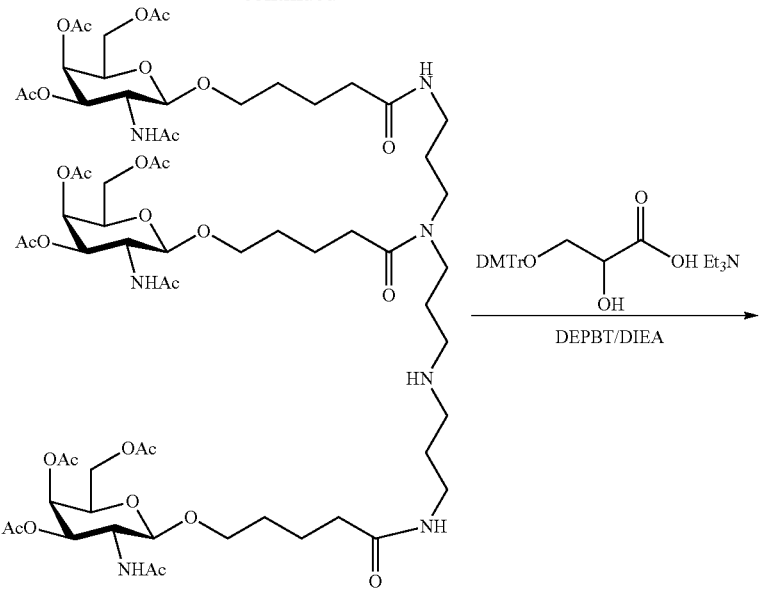
L-8
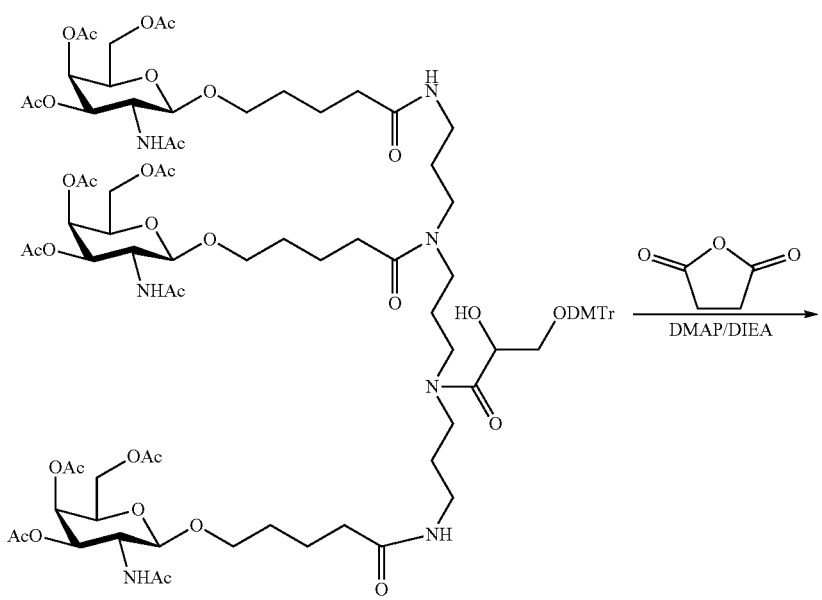
L-7

-continued
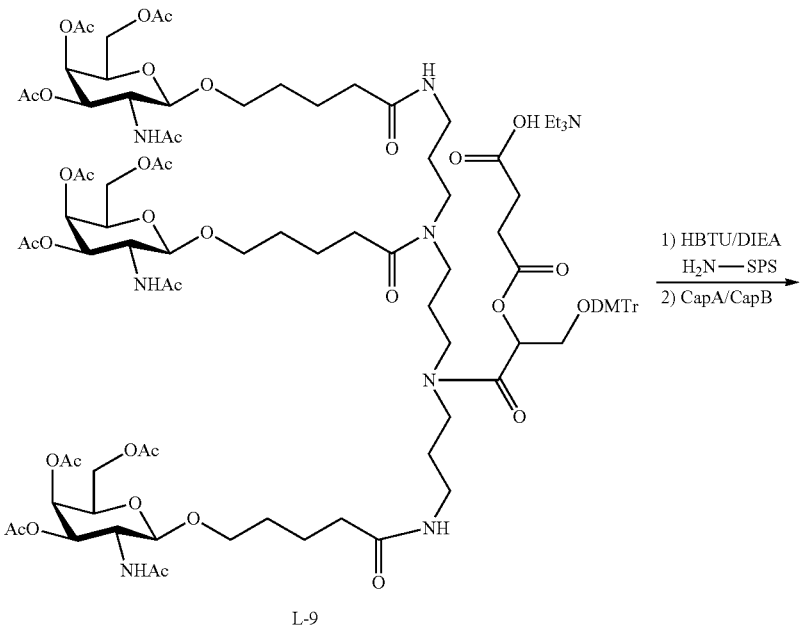
L-9
1) HBTU/DIEA
H$_2$N—SPS
2) CapA/CapB
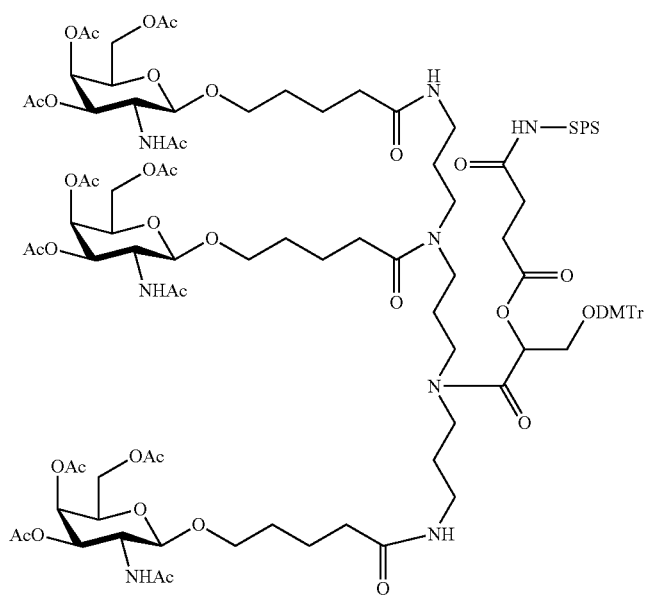
L-10

(1-1-1) Synthesis of a Terminal Segment of the Conjugating Molecule, GAL-5

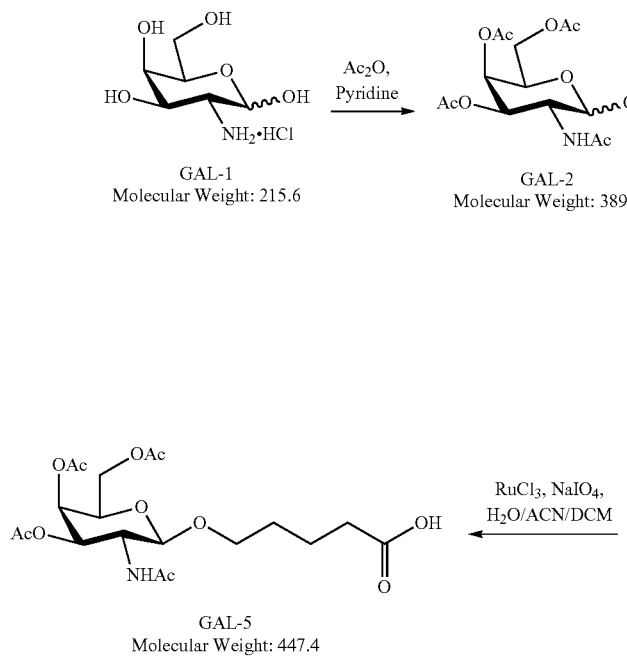

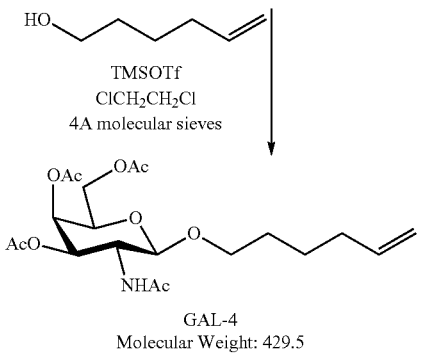

(1-1-1a) Synthesis of GAL-2

100.0 g of GAL-1 (N-acetyl-D-galactosamine hydrochloride, CAS No.: 1772-03-8, purchased from Ning Bo hongxiang bio-chem Co., Ltd., 463.8 mmol) was dissolved in 1000 ml of anhydrous pyridine, to which 540 ml of acetic anhydride (purchased from Enox Inc., 5565.6 mmol) was added in an ice water bath to react for 1.5 hours under stirring at room temperature. The resultant reaction solution was poured into 10 L of ice water and subjected to suction filtration under reduced pressure. The residue was washed with 2 L of ice water, and then added with a mixed acetonitrile/toluene solvent (v/v ratio of acetonitrile:toluene=1:1) until completely dissolved. The solvent was evaporated to give 130.0 g of product GAL-2 as a white solid.

(1-1-1b) Synthesis of GAL-3

GAL-2 (35.1 g, 90.0 mmol) obtained in step (1-1-1a) was dissolved in 213 ml of anhydrous 1,2-dichloroethane, to which 24.0 g of TMSOTf (CAS No.: 27607-77-8, purchased from Macklin Inc., 108.0 mmol) was added in an ice water bath and nitrogen atmosphere to react overnight at room temperature.

400 ml dichloromethane was added to the reaction solution for dilution, filtered with diatomite, and then 1 L saturated aqueous sodium bicarbonate solution was added to the resultant reaction solution and stirred evenly. An organic phase was isolated. The aqueous phase remained was extracted twice, each with 300 ml of dichloroethane, and all organic phases were combined and washed with 300 ml of saturated aqueous sodium bicarbonate solution and 300 ml of saturated brine, respectively. The organic phase was isolated and dried with anhydrous sodium sulfate. The solvent was evaporated under reduced pressure to give 26.9 g of product GAL-3 as a light yellow viscous syrup.

(1-1-1c) Synthesis of GAL-4

GAL-3 (26.9 g, 81.7 mmol) obtained in step (1-1-1b) was dissolved in 136 ml of anhydrous 1,2-dichloroethane, added with 30 g of 4 Å molecular sieve as a dry powder followed by 9.0 g of 5-hexen-1-ol (CAS No.: 821-41-0, purchased from Adamas-beta Inc., 89.9 mmol), and stirred for 30 minutes at room temperature. 9.08 g of TMSOTf (40.9 mmol) was added in an ice bath and nitrogen atmosphere to react overnight under stirring at room temperature. The 4 Å molecular sieve powder was removed by filtration. 300 ml dichloroethane was added to the filtrate for dilution, filtered with diatomite, and then 500 ml of saturated aqueous sodium bicarbonate solution was added to the resultant reaction solution and stirred for 10 minutes for washing. An organic phase was isolated. The aqueous phase was extracted once with 300 ml of dichloroethane. All organic phases were combined and washed with 300 ml of saturated aqueous sodium bicarbonate solution and 300 ml of saturated brine respectively. The organic phase was isolated and dried with anhydrous sodium sulfate. The solvent was evaporated under reduced pressure to give 41.3 g of product GAL-4 as a yellow syrup, which was directly used in the next oxidation reaction without purification.

(1-1-1d) Synthesis of GAL-5

GAL-4 (14.9 g, 34.7 mmol) obtained according to the method described in step (1-1-1c) was dissolved in a mixed solvent of 77 ml of dichloromethane and 77 ml of acetonitrile, added with 103 ml of deionized water and 29.7 g of sodium periodate (CAS No.: 7790-28-5, purchased from Aladdin Inc., 138.8 mmol) respectively, and stirred in an ice bath for 10 minutes. Ruthenium trichloride (CAS No.: 14898-67-0, available from Energy Chemical, 238 mg, 1.145 mmol) was added to react overnight at room temperature. The reaction solution was diluted by adding 300 ml of water, stirred, and adjusted to a pH of about 7.5 by adding saturated sodium bicarbonate. The organic phase isolated was isolated and discarded. The aqueous phase was extracted three times, each with 200 ml of dichloromethane, and the organic phase was discarded. The aqueous phase was adjusted to a pH of about 3 with citric acid solids and extracted three times, each with 200 ml of dichloromethane, and the organic phases were combined and dried with anhydrous sodium sulfate. The solvent was evaporated under reduced pressure to give 6.85 g of product GAL-5 as a white foamy solid. $^1$H NMR (400 MHz, DMSO) δ 12.01 (br, 1H), 7.83 (d, J=9.2 Hz, 1H), 5.21 (d, J=3.2 Hz, 1H), 4.96 (dd, J=11.2, 3.2 Hz, 1H), 4.49 (d, J=8.4 Hz, 1H), 4.07-3.95 (m, 3H), 3.92-3.85 (m, 1H), 3.74-3.67 (m, 1H), 3.48-3.39 (m, 1H), 2.20 (t, J=6.8 Hz, 2H), 2.11 (s, 3H), 2.00 (s, 3H), 1.90 (s, 3H), 1.77 (s, 3H), 1.55-1.45 (m, 4H).

(1-1-2) Synthesis of M-11-T3:

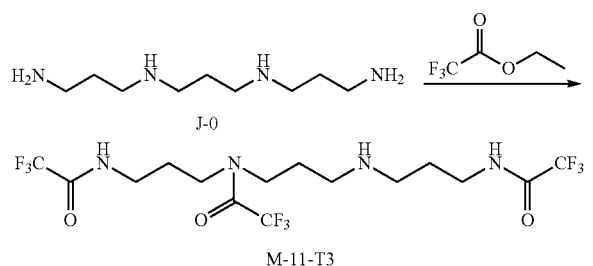

J-0 (1.883 g, 10 mmol, purchased from Alfa Aesar) was dissolved in 25 ml of acetonitrile, added with triethylamine (4.048 g, 40 mmol), and cooled to 0° C. in an ice water bath. Ethyl trifluoroacetate (5.683 g, 40 mmol) was added to react for 22 hours at room temperature. The solvent was evaporated under reduced pressure, and the residue was foam-dried in a vacuum oil pump for 18 hours to give 5.342 g of crude solid product M-11-T3, which was directly used in subsequent reaction without further purification. MS m/z: C15H22F9N4O3, [M+H]+, calcd: 477.35, measured: 477.65.

(1-1-3) Synthesis of M-11-T3-Tr:

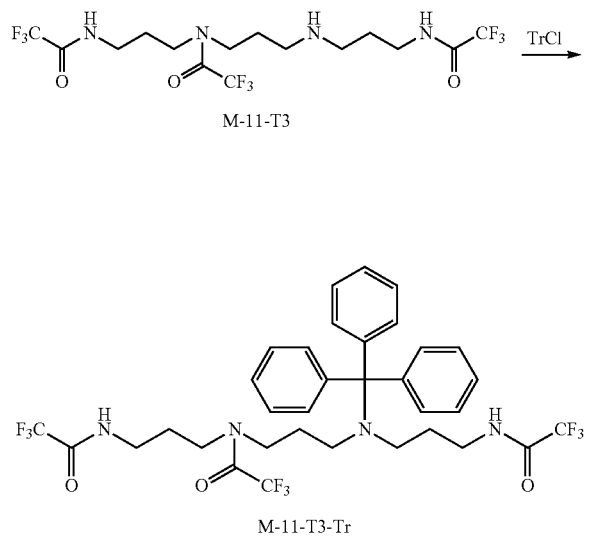

The crude product M-11-T3 (5.342 g, 10 mmol) was dissolved in 50 ml of dichloromethane. The reaction solution was added with TrCl (3.345 g, 12 mmol) and triethylamine (1.518 g, 15 mmol) to react for 20 hours under stirring at room temperature. The reaction solution was washed twice, each with 20 ml of saturated sodium bicarbonate and once with 20 ml of saturated brine. The organic phase was dried with anhydrous sodium sulfate and filtered. The organic solvent was evaporated under reduced pressure, and the residue was foam-dried in a vacuum oil pump overnight to give 7.763 g of crude solid product M-11-T3-Tr. MS m/z: C34H36F9N4O3, [M+Na]+, calcd: 741.25, measured: 741.53. The crude solid product M-11-T3-Tr was then used in the next step for synthesis of M-18-Tr without purification.

(1-1-4) Synthesis of M-18-Tr:

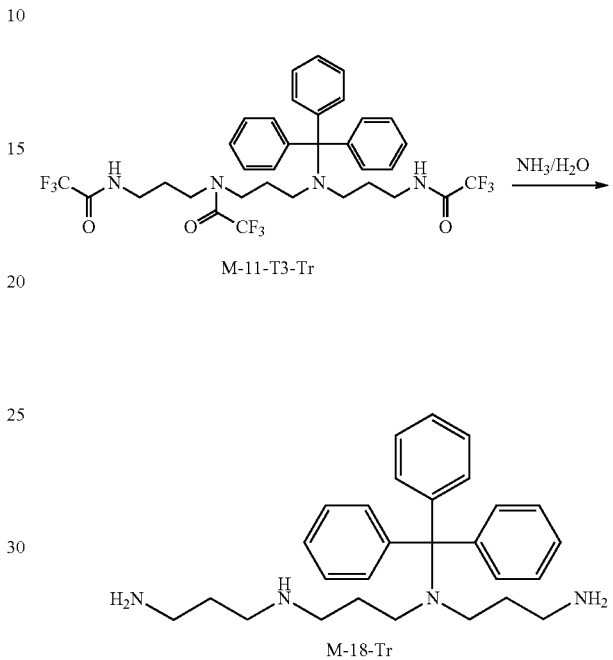

The crude product M-11-T3-Tr (7.763 g, 10 mmol) obtained in step (1-1-3) was dissolved in 100 ml of methanol, and added with 100 ml of aqueous methylamine solution (40 wt %) to react for 23 hours under stirring at 50° C. Insoluble particles were removed by filtration. The solvent was evaporated under reduced pressure, and to the residue was added with 200 ml of mixed solvent of dichloromethane:methanol in a volume ratio of 1:1, washed with 50 ml of saturated sodium bicarbonate. The aqueous phase was extracted three times, each with 50 ml of dichloromethane (DCM). All organic phases were combined, dried with anhydrous sodium sulfate and filtered. The solvent was evaporated under reduced pressure, and the residue was foam-dried in a vacuum oil pump overnight, and purified by using a normal phase silica gel column, 200-300 mesh. The column was packed with petroleum ether, added with 1 wt % triethylamine for neutralizing the acidity of silica gel, and eluted with a gradient elution dichloromethane:methanol:aqueous ammonia (25 wt %)=1:1:0.05-1:1:0.25. The eluate was collected, the solvent was evaporated under reduced pressure, and the residue was foam-dried in a vacuum oil pump to give 2.887 g of pure product M-18-Tr. $^1$H NMR (400 MHz, DMSO) δ7.47-7.39 (m, 6H), 7.32-7.24 (m, 6H), 7.19-7.12 (m, 3H), 2.60-2.47 (m, 4H), 2.46-2.19 (m, 13H), 1.70-1.55 (m, 4H), 1.40 (p, J=6.8 Hz, 2H). MS m/z: C28H39N4, [M+H]+, calcd: 431.65, measured: 432.61.

(1-1-5) Synthesis of L-5-Tr:

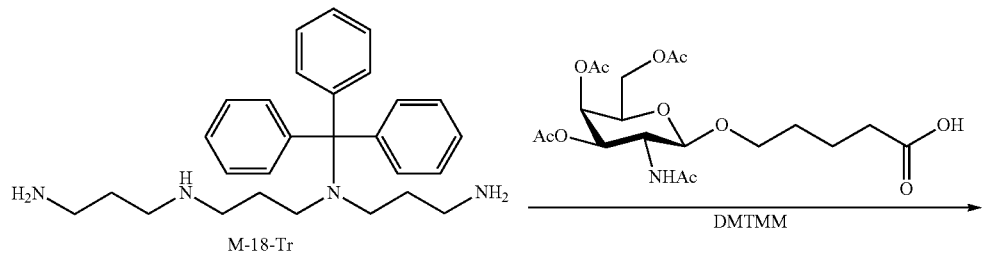

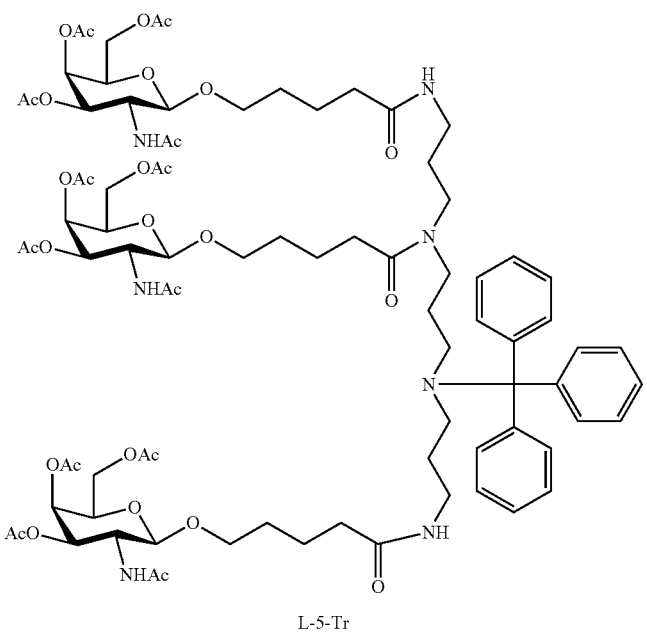

M-18-Tr (2.02 g, 4.69 mmol) obtained in step (1-1-4) and GAL-5 (6.93 g, 15.48 mmol) obtained in step (1-1-1) were mixed and dissolved in 47 ml of acetonitrile, and added with N-methylmorpholine (3.13 g, 30.96 mmol) and 4-(4,6-dimethoxytriazin-2-yl)-4-methylmorpholine hydrochloride (DMTMM, 4.28 g, 15.48 mmol) to react for 2 hours under stirring at room temperature. The reaction solution was diluted with 200 ml of dichloromethane. The organic phase was washed with 100 ml of a saturated sodium bicarbonate solution and 100 ml of saturated brine, dried with anhydrous sodium sulfate, and filtered. Then the solvent was evaporated under reduced pressure to give a crude product. The crude product was purified by using a normal phase silica gel column, 200-300 mesh. The column was packed with petroleum ether, added with 1 wt % triethylamine for neutralizing the acidity of silica gel, and eluted with a gradient elution of dichloromethane:methanol=100:5-100:7. The eluate was collected, and evaporated to dryness under reduced pressure to give 7.49 g of pure product L-5-Tr. $^1$H NMR (400 MHz, DMSO) δ7.83-7.10 (m, 4H), 7.67-7.60 (m, 1H), 7.44-7.34 (m, 6H), 7.33-7.24 (m, 6H), 7.20-7.15 (m, 3H), 5.22 (s, 3H), 4.97 (d, J=11.3 Hz, 3H), 4.49 (d, J=8.4 Hz, 3H), 4.06-3.07 (m, 9H), 3.95-3.83 (m, 3H), 3.77-3.64 (m, 3H), 3.45-3.35 (m, 3H), 3.12-2.87 (m, 8H), 2.30-2.15 (m, 3H), 2.11-1.98 (m, 22H), 1.95-1.84 (m, 11H), 1.81-1.61 (m, 14H), 1.54-1.36 (m, 14H). MS m/z: C85H119N7O30, [M+H]+, calcd: 1718.81, measured: 1718.03.

(1-1-6) Synthesis of L-8:

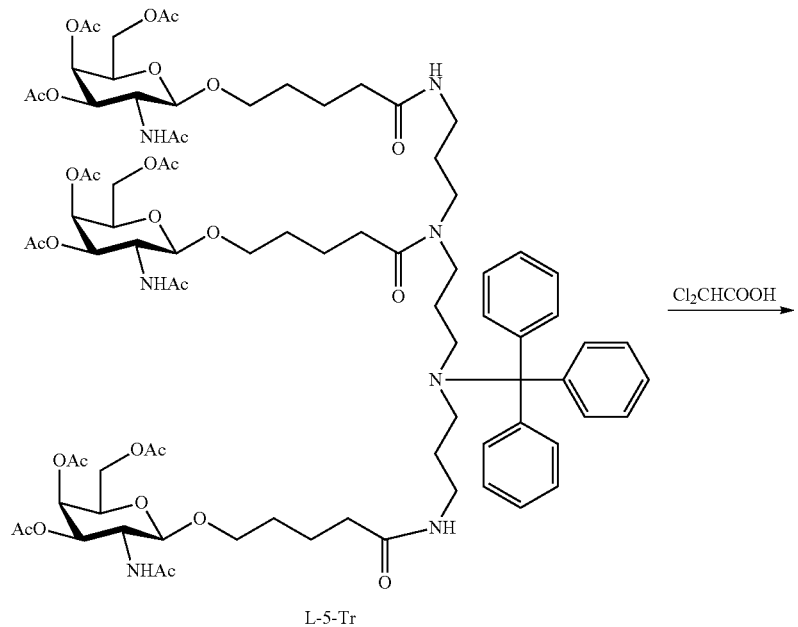

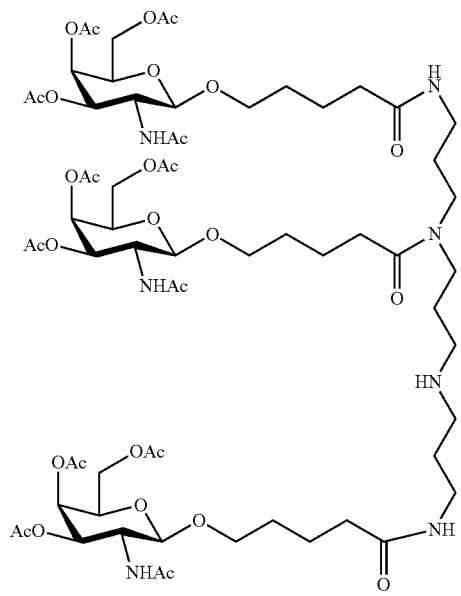

L-5-Tr (5.94 g, 3.456 mmol) obtained in step (1-1-5) was dissolved in 69 ml of dichloromethane, and added with dichloroacetic acid (13.367 g, 103.67 mmol) to react for 2 hours at room temperature. The reaction solution was diluted by adding 100 ml of dichloromethane, washed and adjusted to pH 7-8 with saturated sodium bicarbonate solution. The aqueous phase was extracted six times, each with 30 ml of dichloromethane. All organic phases were combined, dried with anhydrous sodium sulfate, and filtered. Then the solvent was evaporated under reduced pressure to give a crude product. The crude product was purified by using a normal phase silica gel column, 200-300 mesh. The column was adding with 10 wt % triethylamine for neutralizing the acidity of silica gel, equilibrated with 1 wt % triethylamine and eluted with a gradient elution of dichloromethane:methanol=100:30-100:40. The eluate was collected, and the solvent was evaporated under reduced pressure to give 4.26 g of pure product L-8. $^1$H NMR (400 MHz, DMSO) δ 7.84 (d, J=9.0 Hz, 3H), 7.27-7.23 (m, 1H), 7.13-7.18 (m, 1H), 5.22 (d, J=3.1 Hz, 3H), 4.97 (dd, J=11.3, 3.1 Hz, 3H), 4.48 (d, J=8.4 Hz, 3H), 4.09-3.98 (m, 9H), 3.88 (dd, J=19.3, 9.3 Hz, 3H), 3.75-3.66 (m, 3H), 3.44-3.38 (m, 3H), 3.17-3.30 (m, 4H), 3.10-2.97 (m, 4H), 2.35-2.20 (m, 6H), 2.15-2.08 (m, 9H), 2.07-1.98 (m, 13H), 1.94-1.87 (m, 9H), 1.81-1.74 (m, 9H), 1.65-1.42 (m, 18H). MS m/z: $C_{85}H_{119}N_7O_{30}$, [M+H]+, calcd: 1477.59, measured: 1477.23.

(1-1-7a) Synthesis of A-1

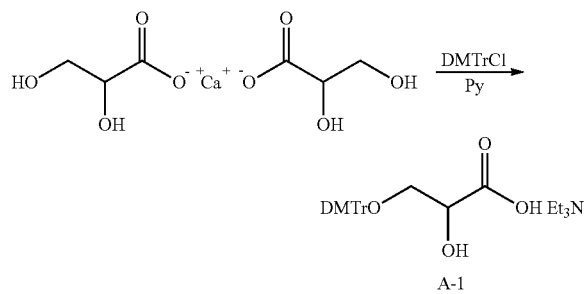

A-1

DMTrCl (4,4'-dimethoxytrityl chloride, 38.12 g, 112.5 mmol) was dissolved in 450 ml of anhydrous pyridine, and added with calcium DL-glycerate hydrate (12.88 g, 45.0 mmol) to react for 22 hours at 45° C. The reaction solution was filtered. The residue was rinsed with 200 ml of DCM, and the filtrate was concentrated to dryness under reduced pressure. The residue was redissolved in 500 ml of dichloromethane and washed twice, each with 200 ml of 0.5 M triethylamine phosphate (pH=7-8). The aqueous phase was extracted twice, each with 200 ml of dichloromethane. All organic phases were combined, dried with anhydrous sodium sulfate, and filtered. The solvent was evaporated under reduced pressure, and the residue was purified by using a normal phase silica gel column, 200-300 mesh, eluted with a gradient elution of petroleum ether:ethyl acetate:dichloromethane:methanol=1:1:1:0.35-1:1:1:0.55. The eluate was collected, and the solvent was evaporated under reduced pressure. The residue was redissolved in 500 ml of dichloromethane, and washed once with 200 ml of 0.5 M triethylamine phosphate. The aqueous phase isolated was extracted twice, each with 200 ml of dichloromethane. All organic phases were combined, dried with anhydrous sodium sulfate, and filtered. The solvent was evaporated under reduced pressure, and the residue was subjected to a reduced pressure in a vacuum oil pump to dryness overnight to give 20.7 g of product A-1 as a white solid. $^1$H NMR (400 MHz, DMSO-$d_6$) δ 7.46 (ddd, J=6.5, 2.3, 1.1 Hz, 1H), 7.40-7.28 (m, 7H), 6.89-6.81 (m, 4H), 4.84 (d, J=5.0 Hz, 1H), 4.36-4.24 (m, 1H), 4.29 (s, 6H), 3.92 (dd, J=12.4, 7.0 Hz, 1H), 3.67 (dd, J=12.3, 7.0 Hz, 1H), 2.52 (q, J=6.3 Hz, 6H), 1.03 (t, J=6.3 Hz, 9H). MS m/z: C24H23O6, [M−H]−, calcd: 407.15, measured: 406.92.

(1-1-7b) Synthesis of L-7:

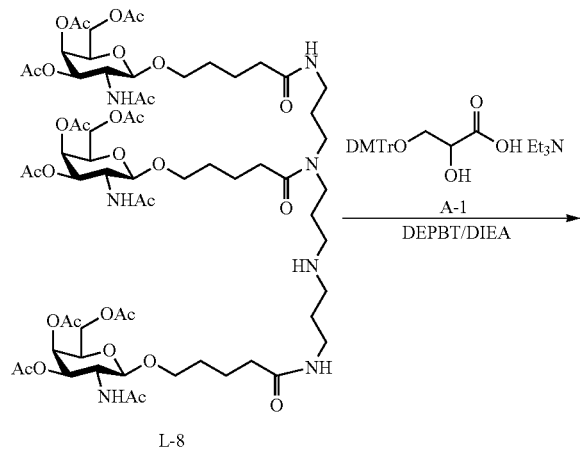

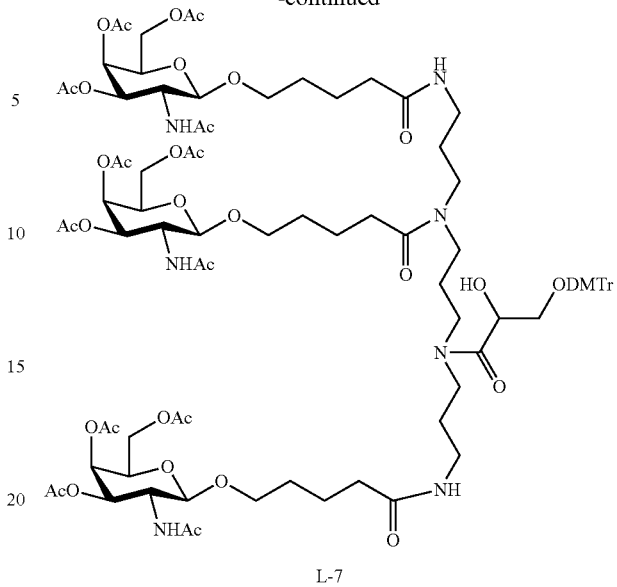

L-7

L-8 (2.262 g, 1.532 mmol) obtained in step (1-1-6) and A-1 (2.342 g, 4.596 mmol) obtained in step (1-1-7a) were mixed and dissolved in 16 ml of dichloromethane, added with 3-(diethoxyphosphoryloxy)-1,2,3-benzotrizin-4(3H)-one (DEPBT, 1.375 g, 4.596 mmol), and further added with diisopropylethylamine (1.188 g, 9.191 mmol) to react for 2 hours under stirring at 25° C. The organic phase was washed with 10 ml of saturated sodium bicarbonate. The aqueous phase was extracted three times, each with 10 ml of dichloromethane. The organic phase was washed with 10 ml of saturated brine, and the aqueous phase was extracted twice, each with 10 ml of dichloromethane, and the organic phases were combined, dried with anhydrous sodium sulfate and filtered. The solvent was evaporated under reduced pressure, and the residue was foam-dried overnight in a vacuum oil pump to give 4.900 g of crude product. The crude product was subjected to a column purification. The column was filled with 120 g normal phase silica gel, 200-300 mesh, added with 20 ml triethylamine for neutralizing the acidity of silica gel. The column was equilibrated with petroleum ether containing 1 wt % triethylamine and eluted with a gradient elution of petroleum ether:ethyl acetate:dichloromethane:N,N-dimethylformamide=1:1:1:0.5-1:1:1:0.6. The eluate was collected, and the solvent was evaporated under reduced pressure to give 2.336 g of pure product L-7. $^1$H NMR (400 MHz, DMSO) δ7.90-7.78 (m, 4H), 7.75-7.64 (m, 1H), 7.38-7.18 (m, 9H), 6.91-6.83 (m, 4H), 5.25-5.10 (m, 4H), 4.97 (dd, J=11.2, 3.2 Hz, 3H), 4.48-4.30 (m, 4H), 4.02 (s, 9H), 3.93-3.84 (m, 3H), 3.76-3.66 (m, 9H), 3.45-3.35 (m, 3H), 3.24-2.98 (m, 10H), 2.30-2.20 (m, 2H), 2.11-1.88 (m, 31H), 1.80-1.40 (m, 28H).MS m/z: C90H128N7O35, [M−DMTr]+, calcd: 1564.65, measured: 1564.88.

(1-1-8) Synthesis of L-9 Conjugating Molecule:

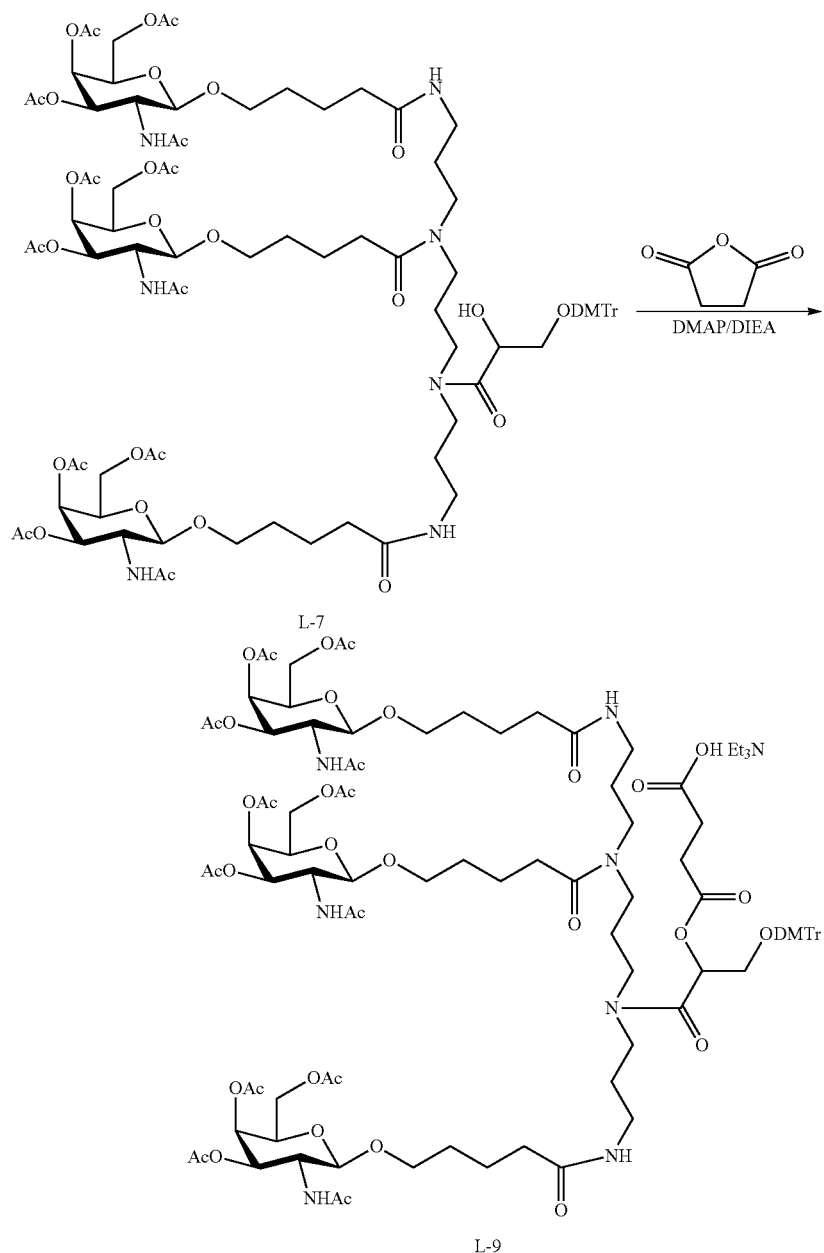

L-7 (2.300 g, 1.26 mmol) obtained in step (1-1-7b), succinic anhydride (0.378 g, 3.78 mmol) and 4-dimethyl-aminopyridine (DMAP, 0.462 g, 3.78 mmol) were mixed and dissolved in 13 ml of dichloromethane, further added with diisopropylethylamine (DIEA, 0.814 g, 6.30 mmol), and stirred for 24 hours at 25° C. The reaction solution was washed with 5 ml of 0.5 M triethylamine phosphate. The aqueous phase was extracted three times, each with 5 ml of dichloromethane. All organic phases were combined, and evaporated under reduced pressure to give 2.774 g of crude product. The crude product was subjected to a column purification. The column was filled with 60 g normal phase silica gel, 200-300 mesh, added with 1 wt % triethylamine for neutralizing the acidity of silica gel. The column was equilibrated with dichloromethane and eluted with a gradient elution of 1 wt % triethylamine-containing dichloromethane:methanol=100:18-100:20. The eluate was collected, and the solvent was evaporated under reduced pressure to give 1.874 g of pure product of L-9 conjugating Molecule. $^1$H NMR (400 MHz, DMSO) δ 8.58 (d, J=4.2 Hz, 1H), 7.94-7.82 (m, 3H), 7.41-7.29 (m, 5H), 7.22 (d, J=8.1 Hz, 5H), 6.89 (d, J=8.3 Hz, 4H), 5.49-5.37 (m, 1H), 5.21 (d, J=3.0 Hz, 3H), 4.97 (d, J=11.1 Hz, 3H), 4.49 (d, J=8.2 Hz, 3H), 4.02 (s, 9H), 3.88 (dd, J=19.4, 9.4 Hz, 3H), 3.77-3.65 (m, 9H), 3.50-3.39 (m, 6H), 3.11-2.90 (m, 5H), 2.61-2.54 (m, 4H), 2.47-2.41 (m, 2H), 2.26-2.17 (m, 2H), 2.15-1.95 (m, 22H), 1.92-1.84 (m, 9H), 1.80-1.70 (m, 10H), 1.65-1.35 (m, 17H), 1.31-1.19 (m, 4H), 0.96 (t, J=7.1 Hz, 9H). MS m/z: C94H132N7O38, [M-DMTr]+, calcd: 1664.72, measured: 1665.03.

(1-1-9) Synthesis of Compound L-10:

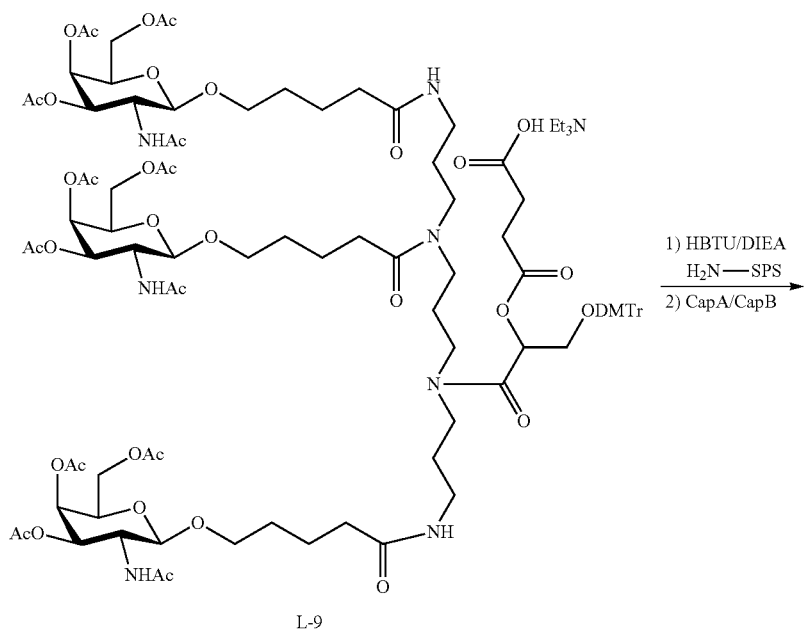

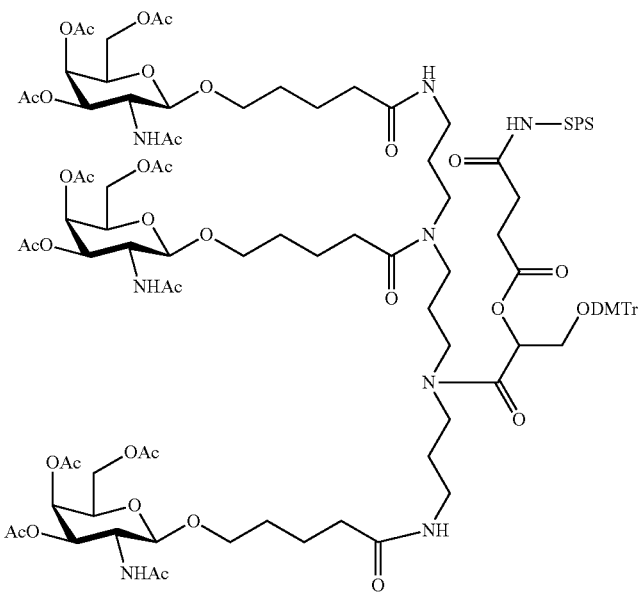

In this step, a compound L-10 was prepared by linking the L-9 Conjugating Molecule to a solid phase support.

The L-9 Conjugating Molecule (0.233 g, 0.1126 mmol) obtained in step (1-1-8), O-benzotriazol-tetramethyluronium hexafluorophosphate (HBTU, 0.064 g, 0.1689 mmol) and diisopropylethylamine (DIEA, 0.029 g, 0.2252 mmol) were mixed and dissolved in 19 ml of acetonitrile, and stirred at room temperature for 5 minutes. Aminomethyl resin (0.901 g, 100-200 mesh, amino loading: 400 µmol/g, purchased from Tianjin Nankai HECHENG S&T Co., Ltd.) was added into the reaction solution. A reaction was performed on a shaker at 25° C. and 220 rpm/min for 15 hours, followed by filtration. The residue was rinsed twice, each with 30 ml of DCM, three times, each with 30 ml of acetonitrile, and once with 30 ml of ethyl ether, and dried for 2 hours in a vacuum oil pump. Then a capping reaction was performed by adding starting materials (CapA, CapB, 4-dimethylaminopyridine (DMAP) and acetonitrile) according to the charge ratio shown in Table 2. A reaction was performed on a shaker at 25° C. and 200 rpm/min for 5 hours. The reaction solution was filtered. The residue was rinsed three times, each with 30 ml of acetonitrile, subjected to suction filteration to dryness, and the mixture was dried overnight under a reduced pressure in a vacuum oil pump to give 1.100 g of compound L-10 (i.e., L-9 Conjugating Molecule linked to a solid phase support), with a loading of 90.8 µmol/g.

TABLE 2

The charge ratio of capping reaction

| Starting Materials | Amount | Level | Lot No. | Manufacturer |
|---|---|---|---|---|
| CapA | 20 ml | — | — | — |
| CapB | 2.3 ml | — | — | — |
| DMAP | 0.01 g | analytical pure | I1422139 | Aladdin |
| acetonitrile | 2.3 ml | spectroscopic pure | O15161001 | CINC (Shanghai) Co., Ltd | wherein CapA and CapB are solutions of capping reagents. CapA is a solution of 20% by volume of N-methylimidazole in a mixture of pyridine/acetonitrile, wherein the volume ratio of pyridine to acetonitrile is 3:5. CapB is a solution of 20% by volume of acetic anhydride in acetonitrile.

(1-2) Synthesis of Sense Strands of Conjugates 1-2 and 15-16

The sequences of the sense strands of Conjugates 1-2 and 15-16 are identical, and so are the preparation methods thereof.

Nucleoside monomers were linked one by one in 3' to 5' direction according to the arrangement order of nucleotides in the sense strand by the phosphoramidite solid phase method, starting the cycles from the Compound L-10 prepared in the above step. The linking of each nucleoside monomer included a four-step reaction of deprotection, coupling, capping, and oxidation or sulfurization. Therein, when a phosphate ester linkage was used between two nucleotides, a four-step reaction of deprotection, coupling, capping, and oxidation was included during linking of the latter nucleoside monomer; and when a phosphorothioate linkage was used between two nucleotides, a four-step reaction of deprotection, coupling, capping, and sulfurization was included during linking of the latter nucleoside monomer. The synthesis condition was given as follows.

The nucleoside monomers were provided in a 0.1 M acetonitrile solution. The conditions were the same for each deprotection reaction, i.e., a temperature of 25° C., a reaction time of 70 seconds, a solution of dichloroacetic acid in dichloromethane (3% v/v) as a deprotection reagent, and a molar ratio of dichloroacetic acid to the protecting group on the solid phase support of 4,4'-dimethoxytrityl of 5:1.

The conditions were the same for each coupling reaction, including a temperature of 25° C., a molar ratio of the nucleic acid sequence linked onto the solid phase support to nucleoside monomers of 1:10, a molar ratio of the nucleic acid sequence linked onto the solid phase support to a coupling reagent of 1:65, a reaction time of 600 seconds, and 0.5 M acetonitrile solution of 5-ethylthio-1H-tetrazole as a coupling reagent.

The conditions were the same for each capping reaction, including a temperature of 25° C. and a reaction time of 15 seconds. A capping reagent was a mixed solution of CapA and CapA in a molar ratio of 1:1; and a molar ratio of the capping reagent to the nucleic acid sequence linked onto the solid phase support was acetic anhydride:N-methylimidazole: the nucleic acid sequence linked onto the solid phase support=1:1:1.

The conditions were the same for each oxidation reaction, including a temperature of 25° C., a reaction time of 15 seconds, and 0.05 M iodine water as an oxidation reagent; and a molar ratio of iodine to the nucleic acid sequence linked onto the solid phase support in the coupling step was 30:1. The reaction was carried out in a mixed solvent of tetrahydrofuran:water:pyridine=3:1:1.

The conditions were the same for each sulfurization reaction, including a temperature of 25° C., a reaction time of 300 seconds, and xanthane hydride as a sulfurization reagent; a molar ratio of the sulfurization reagent to the nucleic acid sequence linked onto the solid phase support in the coupling step was 120:1; the reaction was carried out in a mixed solvent of acetonitrile:pyridine=1:1

The conditions for cleavage and deprotection were as follows. The synthesized nucleotide sequence linked to the support was added into 25 wt % aqueous ammonia to react for 16 hours at 55° C., and the aqueous ammonia was used in an amount of 0.5 ml/μmol. The liquid was removed, and the residue was concentrated in vacuum to dryness.

Purification and desalination: purification of the nucleic acid was achieved by using a preparative ion chromatography column (Source 15Q) with a gradient elution of NaCl. Specifically, eluent A: 20 mM sodium phosphate (pH 8.1), solvent: water/acetonitrile=9:1 (v/v); eluent B: 1.5 M sodium chloride, 20 mM sodium phosphate (pH 8.1), solvent:water/acetonitrile=9:1 (v/v); elution gradient: the ratio of eluent A:eluent B=100:0-50:50. The eluate was collected, combined and desalted by using a reverse phase chromatography column. The specific condition included that a Sephadex column was used for desalination, with Sephadex-G25 as the filler and deionized water for eluting.

Detection: the purity was determined by ion exchange chromatography (IEX-HPLC); and the molecular weight was analyzed by Liquid Chromatography-Mass Spectrometry (LC-MS).

The calculated value of the molecular weight for the sense strand of Conjugate 1 was 7407.22, and the measured value was 7406.4. The calculated value of the molecular weight for the sense strand of Conjugate 2 was 7407.22, and the measured value was 7406.5. Since the measured values were in conformity with the calculated values, it was indicated that a sense strand S with the L-9 Conjugating Molecule conjugated to the 3' terminal was synthesized.

(1-3) Synthesis of Antisense strand of Conjugates 1-2

(1-3A) Preparation of an Antisense Strand of Conjugates 1-2

The antisense strands (AS) of Conjugates 1 and 2 were synthesized by starting the cycles using a universal solid phase support (UnyLinker™ loaded NittoPhase®HL Solid Supports, Kinovate Life Sciences Inc.) according to the method of solid phase phosphoramidite synthesis. The deprotection, coupling, capping, and oxidation or sulfurization reaction in the solid phase synthesis method, the cleavage and deprotection, purification and desalting were conducted under the same conditions as those in the synthesis of the sense strand.

Detection: the purity was determined by ion exchange chromatography (IEX-HPLC); and the molecular weight was analyzed by Liquid Chromatography-Mass Spectrometry (LC-MS). For Conjugate 1, the calculated value was 7208.77 and the measured value was 7208.1. For Conjugate 2, the calculated value was 7170.72 and the measured value was 7170.1. Since the measured values were in conformity with the calculated values, it was indicated that an antisense strand AS with the target sequence was synthesized.

Therein, a vinyl phosphate and 2'-methoxy modified uridine monomer (VP-Um) was synthesized according to the following method:

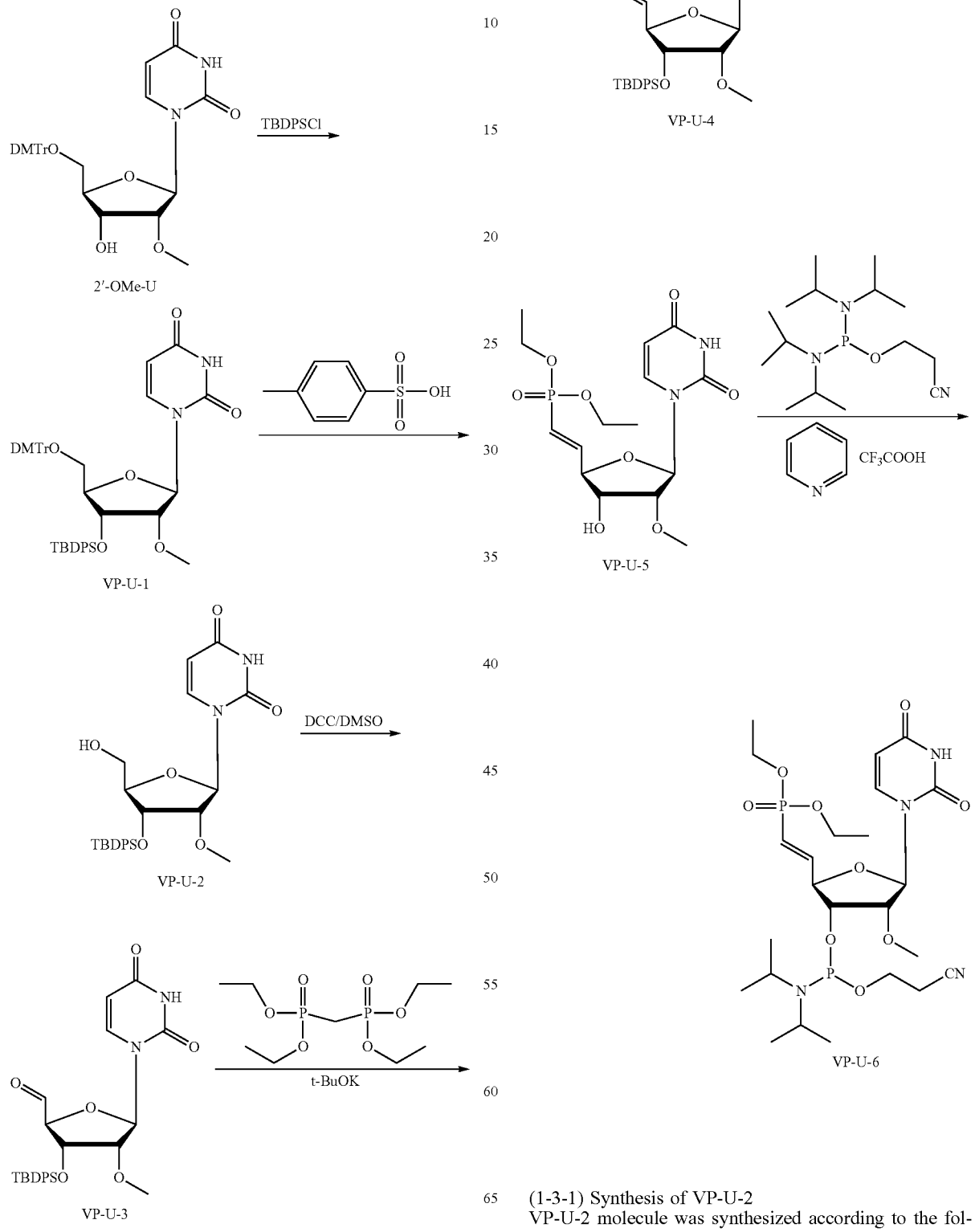

(1-3-1) Synthesis of VP-U-2

VP-U-2 molecule was synthesized according to the following method:

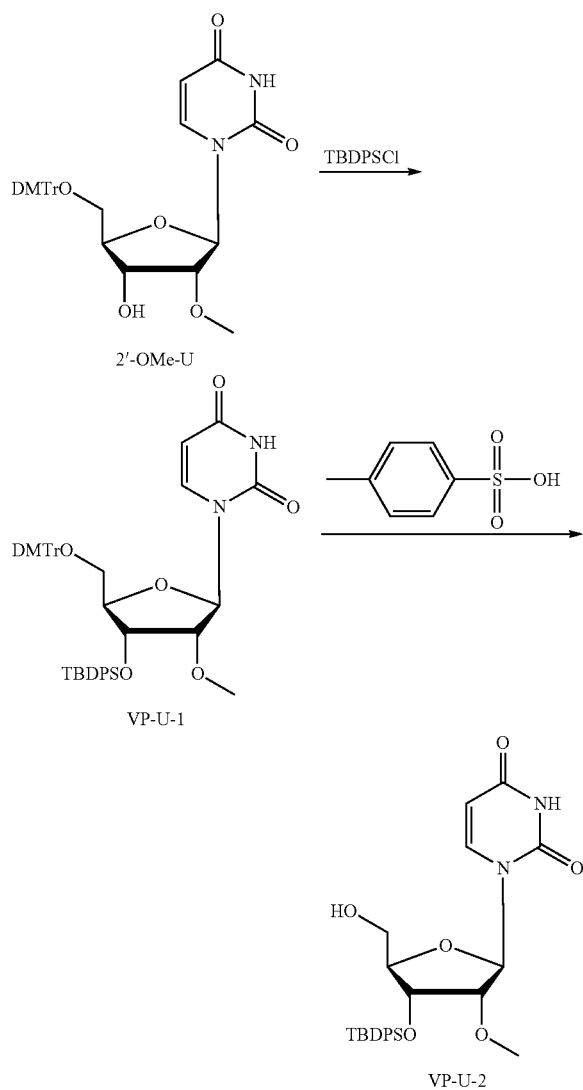

A 2'-methoxy modified uracil nucleoside (2'-OMe-U, 51.30 g, 91.6 mmol), tertbutyl diphenylchlorosilane (TBDP-SCl, 50.35 g, 183.2 mmol), and imidazole (12.47 g, 183.2 mmol) were mixed and dissolved in 450 ml of N,N-dimethylformamide (DMF) to react for 20 hours under stirring at room temperature. DMF was removed by evaporation, and the residue was dissolved with 600 ml of dichloromethane and washed with 300 ml of saturated sodium bicarbonate. The aqueous phase was extracted three times, each with 300 ml of dichloromethane. All organic phases were combined, washed with 5% oxalic acid until an aqueous phase of pH<5 was obtained. The solvent was evaporated to dryness to give a crude product VP-U-1, which was directly used in the subsequent synthesis of VP-U-2.

The crude product VP-U-1 was dissolved in 100 ml of dichloromethane, and then stirred for 10 minutes in an ice bath. 450 ml of 2% p-toluenesulfonic acid solution (with a mixed solvent of methanol and dichloromethane in a volume ratio of 3:7) pre-cooled in a refrigerator at 4° C. was added to react for 10 minutes. The reaction was quenched by addition of 200 ml of saturated sodium bicarbonate. The organic phase was washed by addition of saturated sodium bicarbonate solution to pH=8. Aqueous phases were combined and extracted twice with 200 ml of dichloromethane. All organic phases were combined and washed once with 200 ml of saturated brine. The solvent was evaporated to dryness, and the residue was purified by using a normal phase silica gel column, 200-300 mesh. The column was packed with petroleum ether and eluted with a gradient elution of petroleum ether:ethyl acetate:dichloromethane:methanol=1:1:1:0.05-1:1:1:0.25. The eluate was collected, the solvent was evaporated under reduced pressure, and the residue was foam-dried in a vacuum oil pump to give a total of 40.00 g of pure product VP-U-2. $^1$H NMR (400 MHz, DMSO-d$_6$) δ 7.96 (d, J=7.8 Hz, 1H), 7.64 (dtd, J=5.1, 4.0, 2.2 Hz, 4H), 7.41-7.30 (m, 6H), 6.79 (d, J=4.7 Hz, 1H), 5.73 (d, J=7.6 Hz, 1H), 4.94 (t, J=7.0 Hz, 1H), 4.12 (td, J=4.6, 3.9 Hz, 1H), 4.05 (dd, J=4.8, 4.0 Hz, 1H), 3.96 (t, J=4.7 Hz, 1H), 3.68 (ddd, J=11.8, 7.0, 4.6 Hz, 1H), 3.57-3.46 (m, 1H), 3.39 (s, 3H), 1.05 (s, 8H). MS m/z: C26H33N2O6Si, [M+H]+, calcd: 497.21, Measured: 497.45.

(1-3-2) Synthesis of VP-U-4:

VP-U-2 (19.84 g, 40.0 mmol), dicyclohexylcarbodiimide (DCC, 16.48 g, 80.0 mmol), pyridine (4.20 g, 53.2 mmol), and trifluoroacetic acid (6.61 g, 53.2 mmol) were mixed and dissolved in 200 ml of dimethyl sulfoxide (DMSO) to react for 20 hours under stirring at room temperature. Separately, tetraethyl methylenediphosphate (21.44 g, 74.4 mmol) was dissolved in 120 ml of THF, cooled in an ice bath, added with t-BuOK (11.36 g, 101.2 mmol) at a temperature of the ice bath to react for 10 min, warmed to room temperature to react for 0.5 hour and added into the above reaction solution over about 1 hour. The reaction was carried out for 1 hour at a temperature of the ice bath and then warmed to room temperature to react for 18 hour. The reaction was quenched by addition of water. The aqueous phase isolated was extracted three times, each with 200 ml of dichloromethane. All organic phases were combined and washed once with 200 ml of saturated brine. The solvent was evaporated to dryness, and the residue was purified by using a normal phase silica gel column, 200-300 mesh. The column was packed with petroleum ether and eluted with a gradient elution of petroleum ether:ethyl acetate=1:1-1:4. The eluate was collected, the solvent was evaporated under reduced pressure, and the residue was foam-dried in a vacuum oil pump to give a total of 14.00 g of pure product VP-U-4. $^1$H NMR (400 MHz, DMSO-$d_6$) δ 7.96 (d, J=7.8 Hz, 1H), 7.64 (dtd, J=5.1, 4.0, 2.2 Hz, 4H), 7.41-7.30 (m, 6H), 6.82-6.71 (m, 2H), 5.90 (ddd, J=25.9, 15.0, 1.0 Hz, 1H), 5.73 (d, J=7.6 Hz, 1H), 4.36-4.21 (m, 3H), 4.18 (t, J=4.9 Hz, 1H), 4.05 (ddq, J=9.7, 8.5, 6.9 Hz, 2H), 3.87 (t, J=4.8 Hz, 1H), 3.39 (s, 3H), 1.32 (td, J=6.9, 0.7 Hz, 6H), 1.05 (s, 8H). MS m/z: C31H42N2O8PSi, [M+H]+, calcd: 629.24, measured: 629.51.

(1-3-3) Synthesis of VP-U-5:

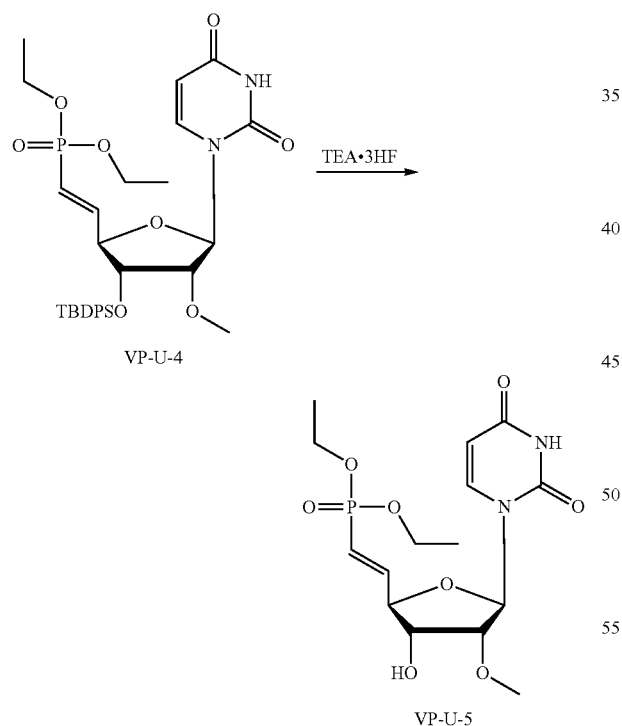

VP-U-4 (14.00 g, 22.29 mmol) was dissolved in 100 ml of tetrahydrofuran, added with triethylamine trihydrofluoride (17.96 g, 111.45 mmol), and stirred at room temperature for 20 hours to react completely. The solvent was directly evaporated to dryness and the residue was dissolved in dichloromethane; the above evaporation and dissolution steps were additionally repeated twice, each with 50 ml of dichloromethane, to give a crude product. The crude product was purified by using a normal phase silica gel column, 200-300 mesh. The column was packed with petroleum ether and eluted with a gradient elution of petroleum ether: ethyl acetate:dichloromethane:methanol=1:1:1:0.05-1:1:1: 0.25. The eluate was collected, the solvent was evaporated under reduced pressure, and the residue was foam-dried in a vacuum oil pump to give a total of 6.70 g of pure product VP-U-5. $^1$H NMR (400 MHz, DMSO-$d_6$) δ 7.96 (d, J=7.8 Hz, 1H), 6.77 (dd, J=15.0, 6.2 Hz, 1H), 5.99-5.82 (m, 2H), 5.73 (d, J=7.6 Hz, 1H), 5.27 (d, J=5.1 Hz, 1H), 5.10 (dd, J=5.3, 4.7 Hz, 1H), 4.29 (ddq, J=9.8, 8.6, 7.0 Hz, 2H), 4.17 (ddd, J=6.2, 5.2, 1.0 Hz, 1H), 4.12-3.98 (m, 3H), 3.39 (s, 2H), 1.32 (td, J=6.9, 0.6 Hz, 6H). MS m/z: C15H24N2O8P, [M+H]+, calcd: 391.13, measured: 391.38.

(1-3-4) synthesis of VP-U-6:

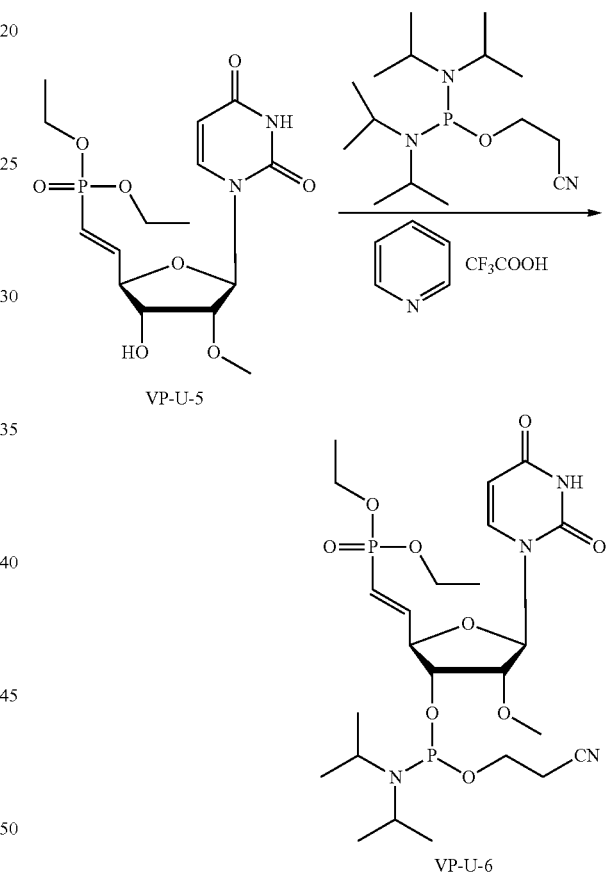

VP-U-5 (391 mg, 1.0 mmol), pyridine trifluoroacetate (0.232 g, 1.2 mmol), N-methylimidazole (0.099 g, 1.2 mmol), and bis(diisopropylamino)(2-cyanoethoxy)phosphine (0.452 g, 1.5 mmol) were added into 10 ml of anhydrous dichloromethane under argon atmosphere to react for 5 hours under stirring at room temperature. The solvent was evaporated to dryness, and then the residue was purified by column chromatography (200-300 mesh normal phase silica gel, with a gradient elution of dichloromethane:acetonitrile (containing 0.5 wt % triethylamine)=3:1-1:3). The eluate was collected and concentrated to remove the solvent to give a total of 508 mg of target product VP-U-6. $^{31}$P NMR (161 MHz, DMSO-$d_6$) δ 150.34, 150.29, 17.07, 15.50. MS m/z: C24H41N4O9P2, [M+H]+, calcd: 591.23, measured:

591.55. It was indicated that VP-U-6 was the target product VP-Um, which involved in the synthesis of RNA strands as a nucleoside monomer.

(1-3B) Preparation of an Antisense Strand of Conjugate 15

The antisense strand of Conjugate 15 only differs from that of Conjugate 1 in the first nucleotide modification at 5'-terminal. During the preparation of an antisense strand according to the method of solid phase phosphoramidite synthesis, after the linking of 2'-methoxy modified uridine monomer as the last nucleoside monomer to be linked, the monomer of Formula (CPR-I) (purchased from Suzhou GenePharma Inc. as Cat #13-2601-XX) was linked to the 5' terminal of the antisense strand by a four-step reaction of deprotection, coupling, capping, and oxidation to form a 5'-phosphate modification.

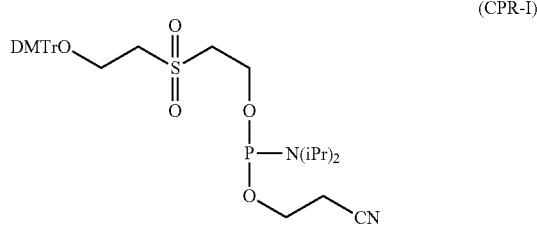

(CPR-I)

During the synthesis, the used universal solid phase support, and the conditions of deprotection, coupling, capping, oxidation or sulfurization reaction, the cleavage and deprotection, purification and desalting are the same as those used in the synthesis of the sense strand.

(1-3C) Preparation of an Antisense Strand of Conjugate 16

The same synthesis procedure as that in the synthesis of the antisense strand of Conjugate 15 was used, except that the above oxidation reaction condition was replaced with a sulfurization reaction condition in the linking of the CPR-I monomer. It was expected that an antisense strand of Conjugate 16 with a 5'-phosphorothioate modification can be prepared.

(1-4) Synthesis of Conjugates 1-2 and 15-16

For Conjugate 1, the S strand and AS strand were dissolved in water for injection to give a solution of 40 mg/mL, respectively. They were mixed in an equimolar ratio, heated for 15 min at 50° C., and then cooled to room temperature to form a double stranded structure via hydrogen bonds. The conjugate was diluted to a concentration of 0.2 mg/mL by using ultra-pure water (homemade by Milli-Q ultra-pure water instrument, with resistivity of 18.2MΩ*cm (25° C.)). The molecular weight was measured by Liquid Chromatography-Mass Spectrometry (LC-MS, purchased from Waters Corp., model: LCT Premier). Since the measured values were in conformity with the calculated values, it was confirmed that the synthesized Conjugate 1 was the designed target double stranded nucleic acid sequence with the L-9 Conjugating Molecule.

For Conjugate 2, it was prepared by the same method and the molecular weight thereof was measured. Since the measured value was in conformity with the calculated value, it was confirmed that the synthesized Conjugate 2 was the designed target double stranded nucleic acid sequence with the L-9 Conjugating Molecule.

For Conjugates 15 and 16, annealing was conducted by the same method, and it was expected that the target conjugates can be prepared.

Conjugates 1, 2, 15 and 16 have a structure as shown by Formula (403).

Preparation Example 2

Preparation of Conjugates 3-14 and Comparative Conjugate 2

It was expected that the subject conjugates can be prepared by using the same method as that in Preparation Example 1, except that: 1) the siRNAs respectively have the sequences as shown in Table 1 corresponding to Conjugates 3-14 and Comparative Conjugate 2; and 2) in the case where the target sequence comprises unmodified nucleotide, in the cleavage and deprotection conditions, after treatment with aqueous ammonia, the product is dissolved in N-methylpyrrolidone in an amount of 0.4 ml/μmol, followed by addition of 0.3 ml/μmol of triethylamine and 0.6 ml/μmol of triethylamine trihydrofluoride, with respect to the amount of the single strand nucleic acid, thereby removing the 2'-TBDMS protection on ribose.

The conjugated siRNA sequences in the subject conjugates are shown in Table 1.

TABLE 1

| Example | No | | Sequence Direction 5'-3' | SEQ ID NO |
|---|---|---|---|---|
| Conjugate 1 | L10-siHB1M1SVP | Sense strand | UmsGmsCmUmAmUmGfCfCfUmCmAmUm CmUmUmCmUmAm | 15 |
| | | Antisense strand | VP-UmsAfsGmAmAmGfAmUmGmAmGm GmCmAfUmAfGmCmAmsGmsCm | 29 |
| Conjugate 2 | L10-siHB2M1SVP | Sense strand | UmsGmsCmUmAmUmGrCfCfUmCmAmUm CmUmUmCmUmAm | 15 |
| | | Antisense strand | VP-UmsAfsGmAmAmGfAmUmGmAmGmGm CmAfUmAfGmCmAmsUmsUm | 30 |
| Conjugate 3 | L10-siHB1M1S | Sense strand | UmsGmsCmUmAmUmGfCfCfUmCmAmUm CmUmUmCmUmAm | 15 |
| | | Antisense strand | UmsAfsGmAmAmGfAmUmGmAmGmGmCm AfUmAfGmCmAmsGmsCm | 16 |

TABLE 1-continued

| | | siRNA conjugates | | |
|---|---|---|---|---|
| Example | No | | Sequence Direction 5'-3' | SEQ ID NO |
| Conjugate 4 | L10-siHB2M1S | Sense strand | UmsGmsCmUmAmUmGfCfCfUmCmAmUm CmUmCmUmAm | 15 |
| | | Antisense strand | UmsAfsGmAmAmGfAmUmGmAmGmGmCm AfUmAfCmCmAmsUmsUm | 17 |
| Conjugate 5 | L10-siHB1M2 | Sense strand | UmGmCmUmAfUmGfGfCfUmCmAmUmCm UmUmCmUmAm | 12 |
| | | Antisense strand | UmAfGmAmAmGfAmUfGfAmGmGmCmAf UmAfGmCmAmGmCm | 13 |
| Conjugate 6 | L10-siHB2M2 | Sense strand | UmGmCmUmAfUmGfCfUmCmAmUmCmUm UmCmUmAm | 12 |
| | | Antisense strand | UmAfGmAmAmGfAmUfGfAmGmGmCmAf UmAfGmCmAmUmUm | 14 |
| Conjugate 7 | L10-siHB1M2SVP | Sense strand | UmsGmsCmUmAfUmGfCfCfUmCmAmUm CmUmCmUmAm | 18 |
| | | Antisense strand | VP-UmsAfsGmAmAmGfAmUfGfAmGmGm CmAfUmAfGmCmAmsGmsCm | 31 |
| Conjugate 8 | L10-siHB2M2SVP | Sense strand | UmsGmsCmUmAfUmGfCfCfUmCmAmUm CmUmCmUmAm | 18 |
| | | Antisense strand | VP-UmsAfsGmAmAmGfAmUfGfAmGmGm CmAfUmAfGmCmAmsUmsUm | 32 |
| Conjugate 9 | L10-siHB1M5SVP | Sense strand | UmsGmsCmUmAfUmGfCfCfUmCmAmUm CmUmCmUmAm | 18 |
| | | Antisense strand | VP-UmsAfsGmAmAmGfAmUmGmAmGmGm CmAfUmAfGmCmAmsGmsCm | 29 |
| Conjugate 10 | L10-siHB1M3SVP | Sense strand | UmsGmsCmUmAfUmGfCmCfUmCmAmUm CmUmCmUmAm | 30 |
| | | Antisense strand | VP-UmsAfsGmAmAmGfAmUmGmAfmGm GmCmAfUmAfGmCmAmsGmsCm | 29 |
| Conjugate 11 | L10-siMB1M4SVP | Sense strand | UmsGmsCmUmAmUmGfCfCfUmCmAmUm CmUmCmUmAm | 15 |
| | | Antisense strand | VP-UmsAfsGmAmAmGfAmUfGmAmGmGm CmAfUmAfGmCmAmsGmsCm | 33 |
| Conjugate 12 | L10-siHB4M1SVP | Sense strand | GmsCmsUmGmCmUmAmUmGfCfCfUmCm AmUmCmUmUmCmUmAm | 34 |
| | | Antisense strand | VP-UmsAfsGmAmAmGfAmUmGmAmGmGm CmAfUmCmCmAmGmCmsGmsCm | 35 |
| Conjugate 13 | L10-siHB1 | Sense strand | UGCUAUGCCUCAUCUUCUA | 36 |
| | | Antisense strand | UAGAAGAUGAGGCAUAGCAGC | 37 |
| Conjugate 14 | L10-siHB2 | Sense strand | UGCUAUGCCUCAUCUUCUA | 38 |
| | | Antisense strand | UAGAAGAUGAGGCAUAGCAUU | 39 |
| Conjugate 15 | L10-siHB1M1SP | Sense strand | UmsGmsCmUmAmUmGfCfCfUmCmAmUm CmUmCmUmAm | 15 |
| | | Antisense strand | P-UmsAfsGmAmAmGfAmUmGmAmGmGm CmAfUmAfGmCmAmsGmsCm | 40 |

TABLE 1-continued siRNA conjugates

| Example | No | | Sequence Direction 5'-3' | SEQ ID NO |
|---|---|---|---|---|
| Conjugate 16 | L10-siHB1M1SPs | Sense strand | UmsGmsCmUmAmUmGfCfCfUmCmAmUm CmUmUmCmUmAm | 15 |
| | | Antisense strand | Ps-UmsAfsGmAmAmGfAmUmGmAmGmGm CmAfUmAfGmCmAmsGmsCm | 41 |
| Conjugate 17 | P10-siHB2M1SVP | Sense strand | UmsGmsCmUmAmUmGFCfCfUmCmAmUm CmUmUmCmUmAm | 15 |
| | | Antisense strand | VP-UmsAfsGmAmAmGfAmUmGmAmGmGm CmAfUmAfGmCmAmsUmsUm | 30 |
| Conjugate 18 | R5-siHB2M1SVP | Sense strand | UmsGmsCmUmAmUmGfCfCfUmCmAmUm CmUmUmCmUmAm | 15 |
| | | Antisense strand | VP-UmsAfsGmAmAmGfAmUmGmAmGmGm CmAfUmAfGmCmAmsUmsUm | 30 |
| Conjugate 19 | LA5-siHB2M1SVP | Sense strand | UmsGmsCmUmAmUmGfCfCfUmCmAmUm CmUmUmCmUmAm | 15 |
| | | Antisense strand | VP-UmsAfsGmAmAmGfAmUmGmAmGmGm CmAfUmAfGmCmAmsUmsUm | 30 |
| Conjugate 20 | LB5-siHB2M1SVP | Sense strand | UmsGmsCmUmAmUmCfCfCfUmCmAmUm CmUmUmCmUmAm | 15 |
| | | Antisense strand | VP-UmsAfsGmAmAmGfAmUmGmAmGmGm CmAfUmAfGmCmAmsUmsUm | 30 |
| Conjugate 21 | V8-siHB2M1SVP | Sense strand | UmsGmsCmUmAmUmGfCfCfUmCmAmUm CmUmUmCmUmAm | 15 |
| | | Antisense strand | VP-UmsAfsGmAmAmGfAmUmGmAmGmGm CmAfUmAfGmCmAmsUmsUm | 30 |
| Conjugate 22 | W8-siHB2M1SVP | Sense strand | UmsGmsCmUmAmUmGfCfCfUmCmAmUm CmUmUmCmUmAm | 15 |
| | | Antisense strand | VP-UmsAFsGmAmAmGfAmUmGmAmGmGm CmAfUmAfGmCmAmsUmsUm | 30 |
| Conjugate 23 | X8-siHB2M1SVP | Sense strand | UmsGmsCmUmAmUmGfCfCfUmCmAmUm CmUmUmCmUmAm | 15 |
| | | Antisense strand | VP-UmsAfsGmAmAmGfAmUmGmAmGmGm CmAfUmAfGmCmAmsUmsUm | 30 |
| Conjugate 24 | Z5-siHB2M1SVP | Sense strand | UmsGmsCmUmAmUmGfCfCfUmCmAmUm CmUmUmCmUmAm | 15 |
| | | Antisense strand | VP-UmsAfsGmAmAmGfAmUmGmAmGmGm CmAfUmAfGmCmAmsUmsUm | 30 |
| Conjugate 25 | FIN-siHB1M1SVP | Sense strand | UmsGmsCmUmAmUmGfCfCfUmCmAmUm CmUmUmCmUmAm | 15 |
| | | Antisense strand | VP-UmsAfsGmAmAmGfAmUmGmAmGmGm CmAfUmAfGmCmAmsGmsCm | 29 |
| Conjugate 26 | FIN-siHB2M1SVP | Sense strand | UmsGmsCmUmAmUmGfCfCfUmCmAmUm CmUmUmCmUmAm | 15 |
| | | Antisense strand | VP-UmsAfsGmAmAmGfAmUmGmAmGmGm CmAfUmAfGmCmAmsUmsUm | 30 |
| Comparative Conjugate 1 | FIN-NC | Sense strand | UUCUCCGAACGUGUCACGU | 42 |
| | | Antisense strand | ACGUGACACGUUCGGAGAAUU | 43 |

TABLE 1-continued siRNA conjugates

| Example | No | | Sequence Direction 5'-3' | SEQ ID NO |
|---|---|---|---|---|
| Comparative Conjugate 2 | L10-siHB3M1SVP | Sense strand | GmsCmsUmGmCmUmAfUfGfCmCmUmCm AmUmCmUmUmAm | 44 |
| | | Antisense strand | VP-UmsAfsAmGmAmUfGmAmGmGmCmAm UmAfGmCfAmGmCmsAmsGm | 45 |
| Comparative Conjugate 3 | FIN-siHB3M1SVP | Sense strand | GmsCmsUmGmCmUmAfUfGfCmCmUmCm AmUmCmUmUmAm | 44 |
| | | Antisense strand | VP-UmsAfsAmGmAmUfGmAmGmGmCmAm UmAfGmCfAmGmCmsAmsGm | 45 |

Preparation Example 3

Preparation of P10-siHB2M1SVP (Conjugate 17)

(3-1) Synthesis of P-10 Compounds

P-10 Compounds were synthesized according to the following process:

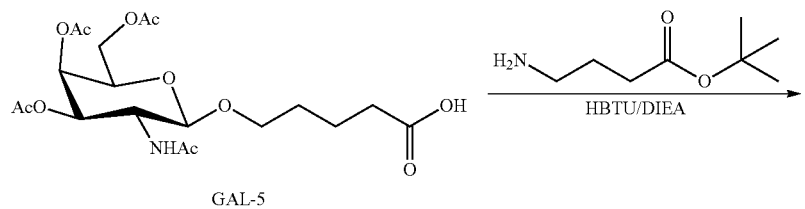

GAL-5

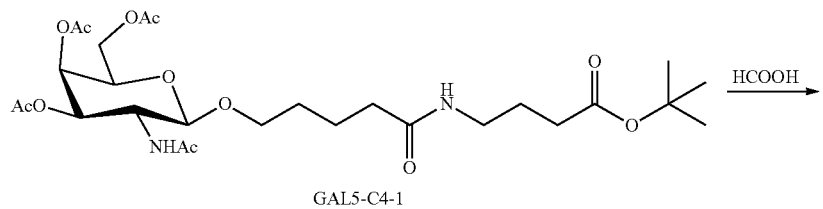

GAL5-C4-1

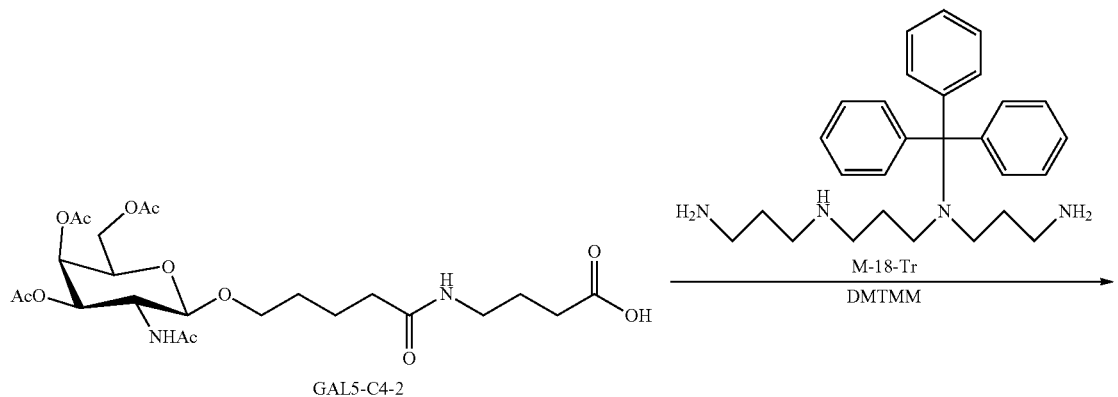

GAL5-C4-2

-continued
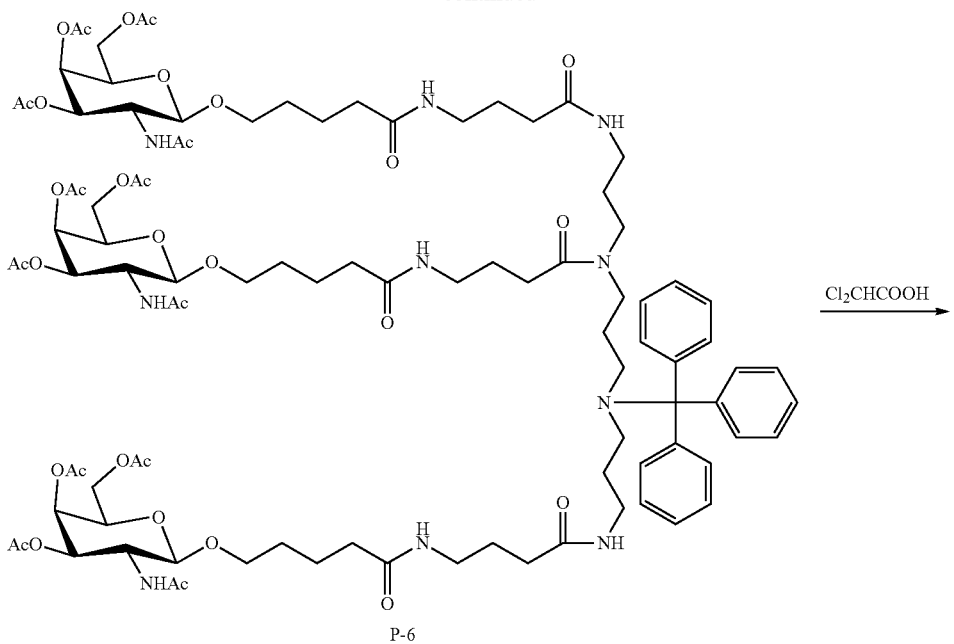
P-6
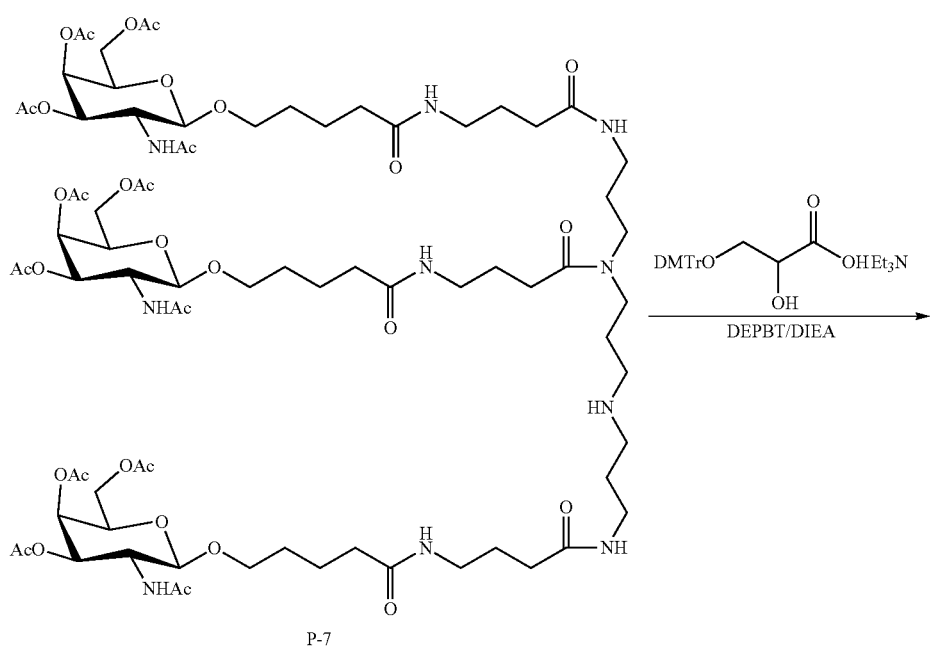
P-7

-continued
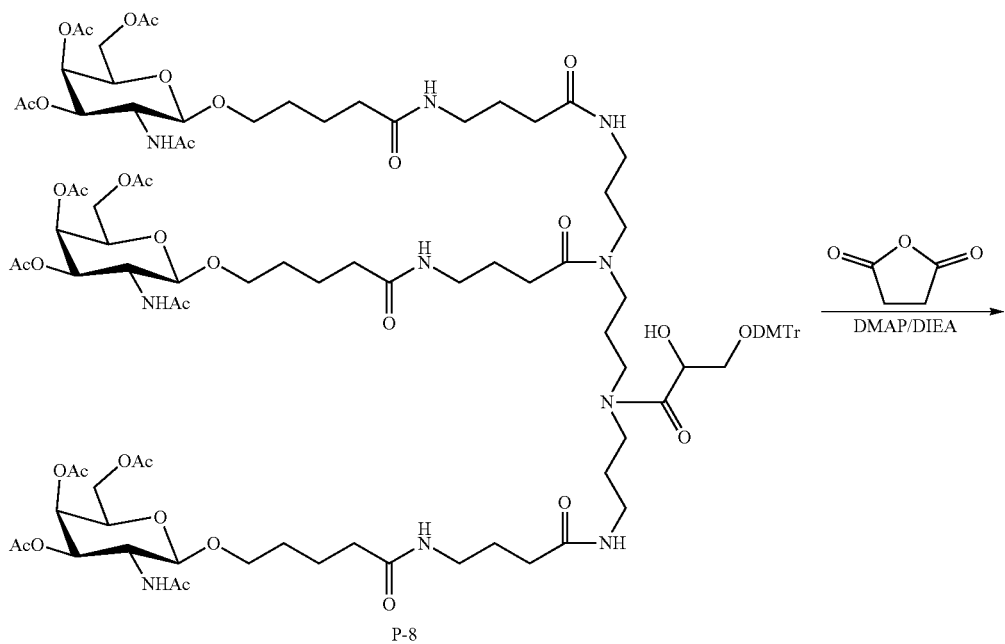
P-8
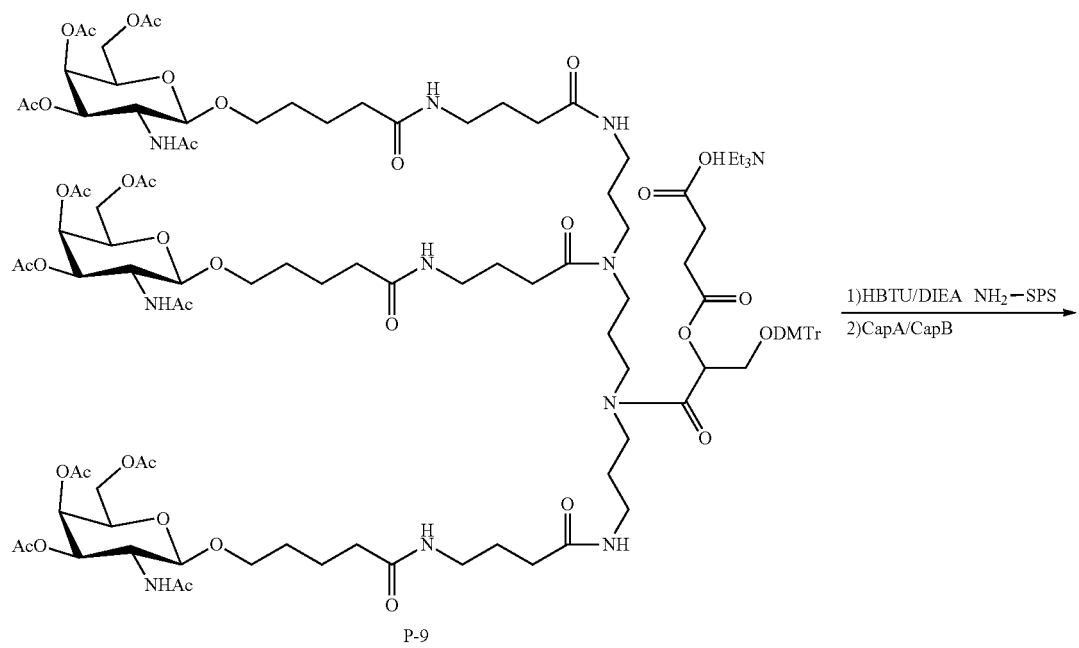
P-9

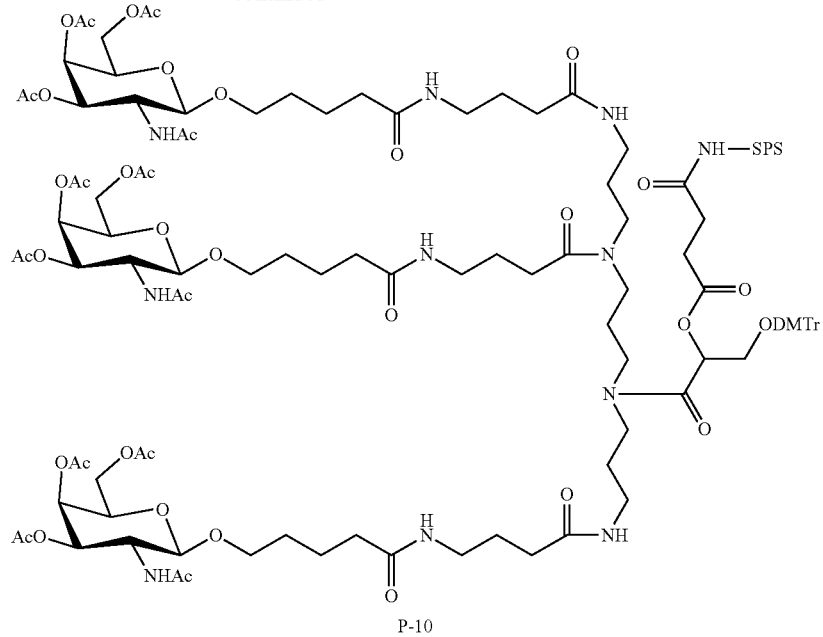

P-10

(3-1-1) Synthesis of GAL5-C4-1

GAL-5 (13.43 g, 30.0 mmol) obtained according to the method described in step (1-1-1) above, t-butyl 4-aminobutyrate hydrochloride (5.87 g, 30.0 mmol), O-benzotriazol-tetramethyluronium hexafluorophosphate (13.65 g, 36.0 mmol) and diisopropylethylamine (11.63 g, 90.0 mmol) were added into 40 ml of N,N-dimethylformamide, dissolved uniformly and then stirred at room temperature to react for 5 hours. 300 ml of saturated aqueous sodium bicarbonate solution was added into the reaction solution, extracted three times, each with 200 ml of ethyl acetate. All organic phases were combined and washed once with 200 ml of saturated brine. The organic phase was isolated and dried with anhydrous sodium sulfate. The solvent was evaporated under reduced pressure to dryness to give 30.3 g of crude product GAL5-C4-1 as oil, which was directly used in the next reaction.

(3-1-2) Synthesis of GAL5-C4-2

The crude product GAL5-C4-1 (30.3 g, 30 mmol) obtained in step (3-1-1) was dissolved in 180 ml of formic acid and stirred at room temperature to react for 16 hours. The solvent was evaporated to dryness. The residue was purified by column chromatography (200-300 mesh normal phase silica gel, with a gradient elution of dichloromethane:methanol=100:18-100:20). The eluate was collected and concentrated to remove the solvents to give a total of 14.84 g of target product GAL5-C4-2.

(3-1-3) Synthesis of P-6:

M-18-Tr (2.02 g, 4.69 mmol) obtained according to the method described in step (1-1-4) and GAL5-C4-2 (8.24 g, 15.48 mmol, combination of 2 batches) obtained in step (3-1-2) were mixed and dissolved in 47 ml of acetonitrile, added with N-methylmorpholine (3.13 g, 30.96 mmol) followed by 4-(4,6-dimethoxytriazin-2-yl)-4-methylmorpholine hydrochloride (DMTMM, 4.28 g, 15.48 mmol) to react for 2 hours under stirring at room temperature. The reaction solution was diluted with 20 ml of dichloromethane. The organic phase was washed with 10 ml of saturated sodium bicarbonate solution and 10 ml of saturated brine, respectively. All organic phases were combined, dried with anhydrous sodium sulfate, and filtered. The solvent was evaporated to dryness under reduced pressure to give a crude product, which was purified by using a normal phase silica gel column, 200-300 mesh. The column was packed with petroleum ether, added with 1 wt % triethylamine for neutralizing the acidity of silica gel, and eluted with a gradient elution of dichloromethane:methanol=100:5-100:7. The eluate was collected, and the solvent was evaporated to dryness under reduced pressure to give a total of 8.27 g of pure product P-6.

(3-1-4) Synthesis of P-7:

P-6 (6.82 g, 3.456 mmol) obtained in step (3-1-3) above was dissolved in 69 ml of dichloromethane, and added with dichloroacetic acid (13.367 g, 103.67 mmol) to react for 2 hours at room temperature. The reaction solution was diluted by adding 100 ml of dichloromethane, washed and adjusted to pH 7-8 with saturated sodium bicarbonate solution. The aqueous phase was extracted six times, each with 30 ml of dichloromethane. All organic phases were combined, dried with anhydrous sodium sulfate, and filtered. Then the solvent was evaporated to dryness under reduced pressure to give a crude product. The crude product was purified by using a normal phase silica gel column, 200-300 mesh. The column was added with 10 wt % triethylamine for neutralizing the acidity of silica gel. The column was equilibrated with 1 wt % triethylamine and eluted with a gradient elution of dichloromethane:methanol=100:30-100:40. The eluate was collected, and the solvent was evaporated to dryness under reduced pressure to give a total of 4.82 g of P-7. MS m/z: C78H127N10O33, [M+H]+, calcd: 1732.91, measured: 1735.73.

(3-1-5) Synthesis of P-8:

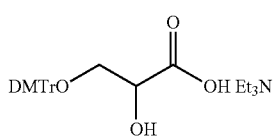

P-7 (2.653 g, 1.532 mmol) and A-1 (2.342 g, 4.596 mmol) were mixed and dissolved in 16 ml of dichloromethane, and added with 3-diethoxyphosphoryl-1,2,3-benzotriazol 4(3H)-one (DEPBT) (1.375 g, 4.596 mmol) followed by diisopropylethylamine (1.188 g, 9.191 mmol) to react for 2 hours under stirring at 25° C. The organic phase was washed with 10 ml of saturated sodium bicarbonate. The aqueous phase was extracted three times, each with 10 ml of dichloromethane. The organic phase was washed with 10 ml of saturated brine. The aqueous phase was extracted twice, each with 10 ml of dichloromethane. All the organic phases were combined, dried with anhydrous sodium sulfate and filtered. The solvent was evaporated to dryness under reduced pressure, and the residue was foam-dried overnight in a vacuum oil pump to give a crude product. The crude product was subjected to a column purification. The column was filled with 120 g normal phase silica gel, 200-300 mesh, added with 20 ml triethylamine for neutralizing the acidity of silica gel. The column was equilibrated with petroleum ether containing 1 wt % triethylamine and eluted with a gradient elution of petroleum ether:ethyl acetate:dichloromethane:N,N-dimethylformamide=1:1:1:0.5-1:1:1:0.6. The eluate was collected, and the solvent was evaporated to dryness under reduced pressure to give a total of 2.793 g of pure product P-8.

(3-1-6) Synthesis of P-9:

P-8 (490 mg, 0.231 mmol), succinic anhydride (69 mg, 0.693 mmol) and 4-dimethylaminopyridine (DMAP, 68 mg, 0.554 mmol) were mixed and dissolved in 2.3 ml of dichloromethane, and added with diisopropylethylamine (DIPEA, 149 mg, 1.155 mmol) to react for 21 hours under stirring at 25° C. The reaction solution was diluted with 50 ml dichloromethane, and then washed with 100 ml of 0.5 M triethylamine phosphate. The aqueous phase was extracted three times, each with 10 ml of dichloromethane. All organic phases were combined, and the solvent was evaporated to dryness under reduced pressure to give a crude product. The crude product was subjected to a column purification. The column was filled with 80 g normal phase silica gel, 200-300 mesh, added with 1 wt % triethylamine for neutralizing the acidity of silica gel. The column was equilibrated with dichloromethane and eluted with a gradient elution of dichloromethane containing 1 wt % triethylamine:methanol=100:18-100:20. The eluate was collected, and the solvent was evaporated to dryness under reduced pressure to give a total of 200 mg of pure product P-9 conjugating molecule. MS m/z: C106H153N10O41, [M-DMTr]+, calcd: 1921.05, measured: 1920.97.

(3-1-7) Synthesis of P-10:

P-10 was prepared by using the same method as in step (1-1-9) of Preparation Example 1, except that: P-9 conjugating molecule was used to replace L-9 conjugating molecule, thereby obtaining P-9 conjugating molecule linked to a solid phase support.

(3-2) Synthesis of P10-siHB2M1SVP Conjugate

Conjugate 17 was prepared by using the same method as those in steps (1-2), (1-3A) and (1-4) of Preparation Example 1, except that P-10 Compound was used to replace L-10 Compound to start the synthesis of a sense strand. It was expected that P10-siHB2M1SVP conjugate with a structure as shown by Formula (404) can be obtained.

Preparation Example 4

Preparation of R5-siHB2M1SVP Conjugate (Conjugate 18)

(4-1) Synthesis of R-5 Compound

R-5 Compound was synthesized by the following method:

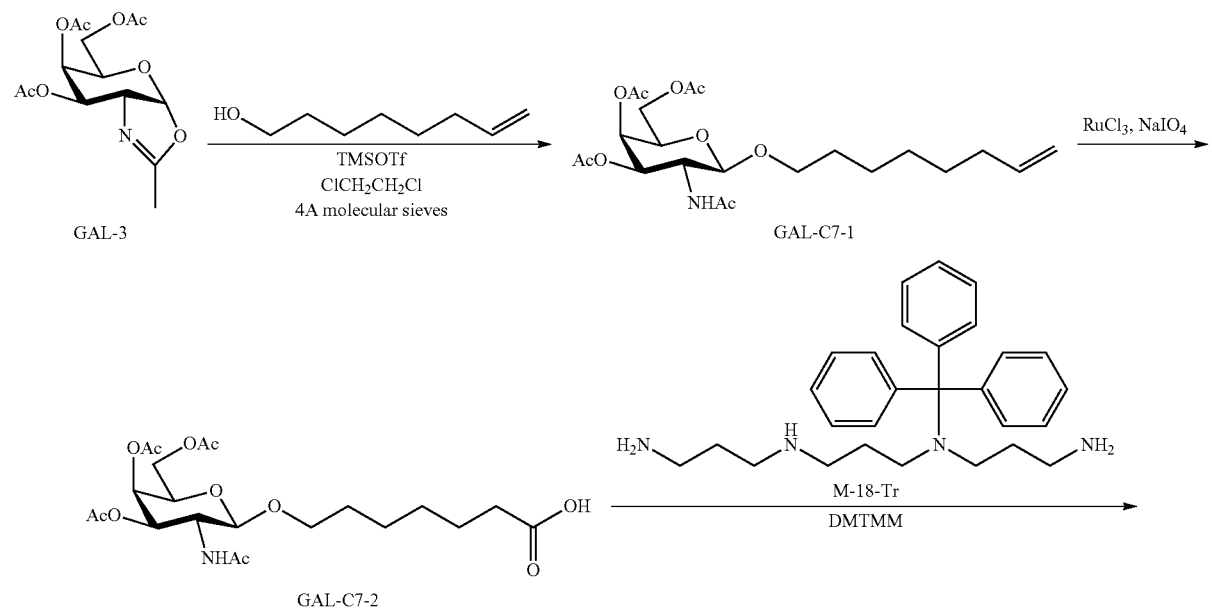

-continued
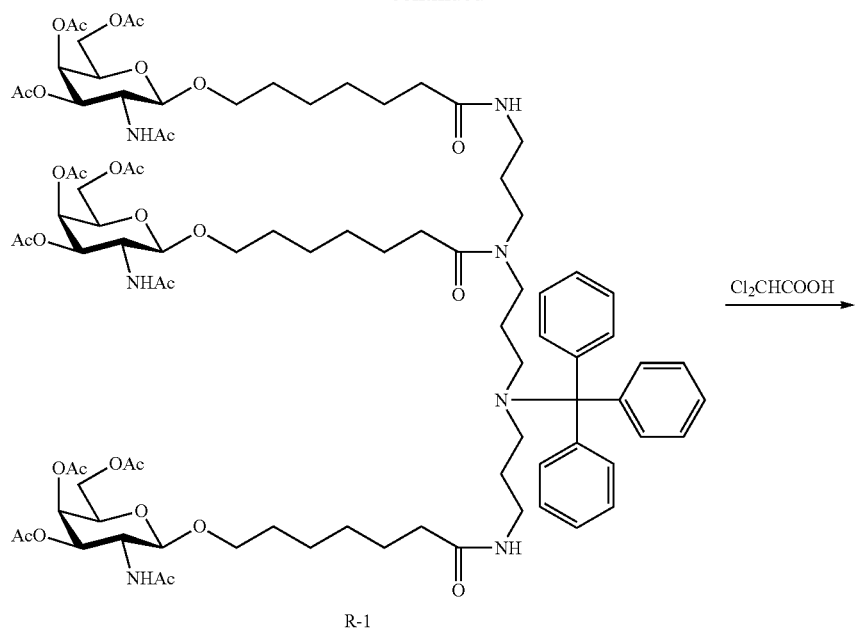
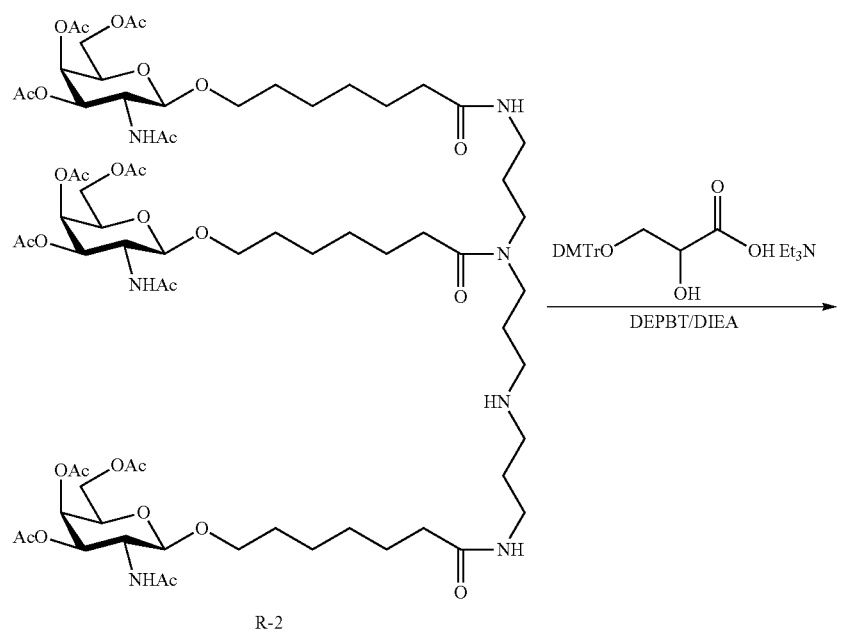

-continued
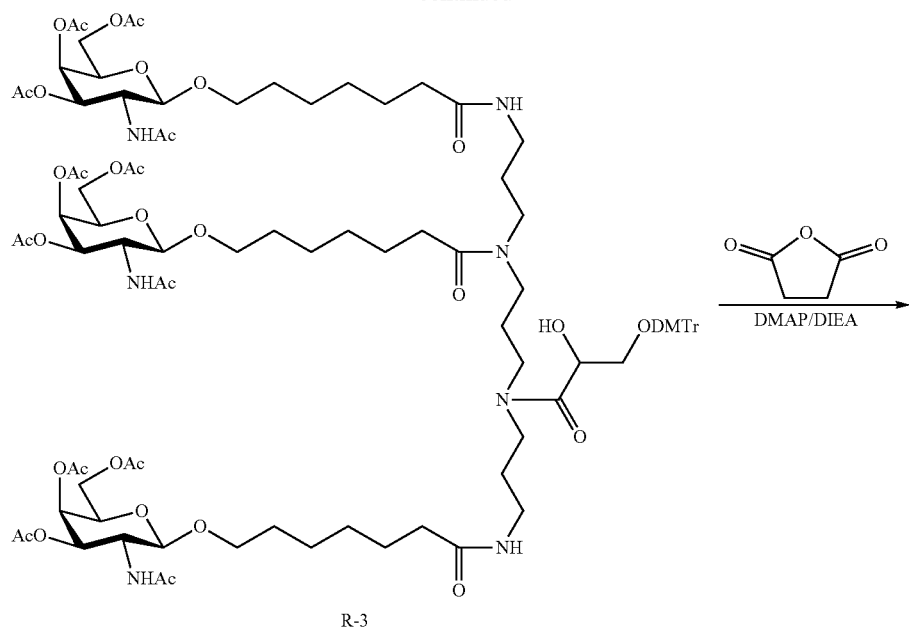
R-3
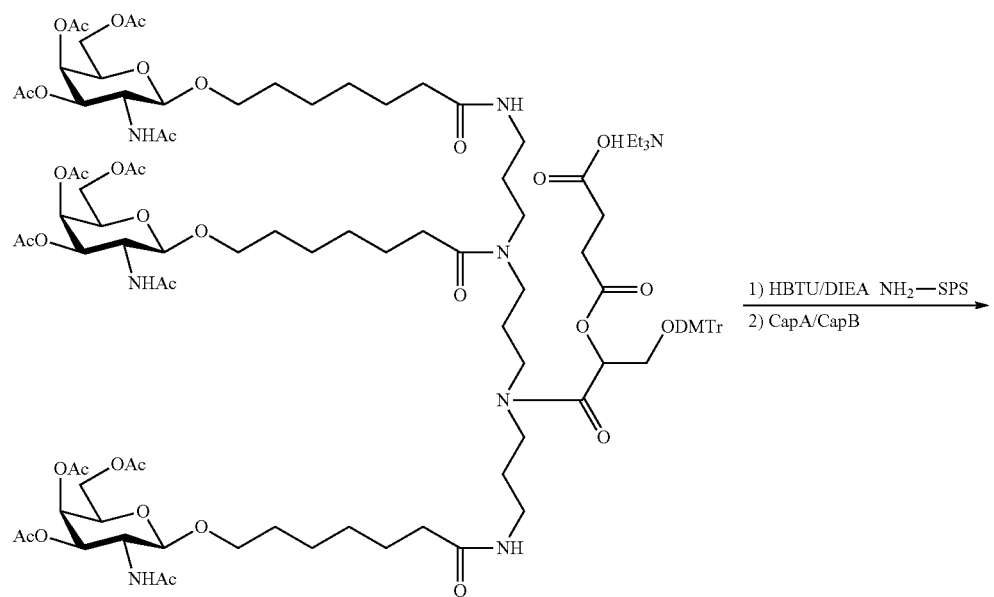
R-4

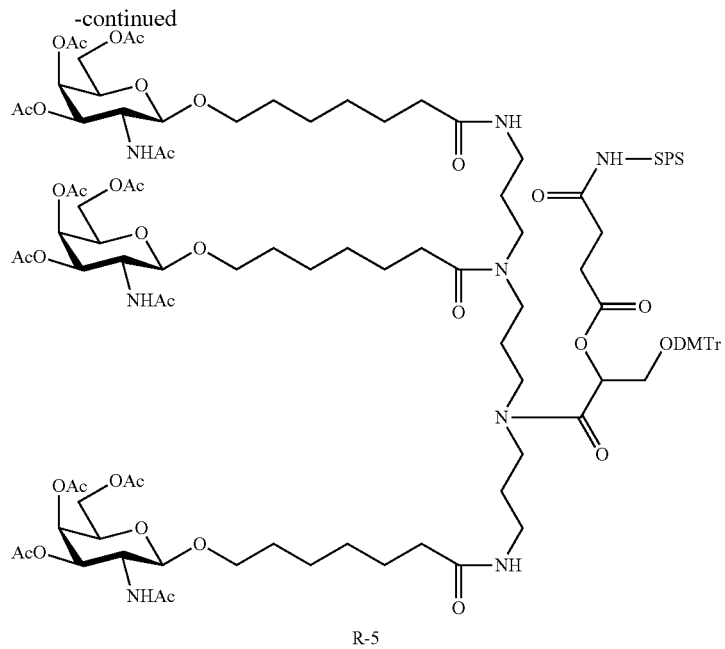

R-5

(4-1-1) Synthesis of GAL-C7-1

GAL-3 (26.4 g, 80.2 mmol) obtained according to the method described in step (1-1-1b) was dissolved in 134 ml of anhydrous 1,2-dichloroethane, and added with 60 g of 4 Å molecular sieve as a powder followed by 7-octen-1-ol (11.3 g, 88.2 mmol) to react for 10 minutes under stirring at room temperature. Trimethylsilyl trifluoromethanesulphonate (8.9 g, 40.1 mmol) was added in an ice bath and nitrogen atmosphere to react for 24 hours under stirring at room temperature. The 4 Å molecular sieve powder was removed by filtration. 500 ml of saturated aqueous sodium bicarbonate solution was added to the filtrate for washing. The organic phase was isolated. The aqueous phase was extracted once with 100 ml of dichloromethane. All organic phases were combined and washed once with 250 ml of saturated brine. The organic phase was isolated and dried with anhydrous sodium sulfate. The solvent was evaporated under reduced pressure to dryness to give 33.3 g of product GAL-C7-1 as yellow syrup, which was directly used in the next oxidation reaction without purification.

(4-1-2) Synthesis of GAL-C7-2

GAL-C7-1 (33.3 g, 72.8 mmol) obtained in step (4-1-1) was dissolved in a mixed solvent of 160 ml of dichloromethane and 160 ml of acetonitrile, added with 216 ml of water and sodium periodate solid (62.3 g, 291.2 mmol) respectively, stirred in an ice water bath for 10 minutes, and added with a catalyst ruthenium trichloride (498 mg, 2.4 mmol). The reaction was naturally warmed to room temperature and stirred for 23 hours. The reaction solution was diluted by adding 200 ml of water, stirred, and adjusted to pH 7.5 by adding saturated sodium bicarbonate. The organic phase isolated was discarded. The aqueous phase remained was extracted three times, each with dichloromethane. The organic phases were discarded. The aqueous phase was adjusted to a pH of about 3 with citric acid solid, extracted three times, each with 200 ml of dichloromethane, and the organic phases were combined, dried with anhydrous sodium sulfate. The solvent was evaporated under reduced pressure, and then the residue was purified by column chromatography (200-300 mesh normal phase silica gel, with a gradient elution of dichloromethane:methanol=100:18-100:20) to give 22.4 g of product GAL-C7-2 as a white foamy solid. MS m/z: C21H32NO11, [M+H]+, calcd: 476.50, measured: 475.94.

(4-1-3) Synthesis of R-1:

M-18-Tr (2.02 g, 4.69 mmol) obtained according to the method described in step (1-1-4) and GAL-C7-2 (7.36 g, 15.48 mmol) were mixed and dissolved in 47 ml of acetonitrile, added with N-methylmorpholine (3.13 g, 30.96 mmol) followed by 4-(4,6-dimethoxytriazin-2-yl)-4-methylmorpholine hydrochloride (DMTMM, 4.28 g, 15.48 mmol) to react for 2 hours under stirring at room temperature. The reaction solution was diluted with 200 ml of dichloromethane. The organic phase was washed with 100 ml of saturated sodium bicarbonate solution and 100 ml of saturated brine, respectively. All organic phases were combined, dried with anhydrous sodium sulfate, and filtered. The solvent was evaporated to dryness under reduced pressure to give a crude product, which was purified by using a normal phase silica gel column, 200-300 mesh. The column was packed with petroleum ether, added with 1 wt % triethylamine for neutralizing the acidity of silica gel, and eluted with a gradient elution of dichloromethane:methanol=100:5-100:7. The eluate was collected and the solvent was evaporated to dryness under reduced pressure to give 7.82 g of pure product R-1.

(4-1-4) Synthesis of R-2:

R-1 (6.23 g, 3.456 mmol) was dissolved in 69 ml of dichloromethane, and added with dichloroacetic acid (13.367 g, 103.67 mmol) to react for 2 hours at room temperature. The reaction solution was diluted by adding 100 ml of dichloromethane, washed and adjust to pH 7-8 with saturated sodium bicarbonate solution. The aqueous phase was extracted six times, each with 30 ml of dichloromethane. All organic phases were combined, dried with anhydrous sodium sulfate, and filtered. Then the solvent was evaporated to dryness under reduced pressure to give a crude product, which was purified by using a normal phase silica gel column, 200-300 mesh. The column was added with 10 wt % triethylamine for neutralizing the acidity of silica gel.

The column was equilibrated with 1 wt % triethylamine and eluted with a gradient elution of dichloromethane:methanol=100:30-100:40. The solvent was evaporated to dryness under reduced pressure to give 4.49 g of pure product R-2.

(4-1-5) Synthesis of R-3:

R-2 (2.391 g, 1.532 mmol) and A-1 (2.342 g, 4.596 mmol) were mixed and dissolved in 16 ml of dichloromethane, and added with 3-(diethoxyphosphoryloxy)-1,2,3-benzotrizin-4 (3H)-one (DEPBT, 1.375 g, 4.596 mmol), followed by diisopropylethylamine (1.188 g, 9.191 mmol) to react for 2 hours under stirring at 25° C. The organic phase was washed with 10 ml of saturated sodium bicarbonate. The aqueous phase was extracted three times, each with 10 ml of dichloromethane. The organic phase was washed with 10 ml of saturated brine. The aqueous phase isolated was extracted twice, each with 10 ml of dichloromethane, and the organic phases were combined, dried with anhydrous sodium sulfate and filtered. The solvent was evaporated to dryness under reduced pressure, and the residue was foam-dried overnight in a vacuum oil pump to give a crude product. The crude product was subjected to a column purification. The column was filled with 120 g normal phase silica gel, 200-300 mesh, added with 20 ml triethylamine for neutralizing the acidity of silica gel. The column was equilibrated with petroleum ether containing 1 wt % triethylamine and eluted with a gradient elution of petroleum ether:ethyl acetate:dichloromethane:N,N-dimethylformamide=1:1:1:0.5-1:1:1:0.6. The solvent was evaporated to dryness under reduced pressure to give 2.642 g of pure product R-3.

(4-1-6) Synthesis of R-4:

R-3 (795 mg, 0.4074 mmol), succinic anhydride (82 mg, 0.8148 mmol) and 4-dimethylaminopyridine (DMAP, 100 mg, 0.8148 mmol) were mixed and dissolved in 4 ml of dichloromethane, and added with diisopropylethylamine (DIPEA, 100 mg, 0.8148 mmol) to react for 18 hours under stirring at 25° C. The reaction solution was washed with 5 ml of 0.5 M triethylamine phosphate. The aqueous phase was extracted three times, each with 5 ml of dichloromethane. All organic phases were combined, and the solvent was evaporated to dryness under reduced pressure to give a crude product. The crude product was subjected to a column purification. The column was filled with 30 g normal phase silica gel, 200-300 mesh, added with 1 wt % triethylamine for neutralizing the acidity of silica gel. The column was equilibrated with dichloromethane and eluted with a gradient elution of dichloromethane containing 1 wt % triethylamine:methanol=100:18-100:20. The eluate was collected, and the solvent was evaporated to dryness under reduced pressure to give 505 mg of pure product of R-4 Conjugating Molecule.

(4-1-7) Synthesis of R-5

R-5 was prepared by using the same method as in step (1-1-9) of Preparation Example 1, except that: R-4 conjugating molecule was used to replace L-9 conjugating molecule, thereby obtaining R-4 conjugating molecule linked to a solid phase support.

(4-2) Synthesis of R5-siHB2M1SVP Conjugate

Conjugate 18 was prepared by using the same method as those in steps (1-2), (1-3A) and (1-4) of Preparation Example 1, except that R-5 Compound was used to replace L-10 Compound to start the synthesis of a sense strand. It was expected that $R_5$-siHB2M1SVP conjugate with a structure as shown by Formula (407) can be obtained.

Preparation Example 5

Preparation of LA5-siHB2M1SVP (Conjugate 19)

It was expected that LA-5 compound can be synthesized according to the following process route:

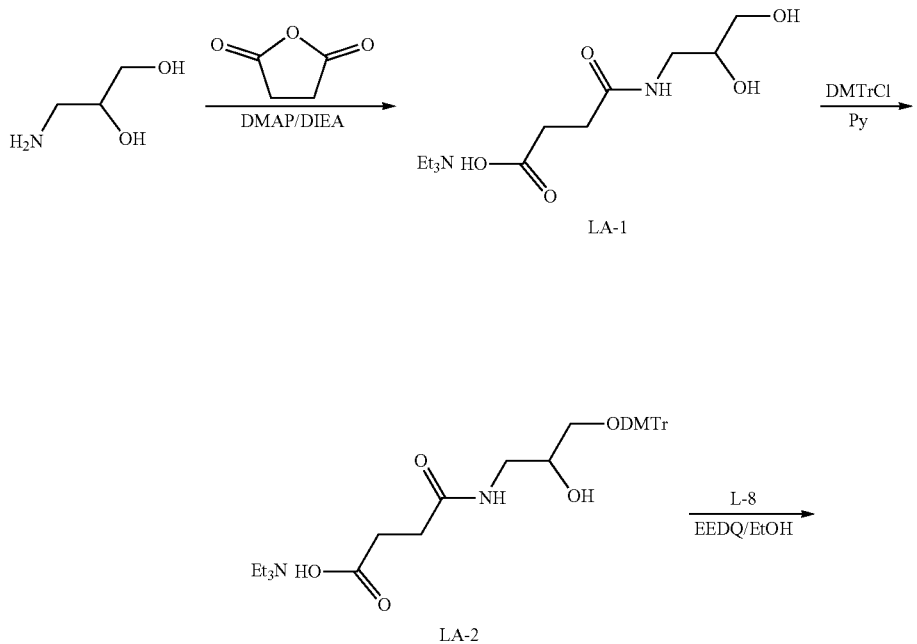

-continued
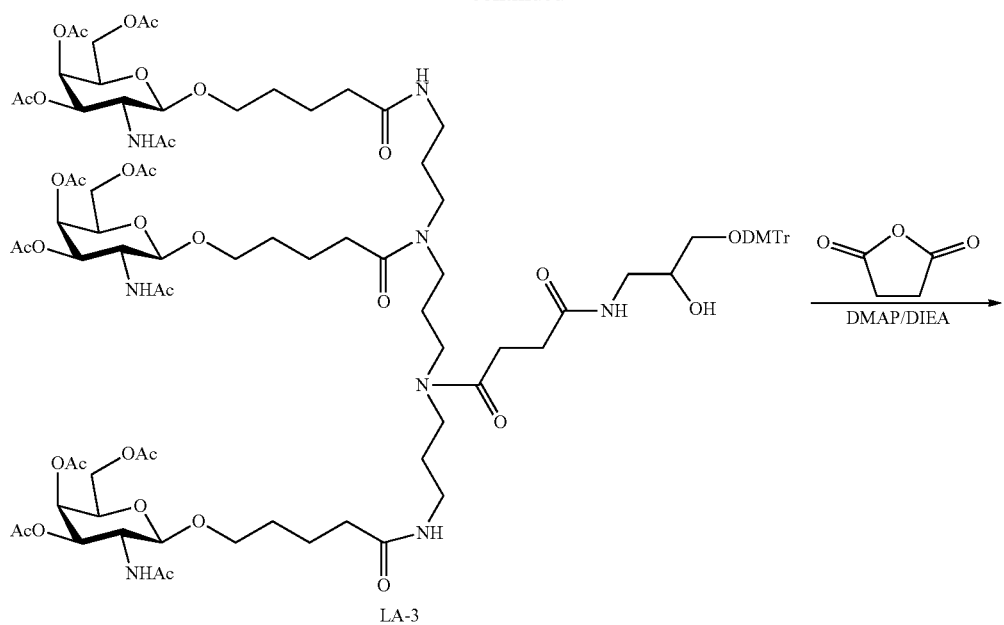
LA-3
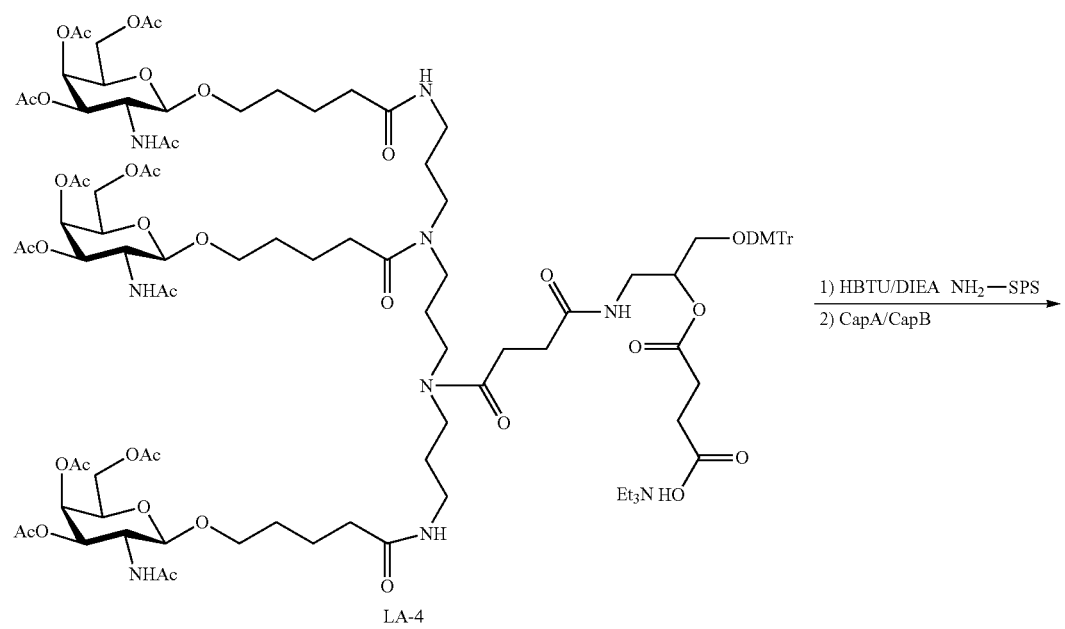
LA-4

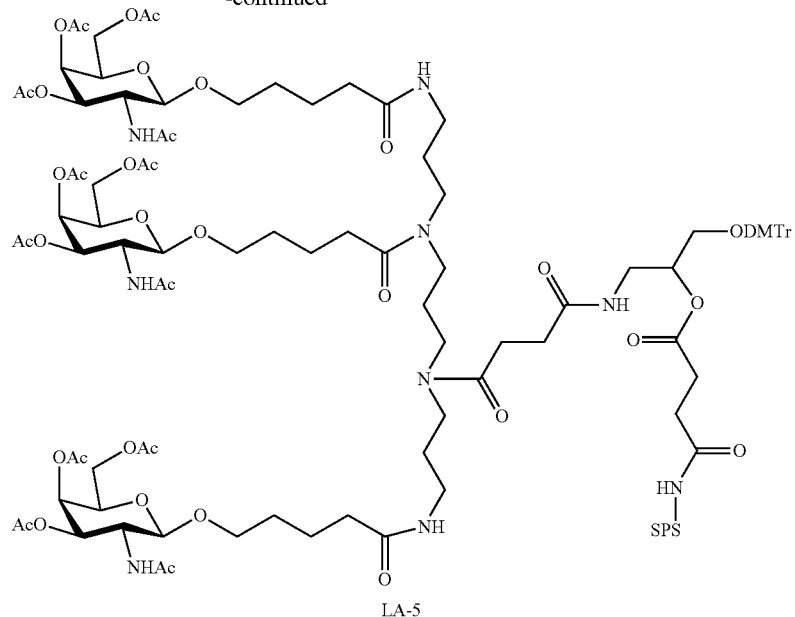

LA-5

Conjugate 19 was prepared by using the same method as those in steps (1-2), (1-3A) and (1-4) of Preparation Example 1, except that LA-5 Compound was used to replace L-10 Compound to start the synthesis of a sense strand. It was expected that LA5-siHB2M1SVP conjugate with a structure as shown by Formula (412) can be obtained.

Preparation Example 6

Preparation of LB5-siHB2M1SVP Conjugate (Conjugate 20)

(6-1) Synthesis of LB-5 Compound

LB-5 compound was synthesized according to the following process:

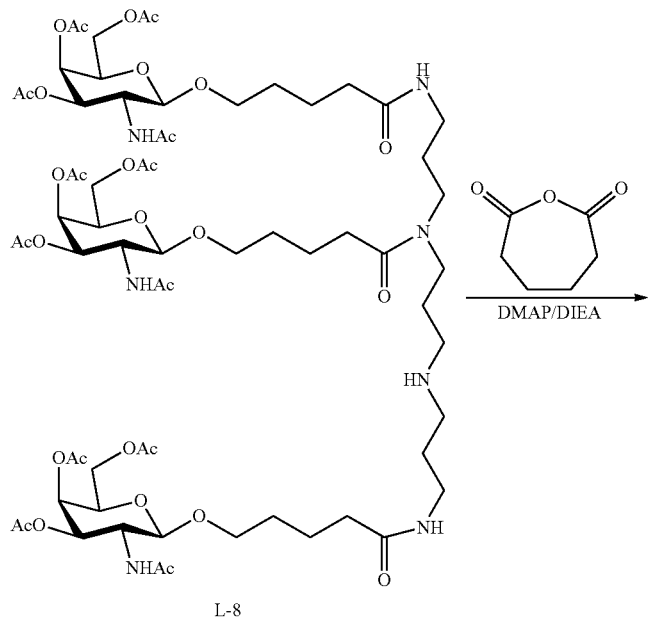

L-8

-continued
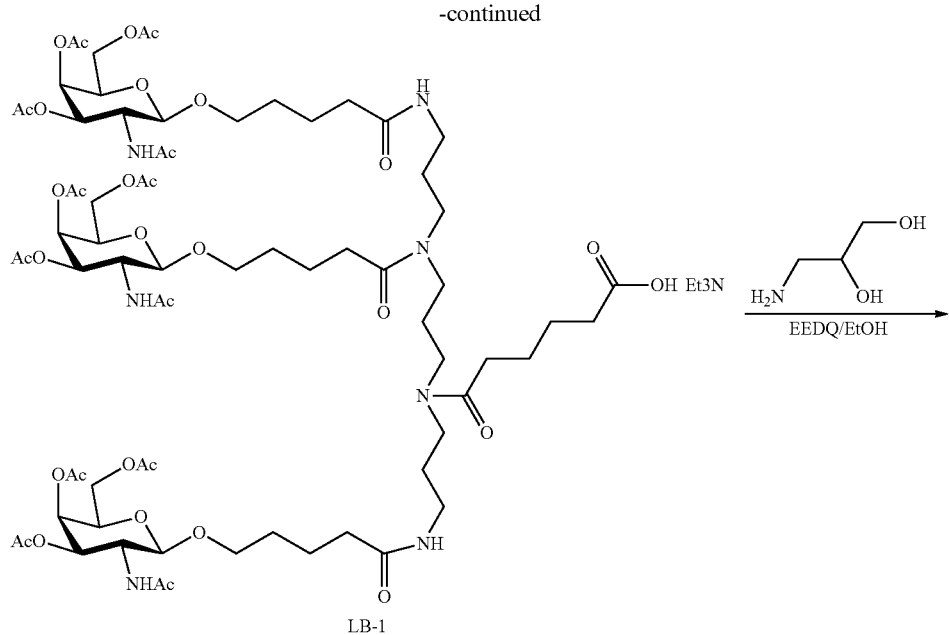
LB-1
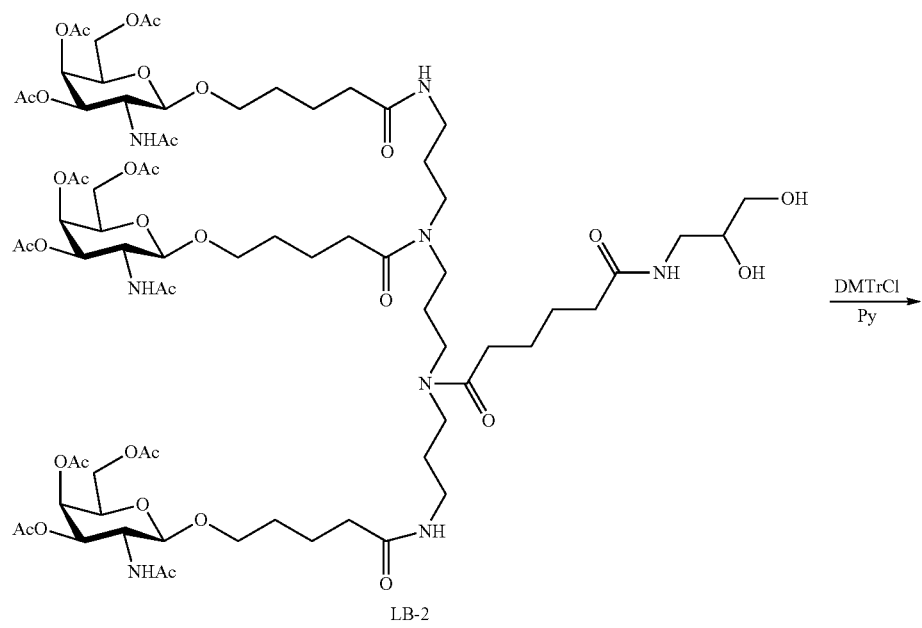
LB-2

-continued
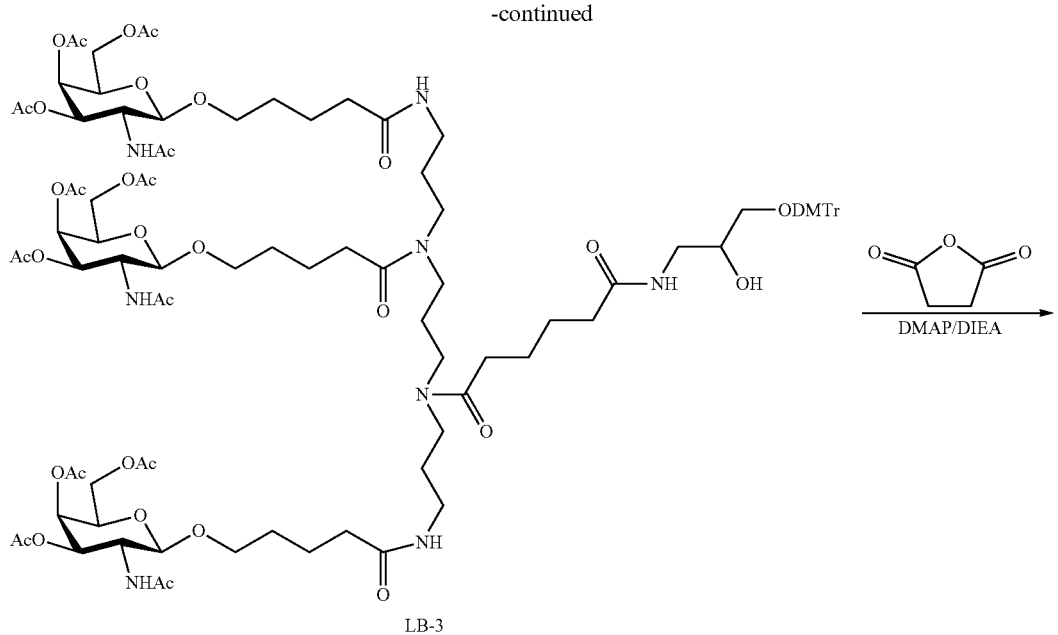
LB-3
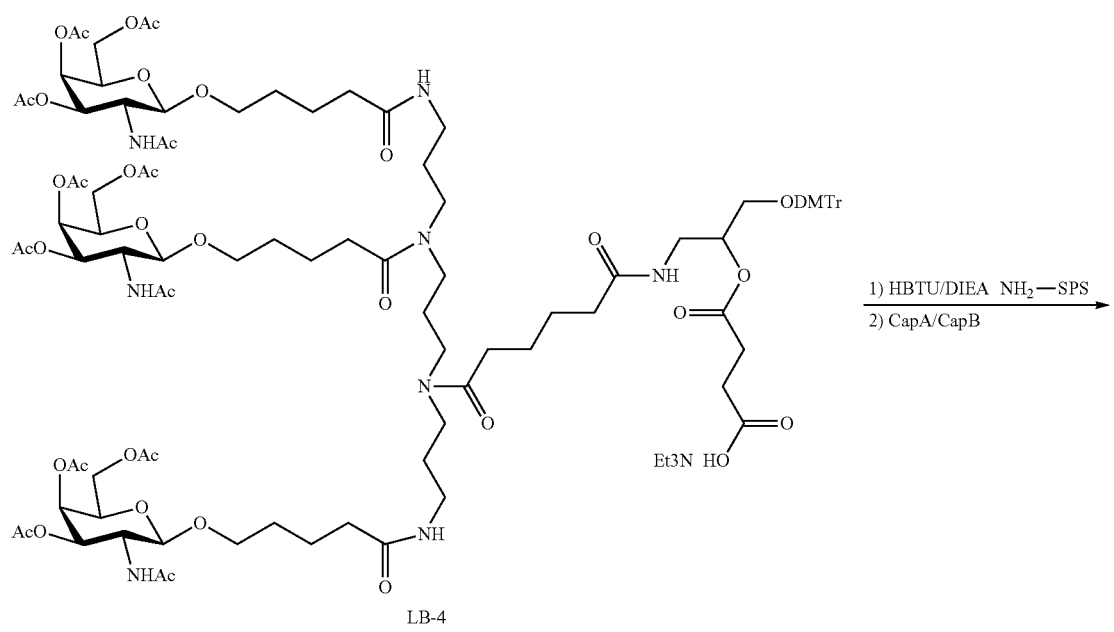
LB-4

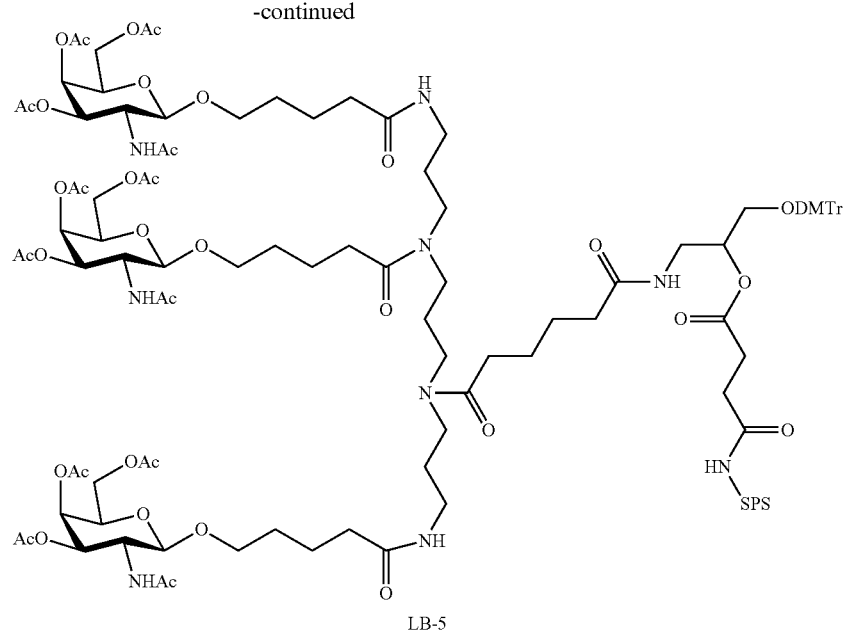

LB-5

(6-1-1) Synthesis of LB-1:

L-8 (5.0 g, 3.386 mmol) obtained according to the method described in step (1-1-6), adipic anhydride (870 mg, 6.772 mmol) and 4-dimethylaminopyridine (DMAP, 827 mg, 6.772 mmol) were mixed and dissolved in 130 ml of dichloromethane, and added with diisopropylethylamine (DIPEA, 2.2 g, 16.931 mmol) to react for 4 hours under stirring at 25° C. The reaction solution was diluted by adding 70 ml dichloromethane, and washed with 0.5 M triethylamine phosphate. The aqueous phase isolated was extracted four times, each with 10 ml of dichloromethane. All organic phases were combined, and the solvent was evaporated to dryness under reduced pressure to give a crude product, which was subjected to a column purification. The column was filled with 120 g normal phase silica gel, 200-300 mesh, added with 1 wt % triethylamine for neutralizing the acidity of silica gel. The column was equilibrated with dichloromethane and eluted with a gradient elution of petroleum ether:ethyl acetate:dichloromethane:methanol=1:1:1:0.2-1:1:1:1. The solvent was evaporated to dryness under reduced pressure to give 4.267 g of pure product LB-1.

(6-1-2) Synthesis of LB-2:

LB-1 (4.697 g, 2.753 mmol, combination of 2 batches) obtained according to the method described in step (6-1-1), 3-amino-1,2-propanediol (313 mg, 3.442 mmol), dimethoxytriazin-2-yl)-4-methylmorpholine hydrochloride (DMTMM, 953 mg, 3.442 mmol) and N-methylmorpholine (700 mg, 6.884 mmol) were sequentially added to the mixed solution of 30 ml of acetonitrile and 3 ml of methanol to react overnight under stirring at room temperature. The solvent was evaporated to dryness, and the residue was purified by column chromatography (200-300 mesh normal phase silica gel, with a gradient elution of dichloromethane:methanol=1:0.07-1:0.5). The eluate was collected and concentrated to remove the solvents to give 3.27 g of target product LB-2.

(6-1-3) Synthesis of LB-3:

LB-2 (2.27 g, 1.353 mmol) was dissolved in 14 ml of anhydrous pyridine, and added with 4,4'-dimethoxytrityl chloride (688 mg, 2.03 mmol) to react overnight under stirring at room temperature. The reaction was quenched by addition of 150 ml of methanol. The solvent was evaporated to dryness, and the residue was purified by column chromatography (200-300 mesh normal phase silica gel, with a gradient elution of dichloromethane:methanol=1:0.05-1:0.2). The eluate was collected and concentrated to remove the solvents to give 1.647 g of target product LB-3.

(6-1-4) Synthesis of LB-4:

LB-3 (822 mg, 0.415 mmol), succinic anhydride (83 g, 0.83 mmol) and 4-dimethylaminopyridine (DMAP, 102 mg, 0.83 mmol) were mixed and dissolved in 4 ml of dichloromethane, added with DIPEA (270 mg, 2.075 mmol), and stirred at 25° C. to react overnight. The reaction solution was washed with 0.5 M triethylamine phosphate for three times. The aqueous phase was extracted three times, each with 2 ml of dichloromethane. All organic phases were combined, and the solvent was evaporated to dryness under reduced pressure to give a crude product, which was subjected to a column purification. The column was filled with normal phase silica gel, 200-300 mesh, added with 5 wt % triethylamine for neutralizing the acidity of silica gel. The column was equilibrated with petroleum ether and eluted with a gradient elution of 1 wt % triethylamine-containing dichloromethane:methanol=100:5-100:20. The solvent was evaporated to dryness under reduced pressure to give 787 mg of pure product, LB-4 conjugating molecule.

(6-1-5) Synthesis of LB-5

LB-5 was prepared by using the same method as in step (1-1-9) of Preparation Example 1, except that: LB-4 conjugating molecule was used to replace L-9 conjugating molecule, thereby obtaining LB-4 conjugating molecule linked to a solid phase support.

(6-2) Synthesis of LB5-siHB2M1SVP Conjugate

Conjugate 20 was prepared by using the same method as those in steps (1-2), (1-3A) and (1-4) of Preparation Example 1, except that LB-5 Compound was used to replace L-10 Compound to start the synthesis of a sense strand. It was expected that LB5-siHB2M1SVP conjugate with a structure as shown by Formula (413) can be obtained.

Preparation Example 7
Preparation of V8-siHB2M1SVP Conjugate (Conjugate 21)
It was expected that V-8 compound can be synthesized according to the following process route:
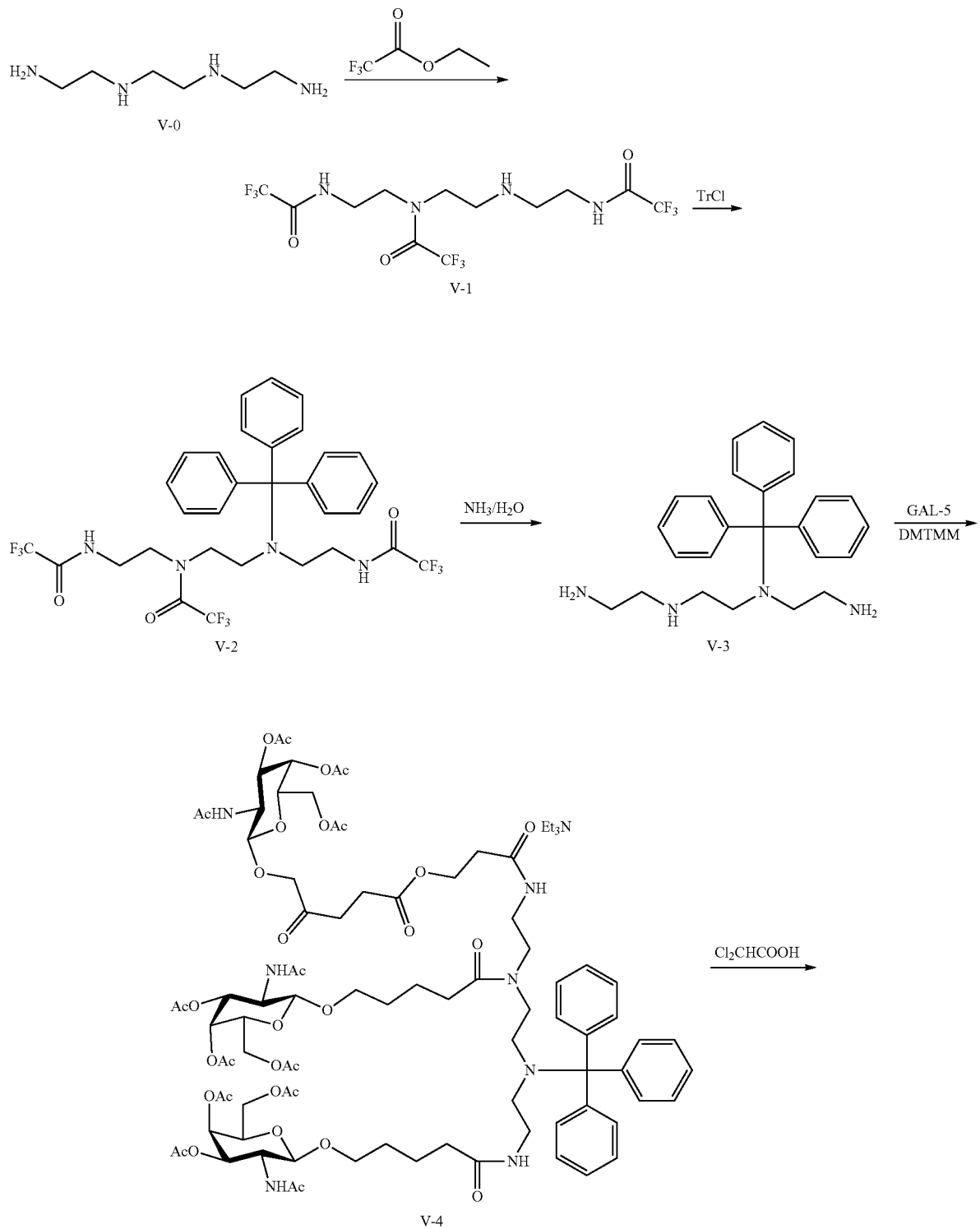

-continued
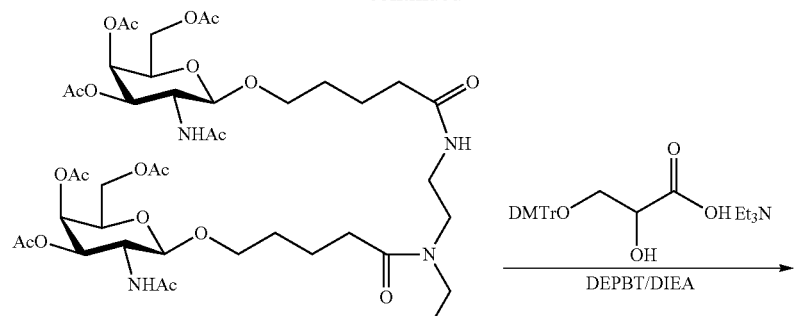
V-5
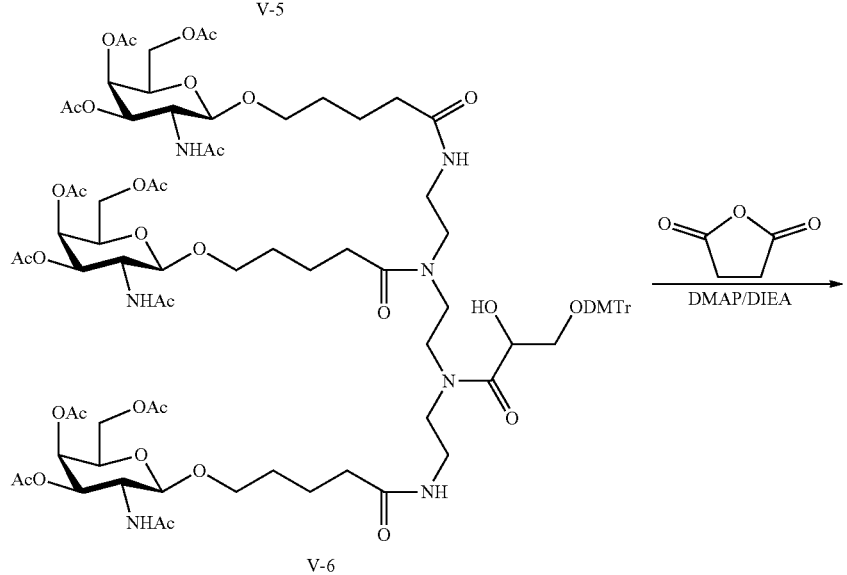
V-6
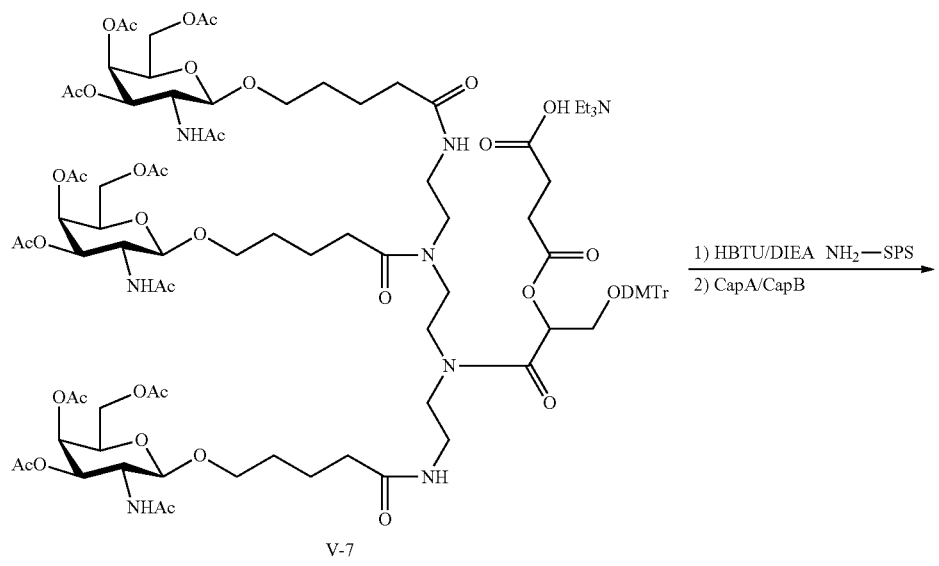
V-7

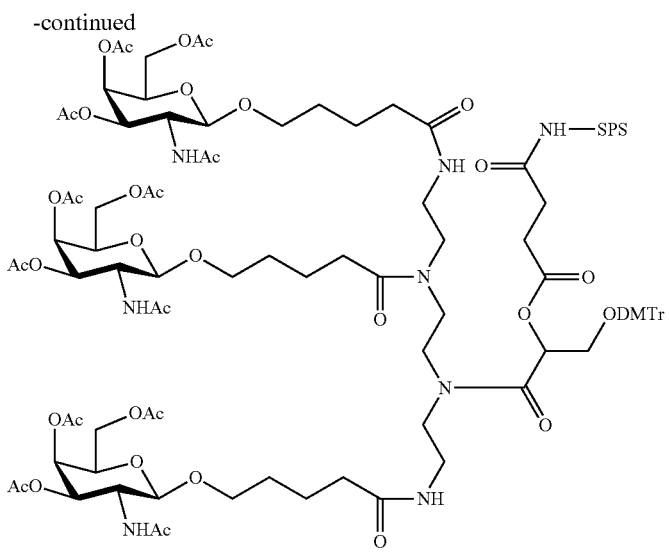

V-8

Conjugate 21 was prepared by using the same method as those in steps (1-2), (1-3A) and (1-4) of Preparation Example 1, except that V-8 Compound was used to replace L-10 Compound to start the synthesis of a sense strand. It was expected that V8-siHB2M1SVP conjugate with a structure as shown by Formula (414) can be obtained.

Preparation Example 8

Preparation of W8-siHB2M1SVP Conjugate (Conjugate 22)

(8-1) Synthesis of W-8 Compound

W-8 compound was synthesized according to the following process:

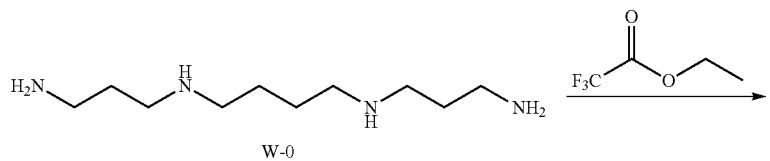

W-0

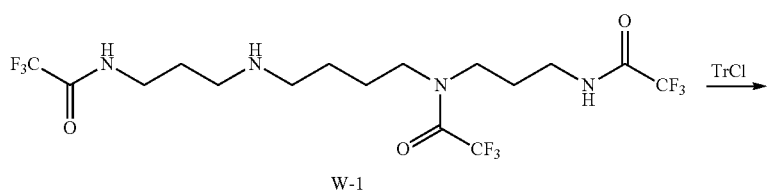

W-1

-continued
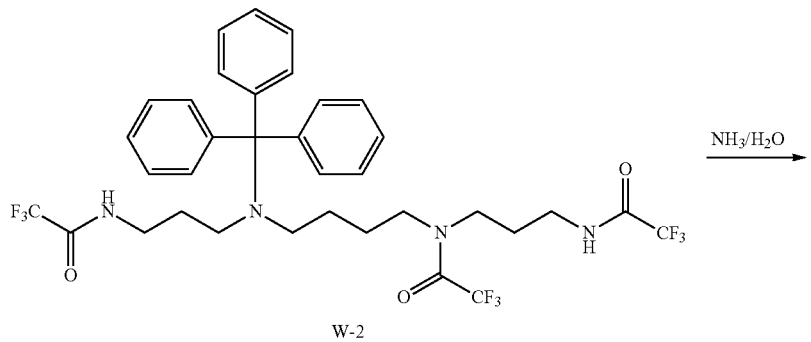
W-2
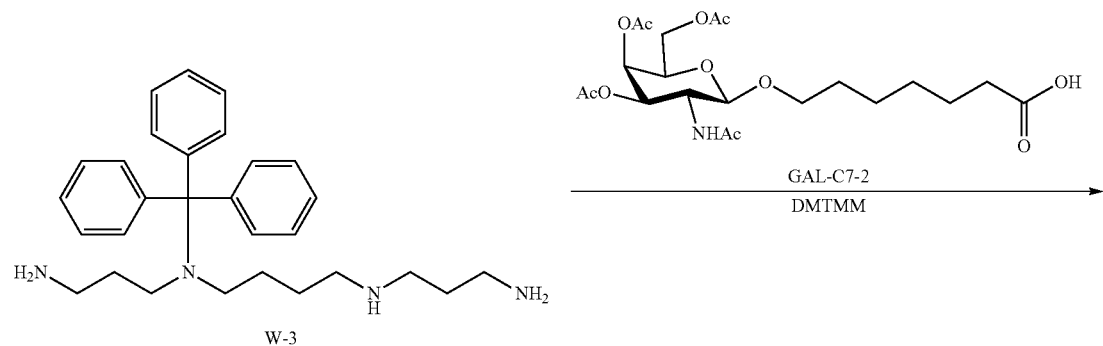
W-3
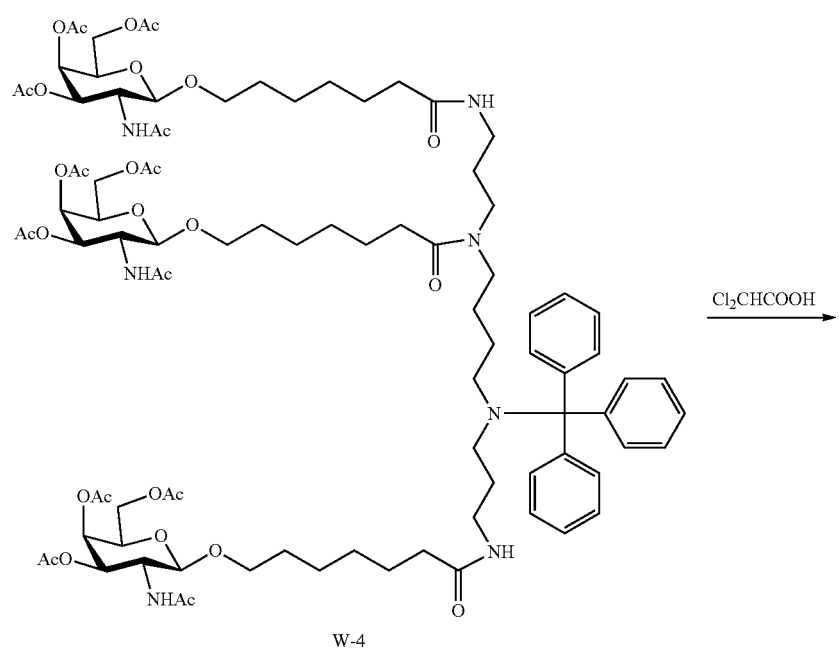
W-4

-continued
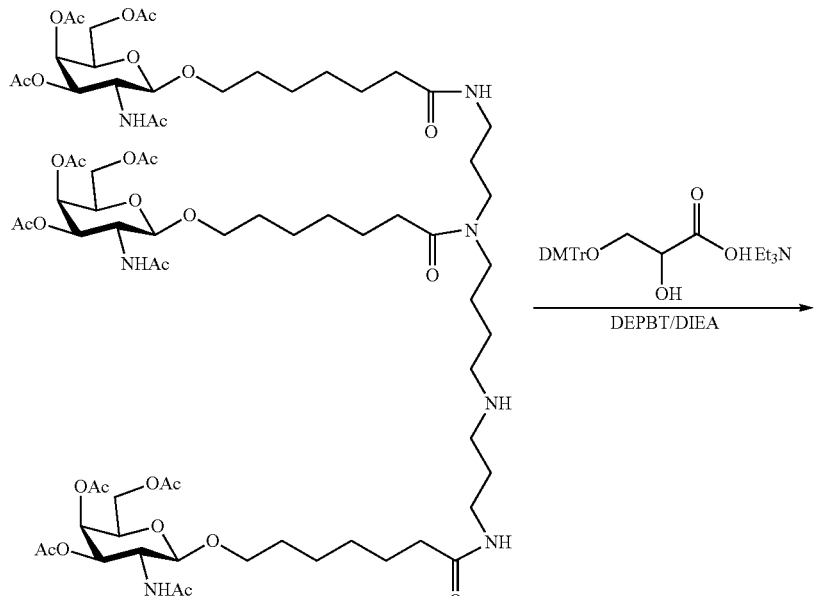
W-5
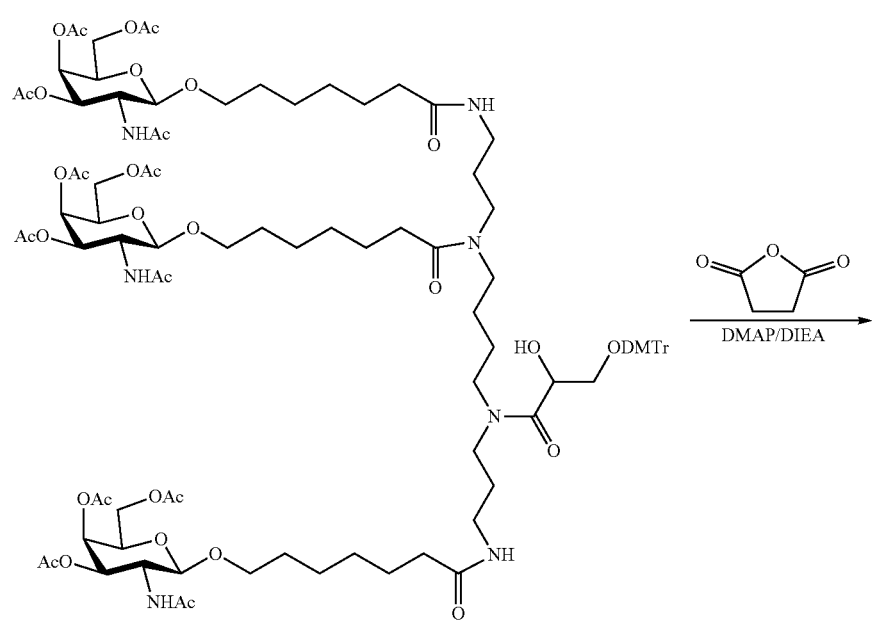
W-6

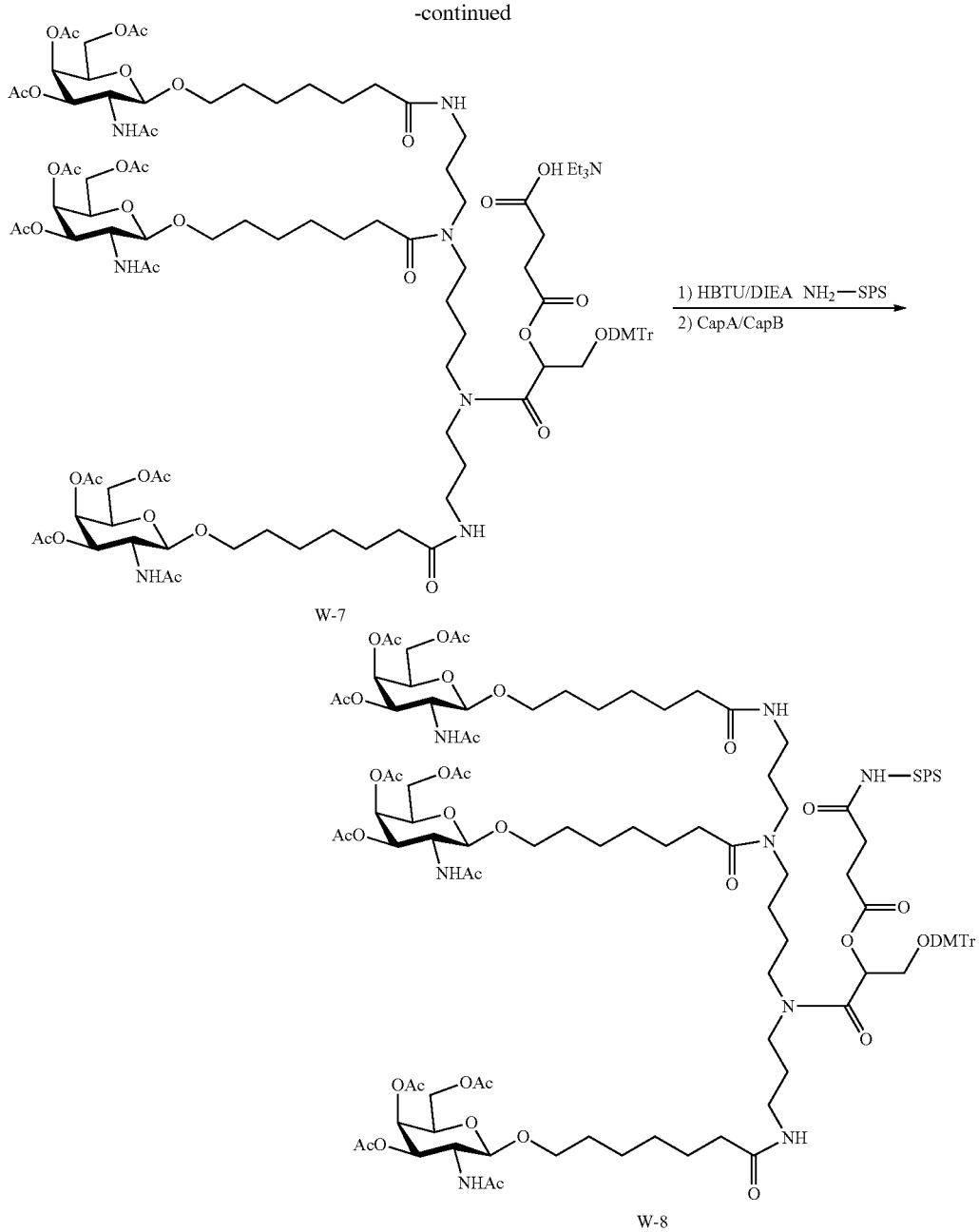

(8-1-1) Synthesis of W-1:

W-0 (2.024 g, 10 mmol) was dissolved in 25 ml of acetonitrile, added with triethylamine (4.048 g, 40 mmol), and cooled to about 0° C. in an ice water bath. Ethyl trifluoroacetate (5.683 g, 40 mmol) was added to react for 22 hours at room temperature. The solvent was evaporated to dryness under reduced pressure, and the residue was foam-dried in a vacuum oil pump for 18 hours to give 5.835 g of crude solid product W-1.

(8-1-2) Synthesis of W-2:

The crude product W-1 (5.835 g, 10 mmol) was dissolved in 50 ml of dichloromethane. TrCl (3.345 g, 12 mmol) and triethylamine (1.518 g, 15 mmol) were added to the reaction solution to react for 20 hours under stirring at room temperature. The reaction solution was washed twice, each with 20 ml of saturated sodium bicarbonate and once with 20 ml of saturated brine. All organic phases were combined, dried with anhydrous sodium sulfate and filtered. The organic solvent was evaporated to dryness under reduced pressure, and the residue was foam-dried in a vacuum oil pump overnight to give 8.012 g of crude solid product W-2, which was used in the next deprotection reaction without treatment.

(8-1-3) Synthesis of W-3:

The crude product W-2 (8.012 g, 10 mmol) was dissolved in 100 ml of methanol, and added with 100 ml of aqueous methylamine solution (40 wt %) to react for 23 hours under stirring at 50° C. Insoluble particles were removed by filtration. The solvent was evaporated to dryness under reduced pressure. The residue was added with 200 ml of mixed solvent of DCM:methanol in a volume ratio of 1:1, and the organic phase was washed with 50 ml of saturated sodium bicarbonate. The aqueous phase was extracted three times, each with 50 ml of dichloromethane. All organic phases were combined, dried with anhydrous sodium sulfate and filtered. The solvent was evaporated to dryness under reduced pressure, and the residue was foam-dried in a vacuum oil pump overnight, and purified by using a normal phase silica gel column, 200-300 mesh. The column was packed with petroleum ether, added with 1 wt % triethylamine for neutralizing the acidity of silica gel, and eluted with a gradient elution of dichloromethane:methanol:aqueous ammonia (25 wt %)=1:1:0.05-1:1:0.25. The eluate was collected. The solvent was evaporated to dryness under reduced pressure, and the residue was foam-dried in a vacuum oil pump to give 3.062 g of pure product W-3.

(8-1-4) Synthesis of W-4:

W-3 (0.675 g, 1.517 mmol) and GAL-C7-2 (2.60 g, 5.46 mmol) were mixed and dissolved in 47 ml of acetonitrile, added with diisopropylethylamine (1.57 g, 12.14 mmol) followed by 3-(diethoxyphosphoryloxy)-1,2,3-benzotrizin-4 (3H)-one (DEPBT, 1.816 g, 6.04 mmol) to react for 2.5 hours under stirring at room temperature. The reaction solution was diluted with 100 ml of dichloromethane. The organic phase was washed with 80 ml of saturated sodium bicarbonate solution and 80 ml of saturated brine, respectively. All organic phases were combined, dried with anhydrous sodium sulfate, and filtered. The solvent was evaporated to dryness under reduced pressure to give a crude product, which was purified by using a normal phase silica gel column, 200-300 mesh. The column was packed with petroleum ether, added with 1 wt % triethylamine for neutralizing the acidity of silica gel, and eluted with a gradient elution of dichloromethane:methanol=100:5-100:7. The eluate was collected, and the solvent was evaporated to dryness under reduced pressure to give 1.610 g of pure product W-4.

(8-1-5) Synthesis of W-5:

W-4 (1.61 g, 0.886 mmol) was dissolved in 125 ml of dichloromethane, and added with dichloroacetic acid (3.5 ml, 42.43 mmol) to react for 1 hour at room temperature. The reaction solution was neutralized by adding 150 ml of pyridine. The solvent was evaporated to dryness under reduced pressure to give a crude product, which was purified by using a normal phase silica gel column, 200-300 mesh. The column was added with 10 wt % triethylamine for neutralizing the acidity of silica gel. The column was equilibrated with 1 wt % triethylamine and eluted with a gradient elution of dichloromethane:methanol=100:30-100:40. The eluate was collected, and the solvent was evaporated to dryness under reduced pressure to give 1.26 g of pure product W-5.

(8-1-6) Synthesis of W-6:

W-5 (1.25 g, 0.793 mmol) and A-1 (1.21 g, 2.38 mmol) obtained according to the method described in step (1-1-7a) were mixed and dissolved in 12 ml of dichloromethane, and added with 3-(diethoxyphosphoryloxy)-1,2,3-benzotrizin-4 (3H)-one (DEPBT, 0.712 g, 2.38 mmol) followed by diisopropylethylamine (0.615 g, 4.76 mmol) to react for 3 hours under stirring at 25° C. The organic phase was washed with 80 ml of saturated sodium bicarbonate. The aqueous phase was extracted three times, each with 10 ml of dichloromethane. All organic phases were combined and washed with 10 ml of saturated brine. The organic phases were combined, dried with anhydrous sodium sulfate, filtered. The solvent was evaporated to dryness under reduced pressure, and the residue was foam-dried overnight in a vacuum oil pump to give a crude product, which was subjected to a column purification. The column was filled with 185 g normal phase silica gel, 200-300 mesh, added with 20 ml triethylamine for neutralizing the acidity of silica gel. The column was equilibrated with petroleum ether containing 1 wt % triethylamine and eluted with a gradient elution of petroleum ether:ethyl acetate:dichloromethane:N,N-dimethylformamide=1:1:1:0.1-1:1:1:0.7. The eluate was collected, and the solvent was evaporated to dryness under reduced pressure to give 1.57 g of pure product W-6.

(8-1-7) Synthesis of W-7:

W-6 (1.238 g, 0.63 mmol), succinic anhydride (0.189 g, 1.89 mmol) and 4-dimethylaminopyridine (DMAP, 0.231 g, 1.89 mmol) were mixed and dissolved in 7 ml of dichloromethane, and added with DIEA (0.407 g, 3.15 mmol) to react for 24 hours under stirring at 25° C. The reaction solution was washed with 5 ml of 0.5 M triethylamine phosphate. The aqueous phase was extracted three times, each with 5 ml of dichloromethane. All organic phases were combined, and the solvent was evaporated to dryness under reduced pressure to give a crude product, which was subjected to a column purification. The column was filled with 30 g normal phase silica gel, 200-300 mesh, added with 1 wt % triethylamine for neutralizing the acidity of silica gel. The column was equilibrated with dichloromethane and eluted with a gradient elution of 1 wt % triethylamine-containing dichloromethane:methanol=100:18-100:20. The eluate was collected, and the solvent was evaporated to dryness under reduced pressure to give 1.033 g of pure product, W-7 Conjugating Molecule. MS m/z: C101H146N7O38, [M-DMTr]+, calcd: 1763.92, measured: 1763.21.

(8-1-8) Synthesis of W-8

W-8 was prepared by using the same method as that in step (1-1-9) of Preparation Example 1, except that: W-7 conjugating molecule was used to replace L-9 conjugating molecule, thereby obtaining W-7 conjugating molecule linked to a solid phase support.

(8-2) Synthesis of W8-siHB2M1SVP Conjugate

Conjugate 22 was prepared by using the same method as those in steps (1-2), (1-3A) and (1-4) of Preparation Example 1, except that W-8 Compound was used to replace L-10 Compound to start the synthesis of a sense strand. It was expected that W8-siHB2M1SVP conjugate with a structure as shown by Formula (415) can be obtained.

Preparation Example 9

Preparation of X8-siHB2M1SVP Conjugate (Conjugate 23)

It was expected that X-8 compound can be synthesized according to the following process route:

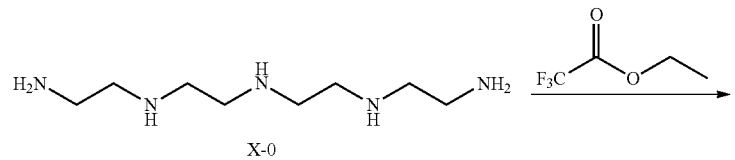

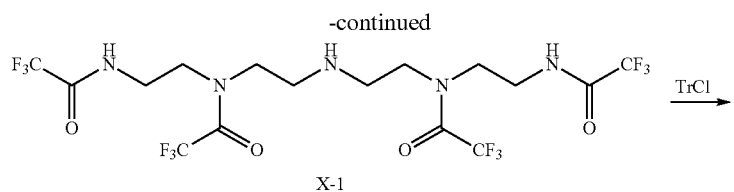
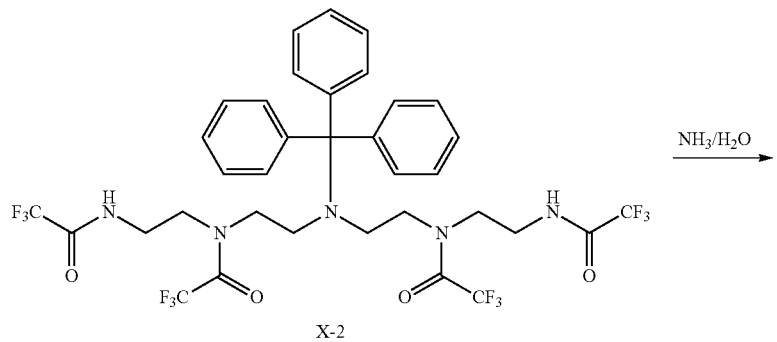
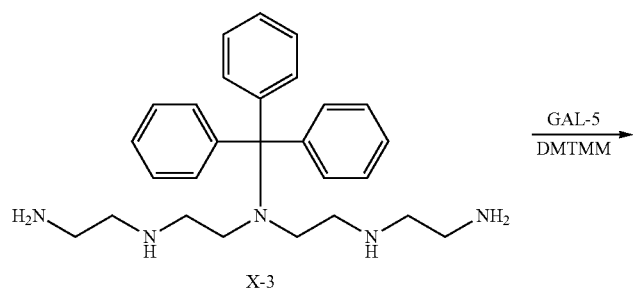
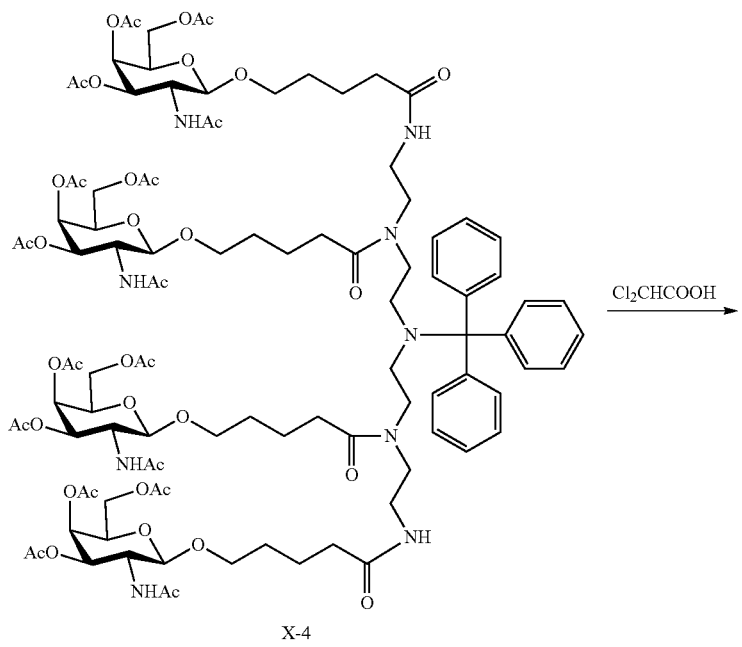

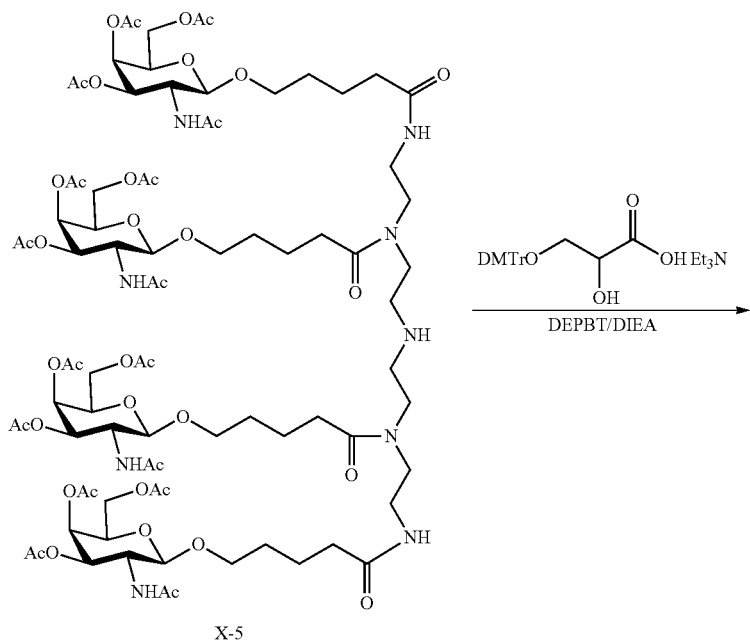
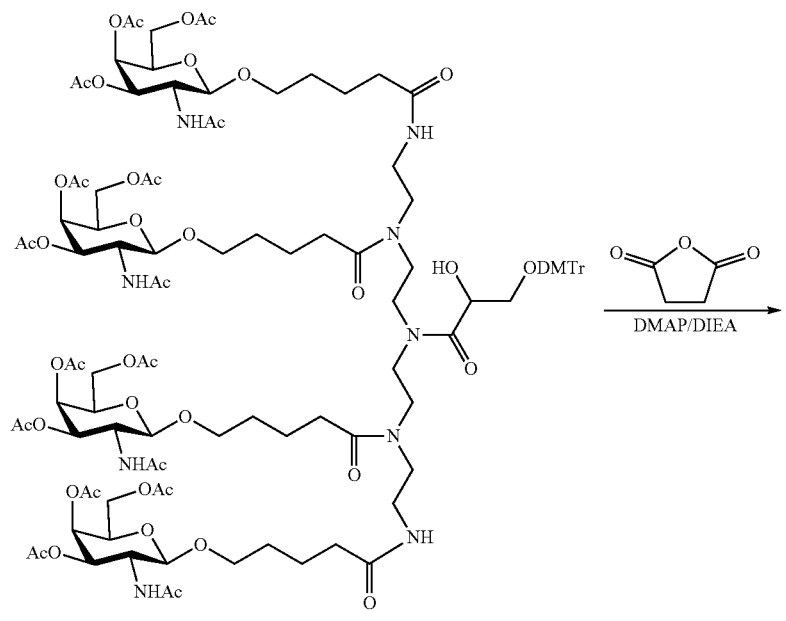

-continued
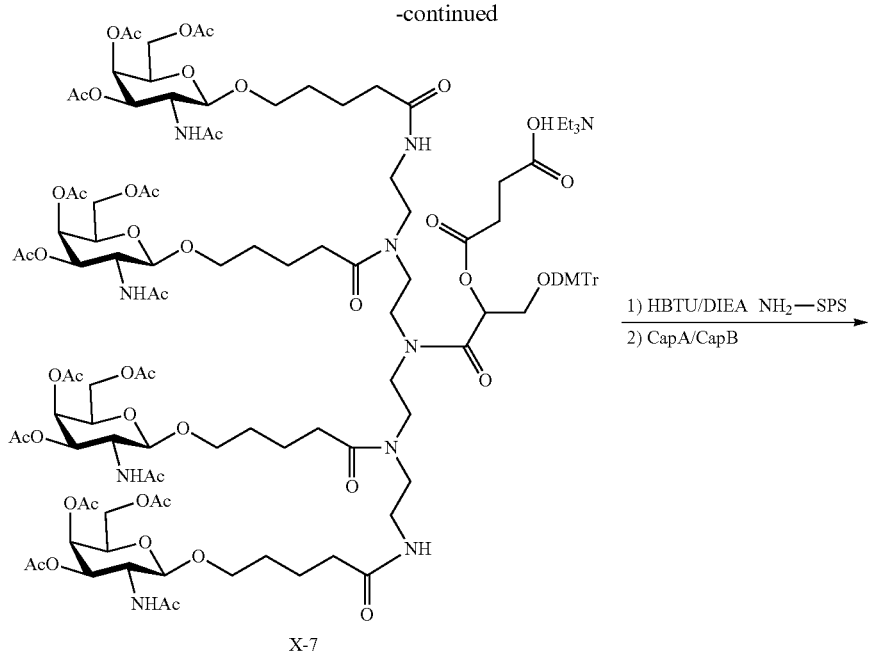
X-7
1) HBTU/DIEA NH₂—SPS
2) CapA/CapB
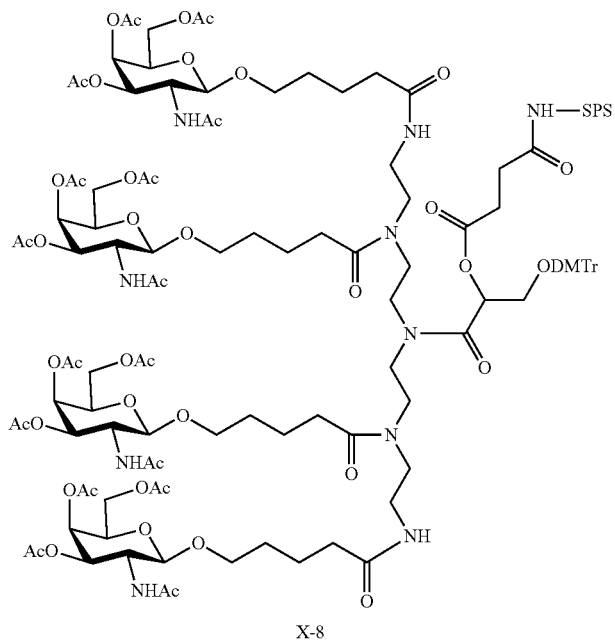
X-8
Conjugate 23 was prepared by using the same method as those in steps (1-2), (1-3A) and (1-4) of Preparation Example 1, except that X-8 Compound was used to replace L-10 Compound to start the synthesis of a sense strand. It was expected that X8-siHB2M1SVP conjugate with a structure as shown by Formula (421) can be obtained.

Preparation Example 10
Preparation of Z5-siHB2M1SVP Conjugate
(Conjugate 24)
(10-1) Synthesis of Z-5 Compound
Z-5 compound was synthesized according to the following process:
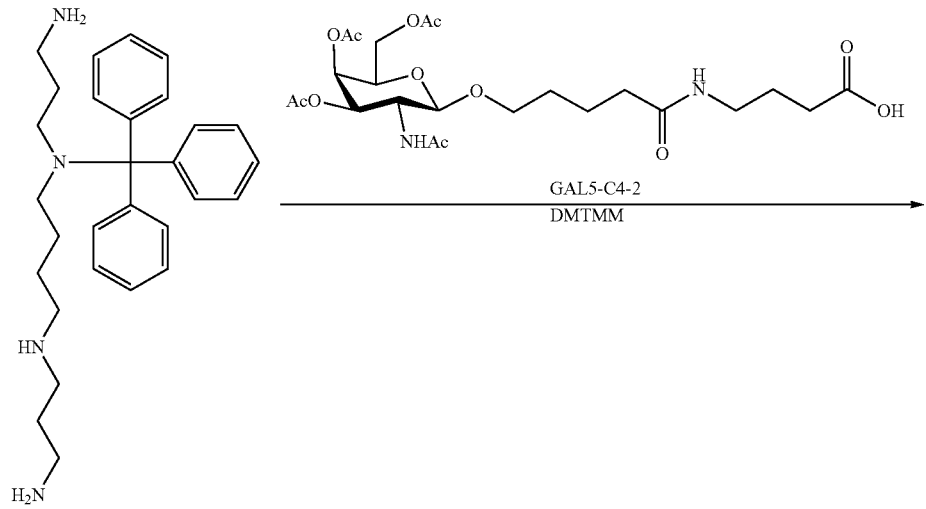
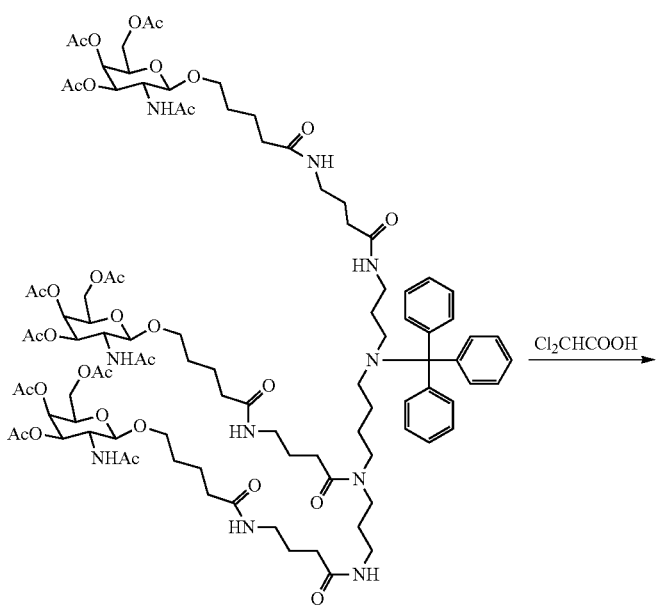

-continued
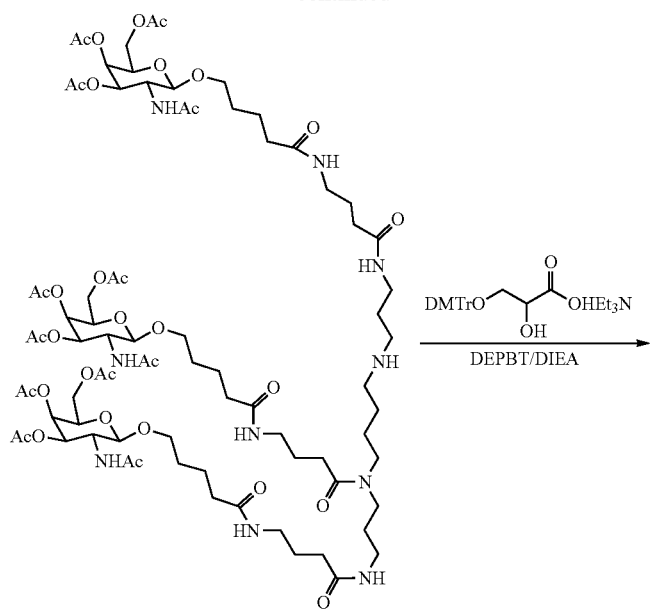
Z-2
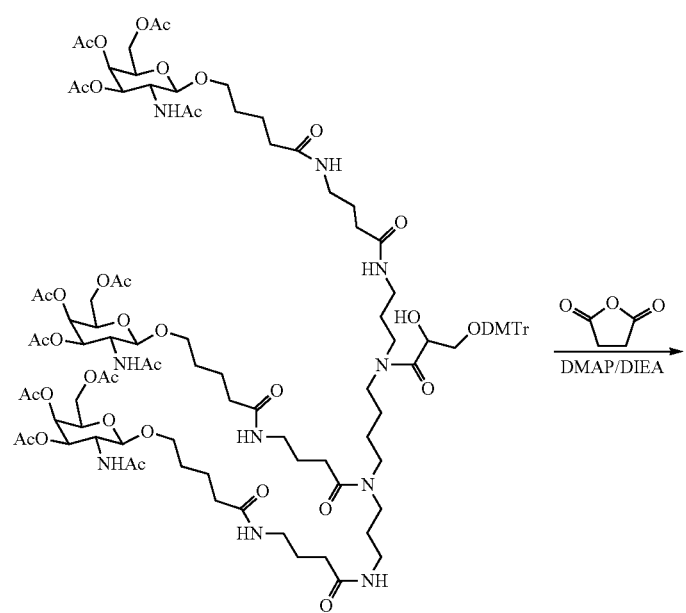
Z-3

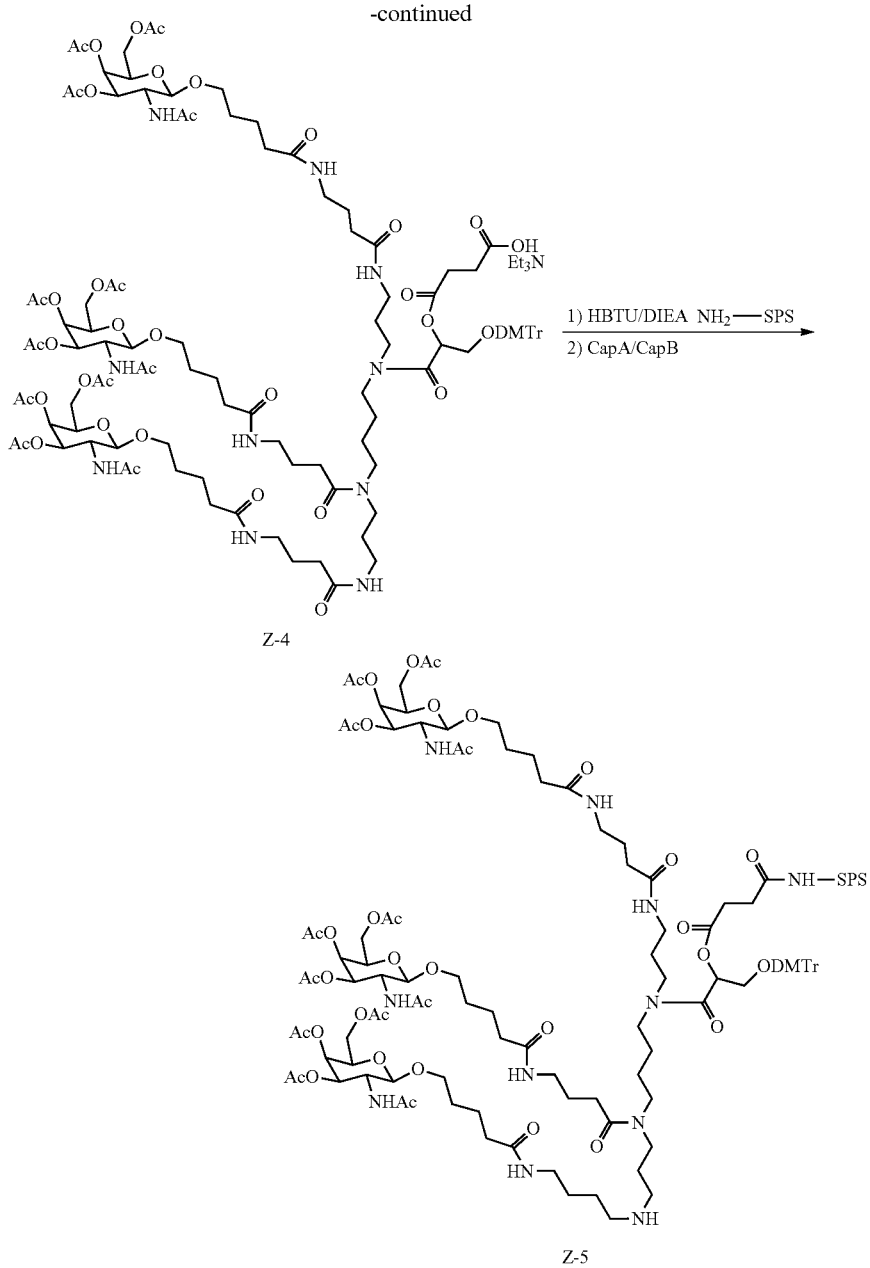

(10-1-1) Synthesis of Z-1:

W-3 (1.50 g, 3.37 mmol) obtained according to the method described in step (8-1-3) and GAL5-C4-2 (7.18 g, 13.48 mmol) obtained according to the method described in step (3-1-2) were mixed and dissolved in 34 ml of dichloromethane, added with diisopropylethylamine (3.48 g, 26.96 mmol) followed by 3-(diethoxyphosphoryloxy)-1,2,3-benzotrizin-4(3H)-one (DEPBT, 4.04 g, 13.48 mmol) to react for 4.5 hours under stirring at room temperature. The reaction solution was diluted with 100 ml of dichloromethane. The organic phase was washed with 80 ml of saturated sodium bicarbonate solution and 80 ml of saturated brine, respectively. All organic phases were combined, dried with anhydrous sodium sulfate, and filtered. The solvent was evaporated to dryness under reduced pressure to give a crude product, which was purified by using a normal phase silica gel column, 200-300 mesh. The column was packed with petroleum ether, added with 1 wt % triethylamine for neutralizing the acidity of silica gel, and eluted with a gradient elution of dichloromethane:methanol=30:1-15:1. The eluate was collected and evaporated to dryness under reduced pressure to give 3.97 g of pure product Z-1. MS m/z: C98H143N10O33, [M+H]+, calcd: 1987.98, measured: 1987.90.

(10-1-2) Synthesis of Z-2:

Z-1 (3.97 g, 2.00 mmol) was dissolved in 250 ml of dichloromethane, and added with dichloroacetic acid (10.941 g, 84.85 mmol) to react for 1 hour at room temperature. The reaction solution was neutralized to neutral by adding pyridine. The solvent was evaporated to dryness under reduced pressure to give a crude product. The column was loaded with 220 g 200-300 mesh normal phase silica gel, and added with 10 wt % pyridine for neutralizing the acidity of silica gel. The column was equilibrated with 1 wt % pyridine and eluted with a gradient elution of dichloromethane:methanol=10:1-2:1. The eluate was collected, and the solvent was evaporated under reduced pressure to give 3.49 g of pure product Z-2. MS m/z: C79H129N10O33, [M+H]+, calcd: 1746.94, measured: 1746.90.

(10-1-3) Synthesis of Z-3:

Z-2 (3.49 g, 2.0 mmol) and A-1 (3.06 g, 6.0 mmol) obtained according to the method described in step (1-1-7a) were mixed and dissolved in 30 ml of dichloromethane, and added with 3-(diethoxyphosphoryloxy)-1,2,3-benzotrizin-4 (3H)-one (DEPBT, 1.80 g, 6.0 mmol) followed by diisopropylethylamine (1.55 g, 12.0 mmol) to react for 3 hours under stirring at 25° C. The reaction solution was diluted with 100 ml dichloromethane. The organic phase was washed twice, each with 30 ml of saturated sodium bicarbonate. The aqueous phase was extracted with 10 ml of dichloromethane. All organic phases were combined and washed with 50 ml of saturated brine. The organic phases were combined and dried with anhydrous sodium sulfate, and filtered. The solvent was evaporated to dryness under reduced pressure, and the residue was foam-dried overnight in a vacuum oil pump to give a crude product, which was subjected to a column purification. The column was filled with 200 g normal phase silica gel, 200-300 mesh, added with 20 ml triethylamine for neutralizing the acidity of silica gel. The column was equilibrated with petroleum ether containing 1 wt % triethylamine and eluted with a gradient elution of dichloromethane:methanol=25:1-15:1. The eluate was collected, and the solvent was evaporated to dryness under reduced pressure to give 2.2 g of pure product Z-3. MS m/z: C103H151N10O38, [M+H]+, calcd: 2136.02, measured: 2136.20.

(10-1-4) Synthesis of Z-4:

Z-3 (2.10 g, 0.983 mmol) was dissolved in 14.8 ml of dichloromethane containing DIEA (0.635 g, 4.915 mmol). 4-dimethylaminopyridin (DMAP, 240 mg, 1.966 mmol) was added to the resultant solution and stirred to clarity. Succinic anhydride (197 mg, 1.966 mmol) was added to react for 18 hours under stirring at 25° C. The reaction solution was diluted by adding 50 ml dichloromethane. The organic phase was washed with 80 ml of 0.5 M triethylamine phosphate. The aqueous phase was extracted twice, each with 50 ml of dichloromethane. All organic phases were combined, and the solvent was evaporated to dryness under reduced pressure to give a crude product, which was subjected to a column purification. The column was filled with 188 g normal phase silica gel, 200-300 mesh, added with 1 wt % triethylamine for neutralizing the acidity of silica gel. The column was equilibrated with dichloromethane and eluted with a gradient elution of dichloromethane containing 1 wt % triethylamine:methanol=10:1-3:1. The eluate was collected, and the solvent was evaporated to dryness under reduced pressure to give 1.95 g of pure product, Z-4 Conjugating Molecule. MS m/z: C107H155N10O41, [M+H]+, calcd: 1935.07, measured: 1935.29.

(10-1-5) Synthesis of Z-5

Z-5 was prepared by using the same method as that in step (1-1-9) of Preparation Example 1, except that: Z-4 conjugating molecule was used to replace L-9 conjugating molecule, thereby obtaining Z-4 conjugating molecule linked to a solid phase support.

(10-2) Synthesis of Z5-siHB2M1SVP Conjugate

Conjugate 24 was prepared by using the same method as those in steps (1-2), (1-3A) and (1-4) of Preparation Example 1, except that Z-5 Compound was used to replace L-10 Compound to start the synthesis of a sense strand. It was expected that Z5-siHB2M1SVP conjugate with a structure as shown by Formula (422) can be obtained.

Preparation Example 11

Preparation of Conjugates 25 and 26, and Comparative Conjugates 1 and 3

In this preparation example, Conjugates 25 and 26, and Comparative Conjugates 1 and 3 (hereinafter referred to as FIN-siHB1M1SVP, FIN-siHB2M1SVP, FIN-NC, and FIN-siHB3M1SVP Conjugates respectively) were synthesized. The sequences of the conjugated siRNAs in the conjugates are shown in Table 1.

(11-1) Synthesis of FIN-2 Conjugating Molecule

FIN-2 conjugating molecule was synthesized with reference to the preparation method described in Rajeev et al., ChemBioChem 2015, 16, 903-908 according to the following process route:

(11-1-1) Synthesis of PRO-10

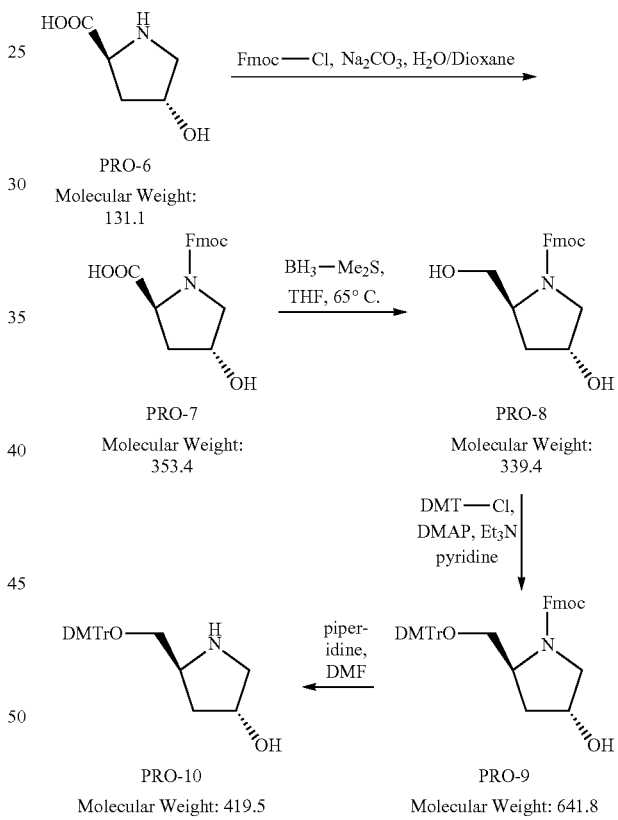

(11-1-1a) Synthesis of PRO-7

2.93 g of PRO-6 (L-hydroxyproline, CAS No.: 51-35-4, purchased from Energy Chemical, 22.4 mmol) was dissolved in 22.5 ml of 1,4-dioxane (CAS No.: 123-91-1) and added with 34 ml of 10% (w/w) aqueous $Na_2CO_3$ solution in the form of suspension. 6.95 g of Fmoc-Cl (9-fluorenylmethyl chloroformate, CAS No.: 28920-43-6, purchased from Energy Chemical, 26.8 mmol) was dissolved in 34 ml of 1,4-dioxane, added into the above suspension in an ice bath, and naturally warmed to room temperature for reaction overnight. The reaction solution was poured into 150 ml of ice water, and extracted three times, each with 100 ml of methyl t-butyl ether. The organic phases were discarded. The aqueous phase was adjusted to pH≤5 with concentrated hydrochloric acid, extracted twice with 100 ml of ethyl acetate, and the organic phases were combined and dried with anhydrous sodium sulfate. The solvent was evaporated to dryness under reduced pressure to give 7.83 g of product PRO-7 as a white foamy solid. $^1$H NMR (400 MHz, DMSO-$d_6$) δ 7.91 (t, J=7.2 Hz, 2H), 7.67 (d, J=7.5 Hz, 2H), 7.48-7.39 (m, 2H), 7.38-7.27 (m, 2H), 5.17 (s, 1H), 4.27 (s, 2H), 4.23-4.11 (m, 2H), 3.55-3.41 (m, 3H), 2.31-2.10 (m, 1H), 2.08-1.88 (m, 1H). HRMS (ESI) m/z calcd. for $C_{20}H_{19}NO_5$ [M−H]−352.1190, measured: 352.1033.

(11-1-1b) Synthesis of PRO-8

7.83 g of PRO-7 (22.2 mmol) was dissolved in 80 ml of THF (CAS No.: 109-99-9), heated to 65° C. in an oil bath, added with 36.6 ml of 2 mol/L solution of $BH_3$-$Me_2S$ in THF (CAS No. 13292-87-0, purchased from J&K Scientific Ltd., 73.2 mmol) under reflux, and refluxed continually to react for 3 hours. The reaction solution was poured out, and the remaining solid was dissolved in methanol. To the resultant reaction solution, methanol was added under stirring until no gas emits, and stirred continually for 30 minutes. The solvent was removed by evaporation under reduced pressure, and then the residue was purified three times, each with petroleum ether, to give 7.1 g of product PRO-8 as a white solid. $^1$H NMR (400 MHz, DMSO-$d_6$) δ 7.91 (t, J=6.7 Hz, 2H), 7.67 (d, J=7.2 Hz, 2H), 7.49-7.39 (m, 2H), 7.38-7.26 (m, 2H), 5.18 (dd, J=6.1, 3.8 Hz, 1H), 4.28 (s, 2H), 4.23-4.13 (m, 2H), 3.55-3.38 (m, 2H), 2.32-2.11 (m, 1H), 2.08-1.89 (m, 1H). HRMS (ESI) m/z calcd for $C_{20}H_{21}NO_4$ [M+Na]+ 362.1368, measured: 362.1012.

(11-1-1c) Synthesis of PRO-9

7.1 g of PRO-8 (21 mmol) was dissolved in 100 ml of pyridine, and added with 14.2 g of DMTr-Cl (4,4'-dimethoxytrityl chloride, 42 mmol) to react for 5 hours under stirring at room temperature. The solvent was removed by evaporation under reduced pressure. The crude product was dissolved in ethyl acetate and filtered to remove salt impurities. The solvent was removed by evaporation under reduced pressure, and then the residue was purified by using a silica gel column. The crude product dissolved in DCM was loaded onto the silica gel column pretreated with pyridine to alkalify the column. DMTr-Cl was eluted with DCM containing 1% (v/v) pyridine, and then the product was eluted with ethyl acetate. The eluate was collected, and the solvent was evaporated to dryness under reduced pressure to give 8.2 g of product PRO-9 as a white solid. HRMS (ESI) m/z calcd for $C_{41}H_{39}NO_6$ [M+Na]+664.2675, measured: 664.2348; C18 RP-HPLC (Lot No.: JJS160324-1); purity: 94.20%.

(11-1-1d) Synthesis of PRO-10

8.2 g of PRO-9 (12.8 mmol) was dissolved in 64 ml of N,N-dimethyl formamide (DMF) and added with 40 ml of piperidine (384 mmol) to react for 30 minutes under stirring at room temperature. The reaction solution was poured into 300 ml of ice water and extracted three times, each with 150 ml of ethyl acetate. The organic phases were combined, washed with 200 ml of saturated brine, and then the organic phases were dried with anhydrous sodium sulfate. The solvent was removed by evaporation under reduced pressure, and then the residue was purified by using a silica gel column. The crude product dissolved in DCM was loaded onto the silica gel column pretreated with pyridine to alkalify the column. Fmoc was eluted with DCM containing 1% (v/v) pyridine, and then the product was eluted with ethyl acetate. The eluate was collected, and the solvent was evaporated to dryness under reduced pressure to give 4.65 g of product PRO-10 as a white solid. $^1$H NMR (400 MHz, DMSO-$d_6$) δ 7.40 (d, J=7.2 Hz, 2H), 7.35-7.18 (m, 7H), 6.93-6.84 (m, 4H), 4.56 (d, J=3.9 Hz, 1H), 4.12 (s, 1H), 3.74 (s, 6H), 3.46-3.37 (m, 1H), 2.88 (ddd, J=18.5, 10.0, 5.5 Hz, 2H), 2.75 (dd, J=8.7, 5.8 Hz, 1H), 2.62 (dd, J=11.0, 2.7 Hz, 1H), 1.74-1.65 (m, 1H), 1.40 (ddd, J=12.9, 8.5, 5.9 Hz, 1H); HRMS (ESI) m/z calcd for $C_{26}H_{29}NO_4$ [M+Na]+442.1994, measured: 442.1999; C18 RP-HPLC (Lot No.: JJS160329-1), purity: 97.07%.

(11-1-2) Synthesis of FIN-1

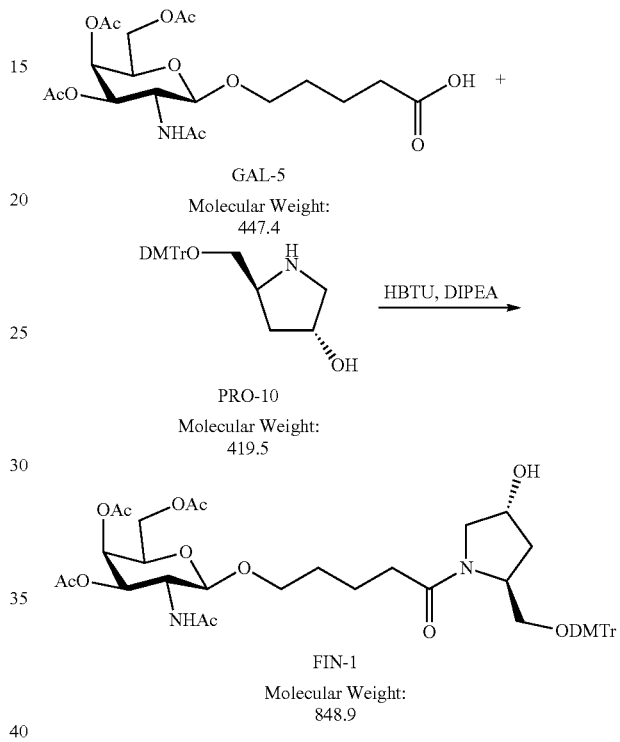

GAL-5 (4.5 g, 10 mmol) obtained according to the method described in step (1-1-1) was dissolved in 40 ml of DMF, sequentially added with 3.9 g of DIPEA (N,N-diisopropylethylamine, CAS No.: 7087-68-5, purchased from Aladdin Inc., 30 mmol) and 3.8 g of HBTU (benzotriazol-N,N,N',N'-tetramethyluronium hexafluorophosphate, CAS No.: 94790-37-2, purchased from Aladdin Inc., 11 mmol), and stirred at room temperature for 10 minutes. PRO-10 (4.2 g, 10 mmol) obtained in step (11-1-1d) was dissolved in 40 ml of DMF, and then added into the above reaction solution. The reaction solution was dried by adding anhydrous sodium sulfate and stirred at room temperature for 2 hours. The reaction solution was poured into 120 ml of ice water and extracted three times, each with 60 ml of ethyl acetate. The organic phases were combined, washed with 20 ml of water and 20 ml of saturated brine, respectively. The organic phase was isolated and dried with anhydrous sodium sulfate. The solvent was removed by evaporation under reduced pressure, and then the residue was purified by using a silica gel column. A sample was loaded onto the silica gel column pretreated with pyridine to alkalify the column, and was eluted with dichloromethane (DCM) solution containing 1% (v/v) triethylamine and 1% (v/v) methanol. The eluate was collected, and the solvent was evaporated to dryness under reduced pressure to give 6.5 g of product FIN-1 as a light yellow foamy solid. $^1$H NMR (400 MHz, DMSO-$d_6$) δ 7.83

(d, J=9.2 Hz, 1H), 7.32 (t, J=6.6 Hz, 4H), 7.20 (td, J=8.9, 3.5 Hz, 5H), 6.93-6.84 (m, 4H), 5.21 (d, J=3.2 Hz, 1H), 5.04-4.90 (m, 2H), 4.49 (s, 1H), 4.40 (d, J=4.4 Hz, 0.8H), 4.31 (d, J=5.0 Hz, 0.2H), 4.15 (s, 1H), 4.03 (s, 3H), 3.93 (s, 1H), 3.74 (s, 7H), 3.59 (dt, J=12.0, 6.0 Hz, 1H), 3.50-3.40 (m, 1H), 3.39-3.25 (m, 3H), 3.13 (dd, J=8.9, 5.2 Hz, 1H), 3.00 (dq, J=9.3, 5.3, 4.3 Hz, 1H), 2.22 (s, 2H), 2.07 (s, 3H), 1.99 (s, 3H), 1.90 (s, 4H), 1.74 (s, 3H), 1.50 (s, 3H), 1.36 (s, 1H). C18 RP-HPLC (Lot Number: LJ160422), purity: 95.45%.

(11-1-3) Synthesis of FIN-2 by evaporation under reduced pressure to give 2.2 g of product as a white powder, FIN-2 conjugating molecule. $^{31}$P NMR (162 MHz, CDCl3) δ 148.04, 147.94, 147.62, 147.19, purity of $^{31}$P NMR: 92%; purity of C18 RP-HPLC: 90.54%.

(11-2) Linking FIN-2 Conjugating Molecule to a Solid Phase Support

The conjugating group (FIN_FIN_FIN) was linked to the 3' terminal of the sense strand of RNA by linking the FIN-2 conjugating molecule obtained in step (11-1-3) to a universal solid phase support (UnyLinker™ loaded NittoPhase®HL

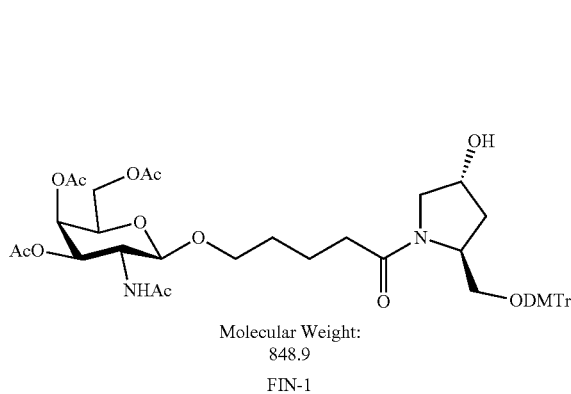

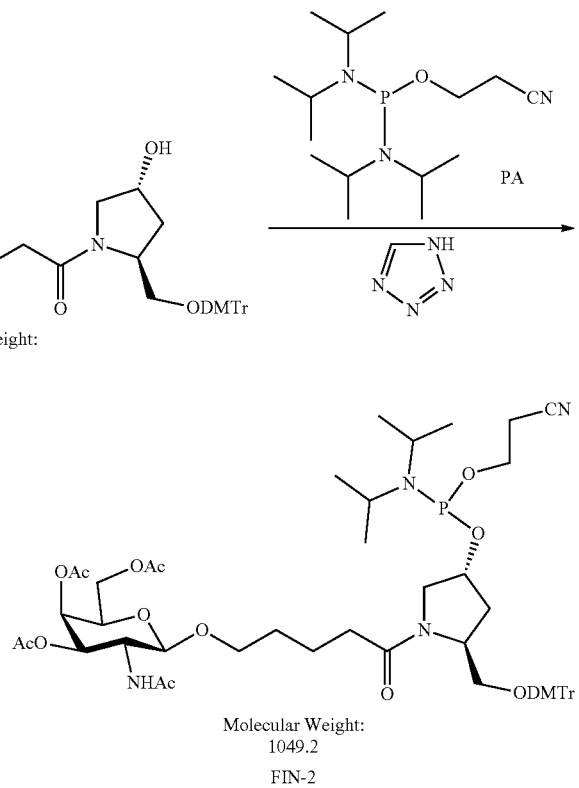

FIN-1 (3.0 g, 3.53 mmol) obtained in step (11-1-2) was azeotropic dehydration with acetonitrile, subjected to suction drying under reduced pressure, and then dissolved in 10 ml of DMF, followed by the addition of 2.13 g of PA (bis(diisopropylamino)(2-cyanoethoxy)phosphine, Adamas Inc., product No. 11356B, 7.06 mmol) and 346 mg tetrazole (CAS No.: 288-94-8, purchased from Aladdin Inc., 4.94 mmol) under nitrogen atmosphere. The mixture was stirred to react at room temperature. The reaction was supplemented with 10 ml of DMF and continually stirred to react for 1 hour. The solvent was removed by evaporation under reduced pressure, and then the residue was purified by silica gel column chromatography. The crude product dissolved in DCM was loaded onto the silica gel column pretreated with pyridine to alkalify the column, and eluted with ethyl acetate. The eluate was collected, and the solvent was evaporated under reduced pressure to give 4.5 g of crude product as a colorless syrup. The crude product was completely dissolved in 50% (v/v) aqueous acetonitrile solution and purified by using a medium pressure column (C-18, 330 g, 300 Å) pretreated with a solution of 1% (v/v) pyridine in acetonitrile to alkalify the column. A product peak was collected by gradient elution and the solvent was removed Solid Supports) by using the nucleic acid solid phase synthesis method through three reaction cycles.

The linking described above was proceeded according to the method described in Rajeev et al., Chem Bio Chem 2015, 16, 903-908. Specifically, started with the above-mentioned universal solid phase support, the hydroxy protecting group was firstly removed from the solid phase support, and the solid phase support was subsequently brought into contact and coupled with the FIN-2 conjugating molecule under the coupling reaction condition in the presence of a coupling agent, and a FIN conjugating molecule linked to the solid phase support was obtained after the capping and oxidation reaction. Moreover, the hydroxy protecting group DMTr was removed from the FIN conjugating molecule linked to the solid phase support, and the solid phase support was further brought into contact and coupled with another FIN-2 conjugating group, followed by capping and oxidation reaction. By repeating the above steps of Deprotection-Coupling-Capping-Oxidation, a third FIN-2 conjugating molecule was linked, and a conjugating group (FIN_FIN_FIN) linked to the solid phase support was thus obtained.

In the reactions described above, the reaction conditions for the deprotection, coupling, capping and oxidation as well as the amounts of the solvents and reagents are the same as those used in the solid phase synthesis method of nucleic acid described in step (1-2) above.

(11-3) Synthesis of Conjugates 25 and 26, and Comparative Conjugates 1 and 3

The subject conjugates were prepared by the same methods as those in steps (1-2), (1-3A), and (1-4) of Preparation Example 1, except that: 1) the compound obtained in step (11-2) was used to start the synthesis of a sense strand; and 2) the conjugated siRNAs had the sequences corresponding to Conjugates 25 and 26, and Comparative Conjugates 1 and 3 shown in Table 1; 3) for Comparative Conjugate 1, since the target sequence comprises unmodified nucleotide, in the cleavage and deprotection conditions, after treatment with aqueous ammonia, the product was dissolved in N-methylpyrrolidone in an amount of 0.4 ml/μmol, followed by addition of 0.3 ml/μmol of triethylamine and 0.6 ml/μmol of triethylamine trihydrofluoride, with respect to the amount of the single strand nucleic acid, thereby removing the 2'-TBDMS protection on ribose.

The molecular weight was measured by Liquid Chromatography-Mass Spectrometry (LC-MS, purchased from Waters Corp., Model: LCT Premier). The results showed that the measured values were in conformity with the calculated values, and thus it was confirmed that the synthesized conjugates were the designed target compounds, which have a structure as shown by Formula (307).

After the preparation of the above conjugates of the present disclosure, they were lyophilized to solid powder via standard process and stored until used. When being used, they can be reconstituted with, for example, water for injection to a solution at a desired concentration.

Experimental Example 1

This Experiment Illustrates the Inhibitory Activity In Vitro of the siRNA Conjugates of the Present Disclosure Experimental Example 1-1

On-Target Activity In Vitro in psiCHECK System

HEK293A cells used in this experimental example were provided by Nucleic Acid Technology Laboratory, Institute of Molecular Medicine, Peking University and cultured in DMEM complete media (Hyclone company) containing 20% fetal bovine serum (FBS, Hyclone company), 0.2v % Penicillin-Streptomycin double-antibiotics (Penicillin-Streptomycin, Gibco, Invitrogen company) at 37° C. in an incubator containing 5% $CO_2$/95% air.

In this experimental example, Conjugates 25 and 26 were investigated in in vitro psiCHECK system for the on-target activity. Specifically, Conjugates 25 and 26 were tested for the activity of targeting completely matching target sequence (in which the nucleotide sequence is complete complementary to the full-length nucleotide sequence of the antisense strand of the conjugate).

According to the method described by Kumico Ui-Tei et al., Functional dissection of siRNA sequence by systematic DNA substitution: modified siRNA with a DNA seed arm is a powerful tool for mammalian gene silencing with significantly reduced off-target effect. Nucleic Acids Research, 2008.36(7), 2136-2151, plasmids for detection were constructed and co-transfected with the siRNA conjugates to be detected into HEK293A cells; and the on-target activity and off-target effect of the siRNA conjugates were reflected by the expression levels of the dual luciferase reporter gene. Specific steps are as follows:

[1] Construction of a Plasmid for Detection

The on-target plasmid was constructed using psiCHECK-2 (Promega™) plasmid. This plasmid contains a target sequence, which is complete complementary to all 21-nucleotide sequence of the antisense strand in the conjugates to be detected. The target sequence was cloned into the Xho I/Not I site of the psiCHECK™-2 plasmid.

[2] Transfection

In a 96-well plate, the siRNA conjugates and the above plasmid were respectively co-transfected according to the instructions of Lipofectamine™ 2000 (Invitrogen). Specifically, 10 ng of plasmid was transfected per well, using 0.2 μL of Lipofectamine™ 2000; and the final concentrations (based on the concentration of siRNA) of the conjugates were 0.1 nM, 0.05 nM, and 0.01 nM in succession. For each group, those untreated with the conjugates were used as control (con). 3 replicate wells were used per group.

[3] Detection 24 hours post co-transfection, the HEK293A cells were lysed by using a dual luciferase reporter gene assay kit (Promega, cat. E2940) according to the instruction manual to detect the expression level of the dual luciferase reporter gene. The Renilla luciferase protein level (Ren) was normalized to the firefly luciferase protein level (Fir). The results are shown in FIG. 1.

The results indicate that Conjugates 25 and 26 both have good inhibitory activity in vitro.

Experimental Example 1-2

Determination of IC50 and Off-Target Detection in In Vitro psiCHECK System

In this experimental example, Conjugate 2 was investigated in in vitro psiCHECK system for the IC50 value and the off-target effect.

According to the method described by Kumico Ui-Tei et al., Functional dissection of siRNA sequence by systematic DNA substitution: modified siRNA with a DNA seed arm is a powerful tool for mammalian gene silencing with significantly reduced off-target effect.

Nucleic Acids Research, 2008.36(7), 2136-2151, plasmids for detection were constructed and co-transfected with the siRNA conjugate to be detected into HEK293A cells; and the on-target activity and off-target effect of the conjugate were reflected by the expression levels of the dual luciferase reporter gene. Specific steps are as follows:

[1] Construction of Plasmids for Detection

Four recombinant plasmids were constructed using psiCHECK™-2 (Promega™) plasmid, in which GSCM indicates the on-target plasmid; and PSCM, GSSM and PSSM indicate the off-target plasmids:

(1) GSCM, containing a target sequence, which is complete complementary to all 21-nucleotide sequence of the antisense strand in the Conjugate 2.

(2) PSCM, containing a target sequence, which is complete consistent with all 21-nucleotide sequence of the antisense strand in the Conjugate 2.

(3) GSSM, containing a target sequence, which is complete complementary to the nucleotide sequence at positions 1-8 from the 5' terminal of antisense strand in the siRNA to be detected; the remaining part of the target sequence corresponds to and completely mismatches with the nucleotide sequence at positions 9-21 from the 5' terminal of antisense strand in the siRNA to be detected. In particular, the nucleotide at any position of positions 9-21 from the 5' terminal of antisense strand in the siRNA to be detected is G, C, A or U, and the nucleotide at the corresponding position of the target sequence is T, A, C or G.

(4) PSSM, containing a target sequence, which is fully complementary to the nucleotide sequence at positions 1-8 from the 5' terminal of sense strand in the siRNA to be detected; the remaining part of the target sequence corresponds to and completely mismatches with the nucleotide sequence at positions 9-19 from the 5' terminal of sense strand in the siRNA to be detected. In particular, the nucleotide at any position of positions 9-19 from the 5' terminal of sense strand in the siRNA to be detected is G, C, A or U; and the nucleotide at the corresponding position of the target sequence is T, A, C or G. In order to have the same length as the GSSM target sequence, two nucleotides CC were added at the 3' terminal of the target sequence.

The target sequence was cloned into the Xho I/Not I site of the psiCHECK™-2 plasmid.

[2] Transfection

In a 96-well plate, the conjugate and each of the above plasmids were co-transfected according to the instructions of Lipofectamine™ 2000 (Invitrogen). Specifically, 10 ng of plasmid was transfected per well, using 0.2 µL of Lipofectamine™ 2000; and the final concentration (based on the concentration of siRNA) of the siRNA conjugate was from 0.1 nM, and double diluted to 0.0001 nM (one plasmid corresponding to 11 groups of siRNA concentrations). 3 replicate wells were used per group.

[3] Detection 24 hours post cultivation, the HEK293A cells were lysed by using a dual luciferase reporter gene assay kit (Promega, cat. E2940) according to the instruction manual to detect the expression level of the dual luciferase reporter gene. For the test group of each specific concentration of the conjugate, those untreated with the conjugate were used as control. The Renilla luciferase protein level (Ren) was normalized to the firefly luciferase protein level (Fir). The dose-response curves were fitted according to the activity results measured at different siRNA concentrations by using Function log (inhibitor) vs. response—Variable slope of Graphpad 5.0 software. The IC50 value of the siRNA to be detected that targets GSCM was calculated based on the dose-effect curve with the formula below:

$$Y = Bot + \frac{Top - Bot}{1 + 10^{(LogIC50-N)} \times HillSlope}$$

wherein:

Y is the expression level of remaining mRNA,

X is the logarithm of the concentration of transfected siRNA,

Bot is the Y value at the bottom of the steady-state phase,

Top is the Y value at the top of the steady-state phase,

Log $IC_{50}$ is the X value when Y is the median value between the bottom and the top, and HillSlope is the slope of the curve. The results are shown in FIG. 2.

Figure 2:
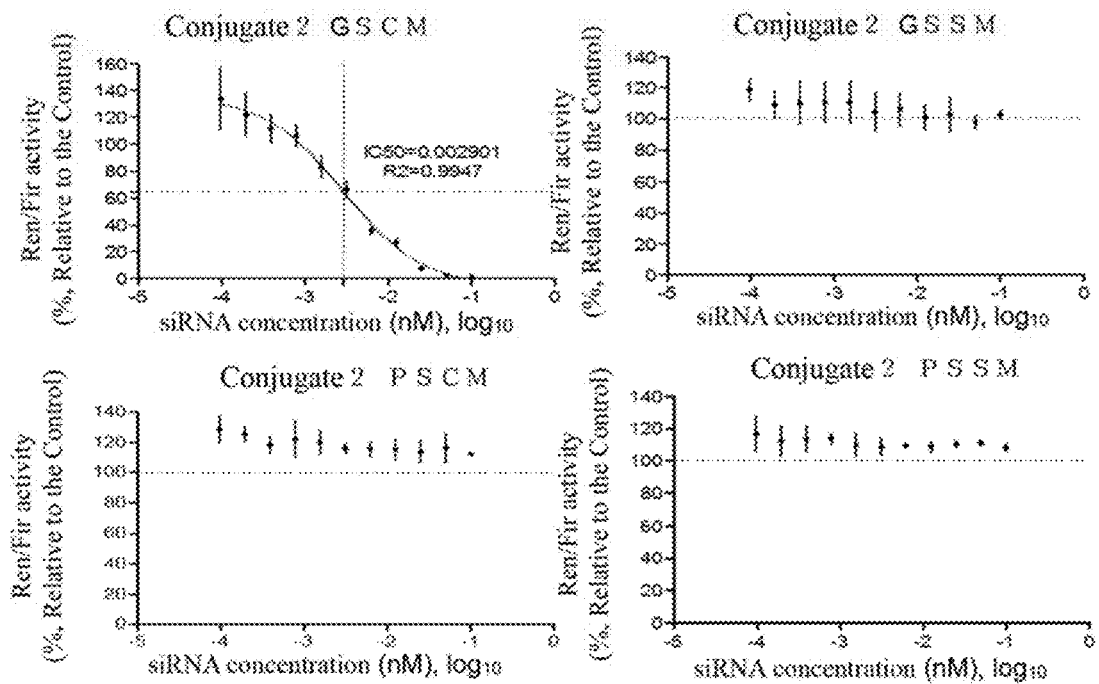
FIG. 2 shows the detection result of the IC50 and off-target effect of Conjugate 2 in psiCHECK system in vitro.

As can be seen from FIG. 2, Conjugate 2 not only has excellent inhibitory effect on the target mRNA, but also exhibits low off-target effect.

Experimental Example 2

This Experiment Illustrates the Stability of the siRNA Conjugates of the Present Disclosure Experimental Example 2-1

Stability of the siRNA Conjugates in the Lysosome Lysate in Vitro

Preparation of test samples treated with the lysosome lysate: Conjugates 1 and 2 (each provided in the form of 0.9% NaCl aqueous solution at a concentration of 20 µM with regard to siRNA, 6 µl for each group, respectively) were individually mixed well with 27.2 µL of sodium citrate aqueous solution (pH 5.0), 4.08 µL of deionized water and 2.72 µL of Tritosomes (commercially available from Xenotech Inc., Cat. R0610LT, No. 1610069, at a final concentration of 0.2 mU/µl), and incubated at a constant temperature of 37° C. 5 µL samples were taken at each time point of 0 h, 5 min, 15 min, 30 min, 1 h, 2 h, 4 h, and 8 h, respectively, each added to 15 µL of 9 M urea solution for denaturation, followed by the addition of 4 µL of 6× loading buffer (purchased from Solarbio Inc., Cat. 20160830), and then immediately cryopreserved in a −80° C. freezer to quench the reaction. 0 h represents the moment when the samples are mixed well with the lysosome lysate and immediately taken out.

Preparation of control samples untreated with the lysosome lysate: 1.5 µL for Conjugate 4 (20 µM) at equal moles was mixed well with 7.5 µL of sodium citrate aqueous solution (pH 5.0) and 1 µL of deionized water, each added to 30 µL of 9 M urea solution for denaturation. Subsequently, 8 µL of 6× loading buffer was added and mixed well, and then the mixture was immediately cryopreserved in a −80° C. freezer to quench the reaction. The control sample was marked as Con in the electrophoretogram.

16 wt % of non-denatured polyacrylamide gel was prepared. 20 µL each of the test samples and the control samples described above was loaded into the gel to perform electrophoresis for 10 minutes under 20 mA constant current and then for 30 minutes under 40 mA constant current. After finishing the electrophoresis, the gel was placed on a shaker and stained with Gelred dye (BioTium, Cat. 13G1203) for 10 minutes. The gel was imaged, observed and photographed. The results are shown in FIG. 3.

Figure 3:
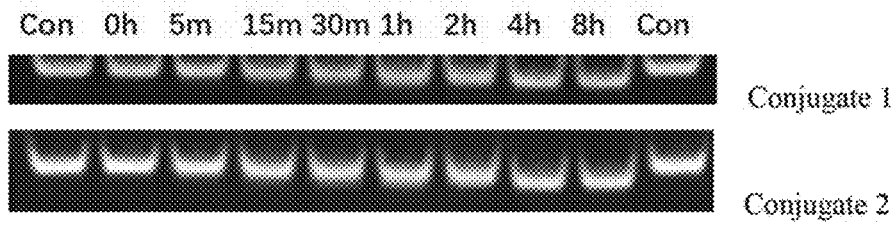
FIG. 3 shows the semiquantitative result of the stability test of the tested siRNA conjugates in the Tritosome in vitro.

FIG. 3 shows the semiquantitative detection result of the stability test of the tested siRNA conjugates in the lysosome in vitro. The results indicate that the conjugates of the present disclosure can remain undegraded in lysosome for a prolonged period of time, showing good stability.

Experimental Example 2-2

Stability of the siRNA Conjugates in Human Plasma

Conjugates 1 and 2 (each provided in the form of 0.9 wt % NaCl aqueous solution at a concentration of 20 µM with regard to siRNA, 12 µl for each group) and Comparative Sequence 1 (20 µM, 12 µl) were individually mixed well with 108 µL of 90% human plasma (diluted in PBS) and incubated at a constant temperature of 37° C. 10 µL samples were taken at each time point of 0 h, 2 h, 4 h, 6 h, 8 h, 24 h, 48 h and 72 h, respectively, and immediately frozen in liquid nitrogen and cryopreserved in a −80° C. freezer. After sampling at each time point, each sample was diluted 5-fold with 1×PBS (pH 7.4) and then taken in a volume of 10 μL for use. Meanwhile, the siRNA (2 μM, 2 μL) or siRNA conjugate (with the siRNA concentration being 2 μM, 2 μL) at equal moles was mixed well with 8 μL of 1×PBS (pH 7.4), thus obtaining 10 μL of samples untreated with human plasma (marked as Con).

20 wt % of non-denatured polyacrylamide gel was prepared. For the above samples for use, all the samples in each group were mixed with 4 μL of loading buffer (aqueous solution of 20 mM EDTA, 36 wt % glycerol, and 0.06 wt % bromophenol blue) and then loaded into the gel to perform electrophoresis for 60 minutes under 80 mA constant current. After finishing the electrophoresis, the gel was stained with 1× Sybr Gold dye (Invitrogen, Cat. 11494) for 15 minutes followed by imaging. The results are shown in FIG. 4.

Comparative Sequence 1:

```
Sense strand:
                                  (SEQ ID NO: 46)
CCUUGAGGCAUACUUCAAA Antisense strand:
                                  (SEQ ID NO: 47)
UUUGAAGUAUGCCUCAAGGUU.
```

Figure 4:
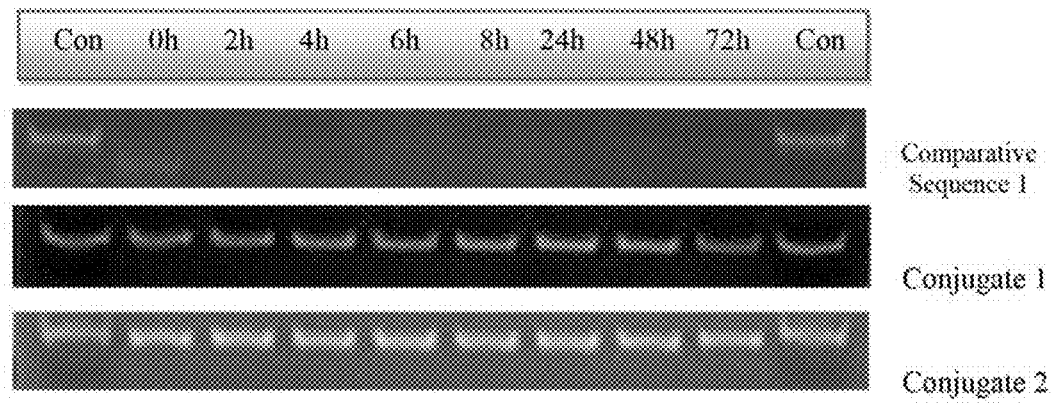
FIG. 4 shows the semiquantitative result of the stability test of the tested siRNA conjugates in the human plasma in vitro.

FIG. 4 shows the semiquantitative detection result of the stability of the tested conjugates in human plasma in vitro.

As can be seen from the results of FIG. 4, the conjugates of the present disclosure remain undegraded in human plasma over a period of up to 72 hours, showing excellent stability in human plasma.

Experimental Example 2-3

Stability of siRNA Conjugate in the Monkey Plasma

In other experiments, the stability of Conjugates 1, Conjugate 2 and Comparative Conjugate 1 were measured in monkey plasma (purchased from HONGQUAN Bio, Cat. HQ70082, diluted in PBS) using the same method as that in Experimental Example 2-2. The results are shown in FIG. 5.

Figure 5:
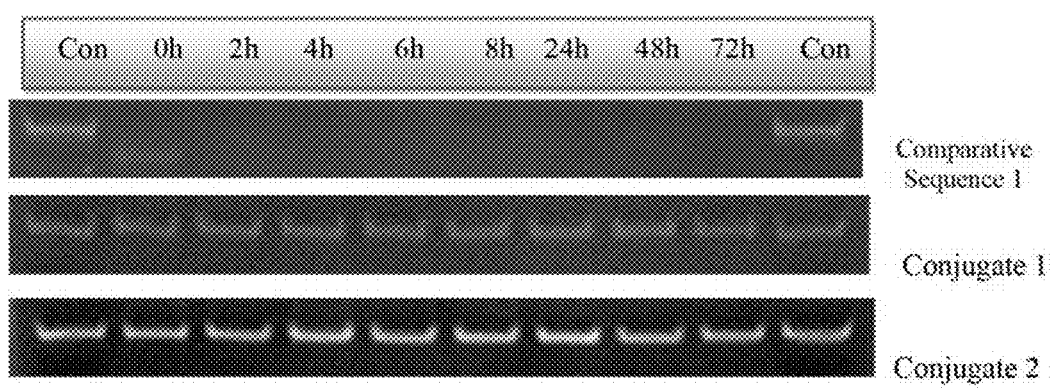
FIG. 5 shows the semiquantitative result of the stability test of the tested siRNA conjugates in the monkey plasma in vitro.

FIG. 5 shows the semiquantitative detection result of the stability of the tested siRNA conjugate in monkey plasma in vitro.

As can be seen from the results of FIG. 5, the siRNA conjugates of the present disclosure can remain undegraded in cynomolgus monkey plasma over a period of up to 72 hours, showing excellent stability in monkey plasma.

Experimental Example 3

This Experimental Example Illustrates the Inhibition of the Conjugate of the Present Disclosure Against HBV mRNA Expression in Mice In this experimental example, the inhibitory efficiency of Conjugate 1 and Comparative Conjugate 2 against HBV mRNA expression in HBV transgenic mice C57BL/6J-Tg (A1b1HBV)44Bri/J was investigated.

The C57BL/6J-Tg (A1b1HBV) 44Bri/J mice were purchased from Department of Laboratory Animal Science, Peking University Health Science Center. HBsAg content in mouse serum was measured using Hepatitis B Virus Surface Antigen Assay Kit (Enzyme-linked Immunosorbent Assay, ELISA) (Shanghai Kehua Bio-engineering Co., Ltd.). Mice with S/COV>10 were selected and randomly divided into groups (all female, 4 mice per group), and respectively numbered; and a normal saline (NS) group was added as a control group. The drug dosages for all animals were calculated according to the body weight (single administration (subcutaneously), different administration dosages of 1 mg/kg and 0.1 mg/kg for Conjugate 1 (in the form of 0.2 mg/ml and 0.02 mg/ml in 0.9% NaCl aqueous solutions), and the dosage volume of 5 mL/kg). Animals were sacrificed at day 7 after administration. The liver was collected and kept with RNA later (Sigma Aldrich), and the liver tissue was homogenized with a tissue homogenizer. Then the total RNA was extracted and obtained by using Trizol according to the standard procedure for total RNA extraction.

The expression level of HBV mRNA in liver tissue was measured by real-time fluorescent qPCR. Specifically, the extracted total RNA was reversely transcribed into cDNA by using ImProm-II™ reverse transcription kit (Promega) according to the instruction thereof, and then the inhibitory efficiency of siRNA against the expression of HBV mRNA in liver tissue was measured by using the fluorescent qPCR kit (Beijing Cowin Biosciences Co., Ltd). In this fluorescent qPCR method, the GAPDH gene was used as an internal control gene; the HBV and GAPDH were detected by using primers for HBV X and GAPDH, respectively.

Sequences of primers for detection are shown in Table 3.

TABLE 3

| Sequences of primers for detection | | |
|---|---|---|
| Genes | Upstream Primers | Downstream Primers |
| HBV X | 5'-CCGTCTGTGCCTTCTCAT CT-3' (SEQ ID NO: 48) | 5'-TAATCTCCTCCCCCAACT CC-3' (SEQ ID NO: 49) |
| GAPDH | 5'-AACTTTGGCATTGTGGAA GGGCTC-3' (SEQ ID NO: 50) | 5'-TGGAAGAGTGGGAGTTGC TGTTGA-3' (SEQ ID NO: 51) |

In this fluorescent qPCR method, the expression of HBV mRNA was expressed as the remaining expression of HBV X gene and calculated by the following equation:

The remaining expression of HBV X gene=(the copy number of HBV X gene in the test group/the copy number of β-actin gene in the test group)/(the copy number of HBV X gene in the control group/the copy number of β-actin gene in the control group)×100%, which is marked as HBV X/β-actin mRNA expression in the figure.

Then, the inhibition percentage of the conjugate against mRNA was calculated according to the following equation:

$$\text{The inhibition percentage of the conjugate against mRNA} = (1-\text{the remaining expression of HBV } X \text{ gene}) \times 100\%,$$

wherein the control group was a group of control mice administered with NS in this experiment and each test group was a group of mice administered with different siRNA conjugates, respectively. The results are shown in FIG. 6.

Figure 6:
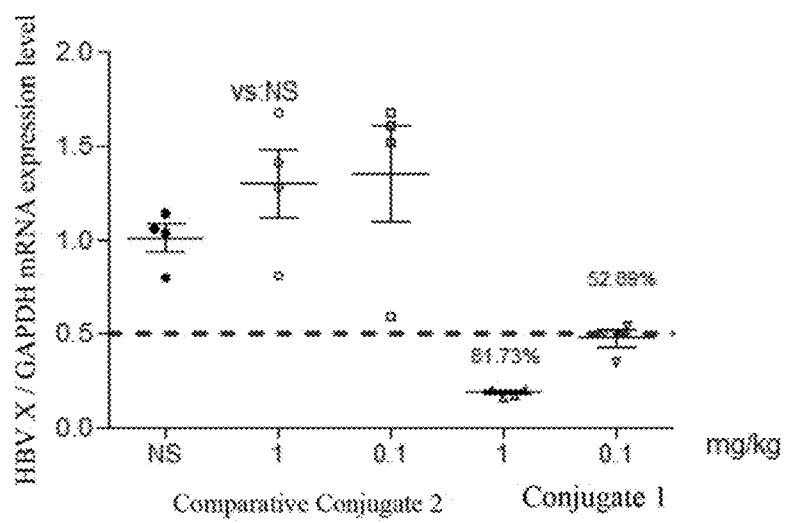
FIG. 6 shows the result of Conjugate 1 for inhibiting HBV mRNA expression in mice.

As can be seen from the results of FIG. 6, Conjugate 1 of the present disclosure described above at the dosage of 1 mg/kg shows an inhibition percentage of up to 81.73% against the target mRNA, exhibiting good inhibitory effect.

Figure 7:
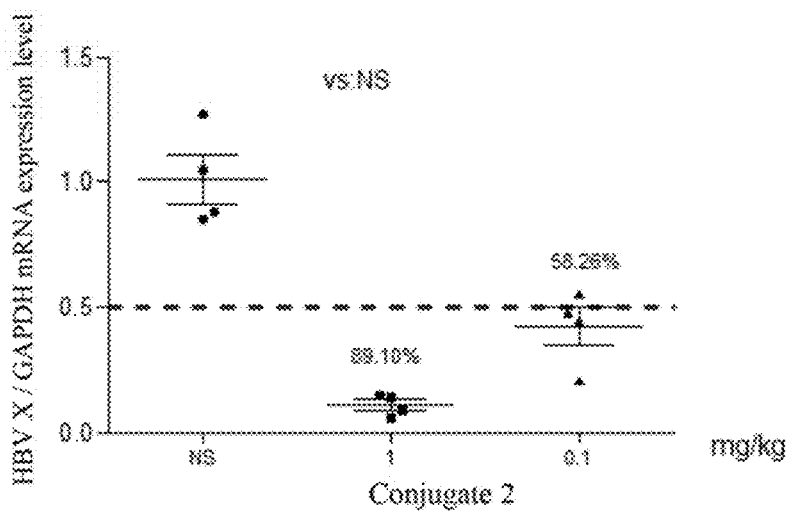
FIG. 7 shows the result of Conjugate 2 for inhibiting HBV mRNA expression in mice.

In other experiments, the expression of HBV mRNA in mice was measured by the same method as that described above, except that the siRNA conjugate administered was replaced with Conjugate 2 for the experiment; and the data were collected at day 7. The results are shown in FIG. 7.

Figure 8:
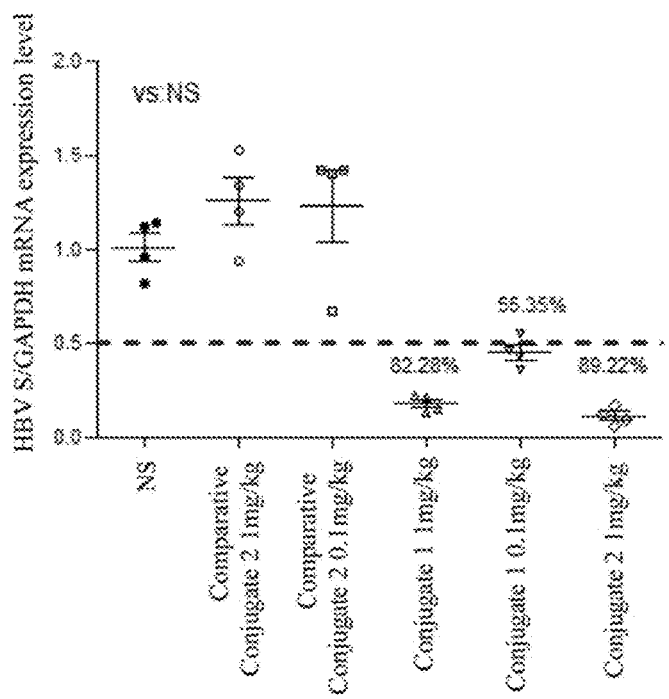
FIG. 8 shows the results of Conjugates 1, 2 and Comparative Conjugate 2 for inhibiting HBV mRNA expression in mice.

In other experiments, the expression of HBV mRNA in mice was measured by the same method as that described above, except that the siRNA conjugate administered was replaced with Conjugates 1, Conjugate 2 and Comparative Conjugate 2 for the experiments. Conjugate 1 and Comparative Conjugate 2 were administered at the two dosages of 1 mg/kg and 0.1 mg/kg, respectively; Conjugate 2 was administered at the dosage of 1 mg/kg; and the detection sequences were replaced with those shown in Table 4. The results are shown in FIG. 8.

TABLE 4

Sequences of primers for detection

| Genes | Upstream Primers | Downstream Primers |
| --- | --- | --- |
| HBV | 5'-CGTTTCTCCTGGCTCAGTTTA-3' (SEQ ID NO: 52) | 5'-CAGCGGTAAAAAGGGACTCAA-3' (SEQ ID NO: 53) |
| GAPDH | 5'-AACTTTGGCATTGTGGAAGGGCTC-3' (SEQ ID NO: 50) | 5'-TGGAAGAGTGGGAGTTGCTGTTGA-3' (SEQ ID NO: 51) |

As can be seen from the results of FIGS. 7 and 8, the conjugates of the present disclosure described above show good inhibitory effects on the target mRNA, and the inhibitory effects on different HBV mRNAs are substantially the same.

Experimental Example 4

This Experiment Illustrates a Time-dependent Test of the Inhibitory Efficiency of the siRNA Conjugates of the Present Disclosure Against the Expression of HBsAg and HBV DNA in Serum of HBV Transgenic Mice The low-concentration AAV-HBV model mice were randomly divided into groups based on HBsAg content in serum (5 mice in each group). Conjugate 2 was administered to each group, and NS was used as a blank control. The drug dosages for all animals were calculated according to the body weight (single administration (subcutaneously), administration dosages of 3 mg/kg and 1 mg/kg (in the form of 0.6 mg/ml and 0.2 mg/ml in 0.9% NaCl aqueous solution), and administration volume of 5 mL/kg). The blood was taken from mouse orbital venous plexus before administration (marked as D0) and at days 7, 14, 21, 28, 56, 84, 98, 112, 126, and 140 after administration, and HBsAg level in serum was measured for each time point.

The blood taken from the orbit was about 100 µl each time, and the serum was no less than 20 µl after centrifugation. The content of HBsAg in serum was measured by using HBsAg CLIA kit (Autobio, CL0310).

The normalized HBsAg level in serum=(the content of HBsAg in the test group after administration/the content of HBsAg in the test group before administration)×100%.

The inhibition percentage against HBsAg=(1−the content of HBsAg in the test group after administration/the content of HBsAg in the test group before administration)×100%, wherein the content of HBsAg was expressed as equivalents (UI) of HBsAg per milliliter (ml) of serum.

Figure 9:
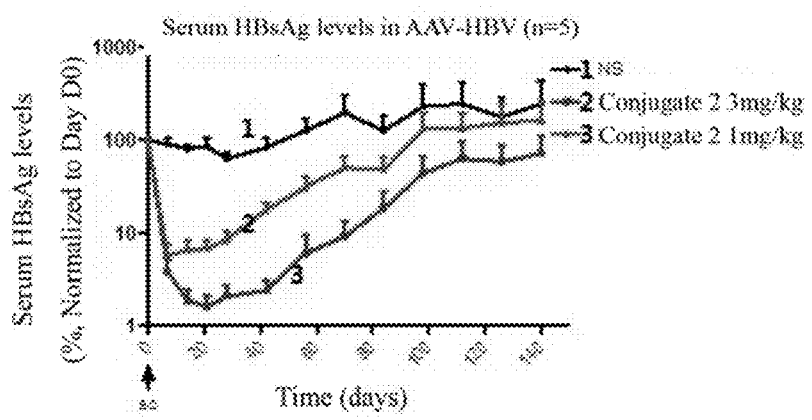
FIG. 9 shows the results of time-dependent tests on the inhibitory efficiency of the siRNA in the tested siRNA Conjugates against serum HBsAg expression in HBV transgenic mice.

The results are shown in FIG. 9.

As can be seen from the results of FIG. 9, the NS negative control group shows no inhibitory effect at different time points after administration; in contrast, Conjugate 2 shows excellent inhibitory effect on HBsAg at different time points after administration, and consistently exhibits high inhibition percentage against HBsAg in serum over a period of up to 100 days, indicating that it can stably and efficiently inhibit the expression of HBV gene over a longer period.

Figure 10:
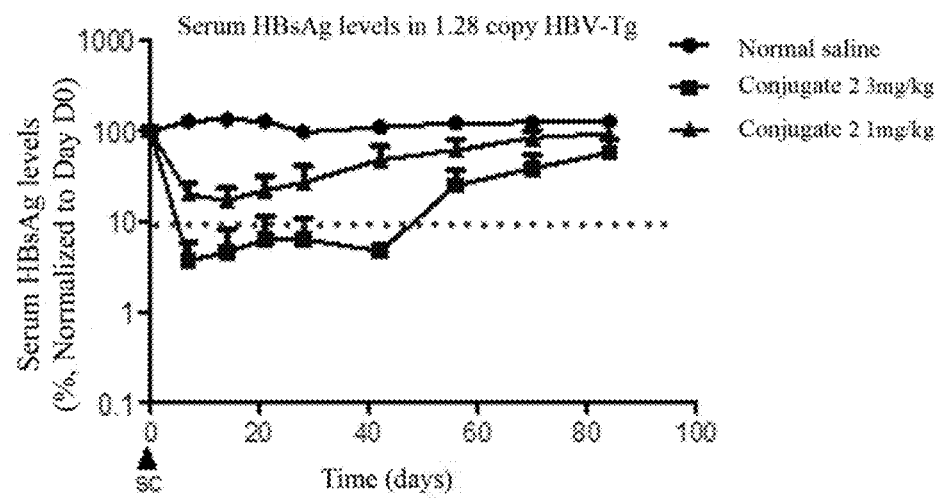
FIG. 10 shows the results of time-dependent tests on the inhibitory efficiency of Conjugate 2 against serum HBsAg expression in 1.28 copy mice.

In further experiments, according to the methods described above, in 1.28 copy mice, two dosage groups (3 mg/kg and 1 mg/kg) of Conjugate 2 were administered respectively. The administration period continued until day 85, and the inhibitory effect on HBsAg was measured according to the methods described above. The results are shown in FIG. 10.

DNA was extracted from the serum according to the instructions of QIAamp 96 DNA Blood Kit. The expression level of HBV DNA was measured by qPCR. The results are shown in FIG. 11.

The normalized HBV DNA level in serum=(the content of HBV DNA in the test group after administration/the content of HBV DNA in the test group before administration)×100%.

The inhibition percentage against HBV DNA=(1−the content of HBV DNA in the test group after administration/the content of HBV DNA in the test group before administration)×100%, wherein the content of HBV DNA was expressed as copies of HBV DNA per milliliter (ml) of serum.

Figure 11:
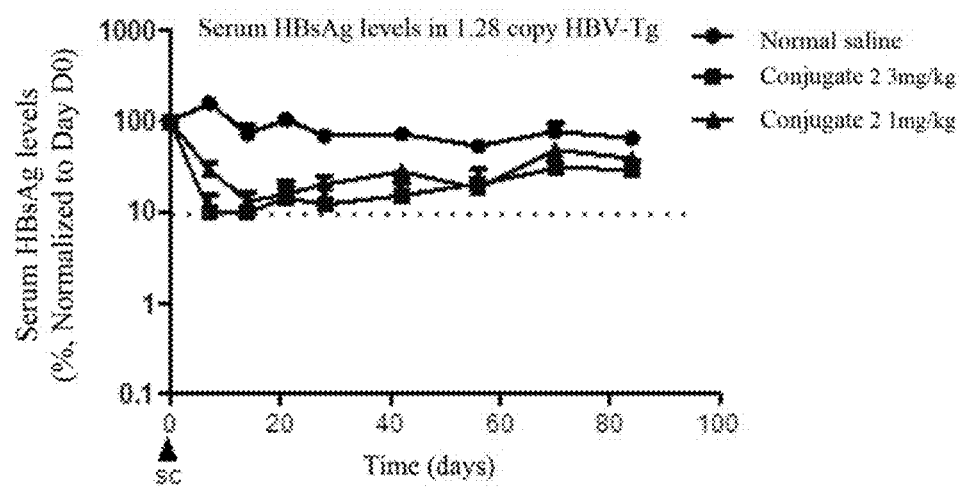
FIG. 11 shows the results of time-dependent tests on the inhibitory efficiency of Conjugate 2 against HBV DNA in 1.28 copy mice.

As can be seen from the results of FIGS. 10 and 11, in 1.28 copy mice, Conjugate 2 of the present disclosure consistently shows highly efficient inhibition against the expression of HBV gene and HBV DNA over a period of 85 days.

Embodiments of the present disclosure are described in detail above, but the present disclosure is not limited to the specific details of the above-described embodiments. Various simple variations of the technical solution of the present disclosure can be made within the scope of the technical concept of the present disclosure, and these simple variations are within the scope of the present disclosure.

It is to be noted that each of the specific technical features described in the above embodiments can be combined in any suitable manner as long as no contradiction is caused. In order to avoid unnecessary repetition, the various possible combination manners are no longer described in the present disclosure.

In addition, various different embodiments of the present disclosure may also be carried out in connection combination as long as it does not contravene the idea of the present disclosure, which should also be regarded as the disclosure of the present disclosure.

What is claimed is:

1. A siRNA, comprising a sense strand and an antisense strand, each nucleotide in the siRNA being independently a modified or unmodified nucleotide, wherein the sense strand comprises a nucleotide sequence I, and the antisense strand comprises a nucleotide sequence II; the nucleotide sequence I and the nucleotide sequence II are at least partly reverse complementary to form a double stranded region; wherein the nucleotide sequence I comprises a nucleotide sequence A, which has the same length as the nucleotide sequence shown in SEQ ID NO: 1 with no more than 3 nucleotide differences; and the nucleotide sequence II comprises a nucleotide sequence B, which has the same length as the nucleotide sequence shown in SEQ ID NO: 2 with no more than 3 nucleotide differences:

$$5'\text{-UGCUAUGCCUCAUCUUCUZ-3'};\quad \text{(SEQ ID NO: 1)}$$

$$5'\text{-Z'AGAAGAUGAGGCAUAGCA-3'};\quad \text{(SEQ ID NO: 2)}$$

wherein,

Z is A; Z' is U; and the nucleotide sequence A comprises a nucleotide $Z_A$ at the position corresponding to Z; the nucleotide sequence B comprises a nucleotide $Z'_B$ at the position corresponding to Z'; the nucleotide Z'B is the first nucleotide at 5' terminal of the antisense strand, wherein each nucleotide in the sense strand and the antisense strand is independently a fluoro modified nucleotide or a non-fluoro modified nucleotide; wherein the fluoro modified nucleotides are in the nucleotide sequences A and B; and in the direction from 5' terminal to 3' terminal, the nucleotides at positions 7, 8 and 9 of the nucleotide sequence A are fluoro modified nucleotides; and in the direction from 5' terminal to 3' terminal, the nucleotides at positions 2, 6, 14 and 16 of the nucleotide sequence B are fluoro modified nucleotides.

2. The siRNA according to claim 1, wherein the nucleotide sequence A is a nucleotide sequence shown in SEQ ID NO: 3; and the nucleotide sequence B is a nucleotide sequence shown in SEQ ID NO: 4:

$$5'\text{-UGCUAUGCCUCAUCUUCUZ}_A\text{-3'};\quad \text{(SEQ ID NO: 3)}$$

$$5'\text{-Z'}_B\text{AGAAGAUGAGGCAUAGCA-3'};\quad \text{(SEQ ID NO: 4)}$$

wherein Z'B is the first nucleotide at 5' terminal of the antisense strand; $Z_A$ is selected from A, U, G or C, and Z'B is a nucleotide complementary to $Z_A$.

3. The siRNA according to claim 1, wherein the nucleotide sequence I further comprises a nucleotide sequence III, and the nucleotide sequence II further comprises a nucleotide sequence IV; the nucleotide sequence III and the nucleotide sequence IV independently of one another are 1-4 nucleotides in length; the nucleotide sequence III is linked to 5' terminal of the nucleotide sequence A; the nucleotide sequence IV is linked to 3' terminal of the nucleotide sequence B; and the nucleotide sequence III and the nucleotide sequence IV have the same length and are substantially reverse complementary or completely reverse complementary; the "substantially reverse complementary" means that there is no more than 1 base mispairing between two nucleotide sequences; the "completely reverse complementary" means that there is no mispairing between two nucleotide sequences.

4. The siRNA according to claim 3, wherein the nucleotide sequence III and the nucleotide sequence IV both are of 1 nucleotide in length, and the base of the nucleotide sequence III is G;

the nucleotide sequence III and the nucleotide sequence IV both are 2 nucleotides in length; in the direction from 5' terminal to 3' terminal, the base composition of the nucleotide sequence III is AG;

the nucleotide sequence III and the nucleotide sequence IV both are 3 nucleotides in length; in the direction from 5' terminal to 3' terminal, the base composition of the nucleotide sequence III is AAG; or the nucleotide sequence III and the nucleotide sequence IV both are 4 nucleotides in length; in the direction from 5' terminal to 3' terminal, the base composition of the nucleotide sequence III is CAAG.

5. The siRNA according to claim 1, wherein the nucleotide sequence II further comprises a nucleotide sequence V, which is 1-3 nucleotides in length and is linked to 3' terminal of the antisense strand, thereby forming a 3' overhang of the antisense strand.

6. The siRNA according to claim 1, wherein the sense strand of the siRNA comprises the nucleotide sequence shown in SEQ ID NO: 3, and the antisense strand comprises the nucleotide sequence shown in SEQ ID NO: 5:

```
                                       (SEQ ID NO: 3)
       5'-UGCUAUGCCUCAUCUUCUZ_A-3';

(SEQ ID NO: 5)
       5'-Z'_BAGAAGAUGAGGCAUAGCAGC-3';
``` or the sense strand of the siRNA comprises the nucleotide sequence shown in SEQ ID NO: 3, and the antisense strand comprises the nucleotide sequence shown in SEQ ID NO: 6:

```
                                       (SEQ ID NO: 3)
       5'-UGCUAUGCCUCAUCUUCUZ_A-3';

(SEQ ID NO: 6)
       5'-Z'_BAGAAGAUGAGGCAUAGCAUU-3';
``` wherein the nucleotide $Z'_B$ is the first nucleotide at 5' terminal of the antisense strand; $Z_A$ is selected from A, U, G or C; and $Z'_B$ is a nucleotide complementary to $Z_A$.

7. The siRNA according to claim 1, wherein each non-fluoro modified nucleotide is a methoxy modified nucleotide, wherein the methoxy modified nucleotide refers to a nucleotide formed by substituting the 2'-hydroxy of the ribose group of the nucleotide with a methoxy group.

8. The siRNA according to claim 1, wherein in the direction from 5' terminal to 3' terminal, the nucleotides at positions 5, 7, 8 and 9 of the nucleotide sequence A in the sense strand of the siRNA are fluoro modified nucleotides, and the nucleotides at the other positions in the sense strand of the siRNA are methoxy modified nucleotides; and in the direction from 5' terminal to 3' terminal, the nucleotides at positions 2, 6, 8, 9, 14 and 16 of the nucleotide sequence B in the antisense strand of the siRNA are fluoro modified nucleotides, and the nucleotides at the other positions in the antisense strand of the siRNA are methoxy modified nucleotides; or in the direction from 5' terminal to 3' terminal, the nucleotides at positions 5, 7, 8 and 9 of the nucleotide sequence A in the sense strand of the siRNA are fluoro modified nucleotides, and the nucleotides at the other positions in the sense strand of the siRNA are methoxy modified nucleotides; and in the direction from 5' terminal to 3' terminal, the nucleotides at positions 2, 6, 14 and 16 of the nucleotide sequence B in the antisense strand of the siRNA are fluoro modified nucleotides, and the nucleotides at the other positions in the antisense strand of the siRNA are methoxy modified nucleotides; or in the direction from 5' terminal to 3' terminal, the nucleotides at positions 7, 8 and 9 of the nucleotide sequence A in the sense strand of the siRNA are fluoro modified nucleotides, and the nucleotides at the other positions in the sense strand of the siRNA are methoxy modified nucleotides; and in the direction from 5' terminal to 3' terminal, the nucleotides at positions 2, 6, 14 and 16 of the nucleotide sequence B in the antisense strand of the siRNA are fluoro modified nucleotides, and the nucleotides at the other positions in the antisense strand of the siRNA are methoxy modified nucleotides.

9. The siRNA according to claim 1, wherein the siRNA is siHBVS3, siHBVS4, siHBVS5, or siHBVS6:

```
siHBVS3
Sense strand:
                                       (SEQ ID NO: 9)
5'-UmGmCmUmAmUmGfCfCfUmCmAmUmCmUmUmCmUmAm-3', Antisense strand:
                                       (SEQ ID NO: 10)
5'-UmAfGmAmAmGfAmUmGmAmGmGmCmAfUmAfGmCmAmGmCm-3', siHBVS4
Sense strand:
                                       (SEQ ID NO: 9)
5'-UmGmCmUmAmUmGfCfCfUmCmAmUmCmUmUmCmUmAm-3', Antisense strand:
                                       (SEQ ID NO: 11)
5'-UmAfGmAmAmGfAmUmGmAmGmGmCmAfUmAfGmCmAmUmUm-3', siHBVS5
Sense strand:
                                       (SEQ ID NO: 12)
5'-UmGmCmUmAfUmGfCfCfUmCmAmUmCmUmUmCmUmAm-3', Antisense strand:
                                       (SEQ ID NO: 13)
5'-UmAfGmAmAmGfAmUfGfAmGmGmCmAfUmAfGmCmAmGmCm-3', siHBVS6
Sense strand:
                                       (SEQ ID NO: 12)
5'-UmGmCmUmAfUmGfCfCfUmCmAmUmCmUmUmCmUmAm-3', Antisense strand:
                                       (SEQ ID NO: 14)
5'-UmAfGmAmAmGfAmUfGfAmGmGmCmAfUmAfGmCmAmUmUm-3',
``` wherein C, G, U, and A represent the base composition of the nucleotides; m represents that the nucleotide adjacent to the left side of the letter m is a methoxy modified nucleotide; f represents that the nucleotide adjacent to the left side of the letter f is a fluoro modified nucleotide.

10. The siRNA according to claim 1, wherein in the siRNA, at least one phosphate group is a phosphorothioate group, and the phosphorothioate linkage exists in at least one of the following positions:

the position between the first and second nucleotides at 5' terminal of the sense strand;

the position between the second and third nucleotides at 5' terminal of the sense strand;

the position between the first and second nucleotides at 3' terminal of the sense strand;

the position between the second and third nucleotides at 3' terminal of the sense strand;

the position between the first and second nucleotides at 5' terminal of the antisense strand;

the position between the second and third nucleotides at 5' terminal of the antisense strand;

the position between the first and second nucleotides at 3' terminal of the antisense strand; and the position between the second and third nucleotides at 3' terminal of the antisense strand.

11. The siRNA according to claim 1, wherein the siRNA is siHBVS7, siHBVS8, siHBVS9, or siHBVS10:

```
siHBVS7
Sense strand:
                                       (SEQ ID NO: 15)
5'-UmsGmsCmUmAmUmGfCfCfUmCmAmUmCmUmUmCmUmAm-3', AntiSense strand:
                                       (SEQ ID NO: 16)
5'-UmsAfsGmAmAmGfAmUmGmAmGmGmCmAfUmAfGmCmAmsGms Cm-3', siHBVS8
Sense strand:
                                       (SEQ ID NO: 15)
5'-UmsGmsCmUmAmUmGfCfCfUmCmAmUmCmUmUmCmUmAm-3', AntiSense strand:
                                       (SEQ ID NO: 17)
5'-UmsAfsGmAmAmGfAmUmGmAmGmGmCmAfUmAfGmCmAmsUms Um-3', siHBVS9
Sense strand:
                                       (SEQ ID NO: 18)
5'-UmsGmsCmUmAfUmGfCfCfUmCmAmUmCmUmUmCmUmAm-3', AntiSense strand:
                                       (SEQ ID NO: 19)
5'-UmsAfsGmAmAmGfAmUfGfAmGmGmCmAfUmAfGmCmAmsGms Cm-3', siHBVS10
Sense strand:
                                       (SEQ ID NO: 18)
5'-UmsGmsCmUmAfUmGfCfCfUmCmAmUmCmUmUmCmUmAm-3', Antisense strand:
                                       (SEQ ID NO: 20)
5'-UmsAfsGmAmAmGfAmUfGfAmGmGmCmAfUmAfGmCmAmsUms Um-3',
``` wherein C, G, U, and A represent the base composition of the nucleotides; m represents that the nucleotide adjacent to the left side of the letter m is a methoxy modified nucleotide; f represents that the nucleotide adjacent to the left side of the letter f is a fluoro modified nucleotide; s represents that the two nucleotides adjacent to both sides of the letter s are linked by a phosphorothioate linkage.

12. The siRNA according to claim 1, wherein the nucleotide at 5'-terminal of the antisense strand is a 5'-phosphate nucleotide or a 5'-phosphate analogue modified nucleotide, wherein the 5'-phosphate nucleotide is a nucleotide having a structure as shown by Formula (2); and the 5'-phosphate analogue modified nucleotide is a nucleotide as shown by any one of Formulae (3) to (6):

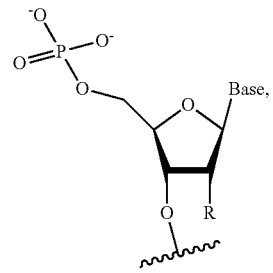

Formula (2)

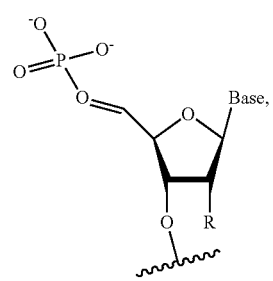

Formula (3)

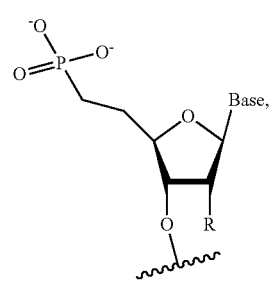

Formula (4)

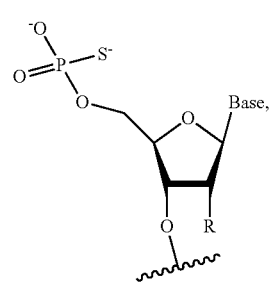

Formula (5)

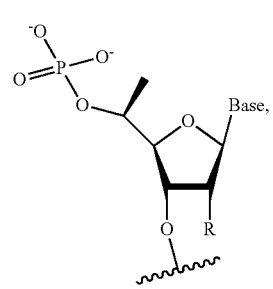

Formula (6)

wherein R is selected from H, OH, methoxy, or F; "Base" represents a base selected from A, U, C, G, or T.

13. The siRNA according to claim 1, wherein the siRNA is siHBVS11, siHBVS12, siHBVS13, siHBVS14, siHBVS15, siHBVS16, siHBVS17, or siHBVS18:

siHBVS11
Sense strand:
(SEQ ID NO: 9)
5'-UmGmCmUmAmUmGfCfCfUmCmAmUmCmUmUmCmUmAm-3', Antisense strand:
(SEQ ID NO: 21)
5'-P1-UmAfGmAmAmGfAmUmGmAmGmGmCmAfUmAfGmCmAm
GmCm-3', siHBVS12
Sense strand:
(SEQ ID NO: 9)
5'-UmGmCmUmAmUmGfCfCfUmCmAmUmCmUmUmCmUmAm-3', Antisense strand:
(SEQ ID NO: 22)
5'-P1-UmAfGmAmAmGfAmUmGmAmGmGmCmAfUmAfGmCmAm
UmUm-3', siHBVS13
Sense strand:
(SEQ ID NO: 12)
5'-UmGmCmUmAfUmGfCfCfUmCmAmUmCmUmUmCmUmAm-3', Antisense strand:
(SEQ ID NO: 23)
5'-P1-UmAfGmAmAmGfAmUfGfAmGmGmCmAfUmAfGmCmAm
GmCm-3', siHBVS14
Sense strand:
(SEQ ID NO: 12)
5'-UmGmCmUmAfUmGfCfCfUmCmAmUmCmUmUmCmUmAm-3', Antisense strand:
(SEQ ID NO: 24)
5'-P1-UmAfGmAmAmGfAmUfGfAmGmGmCmAfUmAfGmCmAmUm
Um-3', siHBVS15
Sense strand:
(SEQ ID NO: 15)
5'-UmsGmsCmUmAmUmGfCfCfUmCmAmUmCmUmUmCmUmAm-3', Antisense strand:
(SEQ ID NO: 25)
5'-P1-UmsAfsGmAmAmGfAmUmGmAmGmGmCmAfUmAfGmCmAms
GmsCm-3', siHBVS16
Sense strand:
(SEQ ID NO: 15)
5'-UmsGmsCmUmAmUmGfCfCfUmCmAmUmCmUmUmCmUmAm-3', Antisense strand:
(SEQ ID NO: 26)
5'-P1-UmsAfsGmAmAmGfAmUmGmAmGmGmCmAfUmAfGmCmAms
UmsUm-3', siHBVS17
Sense strand:
(SEQ ID NO: 18)
5'-UmsGmsCmUmAfUmGfCfCfUmCmAmUmCmUmUmCmUmAm-3', Antisense strand:
(SEQ ID NO: 27)
5'-P1-UmsAfsGmAmAmGfAmUfGfAmGmGmCmAfUmAfGmCmAms
GmsCm-3', siHBVS18
Sense strand:
(SEQ ID NO: 18)
5'-UmsGmsCmUmAfUmGfCfCfUmCmAmUmCmUmUmCmUmAm-3', Antisense strand:
(SEQ ID NO: 28)
5'-P1-UmsAfsGmAmAmGfAmUfGfAmGmGmCmAfUmAfGmCmAms
UmsUm-3';

wherein C, G, U, and A represent the base composition of the nucleotides; m represents that the nucleotide adjacent to the left side of the letter m is a methoxy modified nucleotide; f represents that the nucleotide adjacent to the left side of the letter f is a fluoro modified nucleotide; s represents that the two nucleotides adjacent to both sides of the letter s are linked by a phosphorothioate linkage; P1 represents that the nucleotide adjacent to the right side of P1 is a 5'-phosphate nucleotide or a 5'-phosphate analogue modified nucleotide.

14. A pharmaceutical composition, wherein the pharmaceutical composition comprises the siRNA according to claim 1 and a pharmaceutically acceptable carrier.

15. A siRNA conjugate, comprising the siRNA according to claim 1 and a conjugating group conjugated to the siRNA.

16. The siRNA conjugate according to claim 15, wherein the conjugate has a structure as shown by Formula (308):

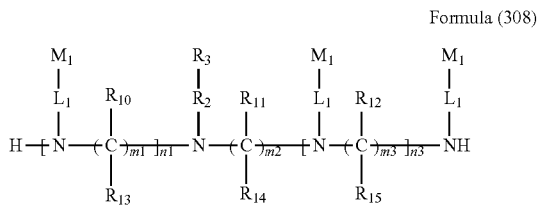

Formula (308)

wherein n1 is an integer of 1-3, and n3 is an integer of 0-4; m1, m2, and m3 independently of one another are an integer of 2-10;

$R_{10}$, $R_{11}$, $R_{12}$, $R_{13}$, $R_{14}$ and $R_{15}$ independently of one another are H, or selected from the group consisting of $C_1$-$C_{10}$ alkyl, $C_1$-$C_{10}$ haloalkyl, and $C_1$-$C_{10}$ alkoxy;

$R_3$ is a group having a structure as shown by Formula (A59):

Formula (A59)

wherein E1 is OH, SH or $BH_2$; Nu is siRNA;

$R_2$ is a linear alkylene of 1 to 20 carbon atoms in length, wherein one or more carbon atoms are optionally replaced with one or more groups selected from the group consisting of: C(O), NH, O, S, CH=N, S(O)$_2$, $C_2$-$C_{10}$ alkenylene, $C_2$-$C_{10}$ alkynylene, $C_6$-$C_{10}$ arylene, $C_3$-$C_{18}$ heterocyclylene, and $C_5$-$C_{10}$ heteroarylene, and wherein $R_2$ optionally has one or more substituents selected from the group consisting of: $C_1$-$C_{10}$ alkyl, $C_6$-$C_{10}$ aryl, $C_5$-$C_{10}$ heteroaryl, $C_1$-$C_{10}$ haloalkyl, —O$C_1$-$C_{10}$ alkyl, —O$C_1$-$C_{10}$ alkylphenyl, —$C_1$-$C_{10}$ alkyl-OH, —O$C_1$-$C_{10}$ haloalkyl, —S$C_1$-$C_{10}$ alkyl, —$SC_1$-$C_{10}$ alkylphenyl, —$C_1$-$C_{10}$ alkyl-SH, —$SC_1$-$C_{10}$ haloalkyl, halo, —OH, —SH, —$NH_2$, —$C_1$-$C_{10}$ alkyl-$NH_2$, —N($C_1$-$C_{10}$ alkyl)($C_1$-$C_{10}$ alkyl), —NH($C_1$-$C_{10}$ alkyl), cyano, nitro, —$CO_2H$, —C(O)O($C_1$-$C_{10}$ alkyl), —CON($C_1$-$C_{10}$ alkyl)($C_1$-$C_{10}$ alkyl), —CONH($C_1$-$C_{10}$ alkyl), —$CONH_2$, —NHC(O)($C_1$-$C_{10}$ alkyl), —NHC(O)(phenyl), —N($C_1$-$C_{10}$ alkyl)C(O)($C_1$-$C_{10}$ alkyl), —N($C_1$-$C_{10}$ alkyl)C(O)(phenyl), —C(O)$C_1$-$C_{10}$ alkyl, —C(O)$C_1$-$C_{10}$ alkylphenyl, —C(O)$C_1$-$C_{10}$ haloalkyl, —OC(O)$C_1$-$C_{10}$ alkyl, —$SO_2$($C_1$-$C_{10}$ alkyl), —$SO_2$(phenyl), —$SO_2$($C_1$-$C_{10}$ haloalkyl), —$SO_2NH_2$, —$SO_2$NH($C_1$-$C_{10}$ alkyl), —$SO_2$NH(phenyl), —$NHSO_2$($C_1$-$C_{10}$ alkyl), —$NHSO_2$(phenyl), and —$NHSO_2$($C_1$-$C_{10}$ haloalkyl);

each L1 is independently a linear alkylene of 1 to 70 carbon atoms in length, wherein one or more carbon atoms are optionally replaced with one or more groups selected from the group consisting of: C(O), NH, O, S, CH=N, S(O)$_2$, $C_2$-$C_{10}$ alkenylene, $C_2$-$C_{10}$ alkynylene, $C_6$-$C_{10}$ arylene, $C_3$-$C_{18}$ heterocyclylene, and $C_5$-$C_{10}$ heteroarylene, and wherein $L_1$ optionally has one or more substituents selected from the group consisting of: $C_1$-$C_{10}$ alkyl, $C_6$-$C_{10}$ aryl, $C_5$-$C_{10}$ heteroaryl, $C_1$-$C_{10}$ haloalkyl, —$OC_1$-$C_{10}$ alkyl, —$OC_1$-$C_{10}$ alkylphenyl, —$C_1$-$C_{10}$ alkyl-OH, —$OC_1$-$C_{10}$ haloalkyl, —$SC_1$-$C_{10}$ alkyl, —$SC_1$-$C_{10}$ alkylphenyl, —$C_1$-$C_{10}$ alkyl-SH, —$SC_1$-$C_{10}$ haloalkyl, halo, —OH, —SH, —$NH_2$, —$C_1$-$C_{10}$ alkyl-$NH_2$, —N(C1-$C_{10}$ alkyl)($C_1$-$C_{10}$ alkyl), —NH($C_1$-$C_{10}$ alkyl), cyano, nitro, —$CO_2H$, —C(O)O($C_1$-$C_{10}$ alkyl), —CON($C_1$-$C_{10}$ alkyl)($C_1$-$C_{10}$ alkyl), —CONH($C_1$-$C_{10}$ alkyl), —$CONH_2$, —NHC(O)($C_1$-$C_{10}$ alkyl), —NHC(O)(phenyl), —N($C_1$-$C_{10}$ alkyl)C(O)($C_1$-$C_{10}$ alkyl), —N($C_1$-$C_{10}$ alkyl)C(O)(phenyl), —C(O)$C_1$-$C_{10}$ alkyl, —C(O)$C_1$-$C_{10}$ alkylphenyl, —C(O)$C_1$-$C_{10}$ haloalkyl, —OC(O)$C_1$-$C_{10}$ alkyl, —$SO_2$($C_1$-$C_{10}$ alkyl), —$SO_2$(phenyl), —$SO_2$($C_1$-$C_{10}$ haloalkyl), —$SO_2NH_2$, —$SO_2$NH($C_1$-$C_{10}$ alkyl), —$SO_2$NH(phenyl), —$NHSO_2$($C_1$-$C_{10}$ alkyl), —$NHSO_2$(phenyl), and —$NHSO_2$($C_1$-$C_{10}$ haloalkyl);

∿ represents a site where a group is linked to the rest of the molecule;

$M_1$ represents a targeting group.

17. The siRNA conjugate according to claim 16, wherein each L1 is independently selected from the connection combinations of one or more of Formulae A1-A26:

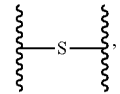 (A1)

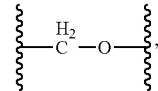 (A2)

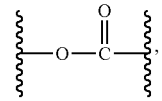 (A3)

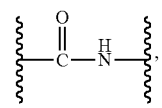 (A4)

-continued

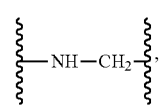 (A5)

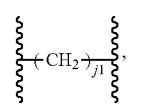 (A6)

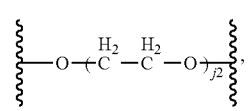 (A7)

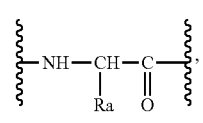 (A8)

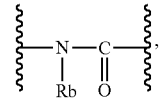 (A9)

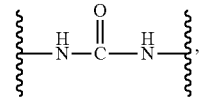 (A10)

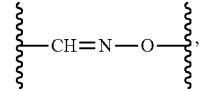 (A11)

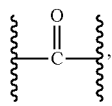 (A12)

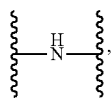 (A13)

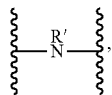 (A14)

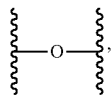 (A15)

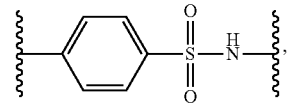 (A16)

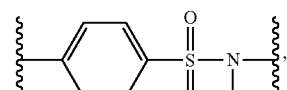 (A17)

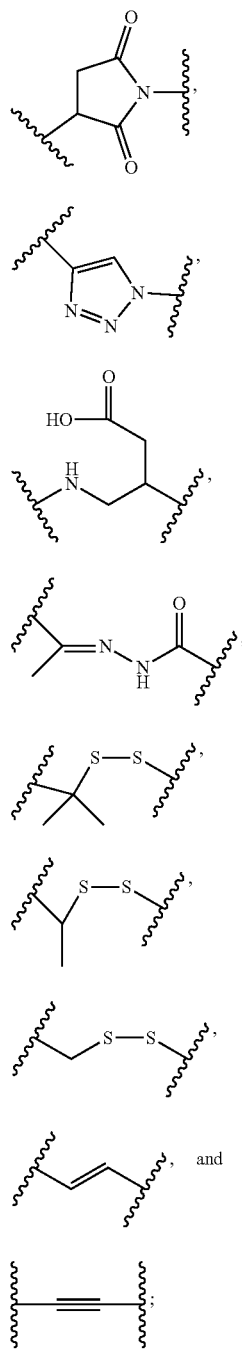
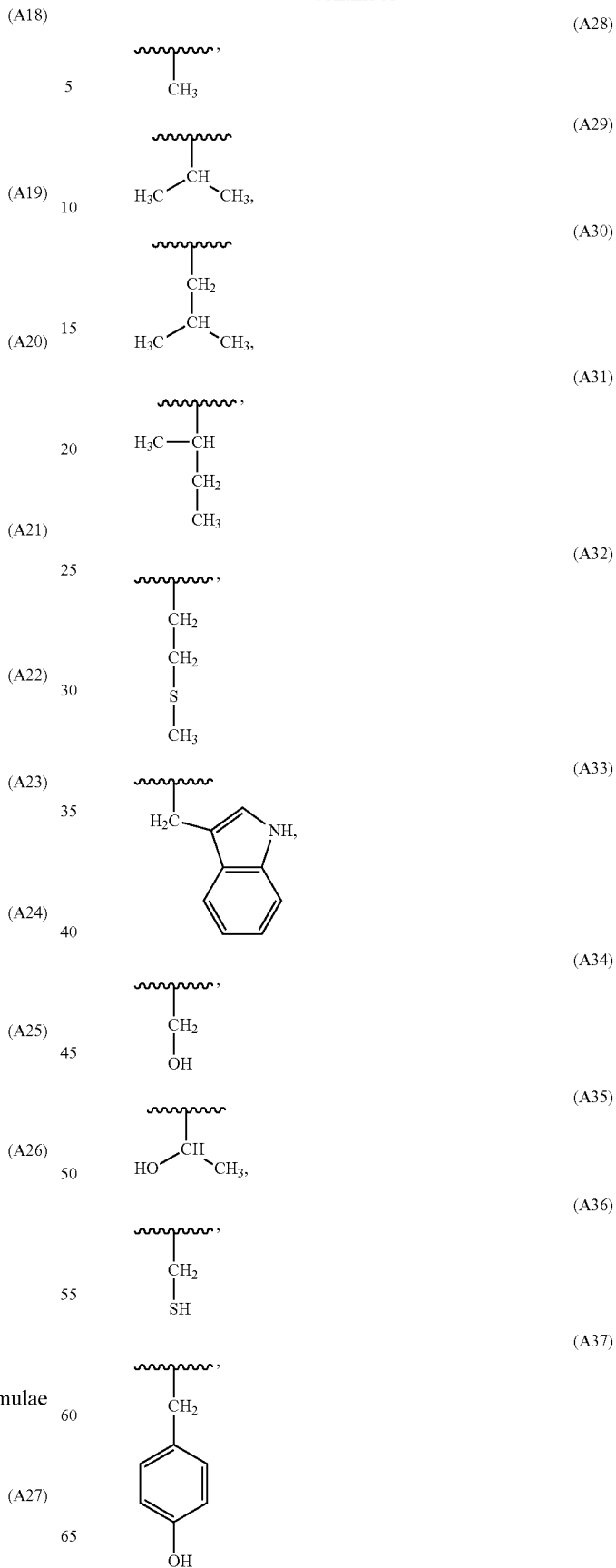
wherein j1 is an integer of 1-20;
j2 is an integer of 1-20;
R' is a $C_1$-$C_{10}$ alkyl;
Ra is selected from the group consisting of Formulae A27-A45, and connection combination thereof:

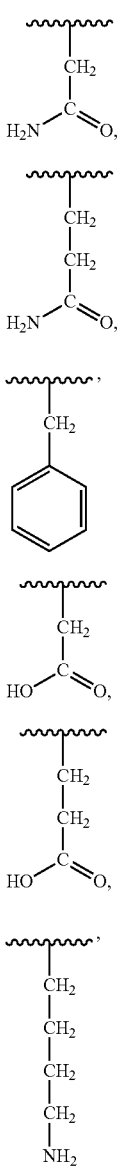

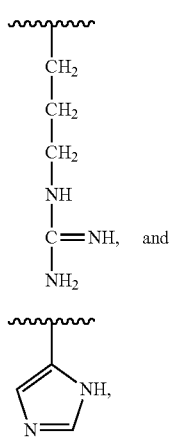

Rb is a $C_1$-$C_{10}$ alkyl.

18. The siRNA conjugate according to claim 16, wherein L1 is selected from the connection combinations of one or more of A1, A4, A5, A6, A8, A10, A11, A13, and thereof; or $L_1$ is selected from the connection combinations of at least two of A1, A4, A8, A10, and A11.

19. The siRNA conjugate according to claim 17, wherein $L_1$ is 3 to 25 atoms in length, or the length of $L_1$ further is 4 to 15 atoms.

20. The siRNA conjugate according to claim 17, wherein m1, m2 and m3 independently of one another are an integer of 2-5; or wherein m1=m2=m3.

21. The siRNA conjugate according to claim 16, wherein each of the targeting groups is independently a ligand that has affinity to the asialoglycoprotein receptors (ASGP-R) on the surface of mammalian hepatocytes.

22. The siRNA conjugate according to claim 21, wherein each of the targeting groups is independently an asialoglycoprotein or saccharide.

23. The siRNA conjugate according to claim 21, wherein at least one or each of the targeting groups is galactose or N-acetylgalactosamine.

24. The siRNA conjugate according to claim 16, wherein the conjugate has a structure as shown by Formula (403), (404), (405), (406), (407), (408), (409), (410), (411), (412), (413), (414), (415), (416), (417), (418), (419), (420), (421), or (422):

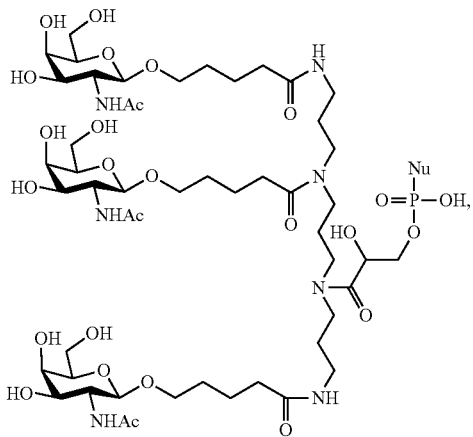

Formula (403)

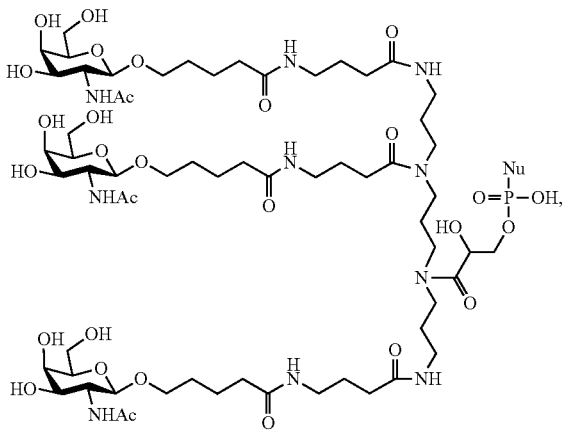

Formula (404)

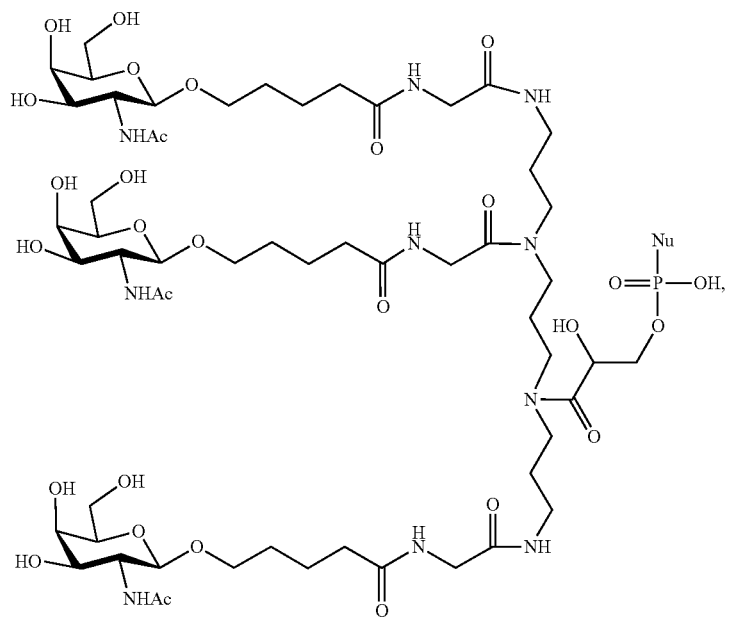
Formula (405)
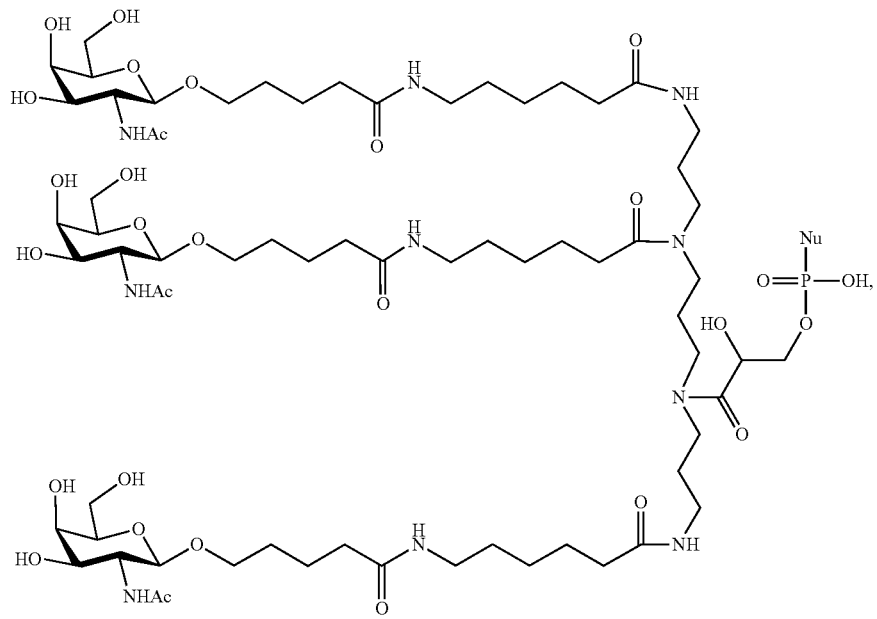
Formula (406)

-continued
Formula (407)
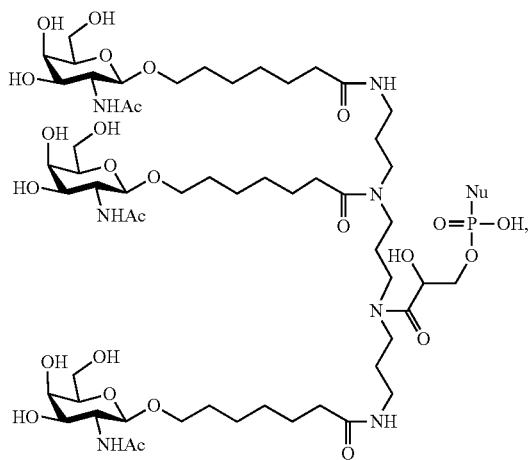
Formula (408)
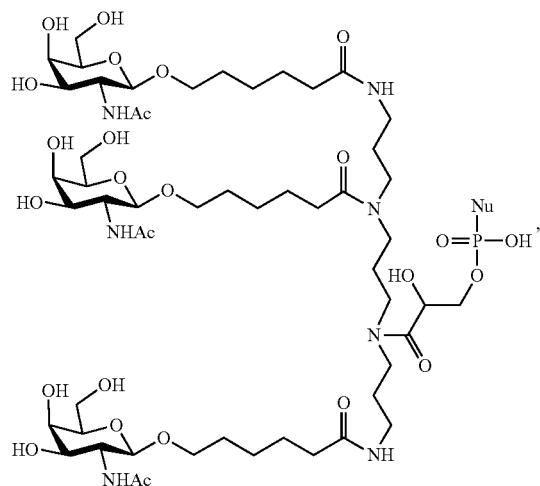
Formula (409)
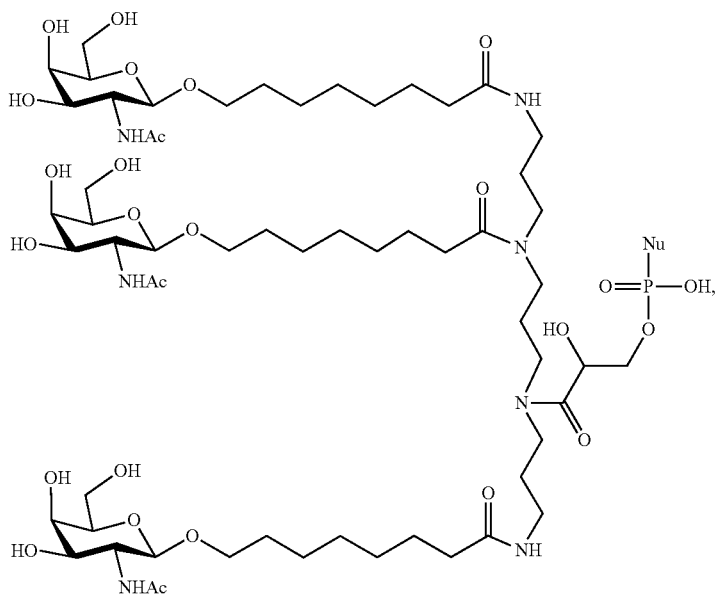

-continued
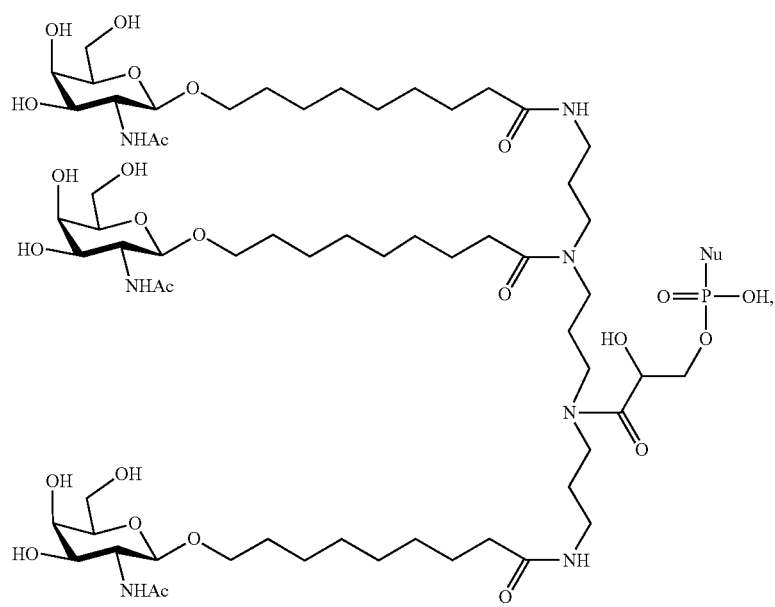
Formula (410)
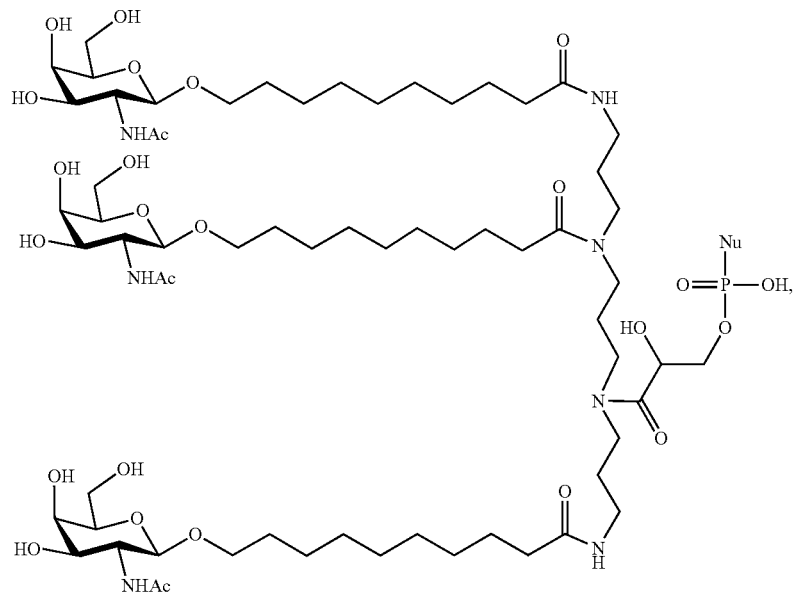
Formula (411)

-continued
Formula (412)
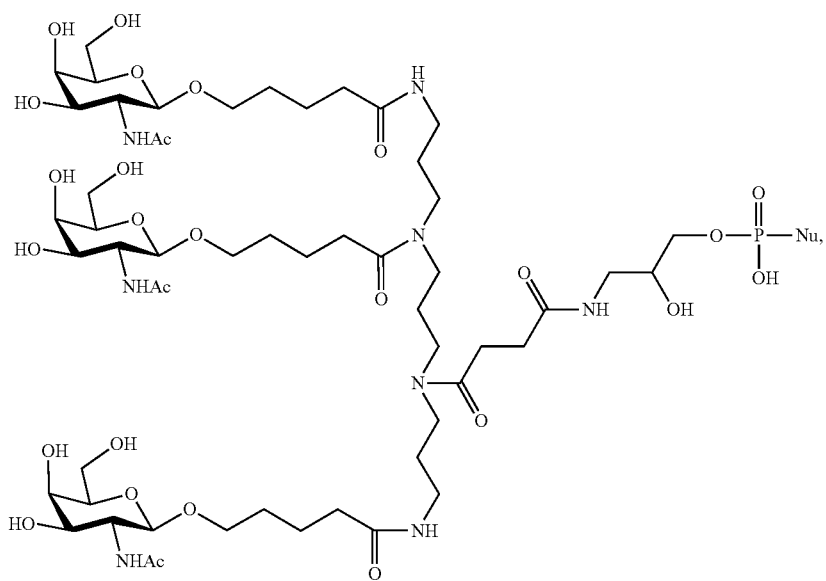
Formula (413)
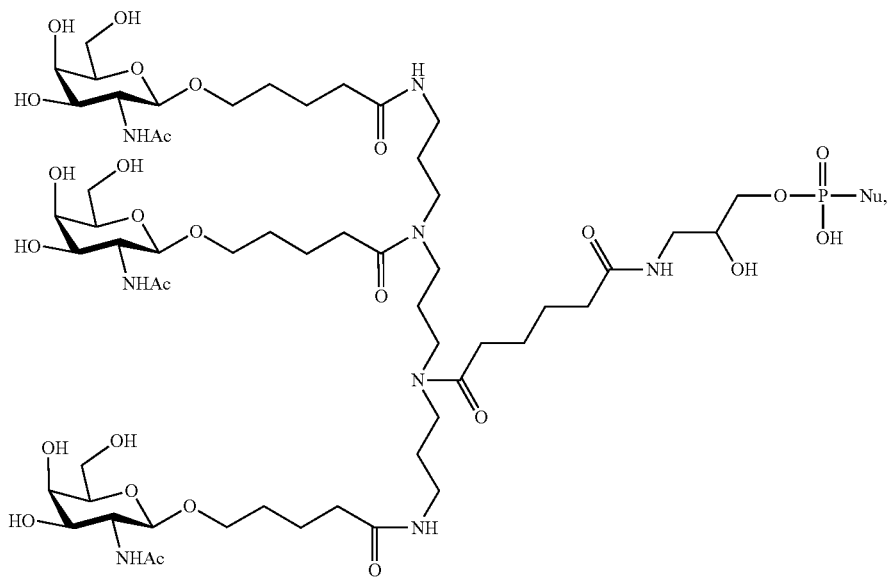

Fromula (414)
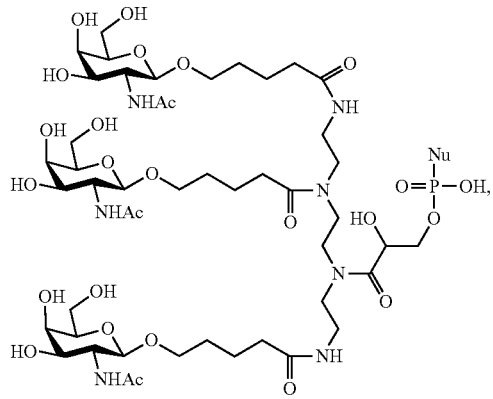
Formula (415)
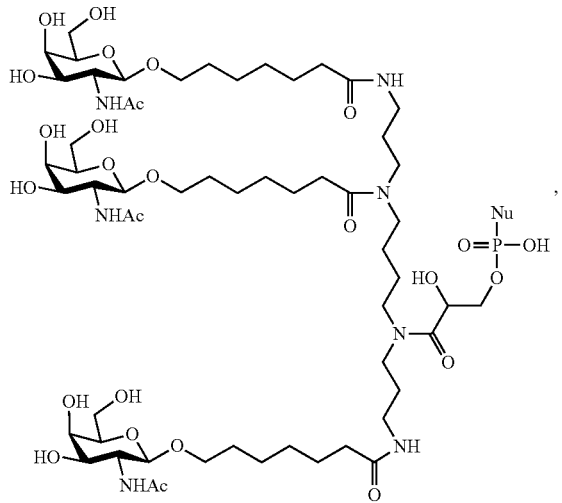
Formula (416)
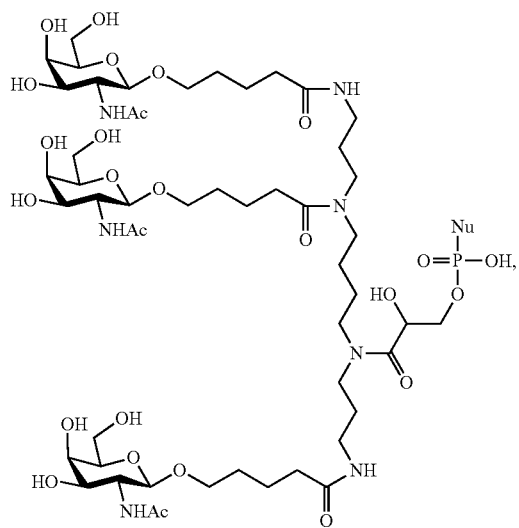
Formula (417)
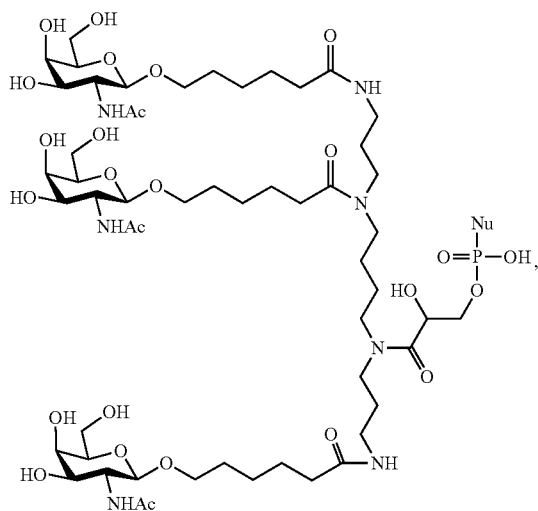

-continued
Formula (418)
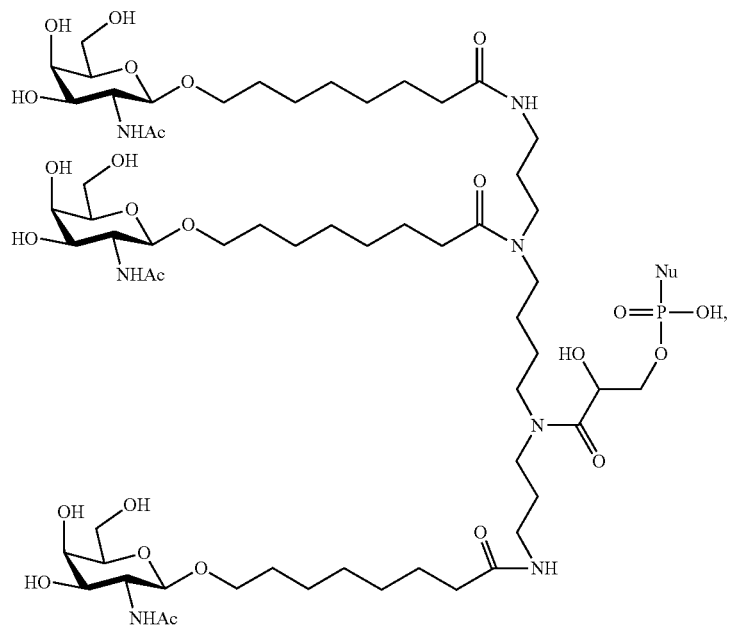
Formula (419)
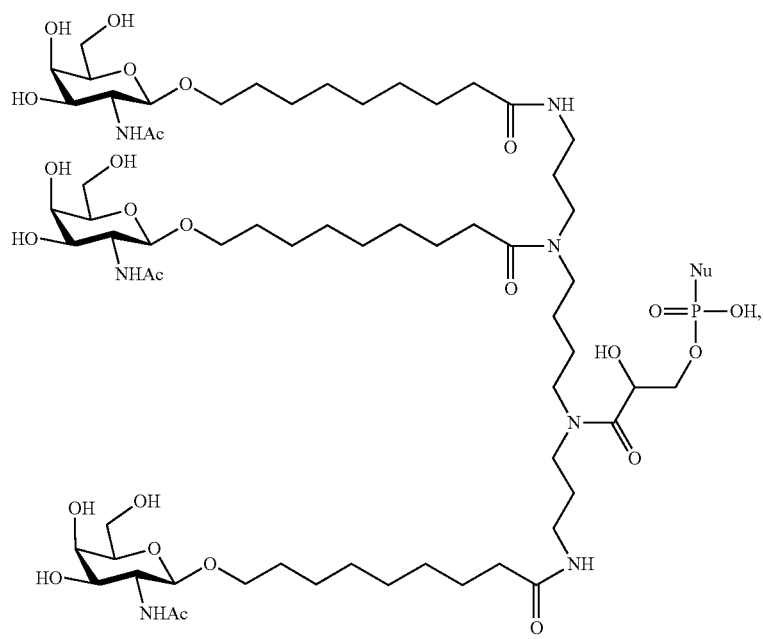

-continued
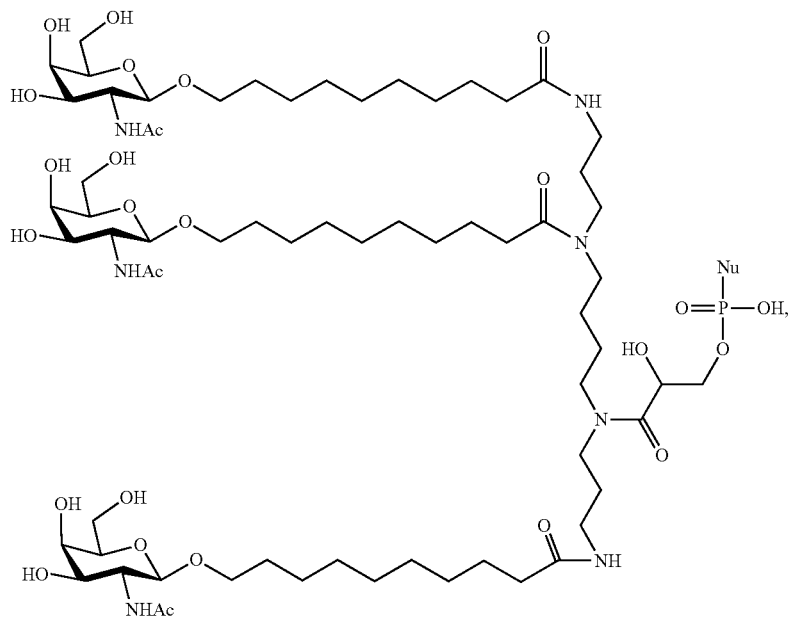
Formula (420)
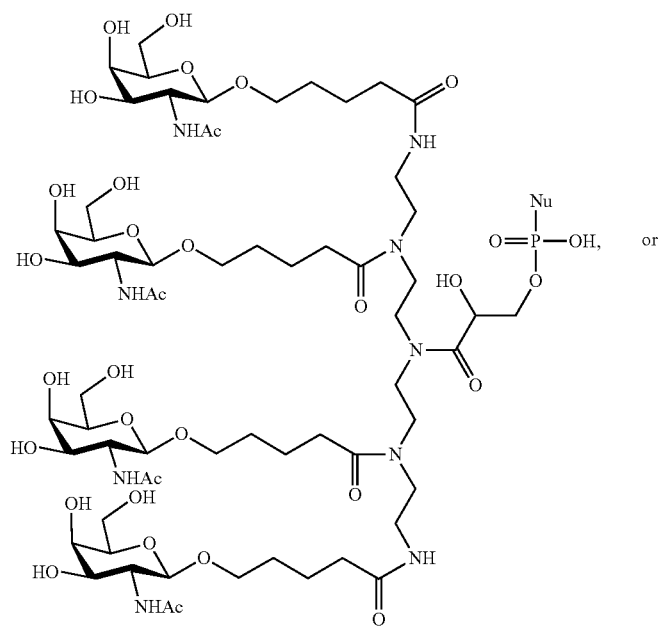
Formula (421)
or

-continued

Formula (422)

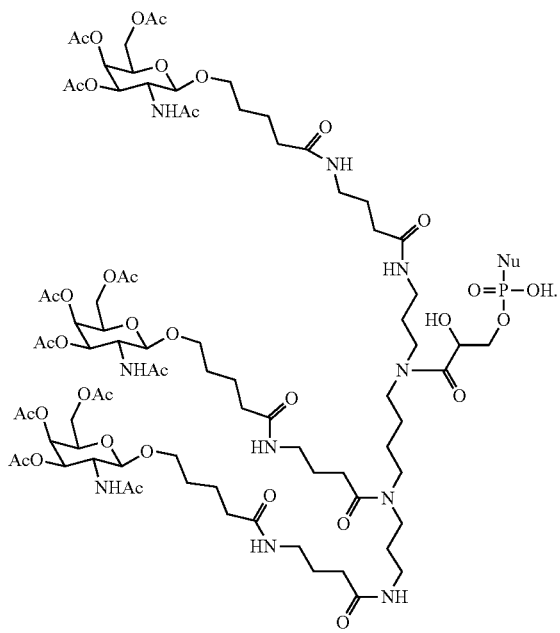

25. The siRNA conjugate according to claim 16, wherein the P atom in Formula A59 is linked to 3' terminal of the sense strand of the siRNA.

26. A method for treating and/or preventing a pathological condition or disease caused by HBV infection, wherein the method comprises administering to a subject in need thereof an effective amount of the siRNA according to claim 1 and/or the siRNA conjugate comprising the same.

* * * * *

UNITED STATES PATENT AND TRADEMARK OFFICE
CERTIFICATE OF CORRECTION

PATENT NO. : 11,414,665 B2  
APPLICATION NO. : 16/763058  
DATED : August 16, 2022  
INVENTOR(S) : Hongyan Zhang et al.

Page 1 of 2

It is certified that error appears in the above-identified patent and that said Letters Patent is hereby corrected as shown below:

In the Specification

In Column 23, Lines 5-16:

" 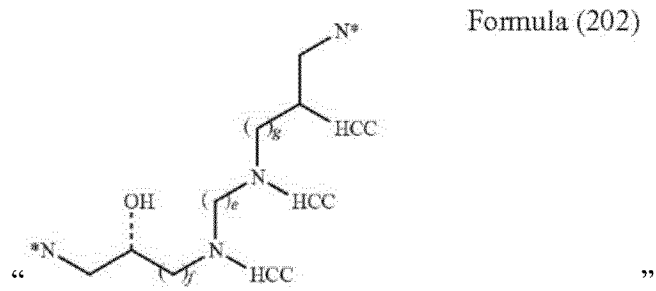 Formula (202) "

Should read:

-- 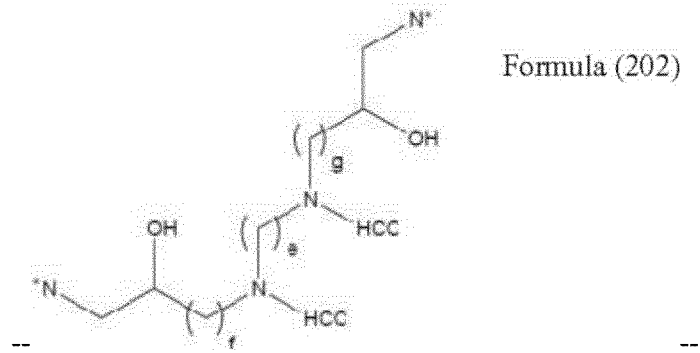 Formula (202) --

Signed and Sealed this  
Eleventh Day of October, 2022

Katherine Kelly Vidal  
*Director of the United States Patent and Trademark Office*

CERTIFICATE OF CORRECTION (continued)
U.S. Pat. No. 11,414,665 B2

In Column 36, Lines 28-51:

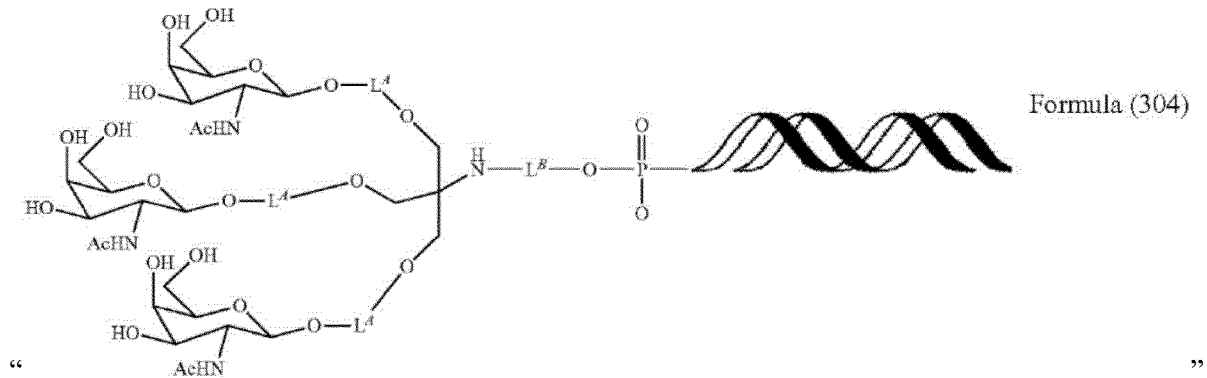
"

Should read:

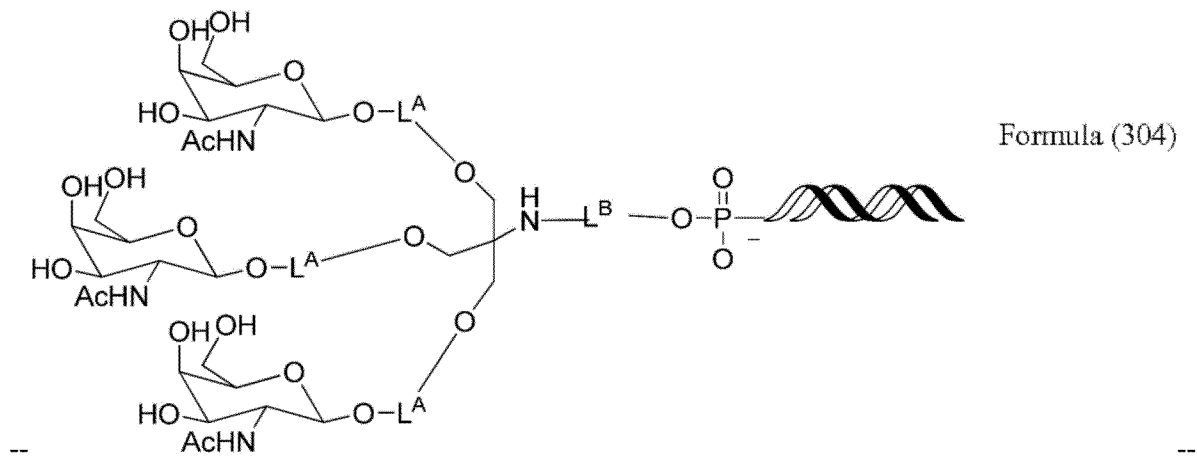
--

In the Claims

In Column 216, Lines 13-23:

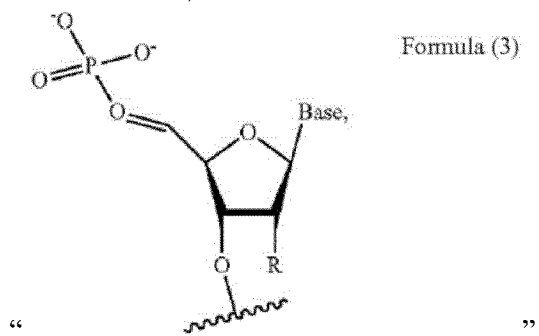
"

Should read:

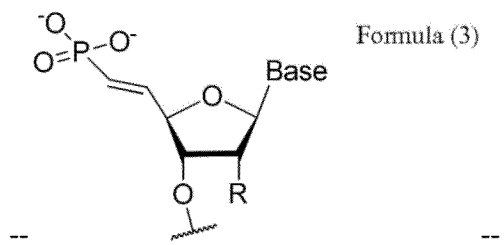
--

SEQUENCE LISTING

<160> NUMBER OF SEQ ID NOS: 53

<210> SEQ ID NO 1
<211> LENGTH: 19
<212> TYPE: RNA
<213> ORGANISM: Artificial Sequence

```
<220> FEATURE:
<223> OTHER INFORMATION: siRNA
<220> FEATURE:
<221> NAME/KEY: misc_feature
<222> LOCATION: (19)..(19)
<223> OTHER INFORMATION: n is A

<400> SEQUENCE: 1
ugcuaugccu caucuucun                                                        19

<210> SEQ ID NO 2
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is U

<400> SEQUENCE: 2
nagaagauga ggcauagca                                                        19

<210> SEQ ID NO 3
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (19)..(19)
<223> OTHER INFORMATION: n is selected from A,U,G and C

<400> SEQUENCE: 3
ugcuaugccu caucuucun                                                        19

<210> SEQ ID NO 4
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is selected from A,U,G and C

<400> SEQUENCE: 4
nagaagauga ggcauagca                                                        19

<210> SEQ ID NO 5
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is selected from A,U,G and C

<400> SEQUENCE: 5
nagaagauga ggcauagcag c                                                     21

<210> SEQ ID NO 6
<211> LENGTH: 21
<212> TYPE: RNA
```

```
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is selected from A,U,G and C

<400> SEQUENCE: 6
nagaagauga ggcauagcau u                                              21

<210> SEQ ID NO 7
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is selected from A,U,G and C

<400> SEQUENCE: 7
nagaagauga ggcauagcag c                                              21

<210> SEQ ID NO 8
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is selected from A,U,G and C

<400> SEQUENCE: 8
nagaagauga ggcauagcau u                                              21

<210> SEQ ID NO 9
<211> LENGTH: 19
<212> TYPE: RNA
<213> ORGANISM: Artificial Sequence
<220> FEATURE:
<223> OTHER INFORMATION: siRNA

<400> SEQUENCE: 9
ugcuaugccu caucuucua                                                 19

<210> SEQ ID NO 10
<211> LENGTH: 21
<212> TYPE: RNA
<213> ORGANISM: Artificial Sequence
<220> FEATURE:
<223> OTHER INFORMATION: siRNA

<400> SEQUENCE: 10
uagaagauga ggcauagcag c                                              21

<210> SEQ ID NO 11
<211> LENGTH: 21
<212> TYPE: RNA
<213> ORGANISM: Artificial Sequence
<220> FEATURE:
<223> OTHER INFORMATION: siRNA

<400> SEQUENCE: 11
uagaagauga ggcauagcau u                                              21
```

```
<210> SEQ ID NO 12
<211> LENGTH: 19
<212> TYPE: RNA
<213> ORGANISM: Artificial Sequence
<220> FEATURE:
<223> OTHER INFORMATION: siRNA

<400> SEQUENCE: 12
ugcuaugccu caucuucua                                                    19

<210> SEQ ID NO 13
<211> LENGTH: 21
<212> TYPE: RNA
<213> ORGANISM: Artificial Sequence
<220> FEATURE:
<223> OTHER INFORMATION: siRNA

<400> SEQUENCE: 13
uagaagauga ggcauagcag c                                                 21

<210> SEQ ID NO 14
<211> LENGTH: 21
<212> TYPE: RNA
<213> ORGANISM: Artificial Sequence
<220> FEATURE:
<223> OTHER INFORMATION: siRNA

<400> SEQUENCE: 14
uagaagauga ggcauagcau u                                                 21

<210> SEQ ID NO 15
<211> LENGTH: 19
<212> TYPE: RNA
<213> ORGANISM: Artificial Sequence
<220> FEATURE:
<223> OTHER INFORMATION: siRNA

<400> SEQUENCE: 15
ugcuaugccu caucuucua                                                    19

<210> SEQ ID NO 16
<211> LENGTH: 21
<212> TYPE: RNA
<213> ORGANISM: Artificial Sequence
<220> FEATURE:
<223> OTHER INFORMATION: siRNA

<400> SEQUENCE: 16
uagaagauga ggcauagcag c                                                 21

<210> SEQ ID NO 17
<211> LENGTH: 21
<212> TYPE: RNA
<213> ORGANISM: Artificial Sequence
<220> FEATURE:
<223> OTHER INFORMATION: siRNA

<400> SEQUENCE: 17
uagaagauga ggcauagcau u                                                 21

<210> SEQ ID NO 18
<211> LENGTH: 19
<212> TYPE: RNA
<213> ORGANISM: Artificial Sequence
<220> FEATURE:
```

```
<223> OTHER INFORMATION: siRNA

<400> SEQUENCE: 18
ugcuaugccu caucuucua                                                    19

<210> SEQ ID NO 19
<211> LENGTH: 21
<212> TYPE: RNA
<213> ORGANISM: Artificial Sequence
<220> FEATURE:
<223> OTHER INFORMATION: siRNA

<400> SEQUENCE: 19
uagaagauga ggcauagcag c                                                 21

<210> SEQ ID NO 20
<211> LENGTH: 21
<212> TYPE: RNA
<213> ORGANISM: Artificial Sequence
<220> FEATURE:
<223> OTHER INFORMATION: siRNA

<400> SEQUENCE: 20
uagaagauga ggcauagcau u                                                 21

<210> SEQ ID NO 21
<211> LENGTH: 21
<212> TYPE: RNA
<213> ORGANISM: Artificial Sequence
<220> FEATURE:
<223> OTHER INFORMATION: siRNA

<400> SEQUENCE: 21
uagaagauga ggcauagcag c                                                 21

<210> SEQ ID NO 22
<211> LENGTH: 21
<212> TYPE: RNA
<213> ORGANISM: Artificial Sequence
<220> FEATURE:
<223> OTHER INFORMATION: siRNA

<400> SEQUENCE: 22
uagaagauga ggcauagcau u                                                 21

<210> SEQ ID NO 23
<211> LENGTH: 21
<212> TYPE: RNA
<213> ORGANISM: Artificial Sequence
<220> FEATURE:
<223> OTHER INFORMATION: siRNA

<400> SEQUENCE: 23
uagaagauga ggcauagcag c                                                 21

<210> SEQ ID NO 24
<211> LENGTH: 21
<212> TYPE: RNA
<213> ORGANISM: Artificial Sequence
<220> FEATURE:
<223> OTHER INFORMATION: siRNA

<400> SEQUENCE: 24
uagaagauga ggcauagcau u                                                 21
```

```
<210> SEQ ID NO 25
<211> LENGTH: 21
<212> TYPE: RNA
<213> ORGANISM: Artificial Sequence
<220> FEATURE:
<223> OTHER INFORMATION: siRNA

<400> SEQUENCE: 25
uagaagauga ggcauagcag c                                              21

<210> SEQ ID NO 26
<211> LENGTH: 21
<212> TYPE: RNA
<213> ORGANISM: Artificial Sequence
<220> FEATURE:
<223> OTHER INFORMATION: siRNA

<400> SEQUENCE: 26
uagaagauga ggcauagcau u                                              21

<210> SEQ ID NO 27
<211> LENGTH: 21
<212> TYPE: RNA
<213> ORGANISM: Artificial Sequence
<220> FEATURE:
<223> OTHER INFORMATION: siRNA

<400> SEQUENCE: 27
uagaagauga ggcauagcag c                                              21

<210> SEQ ID NO 28
<211> LENGTH: 21
<212> TYPE: RNA
<213> ORGANISM: Artificial Sequence
<220> FEATURE:
<223> OTHER INFORMATION: siRNA

<400> SEQUENCE: 28
uagaagauga ggcauagcau u                                              21

<210> SEQ ID NO 29
<211> LENGTH: 21
<212> TYPE: RNA
<213> ORGANISM: Artificial Sequence
<220> FEATURE:
<223> OTHER INFORMATION: siRNA

<400> SEQUENCE: 29
uagaagauga ggcauagcag c                                              21

<210> SEQ ID NO 30
<211> LENGTH: 21
<212> TYPE: RNA
<213> ORGANISM: Artificial Sequence
<220> FEATURE:
<223> OTHER INFORMATION: siRNA

<400> SEQUENCE: 30
uagaagauga ggcauagcau u                                              21

<210> SEQ ID NO 31
<211> LENGTH: 21
<212> TYPE: RNA
<213> ORGANISM: Artificial Sequence
<220> FEATURE:
<223> OTHER INFORMATION: siRNA
```

```
<400> SEQUENCE: 31
uagaagauga ggcauagcag c                                              21

<210> SEQ ID NO 32
<211> LENGTH: 21
<212> TYPE: RNA
<213> ORGANISM: Artificial Sequence
<220> FEATURE:
<223> OTHER INFORMATION: siRNA

<400> SEQUENCE: 32
uagaagauga ggcauagcau u                                              21

<210> SEQ ID NO 33
<211> LENGTH: 21
<212> TYPE: RNA
<213> ORGANISM: Artificial Sequence
<220> FEATURE:
<223> OTHER INFORMATION: siRNA

<400> SEQUENCE: 33
uagaagauga ggcauagcag c                                              21

<210> SEQ ID NO 34
<211> LENGTH: 21
<212> TYPE: RNA
<213> ORGANISM: Artificial Sequence
<220> FEATURE:
<223> OTHER INFORMATION: siRNA

<400> SEQUENCE: 34
gcugcuaugc cucaucuucu a                                              21

<210> SEQ ID NO 35
<211> LENGTH: 23
<212> TYPE: RNA
<213> ORGANISM: Artificial Sequence
<220> FEATURE:
<223> OTHER INFORMATION: siRNA

<400> SEQUENCE: 35
uagaagauga ggcauagcag cgc                                            23

<210> SEQ ID NO 36
<211> LENGTH: 19
<212> TYPE: RNA
<213> ORGANISM: Artificial Sequence
<220> FEATURE:
<223> OTHER INFORMATION: siRNA

<400> SEQUENCE: 36
ugcuaugccu caucuucua                                                 19

<210> SEQ ID NO 37
<211> LENGTH: 21
<212> TYPE: RNA
<213> ORGANISM: Artificial Sequence
<220> FEATURE:
<223> OTHER INFORMATION: siRNA

<400> SEQUENCE: 37
uagaagauga ggcauagcag c                                              21

<210> SEQ ID NO 38
<211> LENGTH: 19
```

```
<212> TYPE: RNA
<213> ORGANISM: Artificial Sequence
<220> FEATURE:
<223> OTHER INFORMATION: siRNA

<400> SEQUENCE: 38
ugcuaugccu caucuucua                                                    19

<210> SEQ ID NO 39
<211> LENGTH: 21
<212> TYPE: RNA
<213> ORGANISM: Artificial Sequence
<220> FEATURE:
<223> OTHER INFORMATION: siRNA

<400> SEQUENCE: 39
uagaagauga ggcauagcau u                                                 21

<210> SEQ ID NO 40
<211> LENGTH: 21
<212> TYPE: RNA
<213> ORGANISM: Artificial Sequence
<220> FEATURE:
<223> OTHER INFORMATION: siRNA

<400> SEQUENCE: 40
uagaagauga ggcauagcag c                                                 21

<210> SEQ ID NO 41
<211> LENGTH: 21
<212> TYPE: RNA
<213> ORGANISM: Artificial Sequence
<220> FEATURE:
<223> OTHER INFORMATION: siRNA

<400> SEQUENCE: 41
uagaagauga ggcauagcag c                                                 21

<210> SEQ ID NO 42
<211> LENGTH: 19
<212> TYPE: RNA
<213> ORGANISM: Artificial Sequence
<220> FEATURE:
<223> OTHER INFORMATION: siRNA

<400> SEQUENCE: 42
uucuccgaac gugucacgu                                                    19

<210> SEQ ID NO 43
<211> LENGTH: 21
<212> TYPE: RNA
<213> ORGANISM: Artificial Sequence
<220> FEATURE:
<223> OTHER INFORMATION: siRNA

<400> SEQUENCE: 43
acgugacacg uucggagaau u                                                 21

<210> SEQ ID NO 44
<211> LENGTH: 19
<212> TYPE: RNA
<213> ORGANISM: Artificial Sequence
<220> FEATURE:
<223> OTHER INFORMATION: siRNA

<400> SEQUENCE: 44
```

```
gcugcuaugc cucaucuua                                              19

<210> SEQ ID NO 45
<211> LENGTH: 21
<212> TYPE: RNA
<213> ORGANISM: Artificial Sequence
<220> FEATURE:
<223> OTHER INFORMATION: siRNA

<400> SEQUENCE: 45
uaagaugagg cauagcagca g                                           21

<210> SEQ ID NO 46
<211> LENGTH: 19
<212> TYPE: RNA
<213> ORGANISM: Artificial Sequence
<220> FEATURE:
<223> OTHER INFORMATION: siRNA

<400> SEQUENCE: 46
ccuugaggca uacuucaaa                                              19

<210> SEQ ID NO 47
<211> LENGTH: 21
<212> TYPE: RNA
<213> ORGANISM: Artificial Sequence
<220> FEATURE:
<223> OTHER INFORMATION: siRNA

<400> SEQUENCE: 47
uuugaaguau gccucaaggu u                                           21

<210> SEQ ID NO 48
<211> LENGTH: 20
<212> TYPE: DNA
<213> ORGANISM: Artificial Sequence
<220> FEATURE:
<223> OTHER INFORMATION: primer

<400> SEQUENCE: 48
ccgtctgtgc cttctcatct                                             20

<210> SEQ ID NO 49
<211> LENGTH: 20
<212> TYPE: DNA
<213> ORGANISM: Artificial Sequence
<220> FEATURE:
<223> OTHER INFORMATION: primer

<400> SEQUENCE: 49
taatctcctc ccccaactcc                                             20

<210> SEQ ID NO 50
<211> LENGTH: 24
<212> TYPE: DNA
<213> ORGANISM: Artificial Sequence
<220> FEATURE:
<223> OTHER INFORMATION: primer

<400> SEQUENCE: 50
aactttggca ttgtggaagg gctc                                        24

<210> SEQ ID NO 51
<211> LENGTH: 24
<212> TYPE: DNA
<213> ORGANISM: Artificial Sequence
```

```
<220> FEATURE:
<223> OTHER INFORMATION: primer

<400> SEQUENCE: 51
tggaagagtg ggagttgctg ttga                                              24

<210> SEQ ID NO 52
<211> LENGTH: 21
<212> TYPE: DNA
<213> ORGANISM: Artificial Sequence
<220> FEATURE:
<223> OTHER INFORMATION: primer

<400> SEQUENCE: 52
cgtttctcct ggctcagttt a                                                 21

<210> SEQ ID NO 53
<211> LENGTH: 21
<212> TYPE: DNA
<213> ORGANISM: Artificial Sequence
<220> FEATURE:
<223> OTHER INFORMATION: primer

<400> SEQUENCE: 53
cagcggtaaa aagggactca a                                                 21
```